United States Patent
Wiles et al.

(10) Patent No.: US 9,828,396 B2
(45) Date of Patent: Nov. 28, 2017

(54) ALKYNE COMPOUNDS FOR TREATMENT OF COMPLEMENT MEDIATED DISORDERS

(71) Applicant: Achillion Pharmaceuticals, Inc., New Haven, CT (US)

(72) Inventors: Jason Allan Wiles, Madison, CT (US); Godwin Pais, Hamden, CT (US); Akihiro Hashimoto, Branford, CT (US); Venkat Rao Gadhachanda, Hamden, CT (US); Qiuping Wang, Bethany, CT (US); Dawei Chen, Guilford, CT (US); Xiangzhu Wang, Branford, CT (US); Atul Agarwal, Hamden, CT (US); Milind Deshpande, Madison, CT (US); Avinash S. Phadke, Branford, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 143 days.

(21) Appl. No.: 14/631,090

(22) Filed: Feb. 25, 2015

(65) Prior Publication Data

US 2015/0239868 A1    Aug. 27, 2015

Related U.S. Application Data

(60) Provisional application No. 61/944,189, filed on Feb. 25, 2014, provisional application No. 62/022,916, (Continued)

(51) Int. Cl.
| | |
|---|---|
| *C07D 401/14* | (2006.01) |
| *C07D 403/14* | (2006.01) |
| *A61K 31/506* | (2006.01) |
| *C07F 9/572* | (2006.01) |
| *C07D 209/42* | (2006.01) |
| *C07D 403/12* | (2006.01) |
| *C07D 471/04* | (2006.01) |
| *C07D 417/06* | (2006.01) |
| *C07D 403/06* | (2006.01) |
| *C07D 417/14* | (2006.01) |

(Continued)

(52) U.S. Cl.
CPC .......... *C07F 9/5728* (2013.01); *A61K 31/404* (2013.01); *A61K 31/407* (2013.01); *A61K 31/4162* (2013.01); *A61K 31/4178* (2013.01); *A61K 31/4184* (2013.01); *A61K 31/4188* (2013.01); *A61K 31/4192* (2013.01); *A61K 31/437* (2013.01); *A61K 31/4439* (2013.01); *A61K 31/4709* (2013.01); *A61K 31/496* (2013.01); *A61K 31/506* (2013.01); *A61K 31/549* (2013.01); *A61K 31/55* (2013.01); *A61K 31/675* (2013.01); *A61K 31/683* (2013.01); *C07B 59/002* (2013.01); *C07D 209/14* (2013.01); *C07D 209/40* (2013.01); *C07D 209/42* (2013.01); *C07D 401/14* (2013.01); *C07D 403/06* (2013.01); *C07D 403/08* (2013.01); *C07D 403/12* (2013.01); *C07D 403/14* (2013.01); *C07D 405/12* (2013.01); *C07D 405/14* (2013.01); *C07D 413/06* (2013.01); *C07D 413/14* (2013.01); *C07D 417/06* (2013.01); *C07D 417/12* (2013.01); *C07D 417/14* (2013.01); *C07D 471/04* (2013.01); *C07D 487/04* (2013.01); *C07D 487/14* (2013.01); *C07D 491/113* (2013.01); *C07D 495/04* (2013.01); *C07D 513/04* (2013.01); *C07F 5/025* (2013.01); *C07F 5/027* (2013.01); *C07F 7/0812* (2013.01); *C07F 9/6561* (2013.01); *C07F 9/65583* (2013.01); *C07F 9/65616* (2013.01); *C07B 2200/05* (2013.01)

(58) Field of Classification Search
None
See application file for complete search history.

(56) References Cited

U.S. PATENT DOCUMENTS

| 6,489,476 B1 | 12/2002 | Dang et al. |
| 6,653,340 B1 | 11/2003 | Babu et al. |

(Continued)

FOREIGN PATENT DOCUMENTS

| WO | WO 93/20099 A2 | 10/1993 |
| WO | WO 95/29697 A1 | 11/1995 |

(Continued)

OTHER PUBLICATIONS

International Search Report and Written Opinion for PCT/US2015/017523 dated May 14, 2015.

(Continued)

*Primary Examiner* — Michael Barker
(74) *Attorney, Agent, or Firm* — Knowles Intellectual Property Strategies, LLC

(57) ABSTRACT

Compounds, methods of use, and processes for making inhibitors of complement factor D comprising Formula I, or a pharmaceutically acceptable salt or composition thereof, wherein $R^{12}$ or $R^{13}$ on the A group is an alkyne ($R^{32}$) are provided. The inhibitors described herein target factor D and inhibit or regulate the complement cascade at an early and essential point in the alternative complement pathway, and reduce factor D's ability to modulate the classical and lectin complement pathways. The inhibitors of factor D described herein are capable of reducing the excessive activation of complement, which has been linked to certain autoimmune, inflammatory, and neurodegenerative diseases, as well as ischemia-reperfusion injury and cancer.

40 Claims, No Drawings

Related U.S. Application Data filed on Jul. 10, 2014, provisional application No. 62/046,783, filed on Sep. 5, 2014.

(51) Int. Cl.

| | |
|---|---|
| C07F 7/08 | (2006.01) |
| C07D 413/14 | (2006.01) |
| C07D 487/04 | (2006.01) |
| C07D 405/14 | (2006.01) |
| C07D 403/08 | (2006.01) |
| C07D 413/06 | (2006.01) |
| C07F 5/02 | (2006.01) |
| C07F 9/6561 | (2006.01) |
| C07F 9/6558 | (2006.01) |
| A61K 31/404 | (2006.01) |
| A61K 31/407 | (2006.01) |
| A61K 31/4162 | (2006.01) |
| A61K 31/4178 | (2006.01) |
| A61K 31/4184 | (2006.01) |
| A61K 31/4188 | (2006.01) |
| A61K 31/4192 | (2006.01) |
| A61K 31/437 | (2006.01) |
| A61K 31/4439 | (2006.01) |
| A61K 31/4709 | (2006.01) |
| A61K 31/496 | (2006.01) |
| A61K 31/549 | (2006.01) |
| A61K 31/55 | (2006.01) |
| A61K 31/675 | (2006.01) |
| A61K 31/683 | (2006.01) |
| C07B 59/00 | (2006.01) |
| C07D 209/14 | (2006.01) |
| C07D 209/40 | (2006.01) |
| C07D 405/12 | (2006.01) |
| C07D 417/12 | (2006.01) |
| C07D 487/14 | (2006.01) |
| C07D 491/113 | (2006.01) |
| C07D 495/04 | (2006.01) |
| C07D 513/04 | (2006.01) |

(56) References Cited

U.S. PATENT DOCUMENTS

| | | |
|---|---|---|
| 9,598,446 B2 | 3/2017 | Gadhachanda et al. |
| 9,643,986 B2 | 5/2017 | Wiles et al. |
| 9,663,543 B2 | 5/2017 | Wiles et al. |
| 9,695,205 B2 | 7/2017 | Wiles et al. |
| 2005/0228000 A1 | 10/2005 | Smallheer et al. |
| 2005/0267108 A1 | 12/2005 | Hsieh et al. |
| 2007/0155712 A1 | 7/2007 | Zahn et al. |
| 2008/0075720 A1 | 3/2008 | Holers et al. |
| 2008/0075728 A1 | 3/2008 | Newman et al. |
| 2008/0108691 A1 | 5/2008 | Hamann et al. |
| 2010/0041628 A1 | 2/2010 | Enomoto et al. |
| 2011/0280808 A1 | 11/2011 | Kroth et al. |
| 2012/0231471 A1 | 9/2012 | Sato et al. |
| 2012/0295884 A1 | 11/2012 | Altmann et al. |
| 2013/0296377 A1 | 11/2013 | Adams et al. |
| 2014/0371133 A1 | 12/2014 | Francois et al. |
| 2015/0141455 A1 | 5/2015 | Altmann et al. |
| 2015/0148374 A1 | 5/2015 | Hommel et al. |
| 2015/0239837 A1 | 8/2015 | Wiles et al. |
| 2015/0239838 A1 | 8/2015 | Phadke et al. |
| 2015/0239893 A1 | 8/2015 | Wang et al. |
| 2015/0239894 A1 | 8/2015 | Gadhachanda et al. |
| 2015/0239895 A1 | 8/2015 | Gadhachanda et al. |
| 2015/0239919 A1 | 8/2015 | Gadhachanda et al. |
| 2015/0239920 A1 | 8/2015 | Gadhachanda et al. |
| 2015/0239921 A1 | 8/2015 | Wiles et al. |
| 2016/0361329 A1 | 12/2016 | Wiles et al. |
| 2016/0362398 A1 | 12/2016 | Wiles et al. |
| 2016/0362399 A1 | 12/2016 | Wiles et al. |
| 2016/0362432 A1 | 12/2016 | Wiles et al. |
| 2016/0362433 A1 | 12/2016 | Wiles et al. |
| 2017/0056428 A1 | 3/2017 | Wiles et al. |
| 2017/0057950 A1 | 3/2017 | Wiles et al. |
| 2017/0057983 A1 | 3/2017 | Wiles et al. |
| 2017/0057993 A1 | 3/2017 | Wiles et al. |
| 2017/0066783 A1 | 3/2017 | Wiles et al. |
| 2017/0189410 A1 | 7/2017 | Gadhachanda et al. |

FOREIGN PATENT DOCUMENTS

| | | |
|---|---|---|
| WO | WO 99/48492 A1 | 9/1999 |
| WO | WO 2004/007501 A1 | 1/2004 |
| WO | WO 2004/045518 A2 | 6/2004 |
| WO | WO 2004/111041 A1 | 12/2004 |
| WO | WO 2008/047831 A1 | 4/2008 |
| WO | WO 2009/091826 A2 | 7/2009 |
| WO | WO 2012/093101 A1 | 7/2012 |
| WO | WO 2012/177782 A1 | 12/2012 |
| WO | WO 2013/166436 A1 | 11/2013 |
| WO | WO 2014/002051 A2 | 1/2014 |
| WO | WO 2014/002052 A1 | 1/2014 |
| WO | WO 2014/002053 A1 | 1/2014 |
| WO | WO 2014/002054 A1 | 1/2014 |
| WO | WO 2014/002057 A1 | 1/2014 |
| WO | WO 2014/002058 A2 | 1/2014 |
| WO | WO 2014/002059 A1 | 1/2014 |
| WO | WO 2014/005150 A1 | 1/2014 |
| WO | WO 2014/009833 A1 | 1/2014 |
| WO | WO 2014/037480 A1 | 3/2014 |
| WO | WO 2014/116880 A1 | 7/2014 |
| WO | WO 2015/130795 A1 | 9/2015 |
| WO | WO 2015/130806 A1 | 9/2015 |
| WO | WO 2015/130830 A1 | 9/2015 |
| WO | WO 2015/130838 A1 | 9/2015 |
| WO | WO 2015/130842 A2 | 9/2015 |
| WO | WO 2015/130845 A1 | 9/2015 |
| WO | WO 2015/130854 A1 | 9/2015 |
| WO | WO 2017/035348 A1 | 3/2017 |
| WO | WO 2017/035349 A1 | 3/2017 |
| WO | WO 2017/035351 A1 | 3/2017 |
| WO | WO 2017/035352 A1 | 3/2017 |
| WO | WO 2017/035353 A1 | 3/2017 |
| WO | WO 2017/035355 A1 | 3/2017 |
| WO | WO 2017/035357 A1 | 3/2017 |
| WO | WO 2017/035360 A1 | 3/2017 |
| WO | WO 2017/035361 A1 | 3/2017 |
| WO | WO 2017/035362 A1 | 3/2017 |
| WO | WO 2017/035401 A1 | 3/2017 |
| WO | WO 2017/035405 A1 | 3/2017 |
| WO | WO 2017/035408 A1 | 3/2017 |
| WO | WO 2017/035409 A1 | 3/2017 |
| WO | WO 2017/035411 A1 | 3/2017 |
| WO | WO 2017/035413 A1 | 3/2017 |
| WO | WO 2017/035415 A1 | 3/2017 |
| WO | WO 2017/035417 A1 | 3/2017 |
| WO | WO 2017/035418 A1 | 3/2017 |
| WO | WO 2017/098328 A2 | 6/2017 |

OTHER PUBLICATIONS

International Search Report and Written Opinion for PCT/US2015/017538 dated May 14, 2015.
International Search Report and Written Opinion for PCT/US2015/017554 dated May 14, 2015.
International Search Report and Written Opinion for PCT/US2015/017583 dated May 27, 2015.
International Search Report and Written Opinion for PCT/US2015/017593 dated Jun. 16, 2015.
International Search Report and Written Opinion for PCT/US2015/017597 dated Jan. 29, 2016.
International Search Report and Written Opinion for PCT/US2015/17600 dated May 27, 2015.
International Search Report and Written Opinion for PCT/US2015/017609 dated May 29, 2015.

(56) References Cited

OTHER PUBLICATIONS

Airey et al. "A Convenient Preparation of Thieno[3,2-c]pyrazole" Synthesis, 2014; 46: 96-100.
Barraclough et al. "Synthesis of (2S,3R)- and (@S,3S)-[3-$^2$H$_1$]-proline via highly selective hydrolysis of a silyl enol ether" Tetrahedron Letters, 2005; 46: 4653-4655.
Barraclough et al. "Two separate and distinct syntheses of stereospecifically deuteriated samples of (2S)-proline" Organic & Biomolecular Chemistry, 2006; 4: 1483-1491.
Cole et al. "Structure of 3,4-Dichloroisocoumarin-Inhibited Factor D" Acta Crystallographica, 1998; D54: 711-717.
De Luca et al. "HIV-1 integrase strand-transfer inhibitors: Design, synthesis and molecular modeling investigation" European Journal of Medicinal Chemistry, 2011; 46: 756-764.
Donthiri et al. "Copper-Catalyzed C—H Functionalization of Pyridines and Isoquinolines with Vinyl Azides: Synthesis of Imidazo Heterocycles" Journal of Organic Chemistry, 2014; 79: 11277-11284.
Dormoy et al. "Synthesis of N-t-Butoxycarbonyl-4,4-dideuterio-L-proline" Synthesis, 1986; 1: 81-82.
Hecker et al. "Liver-Targeted Prodrugs of 2'-C-Methyladenosine for Therapy of Hepatitis C Virus Infection" Journal of Medicinal Chemistry, 2007; 50(16): 3891-3896.
Hruby et al. "Carbon-13 NMR studies of the Peptide hormones oxytocin, arginine vasopressin, isotocin, mesotocin, glumitocin, aspartocin, related analogs, and diastereoisomers. Use of specifically deuterated hormone derivatives for assignments and effects of structural changes on carbon-13 NMR chemical shifts in peptides" Journal of the American Chemical Society, 1979; 101(1): 202-212.
Kobayashi et al. "Carboxylation of alkynylsilanes with carbon dioxide mediated by cesium fluoride in DMSO" Organic & Biomolecular Chemistry, 2013; 11: 3773-3775.
Kuang et al. "Synthesis of (Z)-1-bromo-l-alkenes and terminal alkynes from anti-2,3- dibromoalkanoic acids by microwave-induced reaction" Tetrahedron, 2006; 61(16): 4043-4052.
Mackay et al. "Rapid Synthesis of the N-Methylwelwitindolinone Skeleton" Organic Letters, 2005; 7: 3421-3424.
Okutani et al. "Conversion of Bromoalkenes into Alkynes by Wet Tetra-n-butylammonium Fluoride" Journal of Organic Chemistry, 2009; 74: 442-444.
Quesada et al. "One-pot conversion of activated alcohols into terminal alkynes using manganese dioxide in combination with the Bestmann—Ohira reagent" Tetrahedron Letters, 2005; 46: 6473-6476.
Roth et al. "Further Improvements of the Synthesis of Alkynes from Aldehydes" Synthesis, 2004; 1: 59-62.
Ruiz-Gomez et al. "Structure—Activity Relationships for Substrate-Based Inhibitors of Human Complement Factor B" Journal of Medicinal Chemistry, 2009; 52: 6042-6052.
Tandon et al. "Substrate specificity of human prolyl-4-hydroxylase" Bioorganic and Medicinal Chemistry Letters, 1998; 8(10): 1139-1144.
Tang et al. "Palladium-Catalyzed Carbonylative Sonogashira Coupling of Aryl Bromides via tert-Butyl Isocyanide Insertion" Journal of Organic Chemistry, 2013; 78(7): 3170-3175.
Peifer et al. "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors", J. Med. Chem. 2008, vol. 51, pp. 3814-3824.
Qu et al. "Recent Developments in Low Molecular Weight Complement Inhibitors", Mol. Immunol. 2009. vol. 47 (2-3). pp. 185-195.
International Search Report and Written Opinion for PCT/US2016/048688 dated Dec. 28, 2016.
International Search Report and Written Opinion for PCT/US2016/048690 dated Dec. 28, 2016.
International Search Report and Written Opinion for PCT/US2016/048693 dated Jan. 13, 2017.
International Search Report and Written Opinion for PCT/US2016/048695 dated Dec. 30, 2016.
International Search Report and Written Opinion for PCT/US2016/048696 dated Jan. 5, 2017.
International Search Report and Written Opinion for PCT/US2016/048701 dated Jan. 10, 2017.
International Search Report and Written Opinion for PCT/US2016/048704 dated Dec. 27, 2016.
International Search Report and Written Opinion for PCT/ US2016/048707 dated Jan. 5, 2017.
International Search Report and Written Opinion for PCT/ US2016/048709 dated Jan. 17, 2017.
International Search Report and Written Opinion for PCT/ US2016/048797 dated Dec. 27, 2016.
International Search Report and Written Opinion for PCT/ US2016/048779 dated Dec. 27, 2016.
International Search Report and Written Opinion for PCT/ US2016/048783 dated Feb. 3, 2017.
International Search Report and Written Opinion for PCT/ US2016/048795 dated Feb. 17, 2017.
International Search Report and Written Opinion for PCT/ US2016/048788 dated Jan. 5, 2017.
International Search Report and Written Opinion for PCT/ US2016/048793 dated Dec. 28, 2016.
International Search Report and Written Opinion for PCT/ US2016/048799 dated Dec. 28, 2016.
International Search Report and Written Opinion for PCT/ US2016/048787 dated Jan. 5, 2017.
International Search Report and Written Opinion for PCT/ US2016/048800 dated Jan. 5, 2017.
International Search Report and Written Opinion for PCT/ US2016/048710 dated Jan. 5, 2017.

ALKYNE COMPOUNDS FOR TREATMENT OF COMPLEMENT MEDIATED DISORDERS

CROSS-REFERENCE TO RELATED APPLICATIONS

This application claims the benefit of provisional U.S. Application No. 61/944,189, filed Feb. 25, 2014, provisional U.S. Application No. 62/022,916, filed Jul. 10, 2014, and provisional U.S. Application 62/046,783, filed Sep. 5, 2014. The entirety of each of these applications is hereby incorporated by reference for all purposes.

BACKGROUND

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phaogytosis of antigens), chemotaxis (attracting macrophages and neutrophils), cell lysis (rupturing membranes of foreign cells) and agglutination (clustering and binding of pathogens together).

The complement system has three pathways: classical, alternative and lectin. Complement factor D plays an early and central role in activation of the alternative pathway of the complement cascade. Activation of the alternative complement pathway is initiated by spontaneous hydrolysis of a thioester bond within C3 to produce $C3(H_2O)$, which associates with factor B to form the $C3(H_2O)B$ complex. Complement factor D acts to cleave factor B within the $C3(H_2O)B$ complex to form Ba and Bb. The Bb fragment remains associated with $C3(H_2O)$ to form the alternative pathway C3 convertase $C3(H_2O)Bb$. Additionally, C3b generated by any of the C3 convertases also associates with factor B to form C3bB, which factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. Some examples of disorders mediated by the complement pathway include age-related macular degeneration (AMD), paroxysmal nocturnal hemoglobinuria (PNH), multiple sclerosis, and rheumatoid arthritis.

Age-related macular degeneration (AMD) is a leading cause of vision loss in industrialized countries. Based on a number of genetic studies, there is evidence of the link between the complement cascade and macular degeneration. Individuals with mutations in the gene encoding complement factor H have a fivefold increased risk of macular degeneration and individuals with mutations in other complement factor genes also have an increased risk of AMD. Individuals with mutant factor H also have increased levels of C-reactive protein, a marker of inflammation. Without adequate functioning factor H, the alternative pathway of the complement cascade is overly activated leading to cellular damage. Inhibition of the alternative pathway is thus desired.

Paroxysmal nocturnal hemoglobinuria (PNH) is a non-malignant, hematological disorder characterized by the expansion of hematopoietic stem cells and progeny mature blood cells which are deficient in some surface proteins. PNH erythrocytes are not capable of modulating their surface complement activation, which leads to the typical hallmark of PNH—the chronic activation of complement mediated intravascular anemia. Currently, only one product, the anti-C5 monoclonal antibody eculizumab, has been approved in the U.S. for treatment of PNH. However, many of the patients treated with eculizumab remain anemic, and many patients continue to require blood transfusions. In addition, treatment with eculizumab requires life-long intravenous injections. Thus, there is an unmet need to develop novel inhibitors of the complement pathway.

Factor D is an attractive target for inhibition or regulation of the complement cascade due to its early and essential role in the alternative complement pathway, and its potential role in signal amplification within the classical and lectin complement pathways. Inhibition of factor D effectively interrupts the pathway and attenuates the formation of the membrane attack complex.

While initial attempts have been made to develop inhibitors of factor D, there are currently no small molecule factor D inhibitors in clinical trials. Examples of factor D inhibitors or prolyl compounds are described in the following disclosures.

Biocryst Pharmaceuticals U.S. Pat. No. 6,653,340 titled "Compounds useful in the complement, coagulat and kallikrein pathways and method for their preparation" describes fused bicyclic ring compounds that are potent inhibitors of factor D. Development of the factor D inhibitor BCX1470 was discontinued due to lack of specificity and short half-life of the compound. Novartis PCT patent publication WO2012/093101 titled "Indole compounds or analogues thereof useful for the treatment of age-related macular degeneration" describes certain factor D inhibitors.

Novartis PCT patent publications WO2014/002057 titled "Pyrrolidine derivatives and their use as complement pathway modulators" and WO2014/009833 titled "Complement pathway modulators and uses thereof" describe additional factor D inhibitors with heterocyclic substituents. Additional factor D inhibitors are described in Novartis PCT patent publications WO2014/002051, WO2014/002052, WO2014/002053, WO2014/002054, WO2014/002058, WO2014/002059, and WO2014/005150.

Bristol-Myers Squibb PCT patent publication WO2004/045518 titled "Open chain prolyl urea-related modulators of androgen receptor function" describes open chain prolyl urea and thiourea related compounds for the treatment of androgen receptor-associated conditions, such as age-related diseases, for example, sarcopenia.

Japan Tobacco Inc. PCT patent publication WO1999/048492 titled "Amide derivatives and nociceptin antagonists" describes compounds with a proline-like core and aromatic substituents connected to the proline core through amide linkages useful for the treatment of pain.

Ferring B.V. and Yamanouchi Pharmaceutical Co. ITD. PCT patent publication WO1993/020099 titled "CCK and/or gastrin receptor ligands" describes compounds with a proline-like core and heterocyclic substituents connected to the proline core through amide linkages for the treatment of, for example, gastric disorders or pain.

Alexion Pharmaceuticals PCT patent publication WO1995/029697 titled "Methods and compositions for the treatment of glomerulonephritis and other inflammatory diseases" discloses antibodies directed to C5 of the complement pathway for the treatment of glomerulonephritis and inflammatory conditions involving pathologic activation of the complement system. Alexion Pharmaceutical's anti-C5 antibody eculizumab (Soliris®) is currently the only complement-specific antibody on the market, and is the first and only approved treatment for paroxysmal nocturnal hemoglobinuria (PNH).

Compounds which mediate the complement pathway, and for example, act as factor D inhibitors are needed for treatment of disorders in a host, including a human, associated with misregulation of the complement cascade.

SUMMARY

It has been discovered that a compound of Formula I, or a pharmaceutically acceptable salt or composition thereof, wherein $R^{12}$ or $R^{13}$ on the A group is an alkyne ($R^{32}$), is a superior inhibitor of complement factor D. In one embodiment, the alkyne is directly linked to the A group. In another embodiment, the alkyne is indirectly linked to the A group through a linking moiety, defined further below.

In one embodiment, a method for the treatment of a disorder associated with a dysfunction, including increased activity, of the complement pathway is provided that includes the administration of an effective amount of a compound of Formula I, or a pharmaceutically acceptable salt thereof, optionally in a pharmaceutically acceptable carrier, as described in more detail below.

In one embodiment, the disorder is associated with the alternative complement cascade pathway. In yet another embodiment, the disorder is associated with the complement classical pathway. In a further embodiment, the disorder is associated with the complement lectin pathway. The factor D inhibitors provided herein can thus dampen or inhibit detrimental complement activity in a host, by administration of an effective amount in a suitable manner to a host in need thereof.

Specific embodiments of this invention are directed to certain disease indications. In one embodiment, a method for the treatment of paroxysmal nocturnal hemoglobinuria (PNH) is provided that includes the administration of an effective amount of a compound of Formula I, or a pharmaceutically acceptable salt thereof, optionally in a pharmaceutically acceptable carrier. In another embodiment, a method for the treatment of age-related macular degeneration (AMID) is provided that includes the administration of an effective amount of a compound of Formula I, or a pharmaceutically acceptable salt thereof, optionally in a pharmaceutically acceptable carrier. In another embodiment, a method for the treatment of rheumatoid arthritis is provided that includes the administration of an effective amount of a compound of Formula I, or a pharmaceutically acceptable salt thereof, optionally in a pharmaceutically acceptable carrier. In another embodiment, a method for the treatment of multiple sclerosis is provided that includes the administration of an effective amount of a compound of Formula I, or a pharmaceutically acceptable salt thereof, optionally in a pharmaceutically acceptable carrier.

In other embodiments of the invention, an active compound provided herein can be used to treat or prevent a disorder in a host mediated by complement factor D, or by an excessive or detrimental amount of the C3 amplification loop of the complement pathway. As examples, the invention includes methods to treat or prevent complement associated disorders that are induced by antibody-antigen interactions, a component of an immune or autoimmune disorder or by ischemic injury. The invention also provides methods to decrease inflammation or an immune response, including an autoimmune response, where mediated or affected by factor D.

The disclosure provides compounds of Formula I

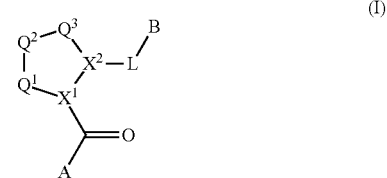

and the pharmaceutically acceptable salts and compositions thereof, wherein:

$Q^1$ is $N(R^1)$ or $C(R^1R^{1'})$;

$Q^2$ is $C(R^2R^{2'})$, $C(R^2R^{2'})$—$C(R^2R^{2'})$, S, O, $N(R^2)$ or $C(R^2R^{2'})O$;

$Q^3$ is $N(R^3)$, S, or $C(R^3R^{3'})$;

$X^1$ and $X^2$ are independently N, CH, or CZ, or $X^1$ and $X^2$ together are C=C; and wherein $Q^1$, $Q^2$, $Q^3$, $X^1$, and $X^2$ are selected such that a stable compound results.

Non-limiting examples of the

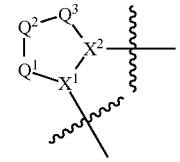

ring are illustrated below (any of which can be otherwise substituted with $R^1$, $R^{1'}$, $R^2$, $R^{2'}$, $R^3$, and $R^{3'}$) as described in more detail below.

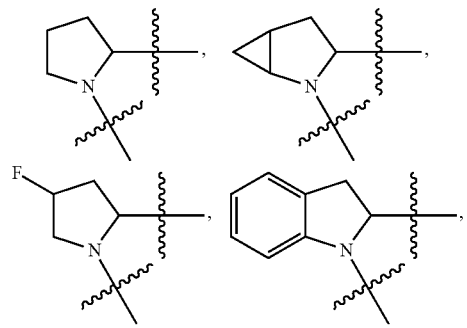

-continued

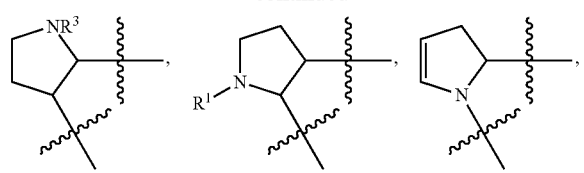
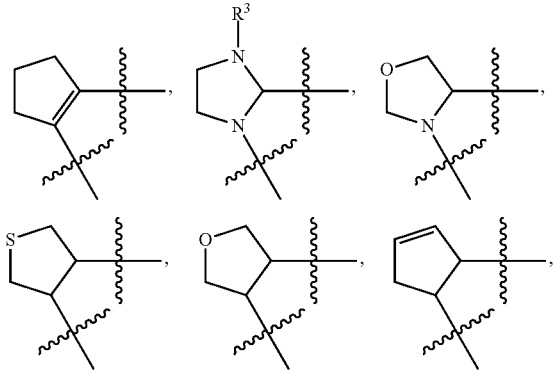
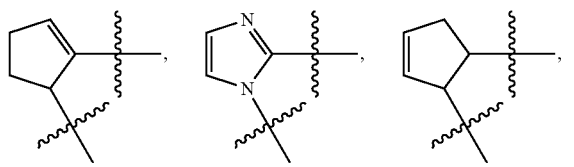
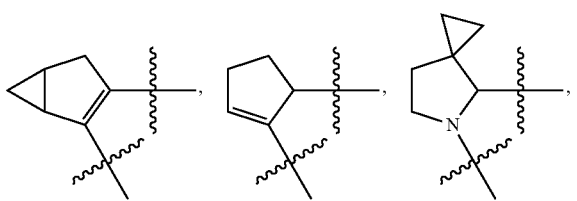
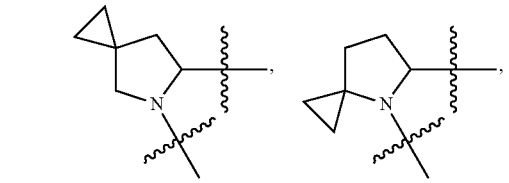
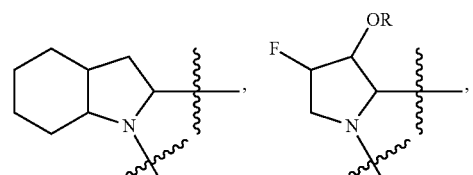
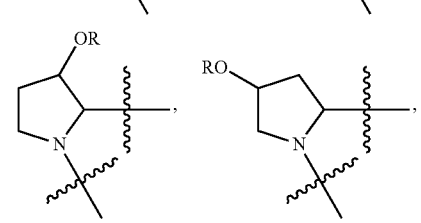
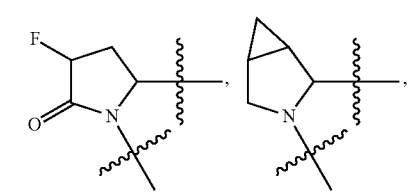

-continued

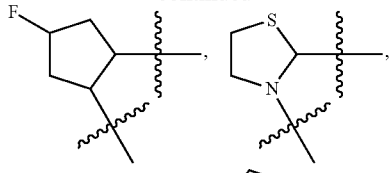
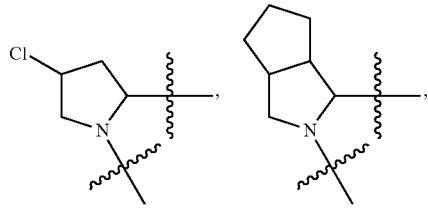
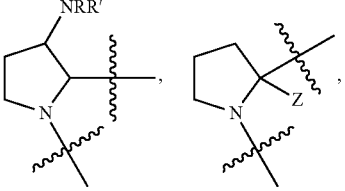
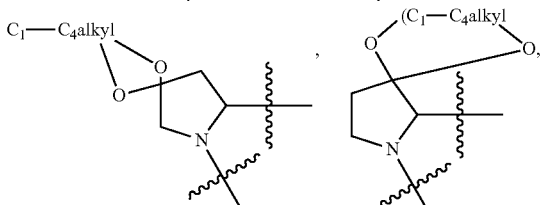
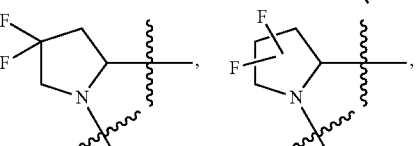
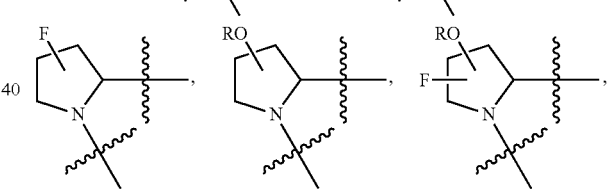
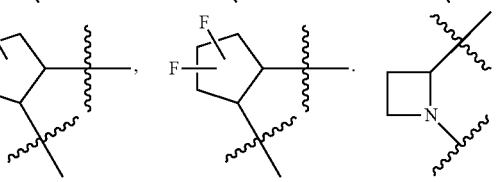
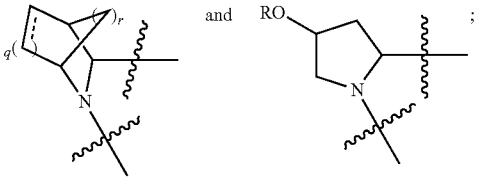

wherein q is 0, 1, 2 or 3 and r is 1, 2 or 3.

R and R' are independently chosen from H, alkyl, cycloalkyl, cycloalkylalkyl, heterocycle, heterocycloalkyl, aryl, arylalkyl, heteroaryl, heteroarylalkyl wherein each group can be optionally substituted or any other substituent group herein that provides the desired properties. In some embodiments, the ring includes one or more chiral carbon atoms. The invention includes embodiments in which the chiral carbon can be provided as an enantiomer, or mixtures of enantiomers, including a racemic mixture. Where the ring includes more than one stereocenter, all of the enantiomers and diastereomers are included in the invention as individual species.

Z is F, Cl, $NH_2$, $CH_3$, $CH_2D$, $CHD_2$, or $CD_3$.

$R^1$, $R^{1'}$, $R^2$, $R^{2'}$, $R^3$, and $R^{3'}$ are independently chosen at each occurrence, as appropriate, and only where a stable compound results, from hydrogen, halogen, hydroxyl, nitro, cyano, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkylN$R^9R^{10}$, —C(O)O$R^9$, —OC(O)$R^9$, —$NR^9$C(O)$R^{10}$, —C(O)N$R^9R^{10}$, —OC(O)N$R^9R^{10}$, —$NR^9$C(O)O$R^{10}$, $C_1$-$C_2$haloalkyl, and $C_1$-$C_2$haloalkoxy, where $R^9$ and $R^{10}$ are independently chosen at each occurrence from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl).

In alternative embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently chosen from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring; each of which spiro ring each of which ring may be unsubstituted or substituted with 1 or more substituents independently chosen from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^2$ may be taken together to form a 3-membered carbocyclic ring; $R^1$ and $R^2$ may be taken together to form a 4- to 6-membered carbocyclic or aryl ring or a 4- to 6-membered heterocyclic or heteroaryl ring containing 1 or 2 heteroatoms independently chosen from N, O, and S; or $R^2$ and $R^3$, if bound to adjacent carbon atoms, may be taken together to form a 3- to 6-membered carbocyclic or aryl ring or a 3- to 6-membered heterocyclic or heteroaryl ring; each of which ring may be unsubstituted or substituted with 1 or more substituents independently chosen from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^{1'}$, $R^2$ and $R^{2'}$, or $R^3$ and $R^{3'}$ can be taken together to form a carbonyl group. In alternative embodiments, $R^1$ and $R^2$ or $R^2$ and $R^3$ can be taken together to form a carbon-carbon double bond.

A is a group chosen from:

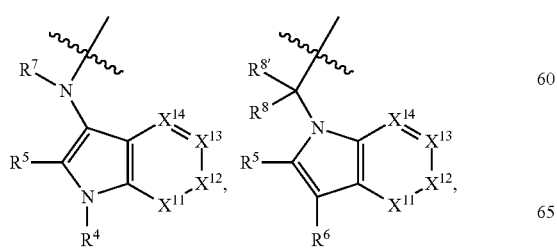

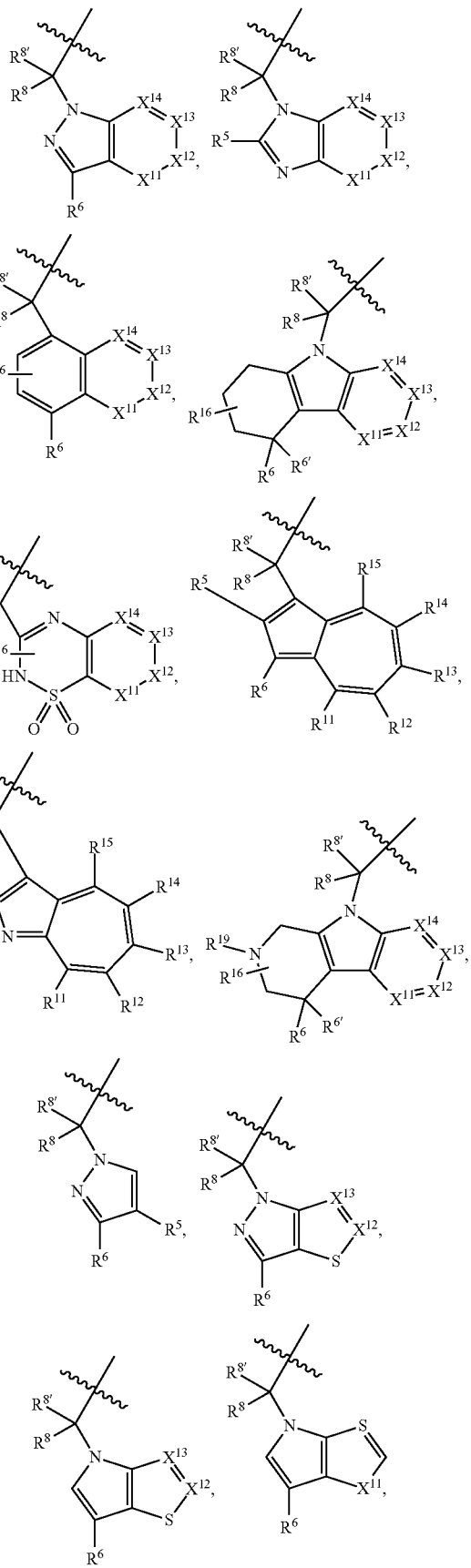

-continued

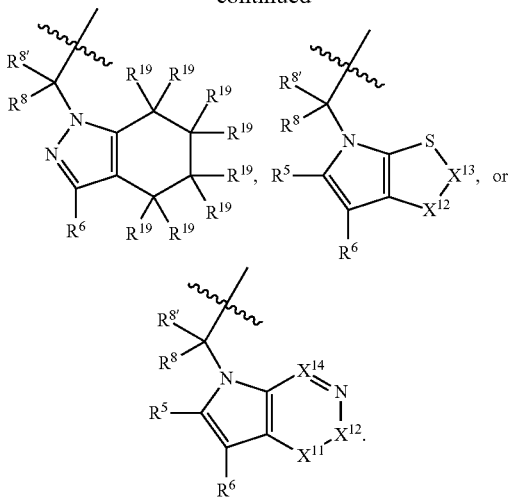

$R^4$ is chosen from —CHO, —CONH$_2$, C$_2$-C$_6$alkanoyl, hydrogen, —SO$_2$NH$_2$, —C(CH$_2$)$_2$F, —CH(CF$_3$)NH$_2$, C$_1$-C$_6$alkyl, —C$_0$-C$_4$alkyl(C$_3$-C$_7$cycloalkyl), —C(O)C$_0$-C$_2$alkyl(C$_3$-C$_7$cycloalkyl),

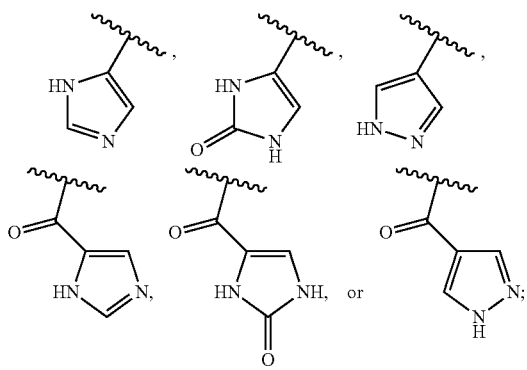

each of which $R^4$ other than hydrogen, —CHO, and —CONH$_2$, is unsubstituted or substituted with one or more of amino, imino, halogen, hydroxyl, cyano, cyanoimino, C$_1$-C$_2$alkyl, C$_1$-C$_2$alkoxy, —C$_0$-C$_2$alkyl(mono- and di-C$_1$-C$_4$alkylamino), C$_1$-C$_2$haloalkyl, and C$_1$-C$_2$haloalkoxy.

$R^5$ and $R^6$ are independently chosen from —CHO, —C(O)NH$_2$, —C(O)NH(CH$_3$), C$_2$-C$_6$alkanoyl, hydrogen, hydroxyl, halogen, cyano, nitro, —COOH, —SO$_2$NH$_2$, vinyl, C$_1$-C$_6$alkyl (including methyl), C$_2$-C$_6$alkenyl, C$_1$-C$_6$alkoxy, —C$_0$-C$_4$alkyl(C$_3$-C$_7$cycloalkyl), —C(O)C$_0$-C$_4$alkyl(C$_3$-C$_7$cycloalkyl), —P(O)(OR$^9$)$_2$, —OC(O)R$^9$, —C(O)OR$^9$, —C(O)N(CH$_2$CH$_2$R$^9$)(R$^{10}$), —NR$^9$C(O)R$^{10}$, phenyl, or 5- to 6-membered heteroaryl.

Each $R^5$ and $R^6$ other than hydrogen, hydroxyl, cyano, and —COOH is unsubstituted or optionally substituted. For example, $R^5$ and $R^6$ other than hydrogen, hydroxyl, cyano, and COOH may be substituted with one or more substituents independently chosen from halogen, hydroxyl, amino, imino, cyano, cyanoimino, C$_1$-C$_2$alkyl, C$_1$-C$_4$alkoxy, —C$_0$-C$_2$alkyl(mono- and di-C$_1$-C$_4$alkylamino), C$_1$-C$_2$haloalkyl, and C$_1$-C$_2$haloalkoxy.

$R^{6'}$ is hydrogen, halogen, hydroxyl, C$_1$-C$_4$alkyl, —C$_0$-C$_4$alkyl(C$_3$-C$_7$cycloalkyl), or C$_1$-C$_4$alkoxy; or $R^6$ and $R^{6'}$ may be taken together to form an oxo, vinyl, or imino group.

$R^7$ is hydrogen, C$_1$-C$_6$alkyl, or —C$_0$-C$_4$alkyl(C$_3$-C$_7$cycloalkyl).

$R^8$ and $R^{8'}$ are independently chosen from hydrogen, halogen, hydroxyl, C$_1$-C$_6$alkyl, —C$_0$-C$_4$alkyl(C$_3$-C$_7$cycloalkyl), C$_1$-C$_6$alkoxy, and (C$_1$-C$_4$alkylamino)C$_0$-C$_2$alkyl; or $R^8$ and $R^{8'}$ are taken together to form an oxo group; or $R^8$ and $R^{8'}$ can be taken together with the carbon that they are bonded to form a 3-membered carbocyclic ring.

$R^{16}$ is absent or may include one or more substituents independently chosen from halogen, hydroxyl, nitro, cyano, C$_1$-C$_6$alkyl, C$_2$-C$_6$alkenyl, C$_2$-C$_6$alkanoyl, C$_1$-C$_6$alkoxy, —C$_0$-C$_4$alkyl(mono- and di-C$_1$-C$_6$alkylamino), —C$_0$-C$_4$alkyl(C$_3$-C$_7$cycloalkyl), C$_1$-C$_2$haloalkyl, and C$_1$-C$_2$haloalkoxy.

$R^{19}$ is hydrogen, C$_1$-C$_6$alkyl, C$_2$-C$_6$alkenyl, C$_2$-C$_6$alkanoyl, —SO$_2$C$_1$-C$_6$alkyl, (mono- and di-C$_1$-C$_6$alkylamino)C$_1$-C$_4$alkyl, —C$_0$-C$_4$alkyl(C$_3$-C$_7$cycloalkyl), —C$_0$-C$_4$alkyl(C$_3$-C$_7$heterocycloalkyl), —C$_0$-C$_4$alkyl(aryl), C$_0$-C$_4$alkyl(heteroaryl), and wherein $R^{19}$ other than hydrogen is unsubstituted or substituted with one or more substituents independently chosen from halogen, hydroxyl, amino, —COOH, and —C(O)OC$_1$-C$_4$alkyl.

$X^{11}$ is N or CR$^{11}$.
$X^{12}$ is N or CR$^{12}$.
$X^{13}$ is N or CR$^{13}$.
$X^{14}$ is N or CR$^{14}$.
No more than 2 of $X^{11}$, $X^{12}$, $X^{13}$, and $X^{14}$ are N.
One of $R^{12}$ and $R^{13}$ is chosen from $R^{31}$ and the other of $R^{12}$ and $R^{13}$ is chosen from $R^{32}$:

$R^{31}$ is chosen from hydrogen, halogen, hydroxyl, nitro, cyano, amino, —COOH, C$_1$-C$_2$haloalkyl, C$_1$-C$_2$haloalkoxy, C$_1$-C$_6$alkyl, —C$_0$-C$_4$alkyl(C$_3$-C$_7$cycloalkyl), C$_2$-C$_6$alkenyl, C$_2$-C$_6$alkanoyl, C$_1$-C$_6$alkoxy, C$_2$-C$_6$alkenyloxy, —C(O)OR$^9$, C$_1$-C$_6$thioalkyl, —C$_0$-C$_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which $R^{31}$ other than hydrogen, halogen, hydroxyl, nitro, cyano, C$_1$-C$_2$haloalkyl, and C$_1$-C$_2$haloalkoxy is unsubstituted or substituted with one or more substituents independently selected from halogen, hydroxyl, nitro, cyano, amino, —COOH, —CONH$_2$ C$_1$-C$_2$haloalkyl, and C$_1$-C$_2$haloalkoxy, and each of which $R^{31}$ is also optionally substituted with one substituent chosen from phenyl and 4- to 7-membered heterocycle containing 1, 2, or 3 heteroatoms independently chosen from N, O, and S; which phenyl or 4- to 7-membered heterocycle is unsubstituted or substituted with one or more substituents independently chosen from halogen, hydroxyl, nitro, cyano, C$_1$-C$_6$alkyl, C$_2$-C$_6$alkenyl, C$_2$-C$_6$alkanoyl, C$_1$-C$_6$alkoxy, (mono- and di-C$_1$-C$_6$alkylamino)C$_0$-C$_4$alkyl, C$_1$-C$_6$alkylester, —C$_0$-C$_4$alkyl)(C$_3$-C$_7$cycloalkyl), C$_1$-C$_2$haloalkyl, and C$_1$-C$_2$haloalkoxy;

$R^{32}$ is —C$_2$-C$_6$alkynylR$^{30}$, and each $R^{32}$ can be optionally substituted. Examples of $R^{32}$ include, for example, but are not limited to,

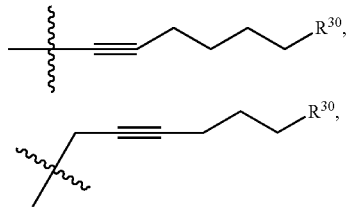

-continued

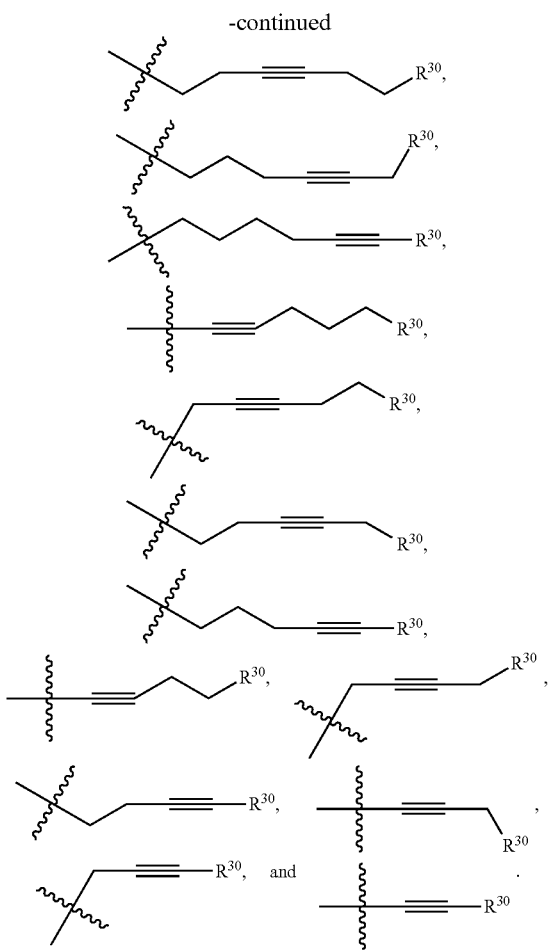

In an alternative embodiment, $R^{12}$ and $R^{13}$ are each independently selected from an $R^{32}$ moiety.

$R^{11}$, $R^{14}$, and $R^{15}$ are independently chosen at each occurrence from hydrogen, halogen, hydroxyl, nitro, cyano, —O(PO)(OR$^9$)$_2$, —(PO)(OR$^9$)$_2$, $C_1$-$C_6$alkyl, $C_2$-$C_6$alkenyl, $C_2$-$C_6$alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl, $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy.

$R^{21}$ and $R^{22}$ are independently chosen at each occurrence from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-$C_4$alkylOC(O)C$_1$-$C_6$alkyl, —$C_1$-$C_4$alkylC(O)OC$_1$-$C_6$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S, and each $R^{21}$ and $R^{22}$ can be optionally substituted.

$R^{23}$ is independently chosen at each occurrence from $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S, (5- or 6-membered unsaturated or aromatic heterocycle)$C_0$-$C_4$alkyl having 1, 2, or 3 heteroatoms independently chosen from N, O, and S, and each $R^{23}$ can be optionally substituted.

$R^{24}$ and $R^{25}$ are taken together with the nitrogen to which they are attached to form a 4- to 7-membered monocyclic heterocycloalkyl group, or a 6- to 10-membered bicyclic heterocyclic group having fused, spiro, or bridged rings, and each $R^{24}$ and $R^{25}$ can be optionally substituted.

$R^{30}$ is independently chosen at each occurrence from hydrogen, $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S; (5- or 6-membered unsaturated or aromatic heterocycle)$C_0$-$C_4$alkyl having 1, 2, or 3 heteroatoms independently chosen from N, O, and S; COOH, Si(CH$_3$)$_3$, COOR$^{30a}$, $C_2$-$C_6$alkanoyl, —B(OH)$_2$, —C(O)(CH$_2$)$_{1-4}$S(O)R$^{21}$, —P(O)(OR$^{21}$)(OR$^{22}$), —P(O)(OR$^{21}$)R$^{22}$, —P(O)R$^{21}$R$^{22}$, —NR$^9$P(O)(NHR$^{21}$)(NHR$^{22}$), —NR$^9$P(O)(OR$^{21}$)(NHR$^{22}$), —NR$^9$P(O)(OR$^{21}$)(OR$^{22}$), —C(S)R$^{21}$, —NR$^{21}$SO$_2$R$^{22}$, —NR$^9$S(O)NR$^{10}$R$^{22}$, —NR$^9$SO$_2$NR$^{10}$R$^{22}$, —SO$_2$NR$^9$COR$^{22}$, —SO$_2$NR$^9$CONR$^{21}$R$^{22}$, —NR$^{21}$SO$_2$R$^{22}$, —C(O)NR$^{21}$SO$_2$R$^{22}$, —C(NH$_2$)NR$^9$R$^{22}$, —C(NH$_2$)NR$^9$S(O)$_2$R$^{22}$, —NR$^9$C(O)OR$^{10}$, —NR$^{21}$OC(O)R$^{22}$, —(CH$_2$)$_{1-4}$C(O)NR$^{21}$R$^{22}$, —C(O)R$^{24}$R$^{25}$, —NR$^9$C(O)R$^{21}$, —C(O)R$^{21}$, —NR$^9$C(O)NR$^9$R$^{10}$, —NR$^9$C(O)NR$^{24}$R$^{25}$, —(CH$_2$)$_{1-4}$OC(O)R$^{21}$, each of which $R^{30}$ can be optionally substituted.

$R^{30a}$ is $C_1$-$C_6$alkyl, $C_2$-$C_6$alkenyl, $C_2$-$C_6$alkynyl, ($C_3$-$C_7$cycloalkyl)$C_0$-$C_4$alkyl-, (aryl)$C_0$-$C_4$alkyl-, (3- to 7-membered heterocycloalkyl)$C_0$-$C_4$alkyl- having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S, each of which $R^{30a}$ can be optionally substituted.

L is a bond or is chosen from the formulas

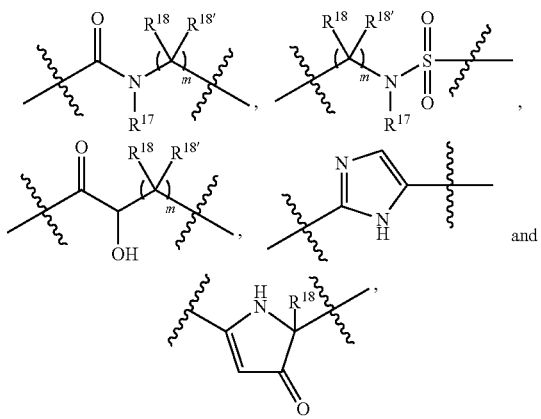

where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently chosen from hydrogen, halogen, hydroxymethyl, and methyl; and m is 0, 1, 2, or 3.

B is a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl).

Each of which B is unsubstituted or substituted with one or more substituents independently chosen from $R^{33}$ and $R^{34}$, and 0 or 1 substituents chosen from $R^{35}$ and $R^{36}$.

$R^{33}$ is independently chosen from halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, and $C_1$-$C_2$haloalkoxy.

$R^{34}$ is independently chosen from nitro, $C_2$-$C_6$alkenyl, $C_2$-$C_6$alkynyl, $C_1$-$C_6$thioalkyl, -JC$_3$-$C_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{21}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)NR$^{22}$, -JC(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)R$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_{1-4}$OC(O)R$^{21}$, and -JC(O)OR$^{23}$; each of which $R^{34}$ may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

$R^{35}$ is independently chosen from naphthyl, naphthyloxy, indanyl, (4- to 7-membered heterocycloalkyl)$C_0$-$C_4$alkyl containing 1 or 2 heteroatoms chosen from N, O, and S, and bicyclic heterocycle containing 1, 2, or 3 heteroatoms independently chosen from N, O, and S, and containing 4- to 7-ring atoms in each ring; each of which $R^{35}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO$_2$R$^9$, $C_1$-$C_2$haloalkyl, and $C_1$-$C_2$haloalkoxy.

$R^{36}$ is independently chosen from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently chosen from N, O, B, and S, each of which $R^{36}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO$_2$R$^9$, —OSi(CH$_3$)$_2$C(CH$_3$)$_3$, —Si(CH$_3$)$_2$C(CH$_3$)$_3$, $C_1$-$C_2$haloalkyl, and $C_1$-$C_2$haloalkoxy.

J is independently chosen at each occurrence from a covalent bond, $C_1$-$C_4$alkylene, —O$C_1$-$C_4$alkylene, $C_2$-$C_4$alkenylene, and $C_2$-$C_4$alkynylene.

Pharmaceutical compositions comprising a compound or salt of Formula I together with a pharmaceutically acceptable carrier are also disclosed.

Methods of treating or preventing disorders mediated by complement cascade factor D, including but not limited to age-related macular degeneration (AMD), retinal degeneration, other ophthalmic diseases (e.g., geographic atrophy), paroxysymal nocturnal hemoglobinuria (PNH), multiple sclerosis (MS), arthritis including rheumatoid arthritis (RA), a respiratory disease or a cardiovascular disease, are provided, comprising administering a therapeutically effective amount of a compound or salt of Formula I to a host, including a human, in need of such treatment are also disclosed.

In another embodiment, an effective amount of an active factor D inhibiting compound is provided to treat an inflammatory or immune disorder, including an autoimmune disorder, that is mediated or affected by factor D. In an alternative embodiment, the compound of Formula I can be used to treat a disorder mediated by the complement pathway, regardless whether it is acting through Factor D.

The present invention includes at least the following features:

(a) a compound of Formula I as described herein, and pharmaceutically acceptable salts and prodrugs thereof (each of which and all subgenuses and species thereof considered individually and specifically described);

(b) Formula I as described herein, and pharmaceutically acceptable salts and prodrugs thereof, for use in treating or preventing disorders mediated by the complement pathway, and for example, cascade factor D, including age-related macular degeneration (AMD), retinal degeneration, paroxysymal nocturnal hemoglobinuria (PNH), multiple sclerosis (MS), and rheumatoid arthritis (RA) and other disorders described further herein;

(c) use of Formula I, and pharmaceutically acceptable salts and prodrugs thereof in the manufacture of a medicament for use in treating or preventing disorders mediated by complement cascade factor D, including age-related macular degeneration (AMD), retinal degeneration, paroxysymal nocturnal hemoglobinuria (PNH), multiple sclerosis (MS), and rheumatoid arthritis (RA) and other disorders described further herein;

(d) a process for manufacturing a medicament intended for the therapeutic use for treating or preventing treating or preventing disorders mediated by complement cascade factor D, including age-related macular degeneration (AMD), retinal degeneration, paroxysymal nocturnal hemoglobinuria (PNH), multiple sclerosis (MS), and rheumatoid arthritis (RA) and other disorders described further herein characterized in that Formula I as described herein is used in the manufacture;

(e) a pharmaceutical formulation comprising an effective host-treating amount of the Formula I or a pharmaceutically acceptable salt or prodrug thereof together with a pharmaceutically acceptable carrier or diluent;

(f) Formula I as described herein in substantially pure form, including substantially isolated from other chemical entities (e.g., at least 90 or 95%);

(g) processes for the manufacture of the compounds of Formula I and salts, compositions, dosage forms thereof; and (h) processes for the preparation of therapeutic products that contain an effective amount of Formula I, as described herein.

DETAILED DESCRIPTION

I. Terminology

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixtures of enantiomers, diastereomers, tautomers, racemates and other isomers, such as rotamers, as if each is specifically described. "Formula I" includes all subgeneric groups of Formula I, such as Formula IA and Formula IB and also includes pharmaceutically acceptable salts of a compound of Formula I, unless clearly contraindicated by the context in which this phrase is used. "Formula I" also includes all subgeneric groups of Formula I, such as Formulas IC-ID, and Formulas II-XXX, and also includes pharmaceutically acceptable salts of all subgeneric groups of Formula I, such as Formulas IA-ID, and Formulas II-XXX, unless contraindicated by the context in which this phrase is used.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Formula I and the use of compounds with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes isotopically modified compounds of Formula I. In one embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively or in addition, isotopes of carbon, e.g., $^{13}C$ and $^{14}C$, may be used. In one embodiment, the isotopic substitution is deuterium for hydrogen at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one embodiments deuterium is 90, 95 or 99% enriched at a desired location. Unless otherwise stated, the enrichment at any point is above natural abundance and enough to alter a detectable property of the drug in a human.

In one embodiment, the substitution of a hydrogen atom for a deuterium atom occurs within an R group substituent on the L-B moiety region. In one embodiment, the substitution of a hydrogen atom for a deuterium atom occurs within an R group selected from any of $R^{18}$, $R^{18'}$, $R^{33}$, $R^{34}$, $R^{35}$, and/or $R^{36}$. In one embodiment, the substitution of a hydrogen atom for a deuterium atom occurs within an R group substituent within the A-carbonyl moiety region. In one embodiment, the substitution of a hydrogen atom for a deuterium atom occurs at $R^{4'}$ $R^5$, $R^6$, $R^{6'}$, $R^7$, $R^8$, $R^{8'}$, $R^{11}$, $R^{12}$, $R^{13}$, $R^{14}$, $R^{15}$, $R^{16}$, $R^{19}$, $R^{21}$, $R^{22}$, $R^{23}$, $R^{30}$, and/or $R^{30a}$. In other embodiments, certain substituents on the proline ring are selectively deuterated. For example, in one embodiment, the substitution of a hydrogen atom for a deuterium atom occurs at R, R', $R^1$, $R^{1'}$, $R^2$, $R^{2'}$, $R^3$, and/or $R^{3'}$. In one embodiment, for example, when any of the R substituents of the proline ring are methyl or methoxy, the alkyl residue is optionally deuterated, e.g., $CD_3$ or $OCD_3$. In certain other embodiments, when two substituents of the proline ring are combined to form a cyclopropyl ring, the unsubstituted methylene carbon is deuterated.

The substitution of a hydrogen atom for a deuterium atom occurs within an R group when at least one of the variables within the R group is hydrogen (e.g., $^2H$ or D) or alkyl (e.g., $CD_3$). For example, when any of R groups are, or contain for example through substitution, methyl or ethyl, the alkyl residue is typically deuterated, e.g., $CD_3$, $CH_2CD_3$ or $CD_2CD_3$.

The compound of the present invention may form a solvate with solvents (including water). Therefore, in one embodiment, the invention includes a solvated form of the active compound. The term "solvate" refers to a molecular complex of a compound of the present invention (including salts thereof) with one or more solvent molecules. Examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C═O)NH$_2$ is attached through carbon of the keto (C═O) group.

The term "substituted", as used herein, means that any one or more hydrogens on the designated atom or group is replaced with a moiety selected from the indicated group, provided that the designated atom's normal valence is not exceeded. For example, when the substituent is oxo (i.e., ═O) then two hydrogens on the atom are replaced. When an oxo group replaces two hydrogens in an aromatic moiety, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates.

A stable compound or stable structure refers to a compound leading to a compound that can be isolated and can be formulated into a dosage form with a shelf life of at least one month.

Any suitable group may be present on a "substituted" or "optionally substituted" position that forms a stable molecule and advances the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; alkylthio including those having one or more thioether linkages; alkylsulfinyl; alkylsulfonyl groups including those having one or more sulfonyl linkages; aminoalkyl groups including groups having one or more N atoms; aryl (e.g., phenyl, biphenyl, naphthyl, or the like, each ring either substituted or unsubstituted aromatic); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated, unsaturated, or aromatic heterocyclic group having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino. In certain embodiments "optionally substituted" includes one or more substituents independently chosen from halogen, hydroxyl, amino, cyano, —CHO, —COOH, —CONH$_2$, $C_1$-$C_6$alkyl, $C_2$-$C_6$alkenyl, $C_2$-$C_6$alkynyl, —$C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, hydroxy$C_1$-$C_6$alkyl, ester, carbamate, urea, sulfonamide, —$C_1$-$C_6$alkyl (heterocyclo), $C_1$-$C_6$alkyl(heteroaryl), —$C_1$-$C_6$alkyl($C_3$-$C_7$cycloalkyl), O—$C_1$-$C_6$alkyl($C_3$-$C_7$cycloalkyl), B(OH)$_2$, phosphate, phosphonate and $C_1$-$C_2$haloalkoxy.

"Alkyl" is a branched or straight chain saturated aliphatic hydrocarbon group. In one embodiment, the alkyl contains from 1 to about 12 carbon atoms, more generally from 1 to about 6 carbon atoms or from 1 to about 4 carbon atoms. In one embodiment, the alkyl contains from 1 to about 8 carbon atoms. In certain embodiments, the alkyl is $C_1$-$C_2$, $C_1$-$C_3$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-$C_4$ alkyl, or —$C_0$-$C_4$alkyl ($C_3$-$C_7$cycloalkyl), the indicated group, in this case cycloalkyl, is either directly bound by a single covalent bond ($C_0$alkyl), or attached by an alkyl chain in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane and 2,3-dimethylbutane. In one embodiment, the alkyl group is optionally substituted as described above.

"Alkenyl" is a branched or straight chain aliphatic hydrocarbon group having one or more carbon-carbon double bonds that may occur at a stable point along the chain. Nonlimiting examples are $C_2$-$C_8$alkenyl, $C_2$-$C_6$alkenyl and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. In one embodiment, the alkenyl group is optionally substituted as described above.

"Alkynyl" is a branched or straight chain aliphatic hydrocarbon group having one or more carbon-carbon triple bonds that may occur at any stable point along the chain, for example, $C_2$-$C_8$alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In one embodiment, the alkynyl group is optionally substituted as described above.

"Alkylene" is a bivalent saturated hydrocarbon. Alkylenes, for example, can be a 1 to 8 carbon moiety, 1 to 6 carbon moiety, or an indicated number of carbon atoms, for example $C_1$-$C_4$alkylene, $C_1$-$C_3$alkylene, or $C_1$-$C_2$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Alkenyloxy" is an alkenyl group as defined covalently bound to the group it substitutes by an oxygen bridge (—O—).

"Alkanoyl" is an alkyl group as defined above covalently bound through a carbonyl (C=O) bridge. The carbonyl carbon is included in the number of carbons, that is C2alkanoyl is a $CH_3(C=O)$— group. In one embodiment, the alkanoyl group is optionally substituted as described above.

"Alkylester" is an alkyl group as defined herein covalently bound through an ester linkage. The ester linkage may be in either orientation, e.g., a group of the formula —O(C=O)alkyl or a group of the formula —(C=O) Oalkyl.

"Amide" or "carboxamide" is —C(O)NR$^a$R$^b$ wherein R$^a$ and R$^b$ are each independently selected from hydrogen, alkyl, for example, $C_1$-$C_6$alkyl, alkenyl, for example, $C_2$-$C_6$alkenyl, alkynyl, for example, $C_2$-$C_6$alkynyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), and —$C_0$-$C_4$alkyl(heteroaryl); or together with the nitrogen to which they are bonded, R$^a$ and R$^b$ can form a $C_3$-$C_7$heterocyclic ring. In one embodiment, the R$^a$ and R$^b$ groups are each independently optionally substituted as described above.

"Carbocyclic group", "carbocyclic ring", or "cycloalkyl" is a saturated or partially unsaturated (i.e., not aromatic) group containing all carbon ring atoms. A carbocyclic group typically contains 1 ring of 3 to 7 carbon atoms or 2 fused rings each containing 3 to 7 carbon atoms. Cycloalkyl substituents may be pendant from a substituted nitrogen or carbon atom, or a substituted carbon atom that may have two substituents can have a cycloalkyl group, which is attached as a spiro group. Examples of carbocyclic rings include cyclohexenyl, cyclohexyl, cyclopentenyl, cyclopentyl, cyclobutenyl, cyclobutyl and cyclopropyl rings. In one embodiment, the carbocyclic ring is optionally substituted as described above. In one embodiment, the cycloalkyl is a partially unsaturated (i.e., not aromatic) group containing all carbon ring atoms. In another embodiment, the cycloalkyl is a saturated group containing all carbon ring atoms.

"Carbocyclic-oxy group" is a monocyclic carbocyclic ring or a mono- or bi-cyclic carbocyclic group as defined above attached to the group it substitutes via an oxygen, —O—, linker.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Hydroxyalkyl" is an alkyl group as previously described, substituted with at least one hydroxyl subsitutuent.

"Aminoalkyl" is an alkyl group as previously described, substituted with at least one amino subsitutuent.

"Halo" or "halogen" indicates independently any of fluoro, chloro, bromo, and iodo.

"Aryl" indicates aromatic groups containing only carbon in the aromatic ring or rings. In one embodiment, the aryl groups contain 1 to 3 separate or fused rings and is 6 to about 14 or 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described above.

The term "heterocycle," or "heterocyclic ring" as used herein refers to a saturated or a partially unsaturated (i.e., having one or more double and/or triple bonds within the ring without aromaticity) carbocyclic radical of 3 to about 12, and more typically 3, 5, 6, 7 to 10 ring atoms in which at least one ring atom is a heteroatom selected from nitrogen, oxygen, phosphorus and sulfur, the remaining ring atoms being C, where one or more ring atoms is optionally substituted independently with one or more substituents described above. A heterocycle may be a monocycle having 3 to 7 ring members (2 to 6 carbon atoms and 1 to 4 heteroatoms selected from N, O, P, and S) or a bicycle having 6 to 10 ring members (4 to 9 carbon atoms and 1 to 6 heteroatoms selected from N, O, P, and S), for example: a bicyclo [4,5], [5,5], [5,6], or [6,6] system. In one embodiment, the only heteroatom is nitrogen. In one embodiment, the only heteroatom is oxygen. In one embodiment, the only heteroatom is sulfur. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, pyrrolidinyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyco[3.1.0]hexanyl, 3-azabicyclo[4.1.0]heptanyl, azabicyclo[2.2.2]hexanyl, 3H-indolyl, quinolizinyl, N-pyridyl ureas, and pyrrolopyrimidine. Spiro moieties are also included within the scope of this definition. Examples of a heterocyclic group wherein 1 or 2 ring carbon atoms are substituted with oxo (=O) moieties are pyrimidinonyl and 1,1-dioxo-thiomorpholinyl. The heterocycle groups herein are optionally substituted independently with one or more substituents described herein.

"Heterocyclicoxy group" is a monocyclic heterocyclic ring or a bicyclic heterocyclic group as described previously linked to the group it substitutes via an oxygen, —O—, linker.

"Heteroaryl" indicates a stable monocyclic aromatic ring which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups are optionally substituted independently with one or more substituents described herein. "Heteroaryloxy" is a heteroaryl group as described bound to the group it substituted via an oxygen, —O—, linker.

"Heterocycloalkyl" is a saturated ring group. It may have, for example, 1, 2, 3, or 4 heteroatoms independently chosen from N, S, and O, with remaining ring atoms being carbon. In a typical embodiment, nitrogen is the heteroatm. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

The term "mono- and/or di-alkylamino" indicates secondary or tertiary alkylamino groups, wherein the alkyl groups are independently chosen alkyl groups, as defined herein. The point of attachment of the alkylamino group is on the nitrogen. Examples of mono- and di-alkylamino groups include ethylamino, dimethylamino, and methyl-propylamino.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

"Pharmaceutical compositions" are compositions comprising at least one active agent, such as a compound or salt of Formula I, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, and includes, in one embodiment, an excipient that is acceptable for veterinary use as well as human pharmaceutical use. A "pharmaceutically acceptable excipient" as used in the present application includes both one and more than one such excipient.

A "patient" or "host" or "subject" is a human or non-human animal in need of modulation of the complement factor D pathway. Typically the host is a human. A "patient" or "host" or "subject" also refers to for example, mammals, primates (e.g., humans), cows, sheep, goats, horses, dogs, cats, rabbits, rats, mice, fish, birds and the like.

A "prodrug" as used herein, means a compound which when administered to a host in vivo is converted into a parent drug. As used herein, the term "parent drug" means any of the presently described chemical compounds that are useful to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

"Providing a compound of Formula I with at least one additional active agent" means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. In certain embodiments the compound of Formula I and the additional active agent need not be prescribed for a patient by the same medical care worker. In certain embodiments the additional active agent or agents need not require a prescription. Administration of the compound of Formula I or the at least one additional active agent can occur via any appropriate route, for example, oral tablets, oral capsules, oral liquids, inhalation, injection, suppositories or topical contact.

A "therapeutically effective amount" of a pharmaceutical composition/combination of this invention means an amount effective, when administered to a patient, to provide a therapeutic benefit such as an amelioration of symptoms, e.g., an amount effective to decrease the symptoms of a macular degeneration. In one embodiment, a therapeutically effective amount is an amount sufficient to prevent a significant increase or will significantly reduce the detectable level of complement factor D in the patient's blood, serum, or tissues.

II. Detailed Description of the Active Compounds

According to the present invention, a compound of Formula I is provided:

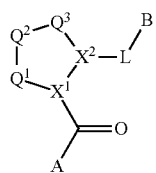
(I)

as well as the pharmaceutically acceptable salts and compositions thereof. Formula I can be considered to have a central core, an L-B substituent, and a (C=O)A substituent. It has been surprisingly discovered that a compound of Formula I, or a pharmaceutically acceptable salt or composition thereof, wherein $R^{12}$ or $R^{13}$ on the A group is an alkyne ($R^{32}$), is a superior inhibitor of complement factor D, and therefore can be used as an effective amount to treat a host in need of complement factor D modulation.

Non-limiting examples of compounds falling within Formula I with variations in the variables e.g., A, B, $R^1$-$R^{3'}$, and L, are illustrated below. The disclosure includes all combinations of these definitions so long as a stable compound results.

Formulas II-XXX

In one aspect, the disclosure includes compounds and salts of Formula II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX and XXX which are within the scope of Formula I. The variables shown in Formula II-XXX carry the definitions set forth in the SUMMARY section for Formula I or any of the definitions set forth in this disclosure.

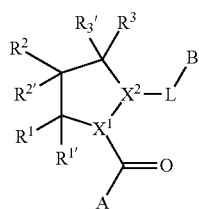

Formula II

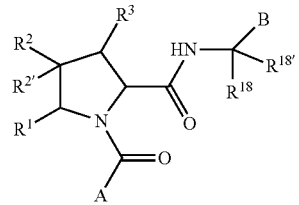

Formula III

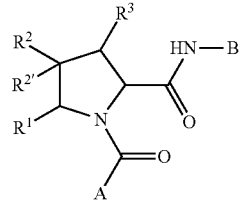

Formula IV

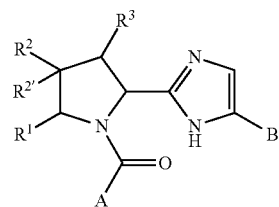

Formula V

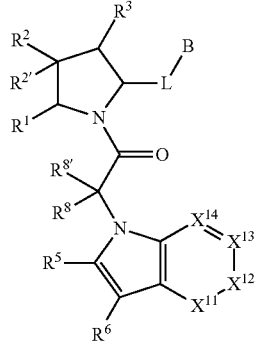

Formula VI

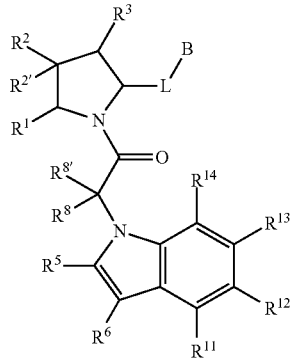

Formula VII

Formula VIII
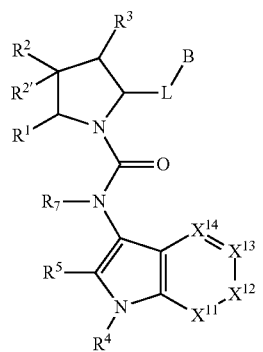
Formula IX
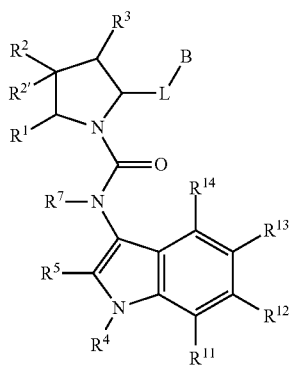
Formula X
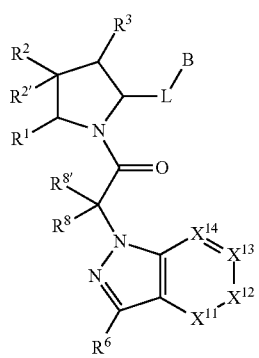
Formula XI
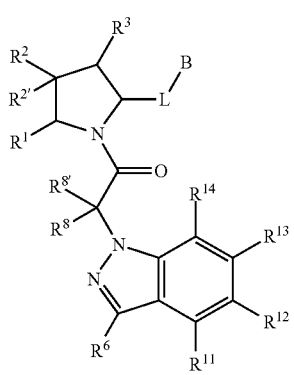
Formula XII
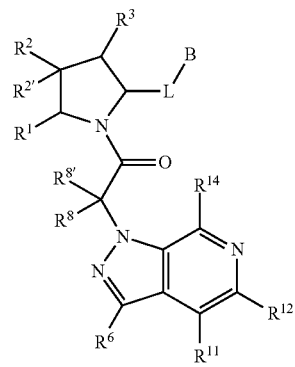
Formula XIII
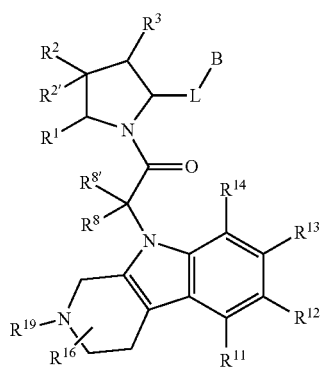
Formula XIV
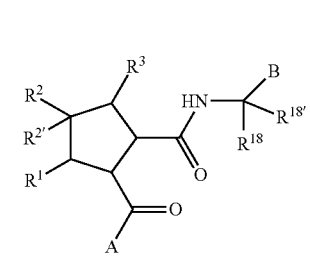
Formula XV
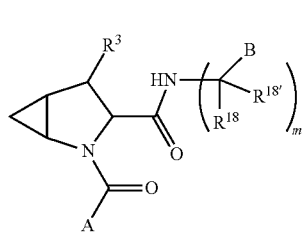
m is 0 or 1.
Formula XVI
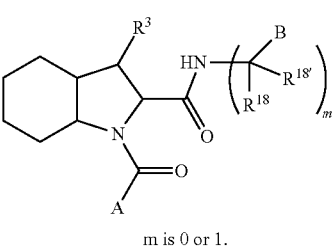
m is 0 or 1.

Formula XVII: m is 0 or 1.

Formula XVIII: m is 0 or 1.

Formula XIX: m is 0 or 1.

Formula XX: m is 0 or 1.

Formula XXI: m is 0 or 1.

Formula XXII

Formula XXIII

Formula XXIV

Formula XXV

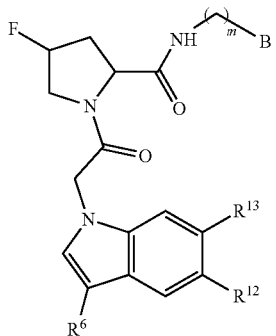

m is 0 or 1.

Formula XXVI

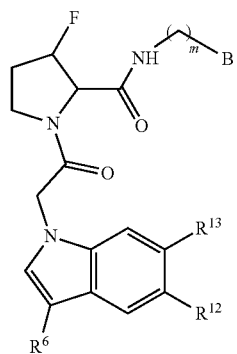

m is 0 or 1.

Formula XXVII

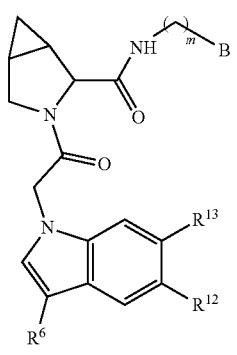

m is 0 or 1.

Formula XXVIII

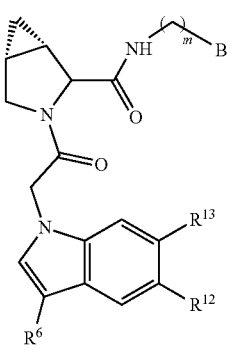

m is 0 or 1.

Formula XXIX

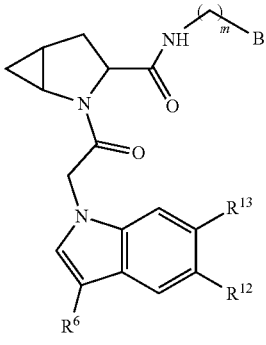

m is 0 or 1.

Formula XXX

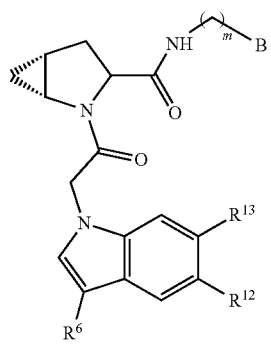

m is 0 or 1.

In these embodiments, it should be understood that where $R^1$ or $R^3$ is attached to a carbon, there can be two independent attachments as in $R^2/R^{2'}$ and these formulas should be considered to include all such variations.

Additionally, the disclosure includes compounds and salts of Formula I and pharmaceutically acceptable compositions thereof, and any of its subformulae (II-XXX) in which at least one of the following conditions is met in the embodiments described below.

The $R^{12}$ and $R^{13}$ Alkynyl Substituents

It has been surprisingly discovered that a compound of Formula I, a pharmaceutically acceptable salt or composition thereof, wherein $R^{12}$ or $R^{13}$ on the A group is an alkyne, is a superior inhibitor of complement factor D. In one embodiment, the alkyne is directly linked to the A group. In another embodiment, the alkyne is indirectly linked to the A group through a linking moiety, wherein the linking moiety is $C_1$-$C_4$alkylene.

One of $R^{12}$ and $R^{13}$ is chosen from $R^{31}$ and the other of $R^{12}$ and $R^{13}$ is chosen from $R^{32}$. In another embodiment each of $R^{12}$ and $R^{13}$ can be independently selected from $R^{32}$.

$R^{31}$ is chosen from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)OR$^9$, $C_1$-$C_6$thioalkyl, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —CONH$_2$ $C_1$-$C_2$haloalkyl, and $C_1$-$C_2$haloalkoxy, and each of which $R^{31}$ is also optionally substituted with one substituent chosen from phenyl and 4- to 7-membered heterocycle containing 1, 2, or 3 heteroatoms independently chosen from N, O, and S; which phenyl or 4- to 7-membered heterocycle is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy;

$R^{32}$ is —$C_2$-$C_6$alkynyl$R^{30}$, and each $R^{32}$ can be optionally substituted. Examples of $R^{32}$ include, for example, but are not limited to,

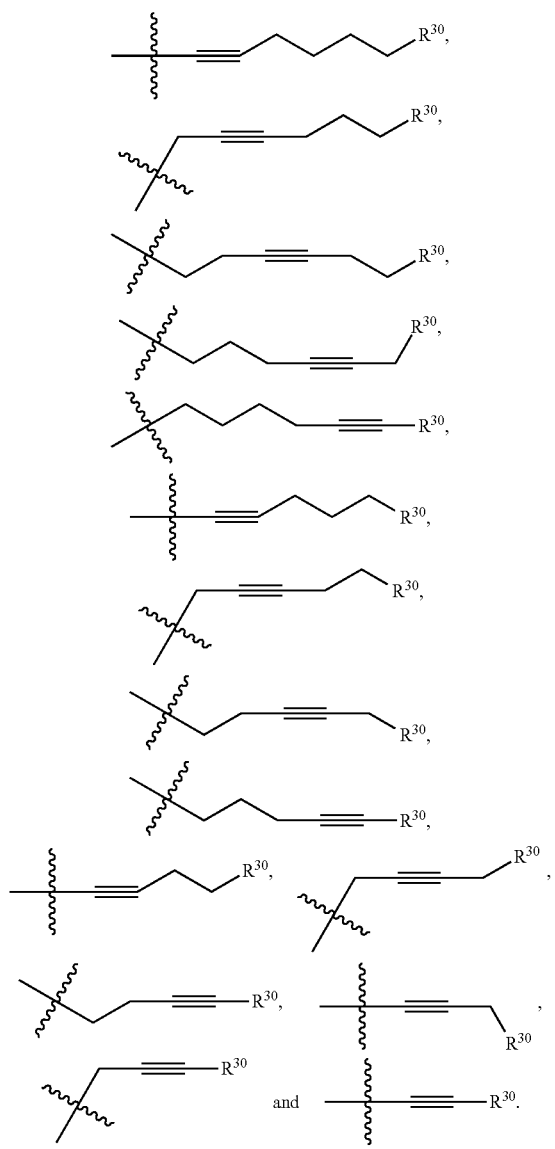

In certain embodiments, $R^{32}$ is selected from:

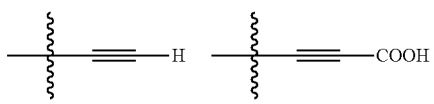

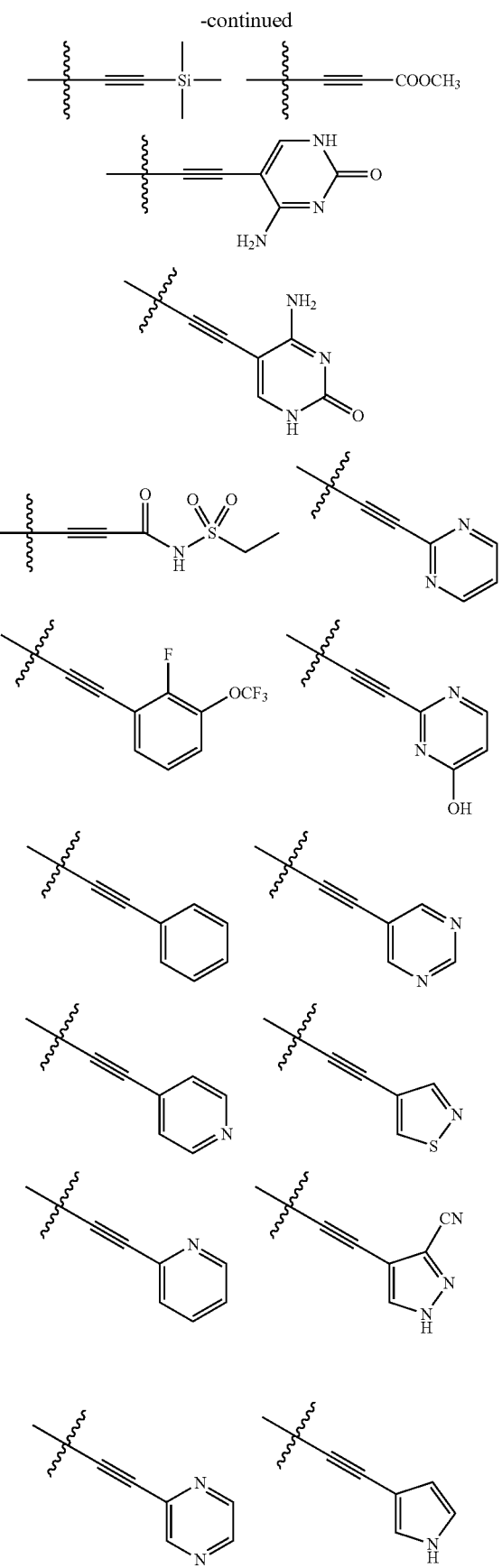

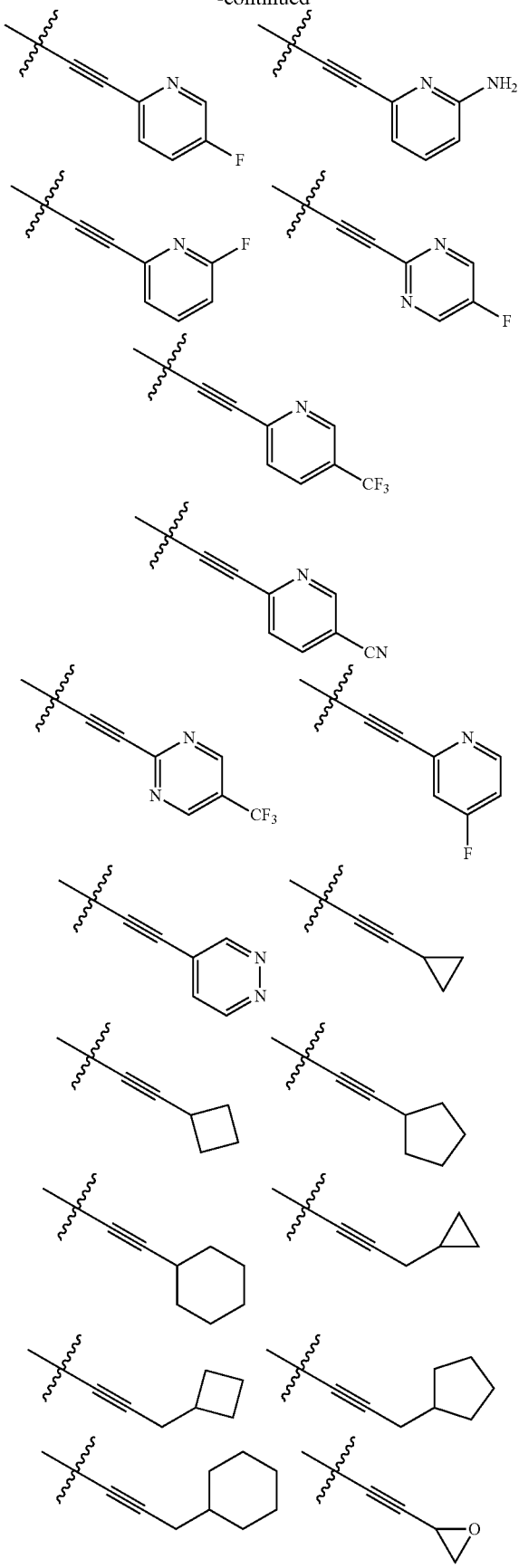
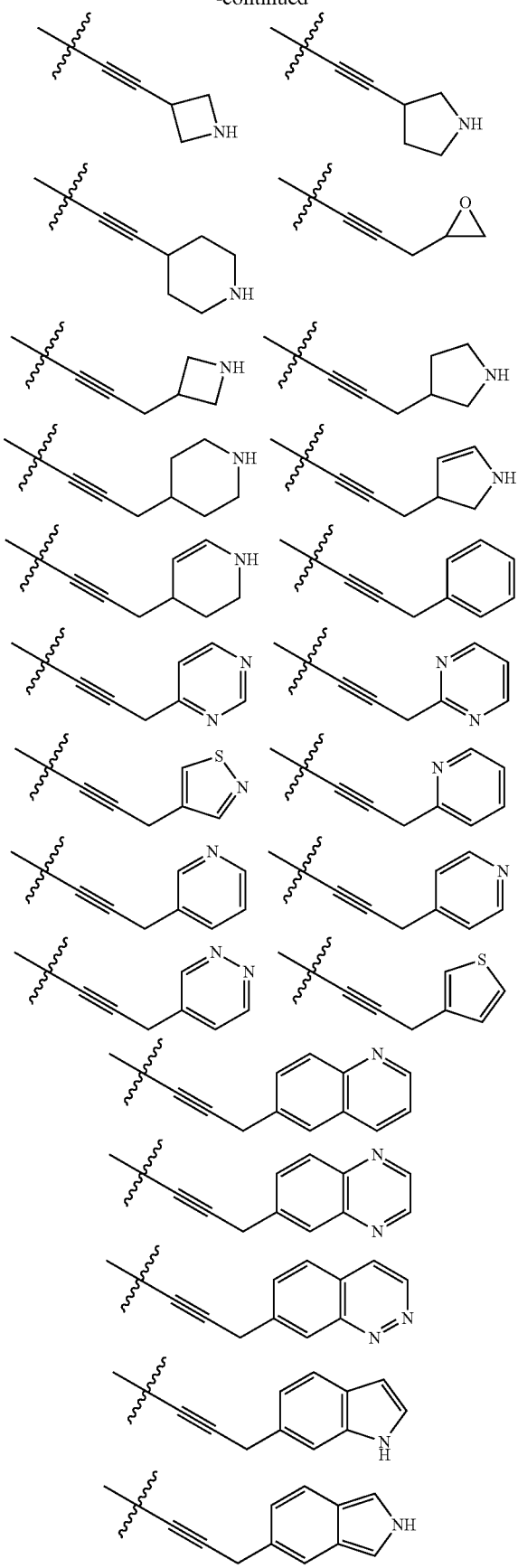

-continued
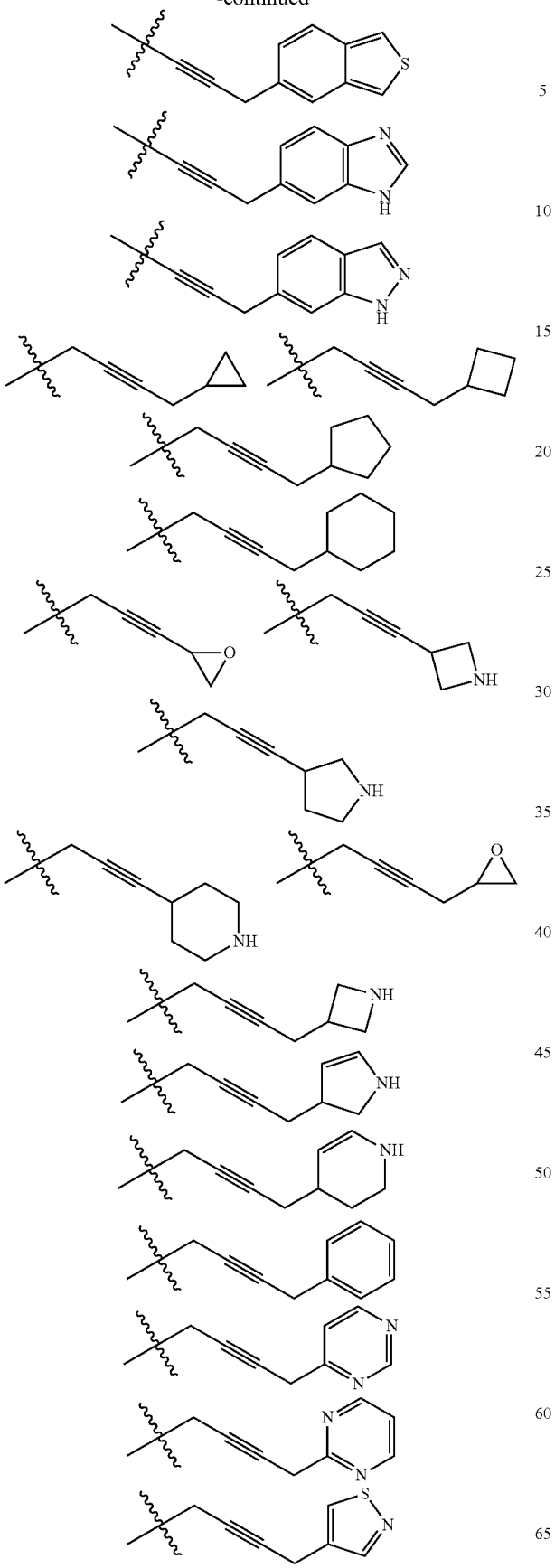
-continued
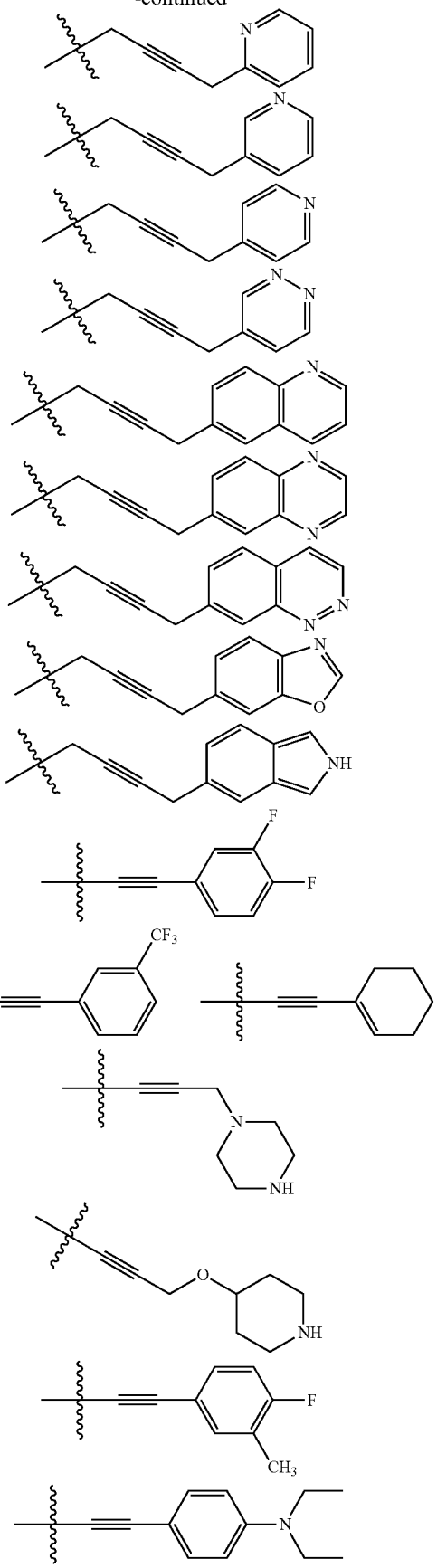

-continued

[Chemical structures shown]

Non-Limiting $R^{12}/R^{13}$ Embodiments

In one embodiment, $R^{12}$ is $R^{32}$.

In one embodiment, $R^{13}$ is $R^{32}$.

In one embodiment, $R^{12}$ is $R^{32}$, which is $C_2$-$C_4$alkynyl$R^{30}$.

In one embodiment, $R^{13}$ is $R^{32}$, which is $C_2$-$C_4$alkynyl$R^{30}$.

In one embodiment, the disclosure provides compounds of Formula I, wherein;

one of $R^{12}$ and $R^{13}$ is H and the other of $R^{12}$ and $R^{13}$ is $R^{32}$, where $R^{32}$ is $C_2$-$C_6$alkynyl$R^{30}$ (which can be, for example, $C_2$-$C_3$alkynyl$R^{30}$, $C_2$-$C_4$alkynyl$R^{30}$, $C_2$-$C_5$alkynyl$R^{30}$, or $C_2$-$C_6$alkynyl$R^{30}$), wherein $R^{30}$ is independently chosen at each occurrence from hydrogen, $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S; (5- or 6-membered unsaturated or aromatic heterocycle)$C_0$-$C_4$alkyl having 1, 2, or 3 heteroatoms independently chosen from N, O, and S; COOH, $Si(CH_3)_3$, COOR$^{30a}$, $C_2$-$C_6$alkanoyl, —C(O)(CH$_2$)$_{1-4}$S(O)R$^{21}$, —P(O)(OR$^{21}$)(OR$^{22}$), —P(O)R$^{21}$R$^{22}$, —NR$^{21}$SO$_2$R$^{22}$, —NR$^9$SO$_2$NR$^{10}$R$^{22}$, —SO$_2$NR$^9$COR$^{22}$, —SO$_2$NR$^9$CONR$^{21}$R$^{22}$, —C(O)NR$^{21}$SO$_2$R$^{22}$, —NR$^9$C(O)OR$^{10}$, —NR$^{21}$OC(O)R$^{22}$, —(CH$_2$)$_{1-4}$C(O)NR$^{21}$R$^{22}$, —C(O)R$^{24}$R$^{25}$, —C(O)R$^{21}$, —NR$^9$C(O)NR$^9$R$^{10}$, —NR$^9$C(O)NR$^{24}$R$^{25}$, —(CH$_2$)$_{1-4}$OC(O)R$^{21}$, each of which $R^{30}$ can be optionally substituted;

wherein $R^9$, $R^{10}$, $R^{21}$, $R^{22}$, $R^{24}$, $R^{25}$, and $R^{30a}$ are as defined in the summary section above.

In another embodiment, the disclosure provides compounds of Formula I, wherein;

$R^1$, $R^{1'}$, $R^2$, and $R^{3'}$ are all hydrogen;

$R^2$ is fluoro and $R^3$ is hydrogen, —C$_0$-C$_4$alkyl(C$_3$-C$_7$cycloalkyl), or —O—C$_0$-C$_4$alkyl(C$_3$-C$_7$cycloalkyl);

$R^5$ is hydrogen, halogen, or $C_1$-$C_2$alkyl;

$R^1$, $R^{13}$, $R^{14}$, and $R^{15}$ if present, are independently chosen at each occurrence from hydrogen, halogen, hydroxyl, amino, $C_1$-$C_4$alkyl, $C_1$-$C_4$alkoxy, —C$_0$-C$_2$alkyl(mono- and di-$C_1$-$C_2$alkylamino), trifluoromethyl, and trifluoromethoxy;

$X^{12}$ is $CR^{12}$; and $R^{12}$ is $C_2$-$C_6$alkynyl$R^{30}$.

In one embodiment, the disclosure provides compounds of Formula I, wherein;

m is 0 or 1;

$R^2$ is halogen, $R^{2'}$ is hydrogen or halogen, and $R^3$ is hydrogen, halogen, —C$_0$-C$_4$alkyl(C$_3$-C$_7$cycloalkyl), or —O—C$_0$-C$_4$alkyl(C$_3$-C$_7$cycloalkyl);

$R^6$ is —C(O)C$_1$-C$_4$alkyl, —C(O)NH$_2$, —C(O)CF$_3$, —C(O)(C$_3$-C$_7$cycloalkyl), or -ethyl(cyanoimino);

one of $R^{12}$ and $R^{13}$ is selected from hydrogen, halogen, $C_1$-$C_4$alkyl, $C_1$-$C_4$alkoxy, trifluoromethyl, and trifluoromethoxy; the other of $R^{12}$ and $R^{13}$ is $R^{32}$, where $R^{32}$ is $C_2$-$C_6$alkynyl$R^{30}$, wherein $R^{30}$ is independently chosen at each occurrence from hydrogen, $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S; (5- or 6-membered unsaturated or aromatic heterocycle)$C_0$-$C_4$alkyl having 1, 2, or 3 heteroatoms independently chosen from N, O, and S; COOH, $Si(CH_3)_3$, COOR$^{30a}$, $C_2$-$C_6$alkanoyl, —B(OH)$_2$, —C(O)(CH$_2$)$_{1-4}$S(O)R$^{21}$, —P(O)(OR$^{21}$)(OR$^{22}$), —P(O)(OR$^{21}$)R$^{22}$, —P(O)R$^{21}$R$^{22}$, —NR$^9$P(O)(NHR$^{21}$)(NHR$^{22}$), —NR$^9$P(O)(OR$^{21}$)(NHR$^{22}$), —NR$^9$P(O)(OR$^{21}$)(OR$^{22}$), —C(S)R$^{21}$, —NR$^{21}$SO$_2$R$^{22}$, —NR$^9$S(O)NR$^{10}$R$^{22}$, —NR$^9$SO$_2$NR$^{10}$R$^{22}$, —SO$_2$NR$^9$COR$^{22}$, —SO$_2$NR$^9$CONR$^{21}$R$^{22}$, —NR$^{21}$SO$_2$R$^{22}$, —C(O)NR$^{21}$SO$_2$R$^{22}$, —C(NH$_2$)NR$^9$R$^{22}$, —C(NH$_2$)NR$^9$S(O)$_2$R$^{22}$, —NR$^9$C(O)OR$^{10}$, —NR$^{21}$OC(O)R$^{22}$, —(CH$_2$)$_{1-4}$C(O)NR$^{21}$R$^{22}$, —C(O)R$^{24}$R$^{25}$, —NR$^9$C(O)R$^{21}$, —C(O)R$^{21}$, —NR$^9$C(O)NR$^9$R$^{10}$, —NR$^9$C(O)NR$^{24}$R$^{25}$, —(CH$_2$)$_{1-4}$OC(O)R$^{21}$, each of which $R^{30}$ can be optionally substituted;

wherein $R^9$, $R^{10}$, $R^{21}$, $R^{22}$, $R^{24}$, $R^{25}$, and $R^{30a}$ are as defined in the summary section above.

In one embodiment, the disclosure provides compounds of Formula I, wherein;

one of $R^{12}$ and $R^{13}$ is hydrogen, hydroxyl, halogen, methyl, or methoxy; and the other of $R^{12}$ and $R^{13}$ is $R^{32}$, where $R^{32}$ is $C_2$-$C_6$alkynyl$R^{30}$, wherein $R^{30}$ is independently chosen at each occurrence from hydrogen, $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S; (5- or 6-membered unsaturated or aromatic heterocycle)$C_0$-$C_4$alkyl having 1, 2, or 3 heteroatoms independently chosen from N, O, and S; COOH, $Si(CH_3)_3$, COOR$^{30a}$, $C_2$-$C_6$alkanoyl, —B(OH)$_2$, —C(O)(CH$_2$)$_{1-4}$S(O)R$^{21}$, —P(O)(OR$^{21}$)(OR$^{22}$), —P(O)(OR$^{21}$)R$^{22}$, —P(O)R$^{21}$R$^{22}$, —NR$^9$P(O)(NHR$^{21}$)(NHR$^{22}$), —NR$^9$P(O)(OR$^{21}$)(NHR$^{22}$), —NR$^9$P(O)(OR$^{21}$)(OR$^{22}$), —C(S)R$^{21}$, —NR$^{21}$SO$_2$R$^{22}$, —NR$^9$S(O)NR$^{10}$R$^{22}$, —NR$^9$SO$_2$NR$^{10}$R$^{22}$, —SO$_2$NR$^9$COR$^{22}$, —SO$_2$NR$^9$CONR$^{21}$R$^{22}$, —NR$^{21}$SO$_2$R$^{22}$, —C(O)NR$^{21}$SO$_2$R$^{22}$, —C(NH$_2$)NR$^9$R$^{22}$, —C(NH$_2$)NR$^9$S(O)$_2$R$^{22}$, —NR⁹C(O)OR¹⁰, —NR²¹OC(O)R²², —(CH₂)₁₋₄C(O)NR²¹R²², —C(O)R²⁴R²⁵, —NR⁹C(O)R²¹, —C(O)R²¹, —NR⁹C(O)NR⁹R¹⁰, —NR⁹C(O)NR²⁴R²⁵, —(CH₂)₁₋₄OC(O)R²¹, each of which R³⁰ can be optionally substituted;

wherein R⁹, R¹⁰, R²¹, R²², R²⁴, R²⁵, and R³⁰ᵃ are as defined in the summary section above.

In one embodiment, R³² may be unsubstituted or substituted with one or more substituents independently chosen from halogen, hydroxyl, nitro, cyano, amino, oxo, —B(OH)₂, —Si(CH₃)₃, —COOH, —CONH₂, —P(O)(OH)₂, C₁-C₆alkyl, C₁-C₆alkoxy, —C₀-C₂alkyl (mono- and di-C₁-C₄alkylamino), C₁-C₆alkylester, C₁-C₄alkylamino, C₁-C₄hydroxylalkyl, C₁-C₂haloalkyl, and C₁-C₂haloalkoxy.

Central Core Moiety

The central core moiety in Formula I is illustrated below:

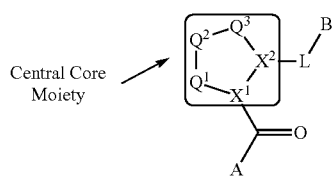

wherein:

Q¹ is N(R¹) or C(R¹R¹');

Q² is C(R²R²'), C(R²R²')—C(R²R²'), S, O, N(R²) or C(R²R²')O;

Q³ is N(R³), S, or C(R³R³');

X¹ and X² are independently N or CH, or X¹ and X² together are C=C; and wherein Q¹, Q², Q³, X¹, and X² are selected such that a stable compound results.

Non-limiting examples of the

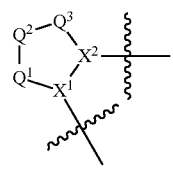

ring are illustrated below (any of which can be otherwise substituted with R¹, R¹', R², R²', R³, and R³') as described in more detail below.

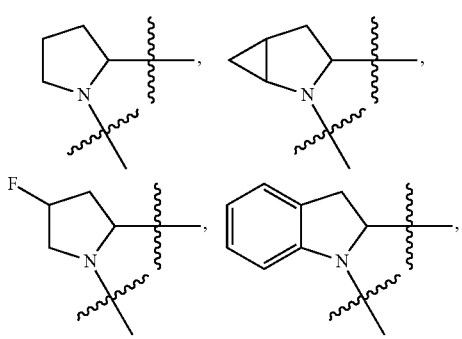

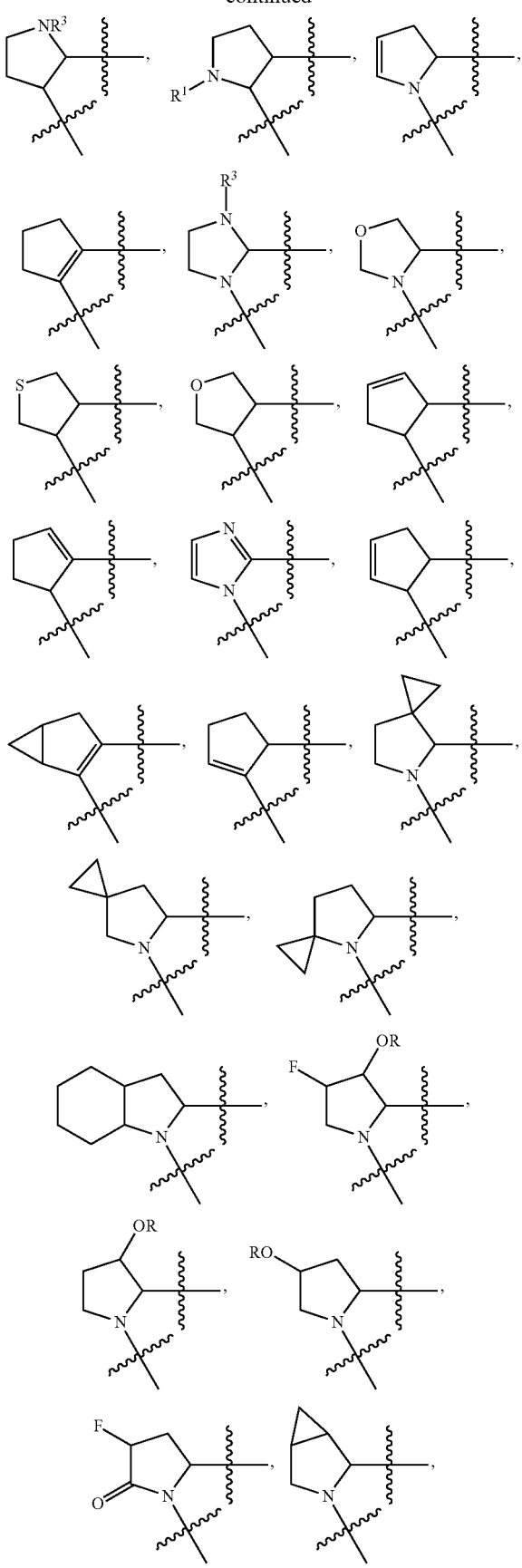

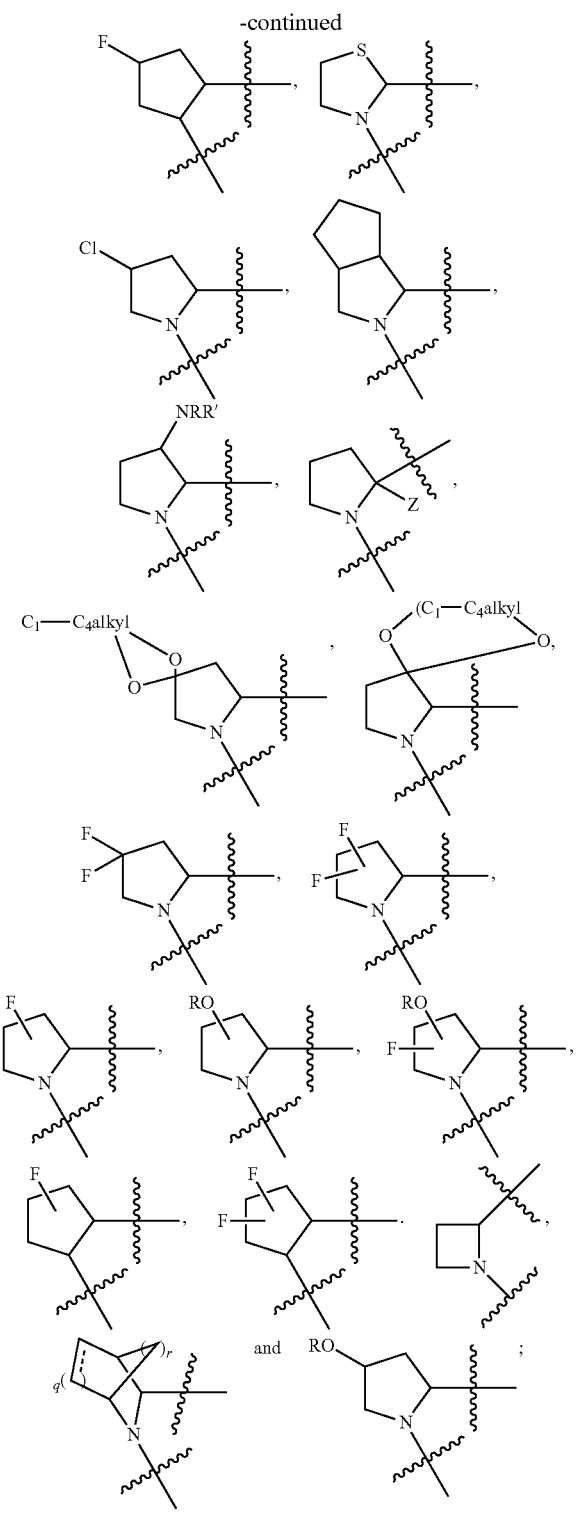

wherein q is 0, 1, 2 or 3 and r is 1, 2 or 3.

R and R' are independently chosen from H, alkyl, cycloalkyl, cycloalkylalkyl, heterocycle, heterocycloalkyl, aryl, aralkyl, heteroaryl, heteroarylalkyl wherein each group can be optionally substituted or any other substituent group herein that provides the desired properties. In some embodiments, the ring includes one or more chiral carbon atoms. The invention includes embodiments in which the chiral carbon can be provided as an enantiomer, or mixtures of enantiomers, including a racemic mixture. Where the ring includes more than one stereocenter, all of the enantiomers and diastereomers are included in the invention as individual species.

Z is F, Cl, $NH_2$, $CH_3$, $CH_2D$, $CHD_2$, or $CD_3$.

$R^1$, $R^{1'}$, $R^2$, $R^{2'}$, $R^3$, and $R^{3'}$ are independently chosen at each occurrence, as appropriate, and only where a stable compound results, from hydrogen, halogen, hydroxyl, nitro, cyano, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkyl$NR^9R^{10}$, —C(O)$OR^9$, —OC(O)$R^9$, —$NR^9$C(O)$R^{10}$, —C(O)$NR^9R^{10}$, —OC(O)$NR^9R^{10}$, —$NR^9$C(O)$OR^{10}$, $C_1$-$C_2$haloalkyl, and $C_1$-$C_2$haloalkoxy, where $R^9$ and $R^{10}$ are independently chosen at each occurrence from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl).

Non-Limiting Central Core Embodiments

In alternative embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently chosen from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring each of which ring may be unsubstituted or substituted with 1 or more substituents independently chosen from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^2$ may be taken together to form a 3-membered carbocyclic ring; $R^1$ and $R^2$ may be taken together to form a 4- to 6-membered carbocyclic or aryl ring or a 4- to 6-membered heterocyclic or heteroaryl ring containing 1 or 2 heteroatoms independently chosen from N, O, and S; or $R^2$ and $R^3$, if bound to adjacent carbon atoms, may be taken together to form a 3- to 6-membered carbocyclic or aryl ring or a 3- to 6-membered heterocyclic or heteroaryl ring each of which ring may be unsubstituted or substituted with one or more substituents independently chosen from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In one embodiment, the central core moiety is proline.

In one embodiment, the central core moiety is 4-fluoroproline.

In one embodiment, $R^1$, $R^{1'}$, $R^{2'}$, $R^3$, and $R^{3'}$, if present, are all hydrogen; and $R^2$ is fluoro.

In one embodiment, $R^1$, $R^{1'}$, $R^{2'}$, and $R^{3'}$, if present, are all hydrogen; and $R^2$ is fluoro and $R^3$ is —$C_0$-$C_4$alkyl($C_3$-$C_7$cycloalkyl) or —O—$C_0$-$C_4$alkyl($C_3$-$C_7$cycloalkyl).

In one embodiment, $R^1$ and $R^2$ are taken together to form a 3- to 6-membered cycloalkyl group, and $R^{1'}$, $R^{2'}$, $R^3$, and $R^{3'}$, where present, are all hydrogen.

In one embodiment, $R^1$, $R^{1'}$, $R^3$, and $R^{3'}$, if present, are all hydrogen, and $R^2$ and $R^{2'}$ are taken together to form a 5- or 6-membered heterocycloalkyl group having 1 or 2 oxygen atoms.

In one embodiment, $R^1$ is hydrogen and $R^2$ is fluoro.

In one embodiment, $R^1$ and $R^2$ are joined to form a 3 membered ring.

The disclosure includes compounds of Formula I in which the central pyrrolidine is vinyl substituted, for example:

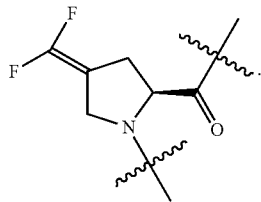 [SMILES: *C(=O)[C@@H]1CC(=C(F)F)CN1*]

In one embodiment, the compound of Formula I has the structure:

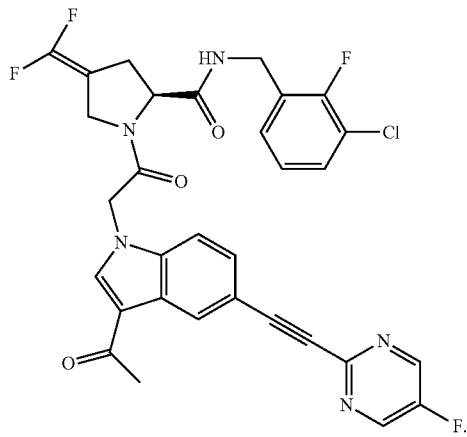 [SMILES: CC(=O)c1cn(CC(=O)N2CC(=C(F)F)C[C@H]2C(=O)NCc2cccc(Cl)c2F)c2ccc(C#Cc3ncc(F)cn3)cc12]

In one embodiment, the central pyrrolidine is modified by addition of a second heteroatom to a pyrrolidine ring, such as N, O, S, or Si, for example:

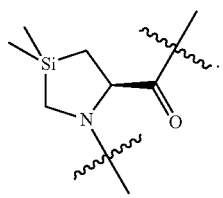 [SMILES: *C(=O)[C@@H]1C[Si](C)(C)CN1*]

Another modification within the scope of the disclosure is joining a substituent on the central pyrrolidine ring to $R^7$ or $R^8$ to form a 5- to 6-membered heterocyclic ring, for example:

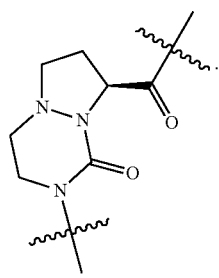 [SMILES: *C(=O)[C@@H]1CCN2CCN(*)C(=O)N12]

Example of compounds having the modifications disclosed above include:

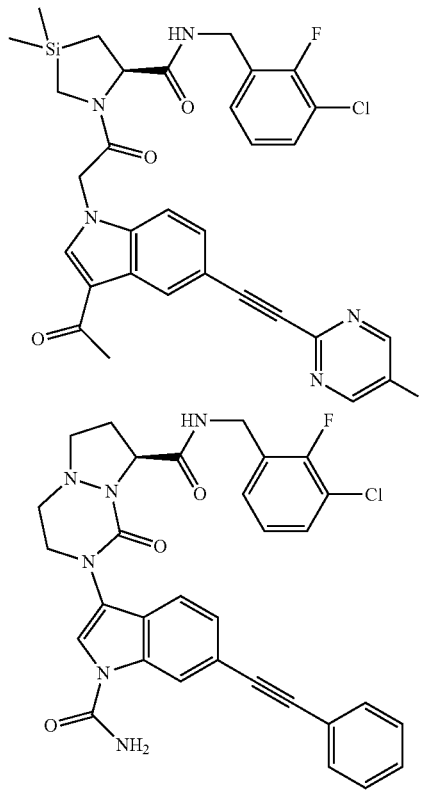

Central Core L-B Substituents

The central core L-B substituents in Formula I are illustrated below:

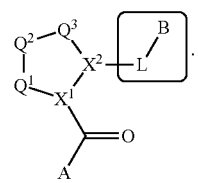

L is a bond or is chosen from the formulas:

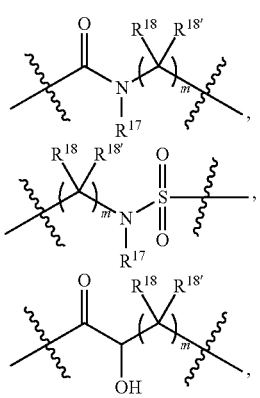

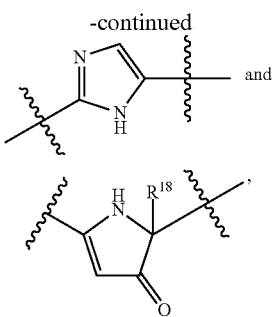 and where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently chosen from hydrogen, halogen, hydroxymethyl, and methyl; and m is 0, 1, 2, or 3.

B is a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl).

Each of which B is unsubstituted or substituted with one or more substituents independently chosen from $R^{33}$ and $R^{34}$, and 0 or 1 substituents chosen from $R^{35}$ and $R^{36}$:

$R^{33}$ is independently chosen from halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, and $C_1$-$C_2$haloalkoxy;

$R^{34}$ is independently chosen from nitro, $C_2$-$C_6$alkenyl, $C_2$-$C_6$alkynyl, $C_1$-$C_6$thioalkyl, -J$C_3$-$C_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$) -JNR$^9$P(O)(OR$^{21}$)(NHR$^{22}$) -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)NR$^{22}$, -JC(NH$_2$)NR$^9$S(O)$_2$R$^{22}$, -JOC(O)NR$^{21}$R$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)R$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_{1-4}$OC(O)R$^{21}$, and -JC(O)OR$^{23}$; each of which R$^{34}$ may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy;

$R^{35}$ is independently chosen from naphthyl, naphthyloxy, indanyl, (4- to 7-membered heterocycloalkyl)$C_0$-$C_4$alkyl containing 1 or 2 heteroatoms chosen from N, O, and S, and bicyclic heterocycle containing 1, 2, or 3 heteroatoms independently chosen from N, O, and S, and containing 4- to 7-ring atoms in each ring; each of which R$^{35}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO$_2$R$^9$, $C_1$-$C_2$haloalkyl, and $C_1$-$C_2$haloalkoxy; and $R^{36}$ is independently chosen from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently chosen from N, O, B, and S, each of which R$^{36}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —SO$_2$R$^9$, —OSi(CH$_3$)$_2$C(CH$_3$)$_3$, —Si(CH$_3$)$_2$C(CH$_3$)$_3$, $C_1$-$C_2$haloalkyl, and $C_1$-$C_2$haloalkoxy.

J is independently chosen at each occurrence from a covalent bond, $C_1$-$C_4$alkylene, —O$C_1$-$C_4$alkylene, $C_2$-$C_4$alkenylene, and $C_2$-$C_4$alkynylene.

In one embodiment, -L-B— is

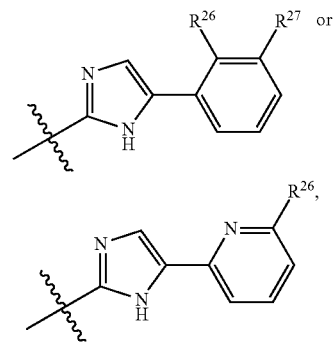

where $R^{26}$ and $R^{27}$ are independently chosen from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, $C_1$-$C_2$haloalkoxy, and $C_1$-$C_2$haloalkylthio.

Non-Limiting L-B Embodiments

In another embodiment, -L-B— is

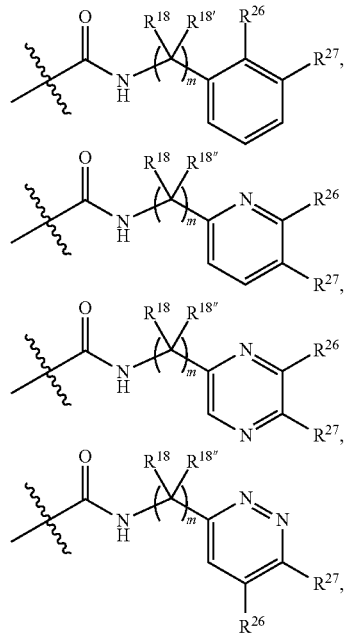

-continued

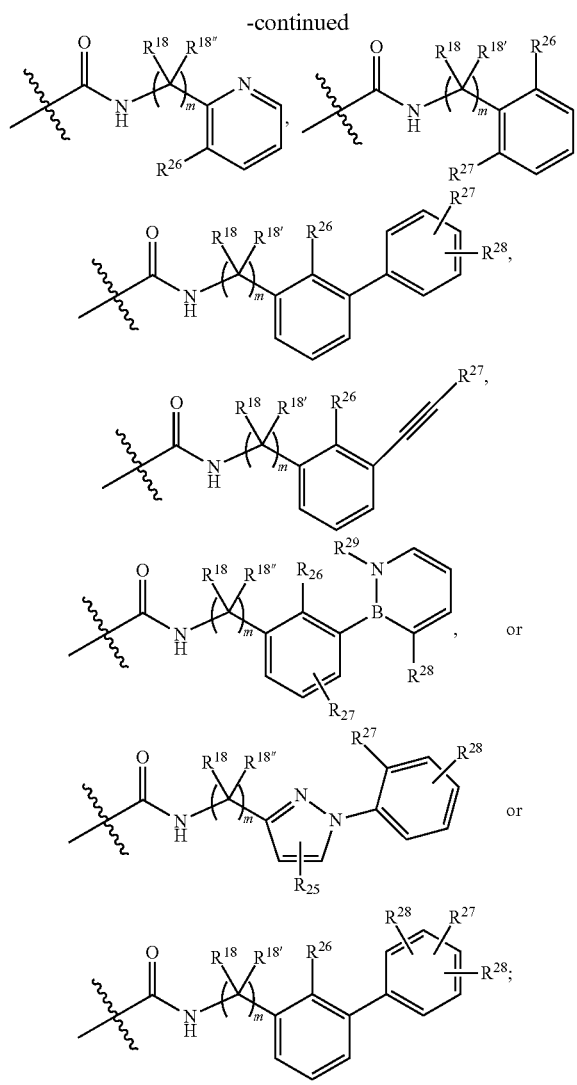

wherein $R^{18}$ and $R^{18'}$ are independently chosen from hydrogen, halogen, hydroxymethyl, and methyl; and m is 0 or 1; and $R^{26}$, $R^{27}$, and $R^{28}$ are independently chosen from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and —$C_0$-$C_4$alkoxy($C_3$-$C_7$cycloalkyl); each of which $R^{26}$, $R^{27}$, and $R^{28}$ other than hydrogen, halogen, hydroxyl, nitro, cyano, is unsubstituted or substituted with one or more substituents independently chosen from halogen, hydroxyl, amino, $C_1$-$C_2$alkoxy, $C_1$-$C_2$haloalkyl, ($C_3$—C7cycloalkyl)$C_0$-$C_4$alkyl-, and $C_1$-$C_2$haloalkoxy; and $R^{29}$ is hydrogen, $C_1$-$C_2$alkyl, $C_1$-$C_2$haloalkyl or —Si(CH$_3$)$_2$C(CH$_3$)$_3$.

In one embodiment, m is 0.

In one embodiment, the disclosure further includes compounds and salts of Formula I in which B is 2-fluoro-3-chlorophenyl. In another embodiment, another carbocyclic, aryl, heterocyclic, or heteroaryl group such as 2-bromopyridin-6-yl, 1-(2,2,2-trifluoroethyl)-1H-pyrazol-3-yl, 2,2-dichlorocyclopropylmethyl, or 2-fluoro-3-trimethylsilylphenyl is used.

In another embodiment, B is phenyl, pyridyl, or indanyl each of which is unsubstituted or substituted with one or more substituents independently chosen from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, —$C_0$-$C_4$alkoxy($C_3$-$C_7$cycloalkyl), (phenyl)$C_0$-$C_2$alkyl, (pyridyl)$C_0$-$C_2$alkyl; each of which substituents other than hydrogen, halogen, hydroxyl, nitro, cyano, is unsubstituted or substituted with one or more substituents independently chosen from halogen, hydroxyl, amino, $C_1$-$C_2$alkyl, $C_1$-$C_2$alkoxy, —OSi(CH$_3$)$_2$C(CH$_3$)$_3$, —Si(CH$_3$)$_2$C(CH$_3$)$_3$, $C_1$-$C_2$haloalkyl, and $C_1$-$C_2$haloalkoxy.

In another embodiment, B is phenyl or pyridyl substituted with 1, 2, or 3 substituents chosen from chloro, bromo, hydroxyl, —SCF$_3$, $C_1$-$C_2$alkyl, $C_1$-$C_2$alkoxy, trifluoromethyl, phenyl and trifluoromethoxy each of which substituents other than chloro, bromo, hydroxyl, —SCF$_3$, can be optionally substitued.

In certain embodiments, B is a 2-fluoro-3-chlorophenyl or a 2-fluoro-3-trifluoromethoxyphenyl group.

In one embodiment, B is pyridyl, optionally substituted with halogen, $C_1$-$C_2$alkoxy, and trifluoromethyl.

In one embodiment, B is phenyl, substituted with 1, 2, or 3 substituents independently selected from halogen, $C_1$-$C_2$alkyl, $C_1$-$C_2$alkoxy, trifluoromethyl, and optionally substituted phenyl.

In one embodiment, $R^{23}$ is independently chosen at each occurrence from ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S.

In one embodiment, B is selected from

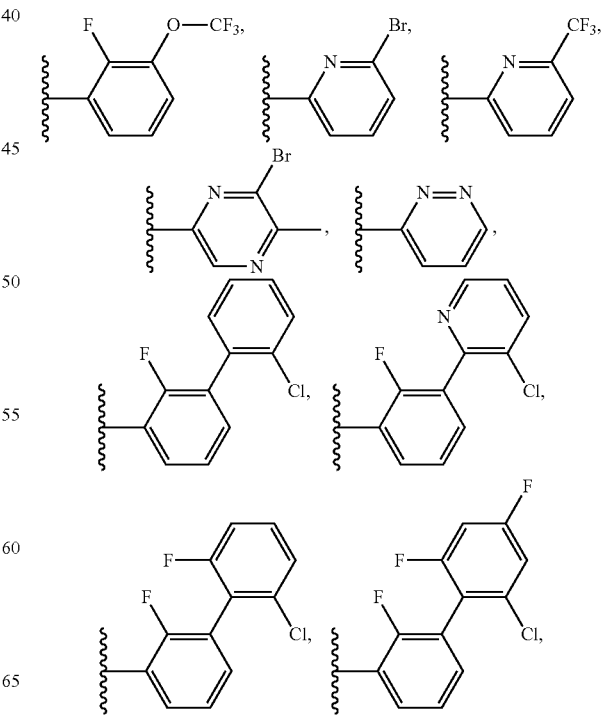

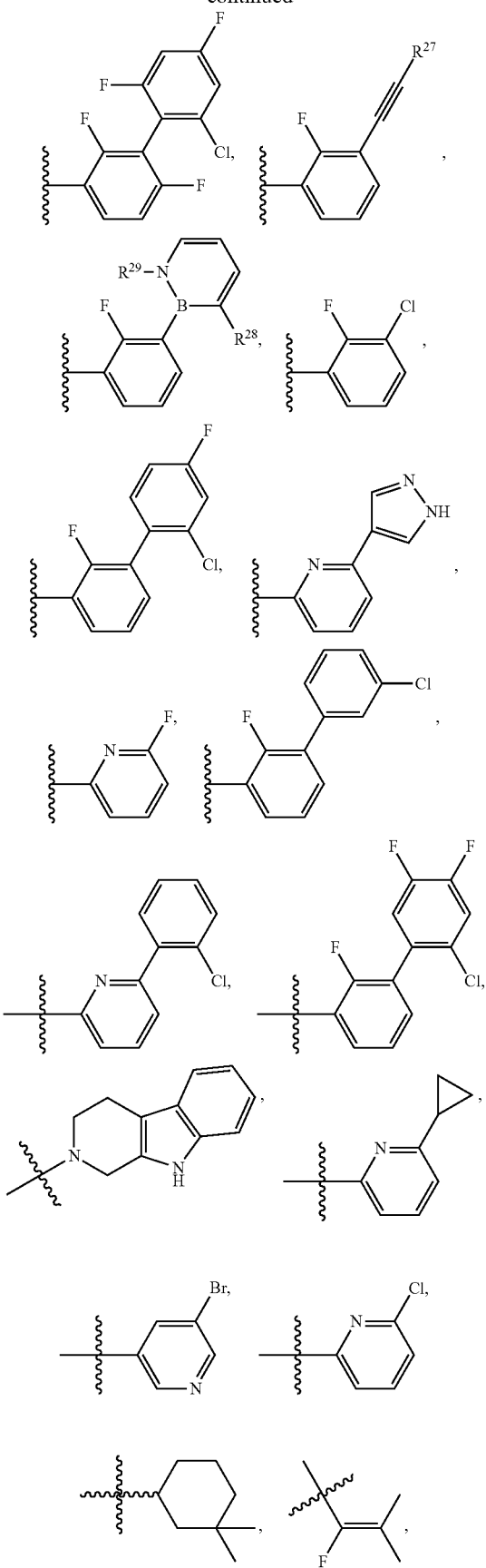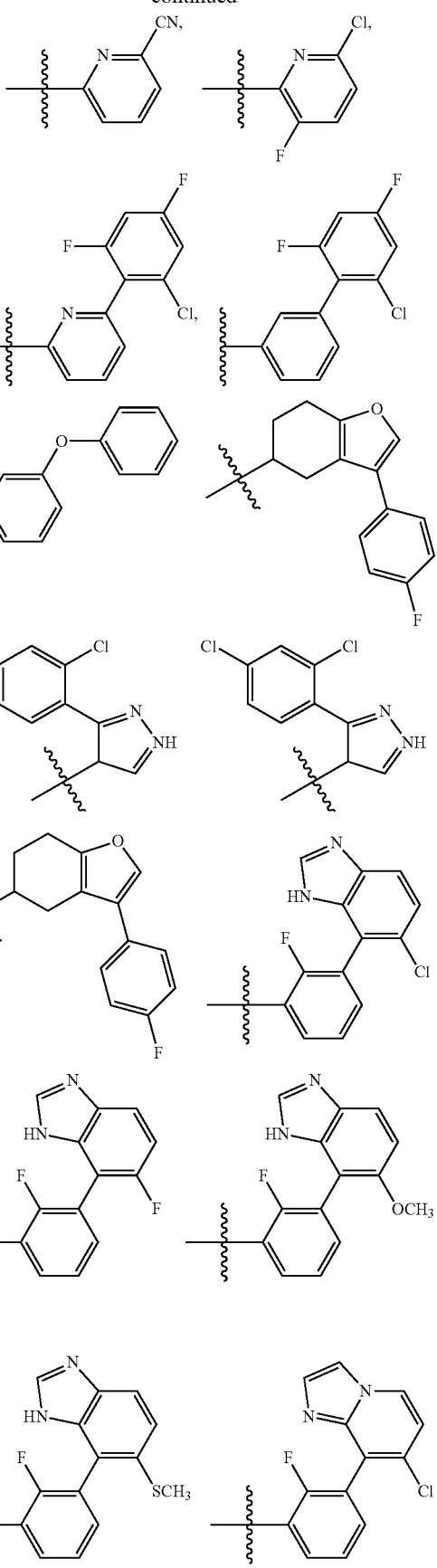

51
-continued
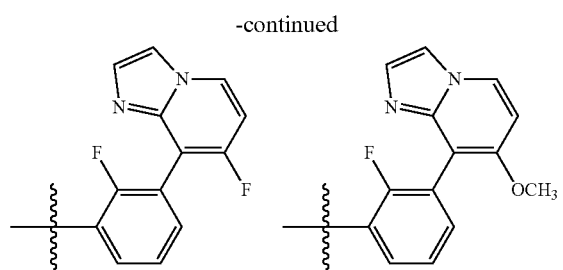
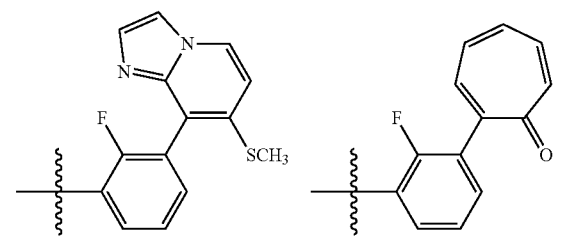
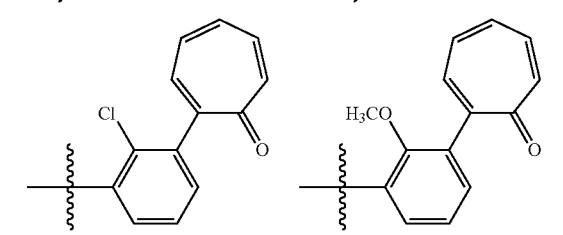
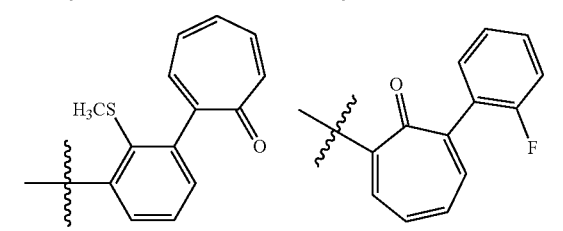
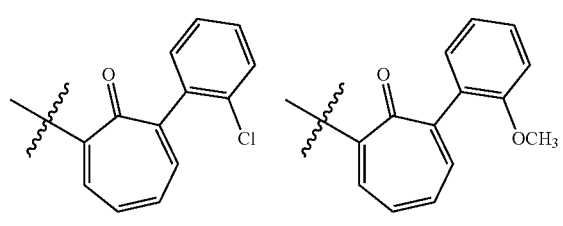
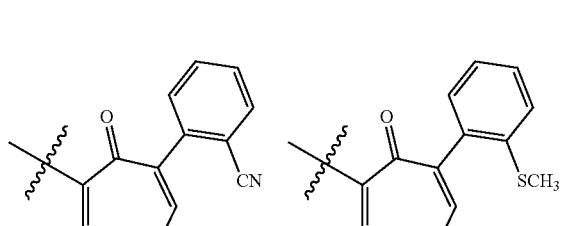
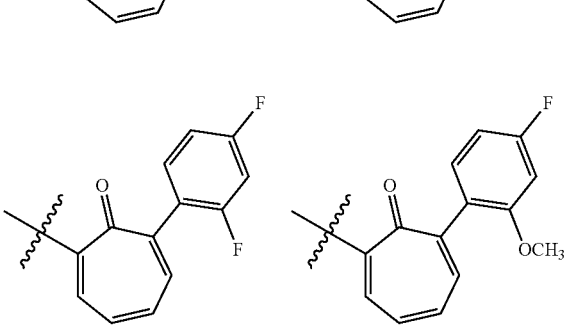
52
-continued
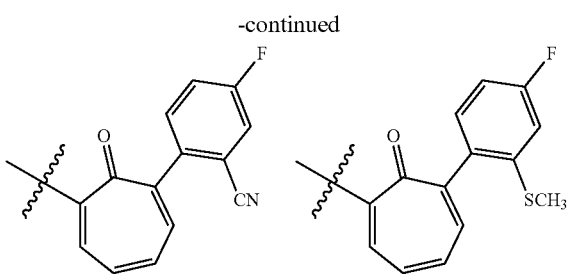
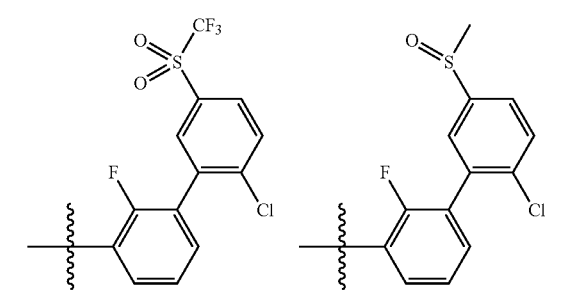
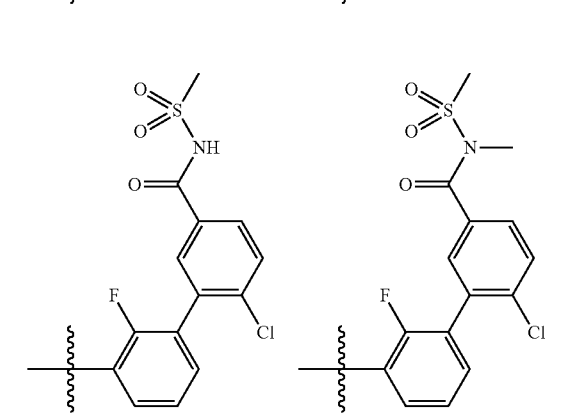
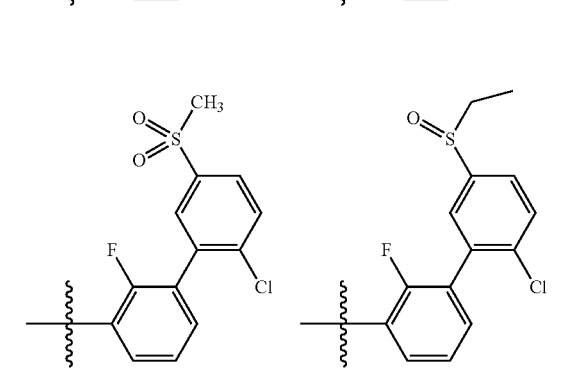
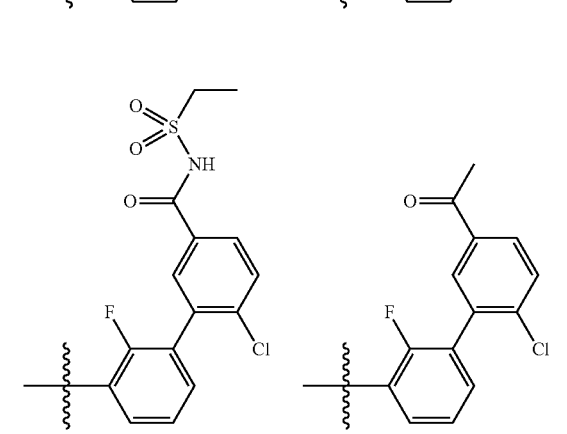

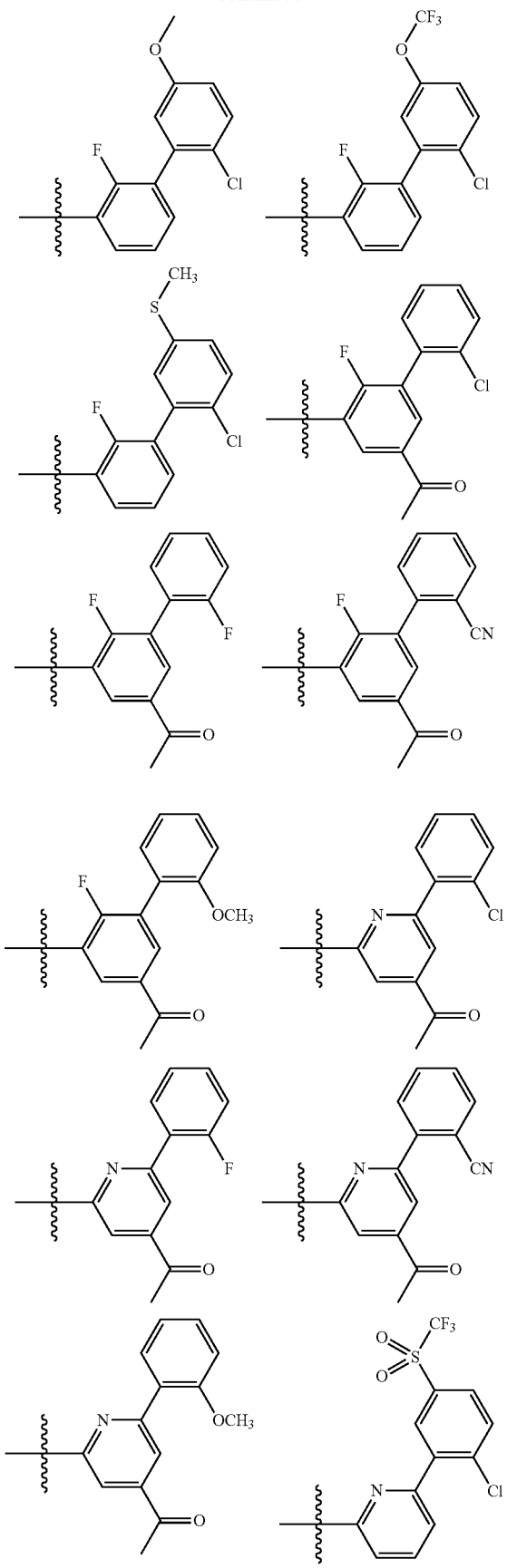
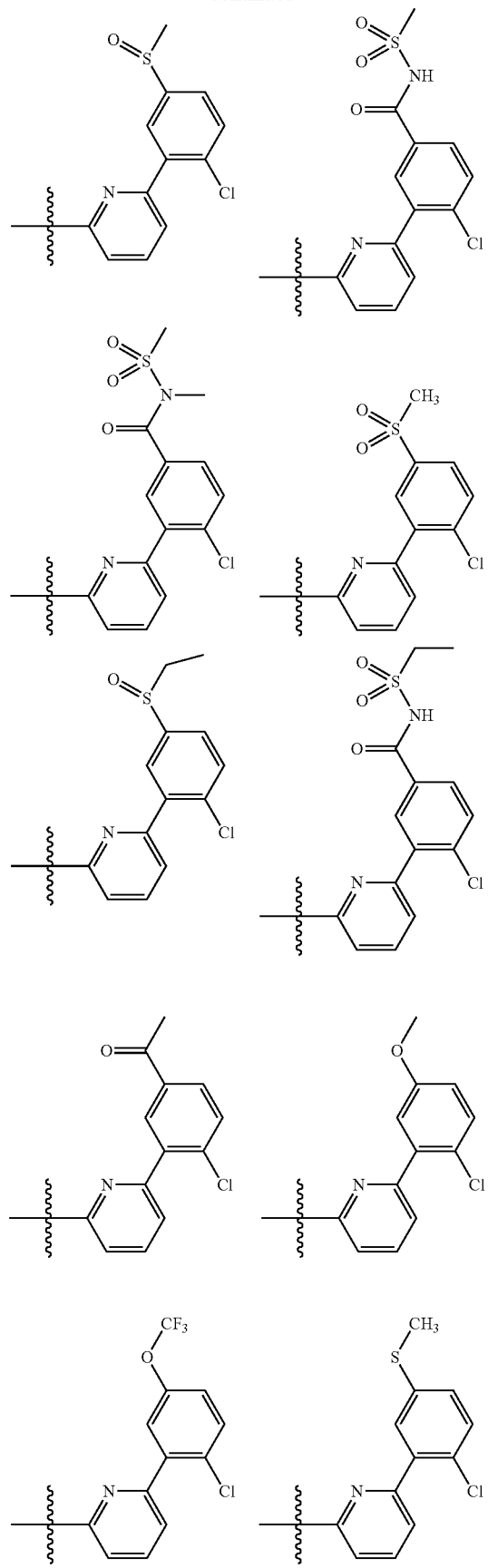

55 56
-continued  -continued
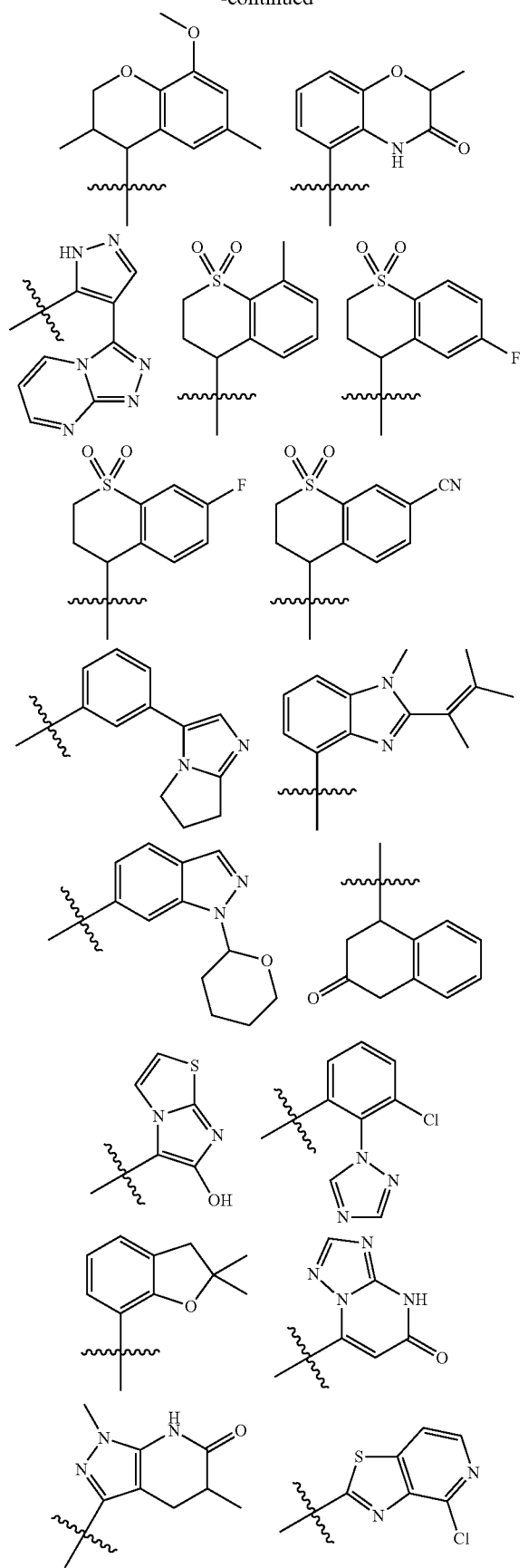
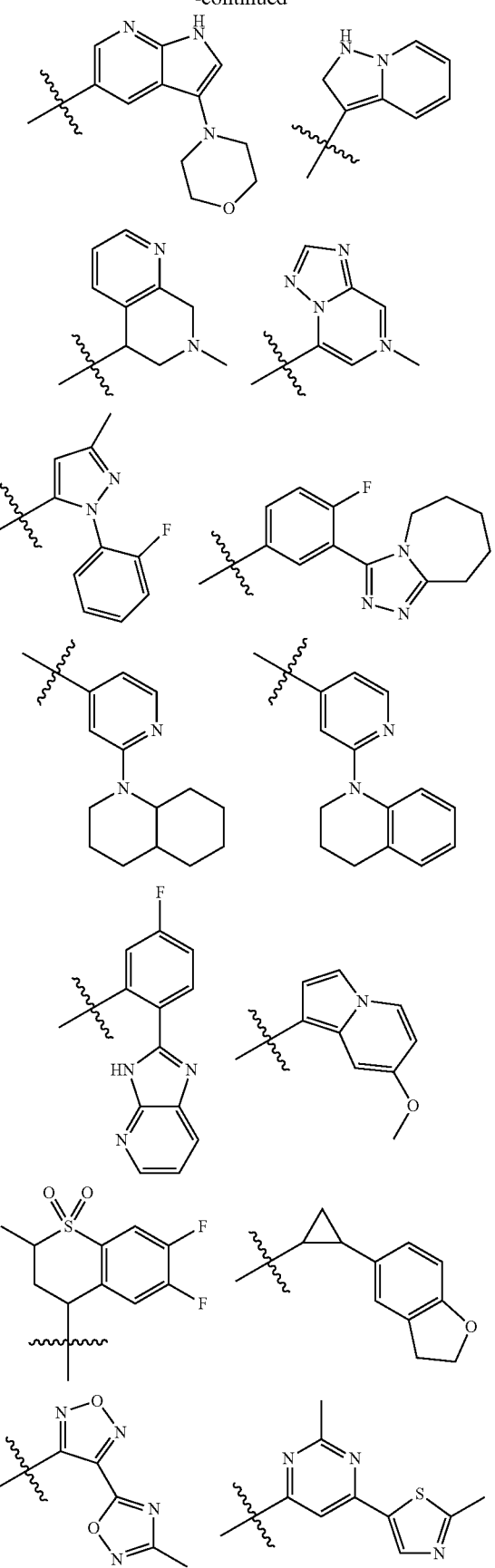

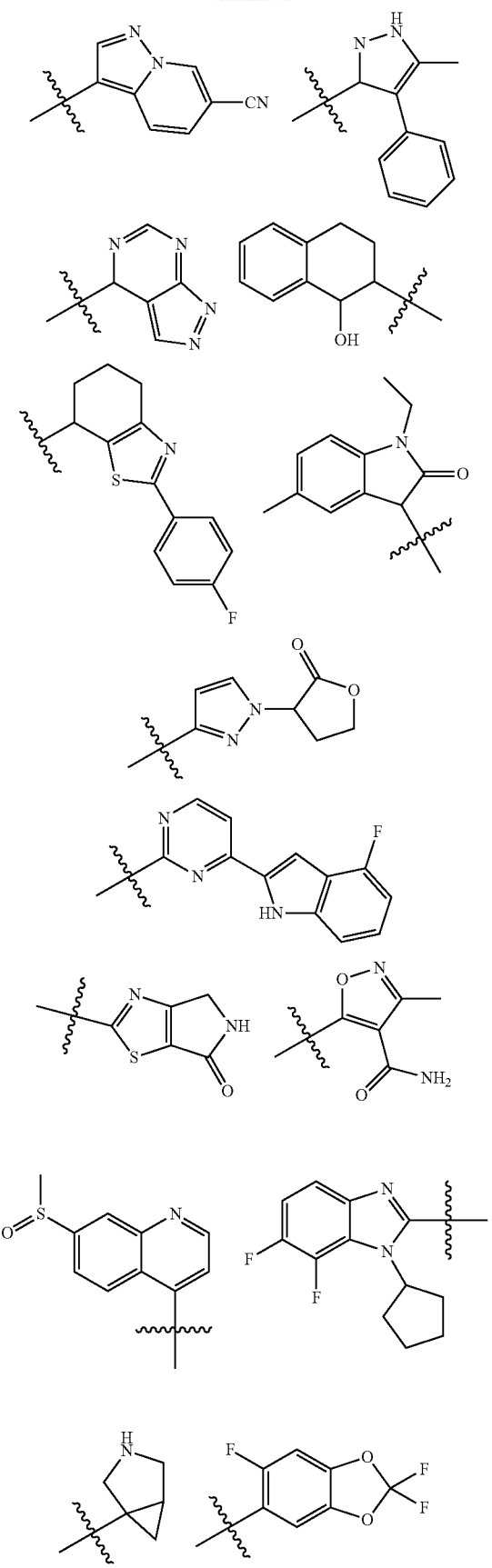
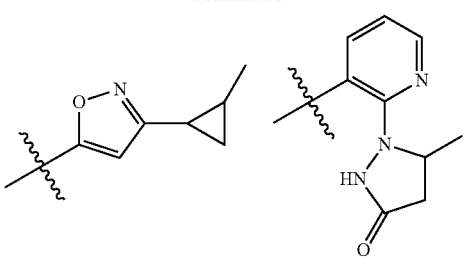
where $R^{27}$ is hydrogen, methyl, or trifluoromethyl; $R^{28}$ is hydrogen or halogen; and $R^{29}$ is hydrogen, methyl, trifluoromethyl, or —Si(CH$_3$)$_2$C(CH$_3$)$_3$.
Central Core (C=O)A Substituent
The central core (C=O)A substituent in Formula I is illustrated below:
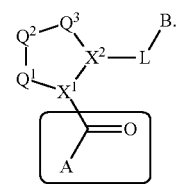
A is a group chosen from:
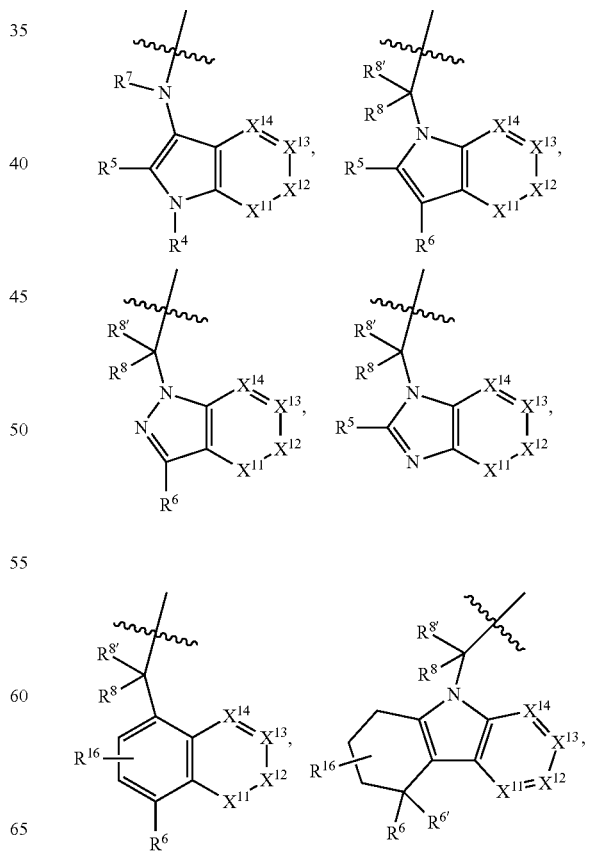

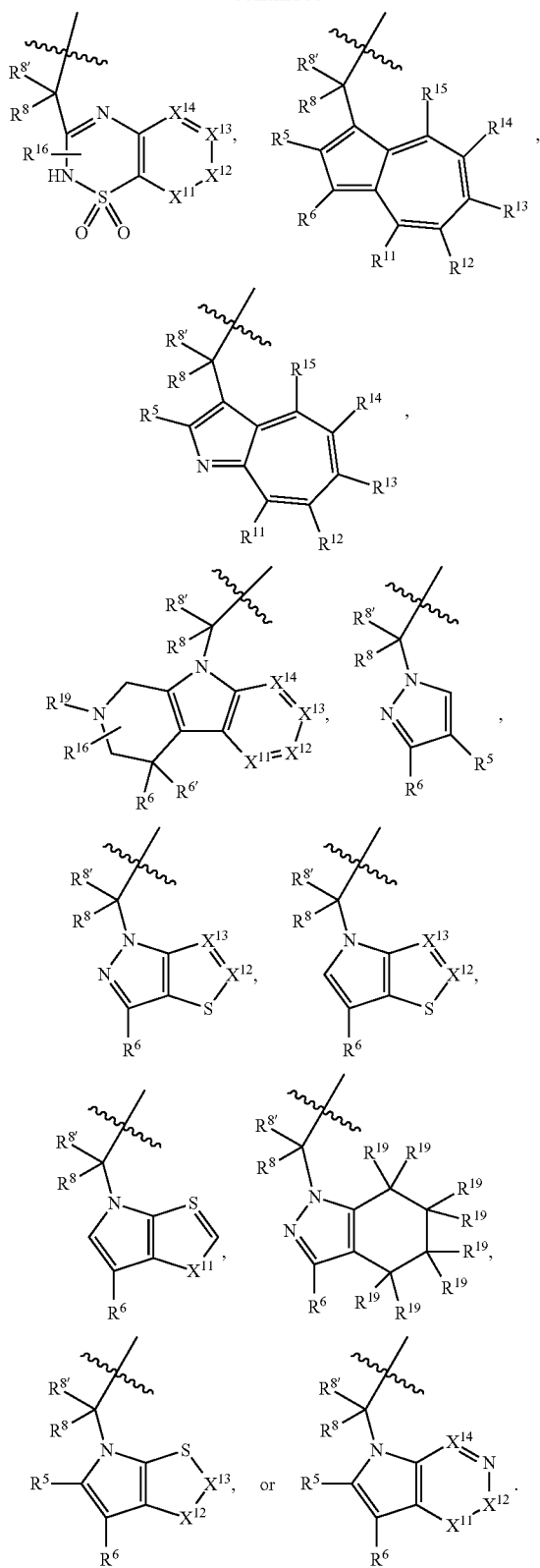

each of which $R^4$ other than hydrogen, —CHO, and —CONH$_2$, is unsubstituted or substituted with one or more of amino, imino, halogen, hydroxyl, cyano, cyanoimino, $C_1$-$C_2$alkyl, $C_1$-$C_2$alkoxy, —$C_0$-$C_2$alkyl(mono- and di-$C_1$-$C_4$alkylamino), $C_1$-$C_2$haloalkyl, and $C_1$-$C_2$haloalkoxy.

$R^5$ and $R^6$ are independently chosen from —CHO, —C(O)NH$_2$, —C(O)NH(CH$_3$), $C_2$-$C_6$alkanoyl, hydrogen, hydroxyl, halogen, cyano, nitro, —COOH, —SO$_2$NH$_2$, vinyl, $C_1$-$C_6$alkyl (including methyl), $C_2$-$C_6$alkenyl, $C_1$-$C_6$alkoxy, —$C_0$-$C_4$alkyl($C_3$-$C_7$cycloalkyl), —C(O)C$_0$-$C_4$alkyl($C_3$-$C_7$cycloalkyl), —P(O)(OR$^9$)$_2$, —OC(O)R$^9$, —C(O)OR$^9$, —C(O)N(CH$_2$CH$_2$R$^9$)(R$^{10}$), —NR$^9$C(O)R$^{10}$, phenyl, or 5- to 6-membered heteroaryl.

Each $R^5$ and $R^6$ other than hydrogen, hydroxyl, cyano, and —COOH is unsubstituted or optionally substituted. For example, $R^5$ and $R^6$, other than hydrogen, hydroxyl, cyano, —COOH, may be substituted with one or more substituents independently chosen from halogen, hydroxyl, amino, imino, cyano, cyanoimino, $C_1$-$C_2$alkyl, $C_1$-$C_4$alkoxy, —$C_0$-$C_2$alkyl(mono- and di-$C_1$-$C_4$alkylamino), $C_1$-$C_2$haloalkyl, and $C_1$-$C_2$haloalkoxy.

$R^{6'}$ is hydrogen, halogen, hydroxyl, $C_1$-$C_4$alkyl, —$C_0$-$C_4$alkyl($C_3$-$C_7$cycloalkyl), or $C_1$-$C_4$alkoxy; or $R^6$ and $R^{6'}$ may be taken together to form an oxo, vinyl, or imino group.

$R^7$ is hydrogen, $C_1$-$C_6$alkyl, or —$C_0$-$C_4$alkyl($C_3$-$C_7$cycloalkyl).

$R^8$ and $R^{8'}$ are independently chosen from hydrogen, halogen, hydroxyl, $C_1$-$C_6$alkyl, —$C_0$-$C_4$alkyl($C_3$-$C_7$cycloalkyl), $C_1$-$C_6$alkoxy, and ($C_1$-$C_4$alkylamino)$C_0$-$C_2$alkyl; or $R^8$ and $R^{8'}$ are taken together to form an oxo group; or $R^8$ and $R^{8'}$ can be taken together with the carbon that they are bonded to form a 3-membered carbocyclic ring.

$R^{16}$ is absent or may include one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, —$C_0$-$C_4$alkyl(mono- and di-$C_1$-$C_6$alkylamino), —$C_0$-$C_4$alkyl($C_3$-$C_7$cycloalkyl), $C_1$-$C_2$haloalkyl, and $C_1$-$C_2$haloalkoxy.

$R^{19}$ is hydrogen, $C_1$-$C_6$alkyl, $C_2$-$C_6$alkenyl, $C_2$-$C_6$alkanoyl, —SO$_2$C$_1$-$C_6$alkyl, (mono- and di-$C_1$-$C_6$alkylamino)$C_1$-$C_4$alkyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), $C_0$-$C_4$alkyl(heteroaryl), and wherein $R^{19}$ other than hydrogen is unsubstituted or substituted with 1 or more substitu- $R^4$ is chosen from —CHO, —CONH$_2$, $C_2$-$C_6$alkanoyl, hydrogen, —SO$_2$NH$_2$, —C(CH$_2$)$_2$F, —CH(CF$_3$)NH$_2$, $C_1$-$C_6$alkyl, —$C_0$-$C_4$alkyl($C_3$-$C_7$cycloalkyl), —C(O)C$_0$-$C_2$alkyl($C_3$-$C_7$cycloalkyl), ents independently chosen from halogen, hydroxyl, amino, —COOH, and —C(O)OC$_1$-C$_4$alkyl.

$X^{11}$ is N or CR$^{11}$.
$X^{12}$ is N or CR$^{12}$.
$X^{13}$ is N or CR$^{13}$.
$X^{14}$ is N or CR$^{14}$.

No more than 2 of $X^{11}$, $X^{12}$, $X^{13}$, and $X^{14}$ are N.

R$^{11}$, R$^{14}$, and R$^{15}$ are independently chosen at each occurrence from hydrogen, halogen, hydroxyl, nitro, cyano, —O(PO)(OR$^9$)$_2$, —(PO)(OR$^9$)$_2$, C$_1$-C$_6$alkyl, C$_2$-C$_6$alkenyl, C$_2$-C$_6$alkynyl, C$_2$-C$_6$alkenyl(aryl), C$_2$-C$_6$alkenyl(cycloalkyl), C$_2$-C$_6$alkenyl(heterocycle), C$_2$-C$_6$alkenyl(heteroaryl), C$_2$-C$_6$alkynyl, C$_2$-C$_6$alkynyl(aryl), C$_2$-C$_6$alkynyl(cycloalkyl), C$_2$-C$_6$alkynyl(heterocycle), C$_2$-C$_6$alkynyl(heteroaryl), C$_2$-C$_6$alkanoyl, C$_1$-C$_6$alkoxy, C$_1$-C$_6$thioalkyl, —C$_0$-C$_4$alkyl(mono- and di-C$_1$-C$_6$alkylamino), —C$_0$-C$_4$alkyl(C$_3$-C$_7$cycloalkyl), —C$_0$-C$_4$alkoxy(C$_3$-C$_7$cycloalkyl), C$_1$-C$_2$haloalkyl, and C$_1$-C$_2$haloalkoxy.

In one embodiment, R$^5$ and R$^6$ are independently chosen from —CHO, —C(O)NH$_2$, —C(O)NH(CH$_3$), C$_2$-C$_6$alkanoyl, and hydrogen.

In one embodiment, each R$^5$ and R$^6$ other than hydrogen, hydroxyl, cyano, and —COOH is unsubstituted or substituted with one or more substituents independently chosen from halogen, hydroxyl, amino, imino, cyano, cyanoimino, C$_1$-C$_2$alkyl, C$_1$-C$_4$alkoxy, —C$_0$-C$_2$alkyl(mono- and di-C$_1$-C$_4$alkylamino), C$_1$-C$_2$haloalkyl, and C$_1$-C$_2$haloalkoxy.

In one embodiment, R$^8$ and R$^{8'}$ are independently hydrogen or methyl.

In one embodiment, R$^8$ and R$^{8'}$ are hydrogen.

In one embodiment, R$^7$ is hydrogen or methyl.

In one embodiment, R$^7$ is hydrogen.

Embodiments of Formulas IA, IB, IC, and ID

To further illustrate the invention, various embodiments of Formula IA, IB, IC and ID are provided. These are presented by way of example to show some of the variations among presented compounds within the invention and can be applied to any of the Formulas I-XXX.

In one aspect, this disclosure includes compounds and salts of Formula IA:

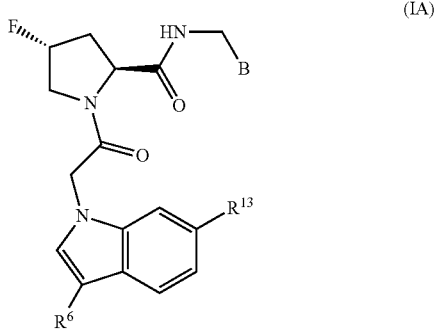

where R$^6$, R$^{13}$, and B may carry any of the definitions set forth herein for this variable.

In another aspect, this disclosure includes compounds and salts of Formula IB, IC, and ID.

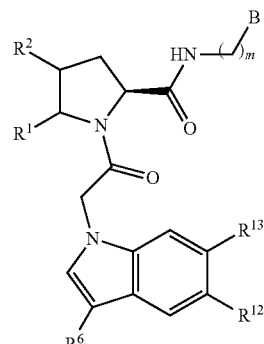

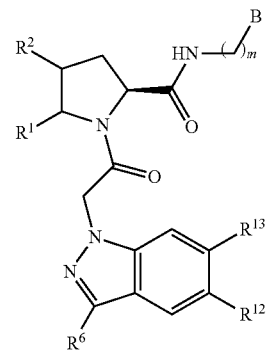

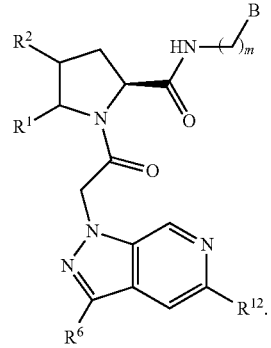

In Formulas IA, IB, IC, and ID, the variables may include any of the definitions set forth herein that results in a stable compound. In certain embodiments, the following conditions apply for Formula IB and IC.

In some embodiments, structures are provided including Formulas IB and IC, wherein m=0, R$^1$ is H, R$^2$ is F, R$^6$ is alkanoyl, R$^{12}$ is alkynylR$^{30}$, R$^{30}$ is heteroaryl, R$^{13}$ is H, and B is heteroaryl.

In some embodiments, structures are provided including Formulas IB and IC, wherein m=0, R$^1$ and R$^2$ are joined to form a 3 membered ring, R$^6$ is alkanoyl, R$^{12}$ is alkynylR$^{30}$, R$^{30}$ is heteroaryl, R$^{13}$ is H, and B is heteroaryl.

In some embodiments, structures are provided including Formulas IB and IC, wherein m=0, R$^1$ is H, R$^2$ is F, R$^6$ is amide, R$^{12}$ is alkynylR$^{30}$, R$^{30}$ is heteroaryl, R$^{13}$ is H, and B is heteroaryl.

In some embodiments, structures are provided including Formulas IB and IC, wherein m=0, R$^1$ and R$^2$ are joined to form a 3 membered ring, R$^6$ is amide, R$^{12}$ is alkynylR$^{30}$, R$^{30}$ is heteroaryl, R$^{13}$ is H, and B is heteroaryl.

In some embodiments, structures are provided including Formulas IB and IC, wherein m=0, R$^1$ is H, R$^2$ is F, R$^6$ is alkanoyl, R$^{12}$ is H, R$^{13}$ is alkynylR$^{30}$, R$^{30}$ is heteroaryl, and B is heteroaryl.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is alkynyl$R^{30}$, $R^{30}$ is heteroaryl, and B is heteroaryl.

In some embodiments, structures are provided including Formulas IB and IC, wherein m=0, $R^1$ is H, $R^2$ is F, $R^6$ is amide, $R^{12}$ is H, $R^{13}$ is alkynyl$R^{30}$, $R^{30}$ is heteroaryl, and B is heteroaryl.

In some embodiments, structures are provided including Formulas IB and IC, wherein m=0, $R^1$ and $R^2$ are joined to form a 3 membered ring, $R^6$ is amide, $R^{12}$ is H, $R^{13}$ is alkynyl$R^{30}$, $R^{30}$ is heteroaryl, and B is heteroaryl.

In some embodiments, structures are provided including Formulas IB and IC, wherein m=0, $R^1$ is H, $R^2$ is F, $R^6$ is alkanoyl, $R^{12}$ is alkynyl$R^{30}$, $R^{30}$ is heteroaryl, $R^{13}$ is H, and B is phenyl.

In some embodiments, structures are provided including Formulas IB and IC, wherein m=0, $R^1$ and $R^2$ are joined to form a 3 membered ring, $R^6$ is alkanoyl, $R^{12}$ is alkynyl$R^{30}$, $R^{30}$ is heteroaryl, $R^{13}$ is H, and B is phenyl.

In some embodiments, structures are provided including Formulas IB and IC, wherein m=0, $R^1$ is H, $R^2$ is F, $R^6$ is amide, $R^{12}$ is alkynyl$R^{30}$, $R^{30}$ is heteroaryl, $R^{13}$ is H, and B is phenyl.

In some embodiments, structures are provided including Formulas IB and IC, wherein m=0, $R^1$ and $R^2$ are joined to form a 3 membered ring, $R^6$ is amide, $R^{12}$ is alkynyl$R^{30}$, $R^{30}$ is heteroaryl, $R^{13}$ is H, and B is phenyl.

In some embodiments, structures are provided including Formulas IB and IC, wherein m=0, $R^1$ is H, $R^2$ is F, $R^6$ is alkanoyl, $R^{12}$ is H, $R^{13}$ is alkynyl$R^{30}$, $R^{30}$ is heteroaryl, and B is phenyl.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is alkynyl$R^{30}$, $R^{30}$ is heteroaryl, and B is phenyl.

In some embodiments, structures are provided including Formulas IB and IC, wherein m=0, $R^1$ is H, $R^2$ is F, $R^6$ is amide, $R^{12}$ is H, $R^{13}$ is alkynyl$R^{30}$, $R^{30}$ is heteroaryl, and B is phenyl.

In some embodiments, structures are provided including Formulas IB and IC, wherein m=0, $R^1$ and $R^2$ are joined to form a 3 membered ring, $R^6$ is amide, $R^{12}$ is H, $R^{13}$ is alkynyl$R^{30}$, $R^{30}$ is heteroaryl, and B is phenyl.

In some embodiments, structures are provided including Formulas IB and IC, wherein m=1, $R^1$ is H, $R^2$ is F, $R^6$ is alkanoyl, $R^{12}$ is alkynyl$R^{30}$, $R^{30}$ is heteroaryl, $R^{13}$ is H, and B is heteroaryl.

In some embodiments, structures are provided including Formulas IB and IC, wherein m=1, $R^1$ and $R^2$ are joined to form a 3 membered ring, $R^6$ is alkanoyl, $R^{12}$ is alkynyl$R^{30}$, $R^{30}$ is heteroaryl, $R^{13}$ is H, and B is heteroaryl.

In some embodiments, structures are provided including Formulas IB and IC, wherein m=1, $R^1$ is H, $R^2$ is F, $R^6$ is amide, $R^{12}$ is alkynyl$R^{30}$, $R^{30}$ is heteroaryl, $R^{13}$ is H, and B is heteroaryl.

In some embodiments, structures are provided including Formulas IB and IC, wherein m=1, $R^1$ and $R^2$ are joined to form a 3 membered ring, $R^6$ is amide, $R^{12}$ is alkynyl$R^{30}$, $R^{30}$ is heteroaryl, $R^{13}$ is H, and B is heteroaryl.

In some embodiments, structures are provided including Formulas IB and IC, wherein m=1, $R^1$ is H, $R^2$ is F, $R^6$ is alkanoyl, $R^{12}$ is H, $R^{13}$ is alkynyl$R^{30}$, $R^{30}$ is heteroaryl, and B is heteroaryl.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is alkynyl$R^{30}$, $R^{30}$ is heteroaryl, and B is heteroaryl.

In some embodiments, structures are provided including Formulas IB and IC, wherein m=1, $R^1$ is H, $R^2$ is F, $R^6$ is amide, $R^{12}$ is H, $R^{13}$ is alkynyl$R^{30}$, $R^{30}$ is heteroaryl, and B is heteroaryl.

In some embodiments, structures are provided including Formulas IB and IC, wherein m=1, $R^1$ and $R^2$ are joined to form a 3 membered ring, $R^6$ is amide, $R^{12}$ is H, $R^{13}$ is alkynyl$R^{30}$, $R^{30}$ is heteroaryl, and B is heteroaryl.

In some embodiments, structures are provided including Formulas IB and IC, wherein m=1, $R^1$ is H, $R^2$ is F, $R^6$ is alkanoyl, $R^{12}$ is alkynyl$R^{30}$, $R^{30}$ is heteroaryl, $R^{13}$ is H, and B is phenyl.

In some embodiments, structures are provided including Formulas IB and IC, wherein m=1, $R^1$ and $R^2$ are joined to form a 3 membered ring, $R^6$ is alkanoyl, $R^{12}$ is alkynyl$R^{30}$, $R^{30}$ is heteroaryl, $R^{13}$ is H, and B is phenyl.

In some embodiments, structures are provided including Formulas IB and IC, wherein m=1, $R^1$ is H, $R^2$ is F, $R^6$ is amide, $R^{12}$ is alkynyl$R^{30}$, $R^{30}$ is heteroaryl, $R^{13}$ is H, and B is phenyl.

In some embodiments, structures are provided including Formulas IB and IC, wherein m=1, $R^1$ and $R^2$ are joined to form a 3 membered ring, $R^6$ is amide, $R^{12}$ is alkynyl$R^{30}$, $R^{30}$ is heteroaryl, $R^{13}$ is H, and B is phenyl.

In some embodiments, structures are provided including Formulas IB and IC, wherein m=1, $R^1$ is H, $R^2$ is F, $R^6$ is alkanoyl, $R^{12}$ is H, $R^{13}$ is alkynyl$R^{30}$, $R^{30}$ is heteroaryl, and B is phenyl.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is alkynyl$R^{30}$, $R^{30}$ is heteroaryl, and B is phenyl.

In some embodiments, structures are provided including Formulas IB and IC, wherein m=1, $R^1$ is H, $R^2$ is F, $R^6$ is amide, $R^{12}$ is H, $R^{13}$ is alkynyl$R^{30}$, $R^{30}$ is heteroaryl, and B is phenyl.

In some embodiments, structures are provided including Formulas IB and IC, wherein m=1, $R^1$ and $R^2$ are joined to form a 3 membered ring, $R^6$ is amide, $R^{12}$ is H, $R^{13}$ is alkynyl$R^{30}$, $R^{30}$ is heteroaryl, and B is phenyl.

Embodiments of Formula VII

To further illustrate the invention, various embodiments of Formula VII. In one aspect, the disclosure includes compounds and salts of Formula VII:

(VII)

wherein:

$R^1$, $R^2$, $R^{2'}$, and $R^3$ are independently chosen from hydrogen, halogen, $C_1$-$C_4$alkyl, $C_1$-$C_4$alkoxy, —$C_0$-

$C_2$alkylNR$^9$R$^{10}$, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy;

R$^8$ and R$^{8'}$ are independently chosen from hydrogen, halogen, and methyl;

R$^5$ is hydrogen, hydroxyl, cyano, —COOH, $C_1$-$C_6$alkyl, $C_1$-$C_6$alkoxy, $C_2$-$C_6$alkanoyl —$C_0$-$C_4$alkyl($C_3$-$C_7$cycloalkyl), —C(O)$C_0$-$C_4$alkyl($C_3$-$C_7$cycloalkyl), $C_1$-$C_2$haloalkyl, or $C_1$-$C_2$haloalkoxy;

R$^6$ is —C(O)CH$_3$, —C(O)NH$_2$, —C(O)CF$_3$, —C(O)(cyclopropyl), or -ethyl(cyanoimino); and R$^{11}$ and R$^{14}$ are independently chosen from hydrogen, halogen, hydroxyl, amino, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —O$C_0$-$C_4$alkyl($C_3$-$C_7$cycloalkyl), $C_1$-$C_2$haloalkyl, and $C_1$-$C_2$haloalkoxy.

Prodrugs of Formula I are also within the scope of the disclosure.

III. Pharmaceutical Preparations

Compounds disclosed herein can be administered as the neat chemical, but can also administered as a pharmaceutical composition, that includes an effective amount for a host in need of treatment of the selected compound of Formula I, as described herein. Accordingly, the disclosure provides pharmaceutical compositions comprising an effective amount of compound or pharmaceutically acceptable salt of Formula I, together with at least one pharmaceutically acceptable carrier. The pharmaceutical composition may contain a compound or salt of Formula I as the only active agent, or, in an alternative embodiment, Formula I and at least one additional active agent. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 25, 50, 100, 200, 250, 300, 400, 500, 600, 700, or 750 mg of active compound, or its salt. The pharmaceutical composition may also include a molar ratio of a compound of Formula I and an additional active agent. For example the pharmaceutical composition may contain a molar ratio of about 0.5:1, about 1:1, about 2:1, about 3:1 or from about 1.5:1 to about 4:1 of an another anti-inflammatory agent.

Compounds disclosed herein may be administered orally, topically, parenterally, by inhalation or spray, sublingually, via implant, including ocular implant, transdermally, via buccal administration, rectally, as an ophthalmic solution, injection, including ocular injection, intraveneous, intraaortal, intracranial, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound for Formula I that achieves the desired result, for example between 0.1 and 99 weight % (wt. %) of a compound of Formula I and usually at least about 5 wt. % of a compound of Formula I. Some embodiments contain from about 25 wt. % to about 50 wt. % or from about 5 wt. % to about 75 wt. % of the compound of Formula I.

The complement factor D inhibitors of the present invention can be administered, for example, either systemically or locally. Systemic administration includes, for example, oral, transdermal, subdermal, intraperitioneal, subcutaneous, transnasal, sublingual, or rectal. Local administration for ocular administration includes: topical, intravitreal, periocular, transscleral, retrobulbar, juxtascleral, sub-tenon, or via an intraocular device. The inhibitors may be delivered via a sustained delivery device implanted intravitreally or transsclerally, or by other known means of local ocular delivery.

IV. Methods of Treatment

The compounds and pharmaceutical compositions disclosed herein are useful for treating or preventing a disorder that is mediated by the complement pathway, and in particular, a pathway that is modulated by complement factor D. In certain embodiments, the disorder is an inflammatory disorder, an immune disorder, an autoimmune disorder, or complement factor D related disorders in a host. In one embodiment, the disorder is an ocular disorder. Complement mediated disorders that may be treated or prevented by the compounds and compositions of this disclosure include, but are not limited to, inflammatory effects of sepsis, systemic inflammatory response syndrome (SIRS), ischemia/reperfusion injury (I/R injury), psoriasis, myasthenia gravis, system lupus erythematosus (SLE), paroxysmal nocturnal hemoglobinuria (PNH), hereditary angioedema, multiple sclerosis, trauma, burn injury, capillary leak syndrome, obesity, diabetes, Alzheimer's dementia, stroke, schizophrenia, epilepsy, age-related macular degeneration, glaucoma, diabetic retinopathy, asthma, allergy, acute respiratory distress syndrome (ARDS), atypical hemolytic uremic syndrome (aHUS), hemolytic uremic syndrome (HUS), cystic fibrosis, myocardial infarction, lupus nephritides, Crohn's disease, rheumatoid arthritis, atherosclerosis, transplant rejection, prevention of fetal loss, biomaterial reactions (e.g. in hemodialysis, inplants), C3 glomerulonephritis, abdominal aortic aneurysm, neuromyelitis optica (NMO), vasculitis, neurological disorders, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during I L-2 therapy, inflammatory disorders, inflammation of autoimmune diseases, adult respiratory distress syndrome, thermal injury including burns or frostbite, myocarditis, post-ischemic reperfusion conditions, balloon angioplasty, post-pump syndrome in cardiopulmonary bypass or renal bypass, hemodialysis, renal ischemia, mesenteric artery reperfusion after aortic reconstruction, immune complex disorders and autoimmune diseases, SLE nephritis, proliferative nephritis, liver fibrosis, hemolytic anemia, tissue regeneration and neural regeneration. In addition, other known complement related disease are lung disease and disorders such as dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome, arthritis, autoimmune heart disease, inflammatory bowel disease, ischemia-reperfusion injuries, Barraquer-Simons Syndrome, hemodialysis, systemic lupus, lupus erythematosus, transplantation, diseases of the central nervous system and other neurodegenerative conditions, glomerulonephritis (including membrane proliferative glomerulonephritis), blistering cutaneous diseases (including bullous pemphigoid, pemphigus, and epidermolysis bullosa), ocular cicatrical pemphigoid, MPGN II, uveitis, adult macular degeneration, diabetic retinopathy, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, postoperative inflammation, and retinal vein occlusion.

In some embodiments, complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

In one embodiment, a method for the treatment of paroxysmal nocturnal hemoglobinuria (PNH) is provided that includes the administration of an effective amount of a compound of Formula I, or a pharmaceutically acceptable salt thereof, optionally in a pharmaceutically acceptable carrier. In another embodiment, a method for the treatment of age-related macular degeneration (AMD) is provided that includes the administration of an effective amount of a compound of Formula I, or a pharmaceutically acceptable salt thereof, optionally in a pharmaceutically acceptable carrier. In another embodiment, a method for the treatment of rheumatoid arthritis is provided that includes the administration of an effective amount of a compound of Formula I, or a pharmaceutically acceptable salt thereof, optionally in a pharmaceutically acceptable carrier. In another embodiment, a method for the treatment of multiple sclerosis is provided that includes the administration of an effective amount of a compound of Formula I, or a pharmaceutically acceptable salt thereof, optionally in a pharmaceutically acceptable carrier. In another embodiment, a method for the treatment of myasthenia gravis is provided that includes the administration of an effective amount of a compound of Formula I, or a pharmaceutically acceptable salt thereof, optionally in a pharmaceutically acceptable carrier. In another embodiment, a method for the treatment of atypical hemolytic uremic syndrome (aHUS) is provided that includes the administration of an effective amount of a compound of Formula I, or a pharmaceutically acceptable salt thereof, optionally in a pharmaceutically acceptable carrier. In another embodiment, a method for the treatment of C3 glomerulonephritis is provided that includes the administration of an effective amount of a compound of Formula I, or a pharmaceutically acceptable salt thereof, optionally in a pharmaceutically acceptable carrier. In another embodiment, a method for the treatment of abdominal aortic aneurysm is provided that includes the administration of an effective amount of a compound of Formula I, or a pharmaceutically acceptable salt thereof, optionally in a pharmaceutically acceptable carrier. In another embodiment, a method for the treatment of neuromyelitis optica (NMO) is provided that includes the administration of an effective amount of a compound of Formula I, or a pharmaceutically acceptable salt thereof, optionally in a pharmaceutically acceptable carrier.

In some embodiments, the present invention provides methods of treating or preventing an inflammatory disorder or a complement related disease, by administering to a host in need thereof an effective amount of a compound of Formula I of the invention. In some embodiments, the present invention provides methods of treating or preventing an inflammatory disorder more generally, an immune disorder, autoimmune disorder, or complement factor D related disease, by providing an effective amount of a compound or pharmaceutically acceptable salt of Formula I to patient with a factor D mediated inflammatory disorder. A compound or salt of Formula I may be provided as the only active agent or may be provided together with one or more additional active agents.

In one embodiment, a method for the treatment of a disorder associated with a dysfunction in the complement cascade is provided that includes the administration of an effective amount of a compound of Formula I, or a pharmaceutically acceptable salt thereof, optionally in a pharmaceutically acceptable carrier. In one embodiment, a method of inhibiting activation of the alternative complement pathway in a subject is provided that includes the administration of an effective amount of a compound of Formula I, or a pharmaceutically acceptable salt thereof, optionally in a pharmaceutically acceptable carrier. In one embodiment, a method of modulating factor D activity in a subject is provided that includes the administration of an effective amount of a compound of Formula I, or a pharmaceutically acceptable salt thereof, optionally in a pharmaceutically acceptable carrier.

"Prevention" as used in this disclosure means decreasing the likelihood of the appearance of symptoms in a patient administered the compound prophylactically as compared to the likelihood of the appearance of symptoms in patients not administered the compound or decreasing the severity of symptoms in a patient administered the compound prophylactically as compared to the severity of symptoms experienced by patients with the disorder or condition who were not administered the compound. In an alternative embodiment, an effective amount of a compound of Formula I is used to prevent or prophylaxis of a complement factor D related disorder.

An effective amount of a pharmaceutical composition/combination of the invention may be an amount sufficient to (a) inhibit the progression of a disorder mediated by the complement pathway, including an inflammatory, immune, including an autoimmune, disorder or complement factor D related disease; (b) cause a regression of an inflammatory, immune, including an autoimmune, disorder or complement factor D related disease; or (c) cause a cure of an inflammatory, immune, including an autoimmune, disorder or complement factor D related disease.

An effective amount of a compound or pharmaceutical composition described herein will also provide a sufficient amount of the active agent when administered to a patient to provide a clinical benefit. Such an amount may be ascertained experimentally, for example by assaying blood concentration of the agent, or theoretically, by calculating bioavailability.

V. Combination Therapy

In one embodiment, a compound or salt of Formula I may be provided in combination or alternation with at least one additional inhibitor of the complement system or a second active compound with a different biological mechanism of action. In one embodiment, a compound or salt of Formula I may be provided in combination with a complement C5 inhibitor or C5 convertase inhibitor. In another embodiment, a compound or salt of Formula I may be provided in combination with eculizumab. In one embodiment, a compound or salt of Formula I may be provided in combination with additional inhibitors of factor D.

In one embodiment, a compound or salt of Formula I may be provided together with a compound that inhibits an enzyme that metabolizes protease inhibitors. In one embodiment, a compound or salt of Formula I may be provided together with ritonavir.

In nonlimiting embodiments, a compound or salt of Formula I may be provided together with a protease inhibitor, a soluble complement regulator, a therapeutic antibody (monoclonal or polyclonal), complement component inhibitors, receptor agonists, or siRNAs.

Nonlimiting examples of active agents in these categories are:

Protease inhibitors: plasma-derived C1-INH concentrates, for example Cetor® (Sanquin), Berinert-P® (CSL Behring, Lev Pharma), and Cinryze®; and recombinant human C1-inhibitors, for example Rhucin®;

Soluble complement regulators: Soluble complement receptor 1 (TP10) (Avant Immunotherapeutics); sCR1-sLex/TP-20 (Avant Immunotherapeutics); MLN-2222/CAB-2 (Millenium Pharmaceuticals); Mirococept (Inflazyme Pharmaceuticals);

Therapeutic antibodies: Eculizumab/Soliris (Alexion Pharmaceuticals); Pexelizumab (Alexion Pharmaceuticals); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S);

Complement component inhibitors: Compstatin/POT-4 (Potentia Pharmaceuticals); ARC1905 (Archemix);

Receptor agonists: PMX-53 (Peptech Ltd.); JPE-137 (Jerini); JSM-7717 (Jerini);

Others: Recombinant human MBL (rhMBL; Enzon Pharmaceuticals).

In an embodiment, the present invention provides a method of treating or preventing age-related macular degeneration (AMD) by administering to a subject in need thereof an effective amount of a composition comprising a compound of the current invention. In one embodiment, the compositions of the present invention are administered in combination with an anti-VEGF agent. Nonlimiting examples of anti-VEGF agents include, but are not limited to, aflibercept (Eylea®; Regeneron Pharmaceuticals); ranibizumab (Lucentis®: Genentech and Novartis); and pegaptanib (Macugen®; OSI Pharmaceuticals and Pfizer); Bevacizumab (Avastin; Genentech/Roche); anecortane acetate, squalamine lactate, and corticosteroids, including, but not limited to, triamcinolone acetonide.

In another embodiment, a compound of Formula I can be combined with a second agent in order to treat a disorder of the eye.

Examples of types of therapeutic agents that can be used in combination for ocular applications include anti-inflammatory drugs, antimicrobial agents, anti-angiogenesis agents, immunosuppressants, antibodies, steroids, ocular antihypertensive drugs and combinations thereof. Examples of therapeutic agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, *vinca* alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluorometholone, rimexolone, anecortave, cyclosporine, methotrexate, tacrolimus and combinations thereof. Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, anterior uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

A compound of Formula I, or a combination of Formula I and another active agent, can be administered into an eye compartment of via injection into the vitreous chamber, subretinal space, subchoroidal space, the episclera, the conjunctiva, the sclera, the anterior chamber, and the cornea and compartments therein (e.g., subepithelial, intrastromal, endothelial).

In an alternative embodiment, a compound of Formula I, or a combination of Formula I and another active agent, can be administered into an eye compartment via binding to a mucosal penetrating particle to treat a condition located in the vitreous chamber, subretinal space, subchoroidal space, the episclera, the conjunctiva, the sclera or the anterior chamber, and the cornea and compartments therein (e.g., subepithelial, intrastromal, endothelial). Mucosal penetrating particles are known in the art, and are described in, for example, PCT published application WO 2013166436 to Kala Pharmaceuticals, incorporated in its entirety herein.

In other embodiments, a composition comprising compound of Formula I suitable for topical administration to an eye is provided. The pharmaceutical composition comprises a plurality of coated particles, comprising a core particle comprising a compound of Formula I, wherein Formula I constitutes at least about 80 wt % of the core particle, and a coating comprising one or more surface-altering agents, wherein the one or more surface-altering agents comprise at least one of a poloxamer, a poly(vinyl alcohol), or a polysorbate. The one or more surface-altering agents is present on the outer surface of the core particle at a density of at least 0.01 molecules/nm. The one or more surface-altering agents is present in the pharmaceutical composition in an amount of between about 0.001% to about 5% by weight. The plurality of coated particles have an average smallest cross-sectional dimension of less than about 1 micron. The pharmaceutical composition also includes one or more ophthalmically acceptable carriers, additives, and/or diluents.

It will be appreciated by one of ordinary skill in the art that particles suitable for use with the presently disclosed methods can exist in a variety of shapes, including, but not limited to, spheroids, rods, disks, pyramids, cubes, cylinders, nanohelixes, nanosprings, nanorings, rod-shaped particles, arrow-shaped particles, teardrop-shaped particles, tetrapod-shaped particles, prism-shaped particles, and a plurality of other geometric and non-geometric shapes. In some embodiments, the presently disclosed particles have a spherical shape.

In one embodiment, the present invention provides a method of treating or preventing paroxysmal nocturnal hemoglobinuria (PNH) by administering to a subject in need thereof an effective amount of a composition comprising a compound of the current invention. In one embodiment, the present invention provides a method of treating or preventing paroxysmal nocturnal hemoglobinuria (PNH) by administering to a subject in need thereof an effective amount of a composition comprising a compound of the current invention in combination or alternation with additional inhibitors of the complement system or another active compound with a different biological mechanism of action. In another embodiment, the present invention provides a method of treating or preventing paroxysmal nocturnal hemoglobinuria (PNH) by administering to a subject in need thereof an effective amount of a composition comprising a compound of the current invention in combination or alternation with eculizumab.

In one embodiment, the present invention provides a method of treating or preventing rheumatoid arthritis by administering to a subject in need thereof an effective amount of a composition comprising a compound of the current invention. In one embodiment, the present invention provides a method of treating or preventing rheumatoid arthritis by administering to a subject in need thereof an effective amount of a composition comprising a compound of the current invention in combination or alternation with an additional inhibitor of the complement system. In another embodiment, the present invention provides a method of treating or preventing rheumatoid arthritis by administering to a subject in need thereof an effective amount of a composition comprising a compound of the current invention in combination or alternation with methotrexate.

In certain embodiments, a compound of Formula I is administered in combination or alternation with at least one anti-rhuematoid arthritis drug selected from: salicylates including aspirin (Anacin, Ascriptin, Bayer Aspirin, Ecotrin) and salsalate (Mono-Gesic, Salgesic); nonsteroidal anti-inflammatory drugs (NSAIDs); nonselective inhibitors of the cyclo-oxygenase (COX-1 and COX-2) enzymes, including diclofenac (Cataflam, Voltaren), ibuprofen (Advil, Motrin), ketoprofen (Orudis), naproxen (Aleve, Naprosyn), piroxicam (Feldene), etodolac (Lodine), indomethacin, oxaprozin (Daypro), nabumetone (Relafen), and meloxicam (Mobic); selective cyclo-oxygenase-2 (COX-2) inhibitors including Celecoxib (Celebrex); disease-modifying anti-rheumatic drugs (DMARDs), including azathioprine (Imuran), cyclosporine (Sandimmune, Neoral), gold salts (Ridaura, Solganal, Aurolate, Myochrysine), hydroxychloroquine (Plaquenil), leflunomide (Arava), methotrexate (Rheumatrex), penicillamine (Cuprimine), and sulfasalazine (Azulfidine); biologic drugs including abatacept (Orencia), etanercept (Enbrel), infliximab (Remicade), adalimumab (Humira), and anakinra (Kineret); corticosteroids including betamethasone (Celestone Soluspan), cortisone (Cortone), dexamethasone (Decadron), methylprednisolone (SoluMedrol, DepoMedrol), prednisolone (Delta-Cortef), prednisone (Deltasone, Orasone), and triamcinolone (Aristocort); gold salts, including Auranofin (Ridaura); Aurothioglucose (Solganal); Aurolate; Myochrysine; or any combination thereof.

In one embodiment, the present invention provides a method of treating or preventing multiple sclerosis by administering to a subject in need thereof an effective amount of a composition comprising a compound of the current invention. In one embodiment, the present invention provides a method of treating or preventing multiple sclerosis by administering to a subject in need thereof an effective amount of a composition comprising a compound of the current invention in combination or alternation with additional inhibitors of the complement system. In another embodiment, the present invention provides a method of treating or preventing multiple sclerosis by administering to a subject in need thereof an effective amount of a composition comprising a compound of the current invention in combination or alternation with a corticosteroid. Examples of corticosteroids include, but are not limited to, prednisone, dexamethasone, solumedrol, and methylprednisolone.

In one embodiment, a compound of Formula I is combined with at least one anti-multiple sclerosis drug selected from: Aubagio (teriflunomide), Avonex (interferon beta-1a), Betaseron (interferon beta-1b), Copaxone (glatiramer acetate), Extavia (interferon beta-1b), Gilenya (fingolimod), Lemtrada (alemtuzumab), Novantrone (mitoxantrone), Plegridy (peginterferon beta-1a), Rebif (interferon beta-1a), Tecfidera (dimethyl fumarate), Tysabri (natalizumab), Solu- Medrol (methylpredni solone), High-dose oral Deltasone (prednisone), H.P. Acthar Gel (ACTH), and combinations thereof.

In one aspect, a compound or salt of Formula I may be provided in combination or alternation with an immunosuppressive agent or an anti-inflammatory agent.

In one embodiment of the present invention, a compound described herein can be administered in combination or alternation with at least one immunosuppressive agent. The immunosuppressive agent as nonlimiting examples, may be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA41g (Abatacept), belatacept, LFA31g, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

Examples of anti-inflammatory agents include methotrexate, dexamethasone, dexamethasone alcohol, dexamethasone sodium phosphate, flurometholone acetate, flurometholone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucorticoids, diclofenac, and any combination thereof. In one embodiment, a compound of Formula I is combined with one or more non-steroidal anti-inflammatory drugs (NSAIDs) selected from naproxen sodium (Anaprox), celecoxib (Celebrex), sulindac (Clinoril), oxaprozin (Daypro), salsalate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

VI. Process of Preparation of Compounds of Formula I

Abbreviations
(Boc)$_2$O di-tert-butyl dicarbonate
ACN Acetonitrile
ACOET, ETOAC ethyl acetate
CH$_3$OH, MeOH Methanol
CsF Cesium fluoride
CuI Cuprous iodide
DCM, CH$_2$Cl$_2$ Dichloromethane
DIEA, DIPEA N,N-diisopropylethylamine
DMA N,N-dimethylacetamide
DMF N,N-dimethylformamide
DMSO Dimethylsulfoxide
DPPA diphenyl phosphoryl azide
Et$_3$N, TEA Triethylamine
EtOAc Ethyl acetate
HATU 1-[Bis(dimethylamino)methylene]-1H-1,2,3-triazolo [4,5-b]pyridinium 3-oxide hexafluorophosphate
$^i$Pr$_2$NEt N,N-diisopropylethylamine
K$_2$CO$_3$ Potassium carbonate
Na$_2$SO$_4$ Sodium sulfate
NaCl Sodium chloride
NaH Sodium hydride
NaHCO$_3$ Sodium bicarbonate
NEt$_3$ Trimethylamine
Pd(dppf)Cl$_2$ [1,1'-Bis(diphenylphosphino) ferrocene]dichloropalladium(II)
Pd(PPh$_3$)$_2$Cl$_2$ Bis(triphenylphosphine)palladium(II) dichloride
Pd(PPh$_3$)$_4$ Tetrakis(triphenylphosphine)palladium(0)
RT Room temperature
tBuOK potassium tert-butoxide
TEA Trimethylamine
Tf$_2$O trifluoromethanesulfonic anhydride
TFA Trifluoroacetic acid
THF Tetrahydrofuran
TMSBr Bromotrimethylsilane
$t_R$ Retention time General Methods All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products was confirmed by standard analytical techniques, including NMR spectroscopy and mass spectrometry.

LC Method A
Instrument: Waters Acquity Ultra Performance LC
Column: ACQUITY UPLC BEH C18 2.1×50 mm, 1.7 μm
Column Temperature: 40° C.
Mobile Phase: Solvent A: H$_2$O+0.05% FA; Solvent B: CH$_3$CN+0.05% FA
Flow Rate: 0.8 mL/min
Gradient: 0.24 min @ 15% B, 3.26 min gradient (15-85% B), then 0.5 min @ 85% B.
Detection: UV (PDA), ELS, and MS (SQ in EI mode)
LC Method B
Instrument: Shimadzu LC-2010A HT
Column: Athena, C18-WP, 50×4.6 mm, 5 μm
Column Temperature: 40° C.
Mobile Phase: Solvent A: H$_2$O/CH$_3$OH/FA=90/10/0.1; Solvent B: H$_2$O/CH$_3$OH/FA=10/90/0.1
Flow Rate: 3 mL/min
Gradient: 0.4 min @ 30% B, 3.4 min gradient (30-100% B), then 0.8 min @ 100% B
Detection: UV (220/254 nm)

Example 1. General Route of Synthesis

A compound of the present invention can be prepared, for example, from a central core. In one embodiment, for example, the central core Structure 1 is an N-protected aminoacid where $X^1$ is nitrogen and PG=protecting group. In one embodiment, the central core is coupled to an amine to generate an amide of Structure 2 (wherein L-B includes a C(O)N moiety). Structure 2 can then be deprotected to generate Structure 3. Structure 3 is coupled to Structure 4 (A-COOH) to generate a second amide bond, forming a compound within Formula I. The chemistry is illustrated in Route 1.

Route 1

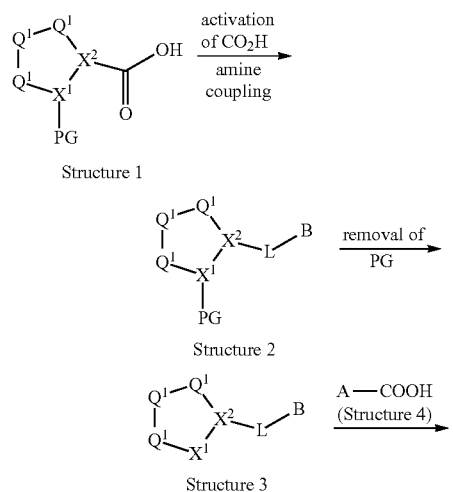

Structure 1

Structure 2

Structure 3

Formula I

In an alternative embodiment, central core Structure 5 is reacted with a heterocyclic or heteroaryl compound to generate a compound of Structure 6. In one embodiment, Structure 6 is deprotected to generate a carboxylic acid, Structure 7. In one embodiment, Structure 7 is coupled to an amine to generate a compound of Formula I. This chemistry is illustrated in Route 2.

Route 2

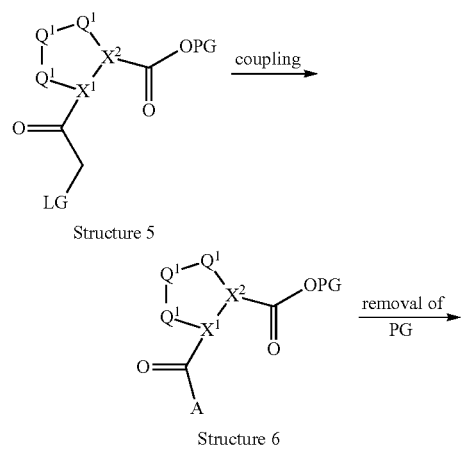

Structure 5

Structure 6

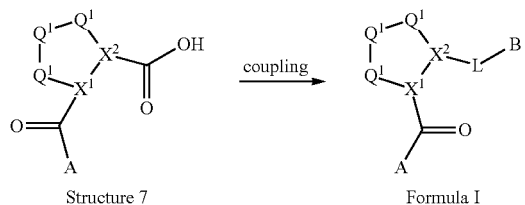

Structure 7

Formula I

In an alternative embodiment, Structure 8 is deprotected to generate an amine which is Structure 9. Structure 9 is then coupled to generate an amide which is Structure 6. Structure 6 is then deprotected to generate a carboxylic acid which is Structure 7. Structure 7 is then coupled to form the amide which falls within Formula I. The chemistry is illustrated in Route 3.

Route 3

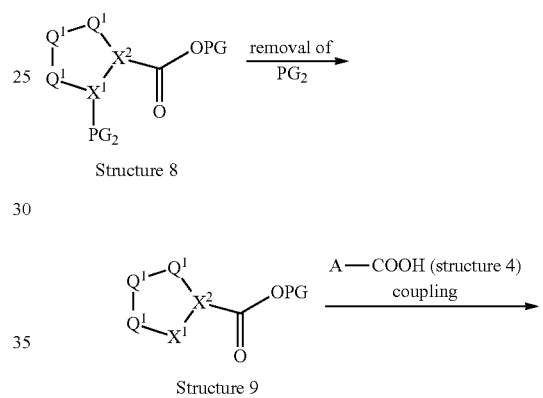

Structure 8

Structure 9

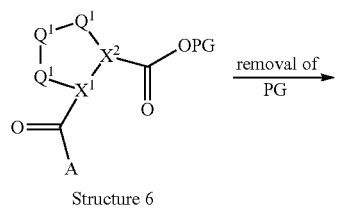

Structure 6

Structure 7

Formula I

In an alternate embodiment, a heteroaryl or aryl moiety, 4-1, is coupled to a central core to generate 4-2. The protected acid, 4-2 is deblocked to form the carboxylic acid, 4-3. The carboxylic acid is then coupled to form an amide (L-B) which is 4-4. The heteroaryl or aryl moiety, A', can then be further derivitized to add substituents at the $X^{11}$, $X^{12}$, $X^{13}$ and $X^{14}$ positions to generate compounds of Formula I. This chemistry is illustrated in Route 4.

Route 4

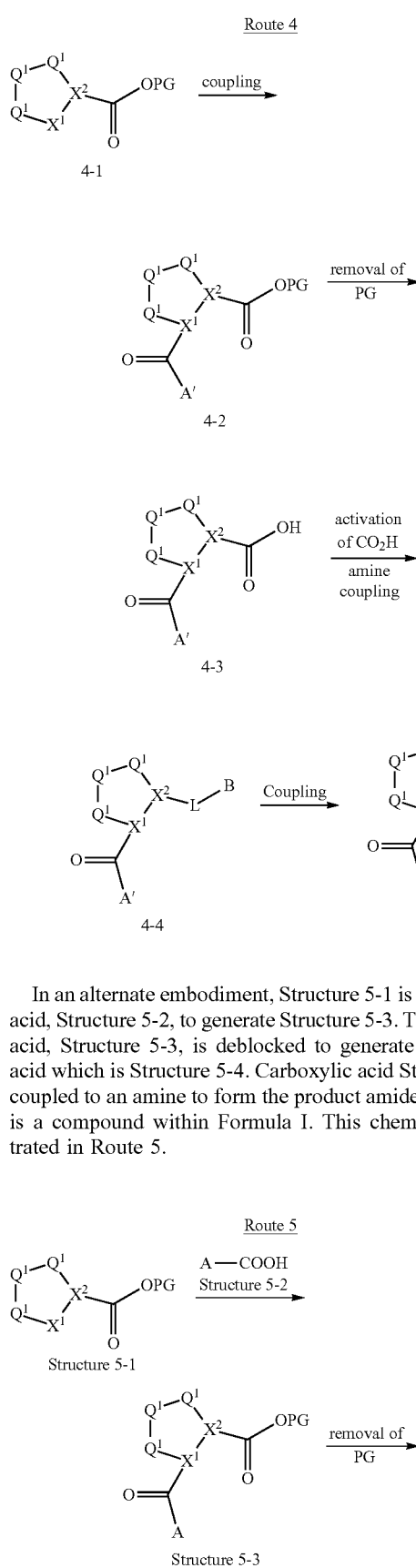

In an alternate embodiment, Structure 5-1 is coupled to an acid, Structure 5-2, to generate Structure 5-3. The carboxylic acid, Structure 5-3, is deblocked to generate a carboxylic acid which is Structure 5-4. Carboxylic acid Structure 5-4 is coupled to an amine to form the product amide (L-B) which is a compound within Formula I. This chemistry is illustrated in Route 5.

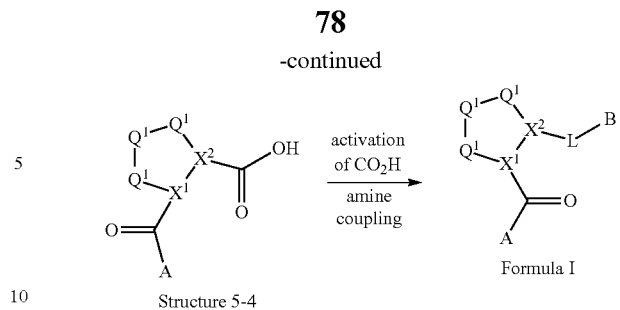

In an alternate embodiment, Structure 6-1 is coupled to an amine to generate an amide (L-B) which is Structure 6-2. Structure 6-2 is coupled to an amine to generate compounds within Formula I. This chemistry is illustrated in Route 6.

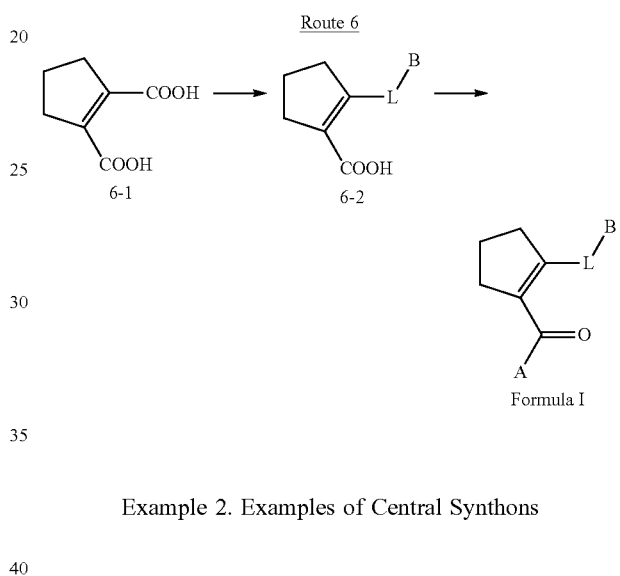

Example 2. Examples of Central Synthons

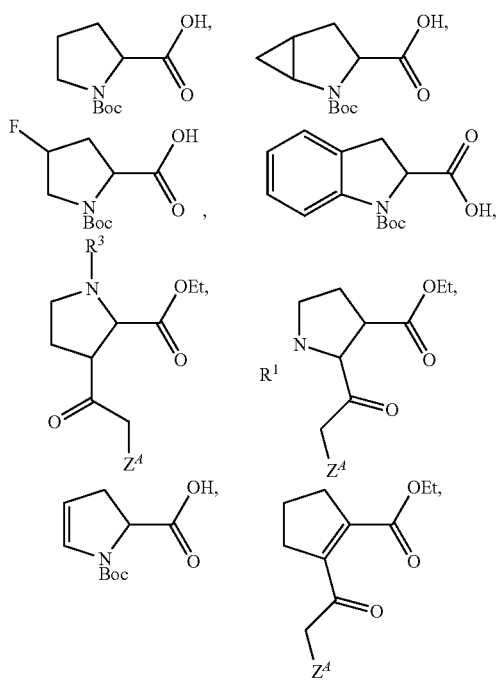

-continued
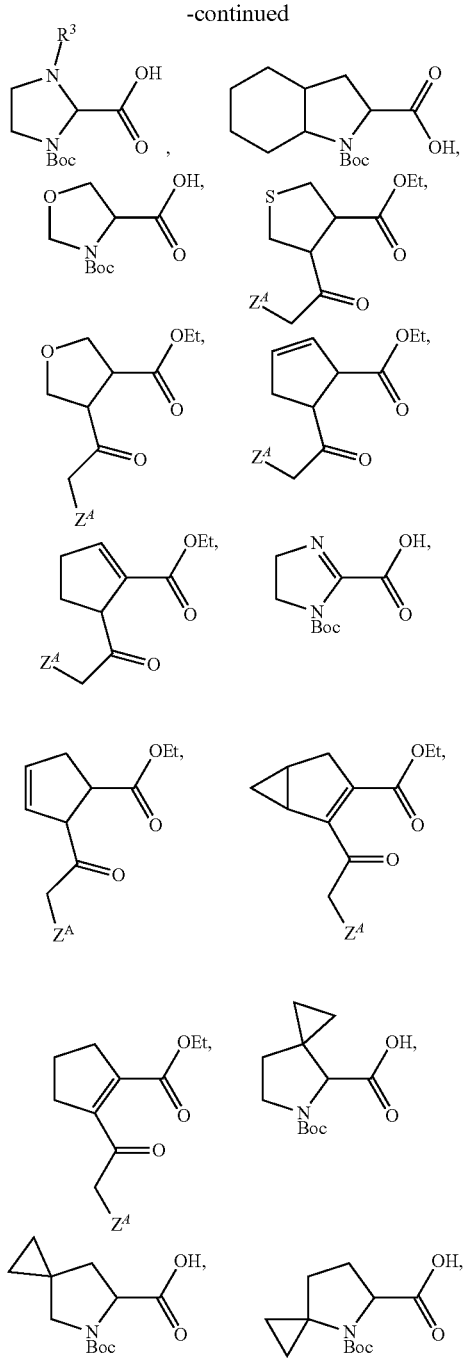
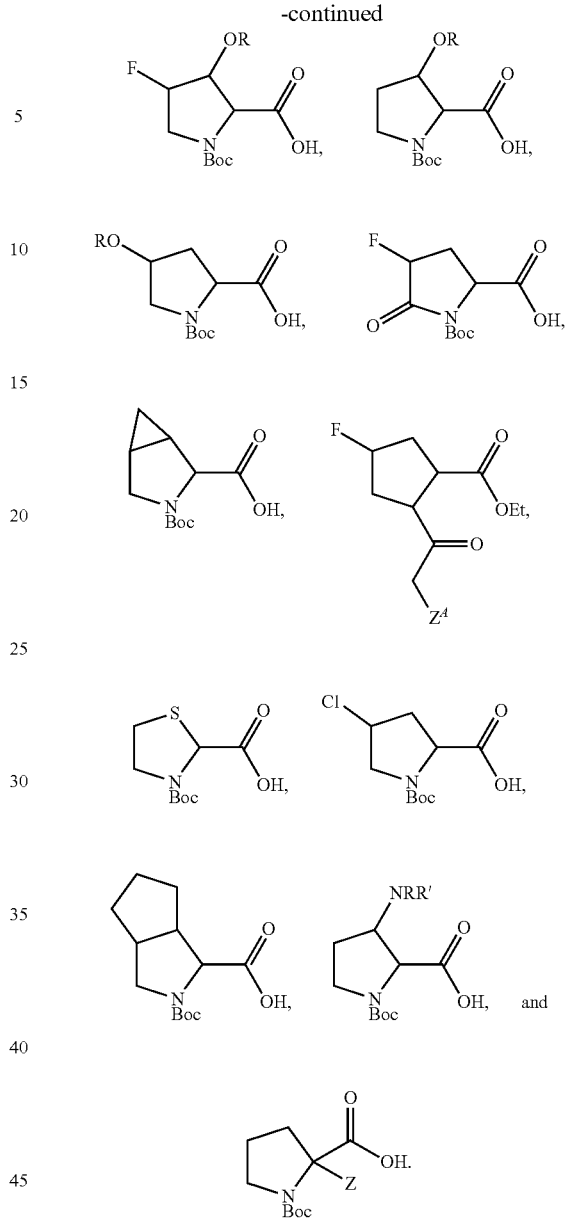
$Z^a$ is halogen.
In one embodiment, deuterated L-proline synthons are disclosed. Deuterated synthons include, but are not limited to, for example, the following compounds:
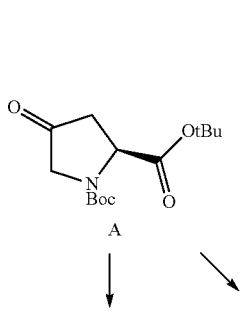
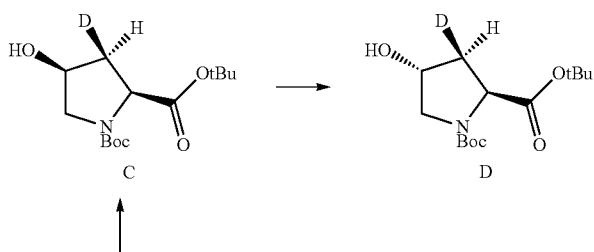

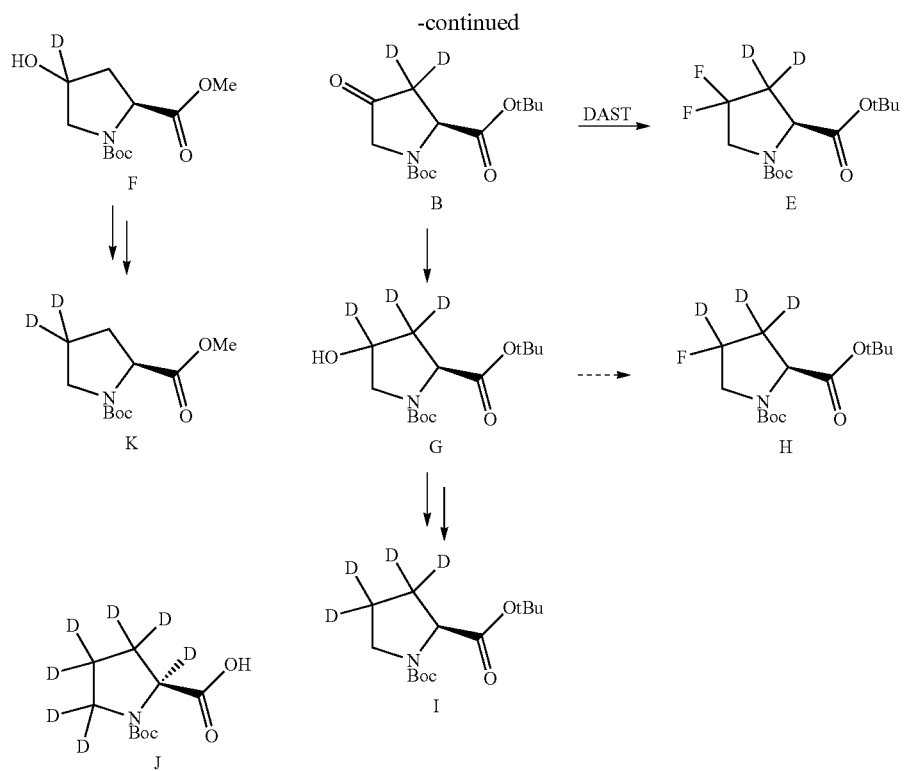

Structure A can be treated with deuterium oxide to generate Structure B. See, Barraclough, P. et al. Tetrahedron Lett. 2005, 46, 4653-4655; Barraclough, P. et al. Org. Biomol. Chem. 2006, 4, 1483-1491 and WO 2014/037480 (p. 103). Structure B can be reduced to generate Structure C. See, Barraclough, P. et al. Tetrahedron Lett. 2005, 46, 4653-4655; Barraclough, P. et al. Org. Biomol. Chem. 2006, 4, 1483-1491. Structure C can be treated with Mitsunobu reaction conditions to generate Structure D. Structure B can be treated with DAST to generate Structure E. See, WO 2014/037480. Structure A can be treated with sodium borodeuteride to generate Structure F. See, Dormoy, J. -R.; Castro, B. *Synthesis* 1986, 81-82. Compound F can be used to generate Structure K. See, Dormoy, J. -R.; Castro, B. *Synthesis* 1986, 81-82. Structure B can be treated with a deuterated reducing agent, for example sodium borodeuteride to generate Structure G. Structure G can be treated with DAST to generate Structure H. Structure F can be used to generate Structure K. See, Dormoy, J. -R.; Castro, B. *Synthesis* 1986, 81-82. Structure G can be used to generate Structure I. Structure J can be prepared according to Hruby, V. J. et al. *J. Am. Chem. Soc.* 1979, 101, 202-212. Structures A-J can be used to prepare compounds of Formula I.

Example 3. Preparation of Central-L-B Synthons

Routes 1a, 1b and 1c.

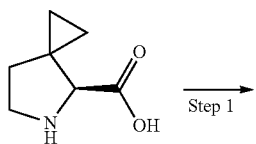

(1a)

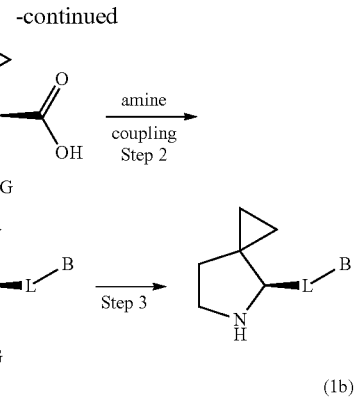

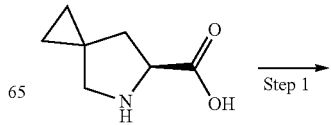

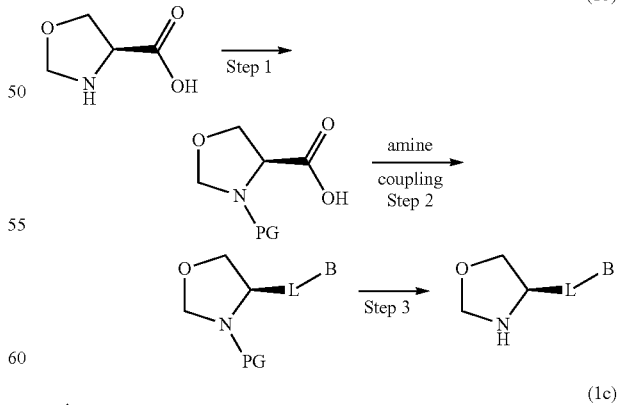

(1b)

(1c)

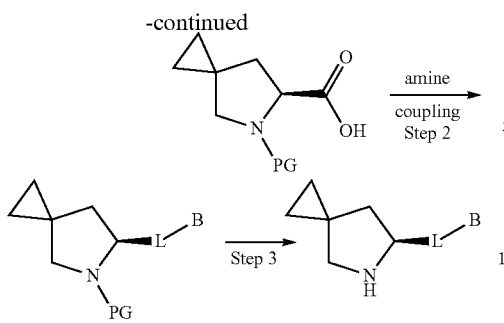

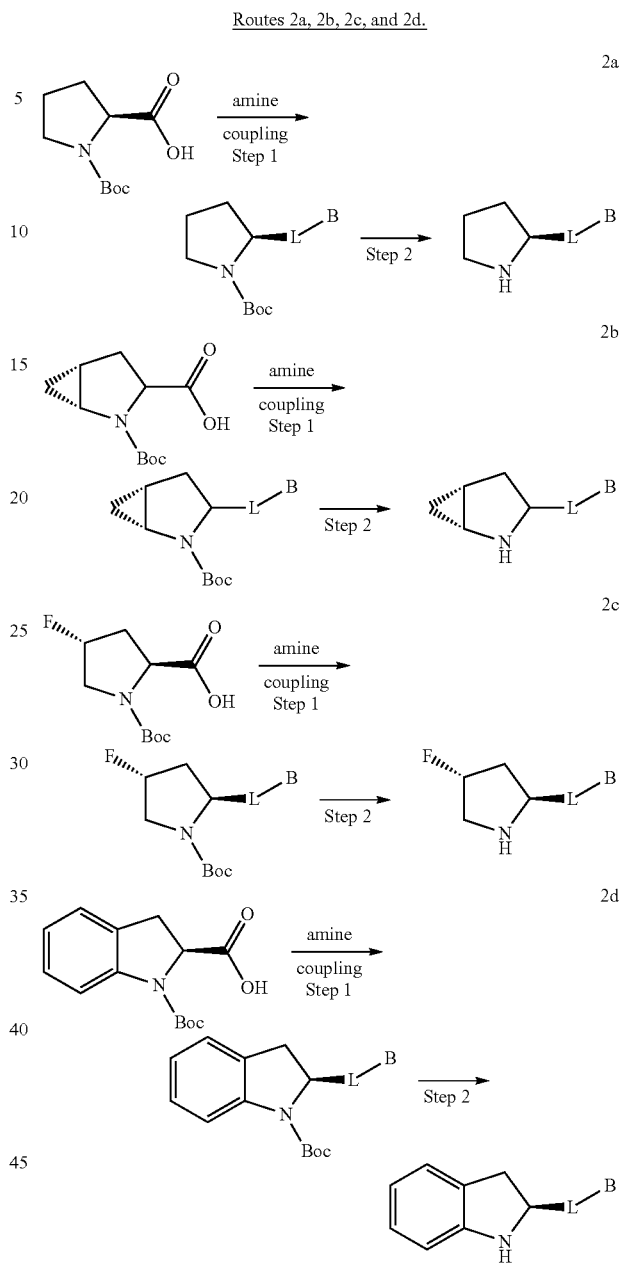

Routes 2a, 2b, 2c, and 2d.

In Route 1a, 5-azaspiro[2.4]heptane-4,5-dicarboxylic acid, 5-(1,1-dimethylethyl) ester, (4S)—, CAS 209269-08-9, can be prepared as described in Tandon, M. et al. Bioorg. Med. Chem. Lett. 1998, 8, 1139-1144. In Step 2, the protected azaspiro[2.4]heptane is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1b, (4S) 4-oxazolidinecarboxylic acid, hydrochloride is treated with an amine protecting reagent. In one embodiment, the amine protecting reagent is di-tert-butyl dicarbonate. In another embodiment, 3,4-oxazolidinedicarboxylic acid, 3-(1,1-dimethylethyl) ester, (4S)—, is commercially available from JPM2 Pharmaceuticals. In one embodiment the reaction is carried out in an organic solvent in the presence of a base. In one embodiment, the organic solvent is acetonitrile. In one embodiment, the base is 4-dimentylaminopyridine (DMAP). In Step 2, the protected 4-oxazolidinecarboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1c, (S)-5-(tert-Butoxycarbonyl)-5-azaspiro[2.4] heptane-6-caboxylic acid, CAS 1129634-44-1, is commercially available from Ark Pharm. In Step 2, the carboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 2a, commercially available Boc-L-proline is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2b, commercially available (1R, 3S, 5R)-2-[(tert-butoxy)carbonyl]-2-azabicyclo[3.1.0]hexane-3-carboxylic acid, from Enamine, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2c, commercially available (2S,4R)-1-(tert-butoxycarbonyl)-4-fluoropyrrolidine-2-carboxylic acid, from Manchester Organics, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2d, commercially available (S)-1-(tert-butoxycarbonyl)indoline-2-carboxylic acid, from Chem-Impex, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane. This chemistry is illustrated in Scheme 2.

Additional starting materials that can readily be converted to Central-L-B— Synthons include, but are not limited to: (S)-1-(tert-butoxycarbonyl)-2,3-dihydro-1H-pyrrole-2-carboxylic acid, CAS 90104-21-5, available from Ark Pharm; cyclopent-1-ene-1,2-dicarboxylic acid, CAS 3128-15-2, purchased from Ark Pharm; imidazole, 1H-imidazole-1,2-dicarboxylic acid, 1-(1,1-dimethylethyl) 2-ethyl ester, CAS 553650-00-3, commercially available from FCH Group; Boc-L-octahydroindole-2-carboxylic acid can be purchased from Chem Impex. The compound,

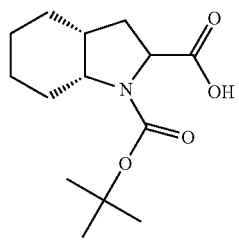 [SMILES: CC(C)(C)OC(=O)N1C(C(=O)O)C[C@H]2CCCC[C@H]21]

can be prepared according to the procedures disclosed in WO 2004/111041; (S)-Boc-5-oxopyrrolidine-2-carboxylic acid is available from the Aldrich Chemical Co.; (1S,2S,5R)-3-(tert-butoxycarbonyl)-3-azabicyclo[3.3.0]hexane-2-carboxylic acid is available from Ark Pharm; (S)-3-Boc-thiazolidine-2-carboxylic acid is available from Alfa Aesar; (2S,4R)-1-(tert-butoxycarbonyl)-4-chloropyrrolidine-2-carboxylic acid is available from Arch Bioscience; (1 S,3 aR,6aS)-2-(tert-butoxycarbonyl)octahydrocyclopenta[c] pyrrole-1-carboxylic acid is available from Ark Pharm; 1,2-pyrrolidinedicarboxylic acid, 3-[[(phenylmethoxy)carbonyl]amino]-, 1-(1,1-dimethylethyl) ester, (2S,3R) can be prepared as disclosed in WO 2004/007501. The Cbz group can be removed and the amino group can be alkylated to generate central core compounds of the present invention.

The compound

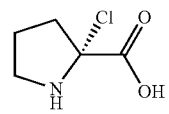

can be prepared as disclosed by Braun, J. V.; Heymons, Albrecht Berichte der Deutschen Chemischen Gesellschaft [Abteilung] B: Abhandlungen (1930) 63B, 502-7.

The compounds (2S,3 S,4S)-4-fluoro-3-methoxy-pyrrolidine-1,2-dicarboxylic acid 1-tert-butyl ester and (2R,3R,4R)-3-fluoro-4-methoxy-pyrrolidine-1,2-dicarboxylic acid 1-tert-butyl ester can be prepared as a mixture according to WO 2012/093101 to Novartis and the regioisomers can be ultimately separated once coupled to generate the central core-L-B synthons. The compound (S)-Boc-5-oxopyrrolidine-2-carboxylic acid is available from the Aldrich Chemical Co.

Example 4. Preparation of Alkynyl Synthons

Alkynyl synthons include but are not limited to:

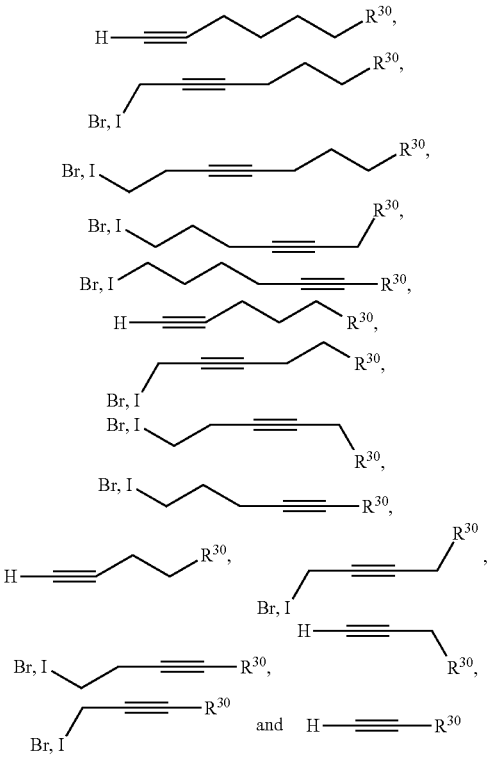

wherein $R^{30}$ is independently chosen at each occurrence from hydrogen, $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S; (5- or 6-membered unsaturated or aromatic heterocycle)$C_0$-$C_4$alkyl having 1, 2, or 3 heteroatoms independently chosen from N, O, and S; COOH, Si$(CH_3)_3$, COOR$^{30a}$, $C_2$-$C_6$alkanoyl, —B(OH)$_2$, —C(O)(CH$_2$)$_{1-4}$S(O)R$^{21}$, —P(O)(OR$^{21}$)(OR$^{22}$), —P(O)(OR$^{21}$)R$^{22}$, —P(O)R$^{21}$R$^{22}$, —NR$^9$P(O)(NHR$^{21}$)(NHR$^{22}$), —NR$^9$P(O)(OR$^{21}$)(NHR$^{22}$), —NR$^9$P(O)(OR$^{21}$)(OR$^{22}$), —C(S)R$^{21}$, —NR$^{21}$SO$_2$R$^{22}$, —NR$^9$S(O)NR$^{10}$R$^{22}$, —NR$^9$SO$_2$NR$^{10}$R$^{22}$, —SO$_2$NR$^9$COR$^{22}$, —SO$_2$NR$^9$CONR$^{21}$R$^{22}$, —NR$^{21}$SO$_2$R$^{22}$, —C(O)NR$^{21}$SO$_2$R$^{22}$, —C(NIH2)NR$^9$R$^{22}$, —C(NH$_2$)NR$^9$S(O)$_2$R$^{22}$, —NR$^9$C(O)OR$^{10}$, —NR$^{21}$OC(O)R$^{22}$, —(CH$_2$)$_{1-4}$C(O)NR$^{21}$R$^{22}$, —C(O)R$^{24}$R$^{25}$, —NR$^9$C(O)R$^{21}$, —C(O)R$^{21}$, —NR$^9$C(O)NR$^9$R$^{10}$, —NR$^9$C(O)NR$^{24}$R$^{25}$, —(CH$_2$)$_{1-4}$OC(O)R$^{21}$, each of which R$^{30}$ can be optionally substitutent;

R$^{30a}$ is $C_1$-$C_6$alkyl, $C_2$-$C_6$alkenyl, $C_2$-$C_6$alkynyl, ($C_3$-$C_7$cycloalkyl)$C_0$-$C_4$alkyl-, (aryl)$C_0$-$C_4$alkyl-, (3- to 7-membered heterocycloalkyl)$C_0$-$C_4$alkyl- having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S, each of which R$^{30a}$ can be optionally substituted.

Alkyne synthons can be prepared and coupled by a person skilled in the art. For example, Amashiro discloses alkynyl amines in WO 2008/047831. Aryl alkynes are disclosed in Tang, T. et al., J. Org. Chem., 2013, 78, 3170-3175. Alkynes can be synthesized from primary alcohols; see, Quesada, R. and Taylor, R. J. K., Tett. Lett., 2005, 46, 6473-6476. Alkynes can be synthesized from aldehydes using an in situ preparation of dimethyldiazomethylphosphonate; see Roth, G. J. et al., Synthesis, 2004, 59-62. Bromoalkenes can be converted to alkynes; see, Okutani, M. and Mori, Y., J. Org. Chem., 2009, 74, 442-444. (Z)-1-Bromoalkenes can be converted to alkynes; see, Kuang, C., et al., Tetrahedron, 2005, 61, 4043-4052.

Example 5. Preparation of A-C(O)— Moiety

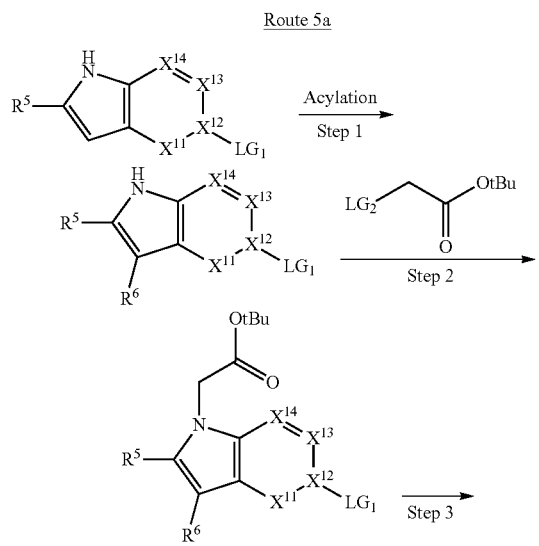

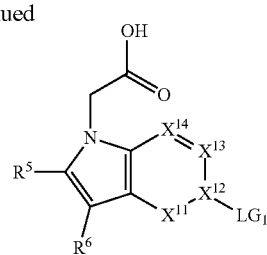

In Step 1 of Route 5a, the stating material is treated with an organic solvent, an acylating reagent and a catalyst to add the R$^6$ substitutent. In one embodiment, the organic solvent is toluene. In one embodiment, the acylating reagent is acetyl chloride. In one embodiment, the catalyst is tin tetrachloride. In another embodiment, the starting material in Step 1 is treated with an inorganic cyanide and organometallic catalyst to generate a cyano group at the R$^6$ position. The cyano group is treated with a oxime to generate an amide at the R$^6$ position. In Step 2, the nitrogen of the heteroaryl ring is treated with a tert-butyl haloacetate, an organic solvent and a base. In one embodiment, the halo group, LG$_2$, is bromine. In one embodiment, the organic solvent is acetonitrile. In one embodiment, the base is potassium carbonate. In Step 3, the tert-butyl ester is treated with an organic acid and an organic solvent to generate an acid. In one embodiment, the organic acid is trifluoroacetic acid. In one embodiment, the organic solvent is dichloromethane. This chemistry is illustrated in Route 5a.

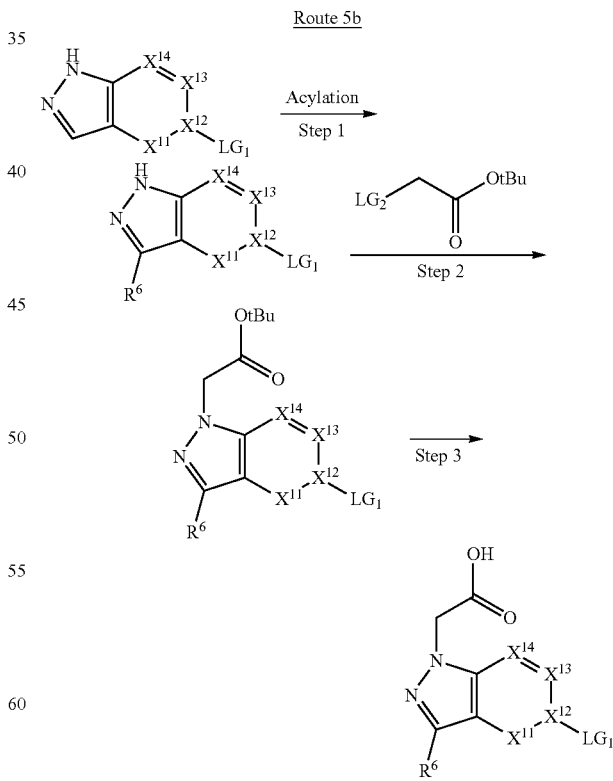

In Step 1 of Route 5b, the stating material is treated with an organic solvent, an acylating reagent and a catalyst to add the R$^6$ substitutent. In one embodiment, the organic solvent is toluene. In one embodiment, the acylating reagent is acetyl chloride. In one embodiment, the catalyst is tin tetrachloride. In another embodiment, the starting material in Step 1 is treated with an inorganic cyanide and organometallic catalysts to add a cyano group at the $R^6$ position. The cyano group is treated with an oxime to generate an amide at the $R^6$ position. In Step 2, the nitrogen of the heteroaryl ring is treated with a tert-butyl haloacetate, an organic solvent and a base. In one embodiment, the halo group, $LG_2$, is bromine. In one embodiment, the organic solvent is acetonitrile. In one embodiment, the base is potassium carbonate. In Step 3, the tert-butyl ester is treated with an organic acid and an organic solvent to generate a carboxylic acid. In one embodiment, the organic acid is trifluoroacetic acid. In one embodiment, the organic solvent is dichloromethane. This chemistry is illustrated in Route 5b.

Example 6: Coupling of Central-L-B Synthons to —C(O)— Moieties

As illustrated in Scheme 6a, central-LB synthons and a carboxylic acid (C(O)-A) are combined and treated with an organic solvent, a base, and coupling agent. In one embodiment, the solvent is DMF. In one embodiment, the base is N,N-diisopropylethylamine. In one embodiment the coupling reagent is (1-[bis(dimethylamino)methylene]-1H-1,2,3-triazolo[4,5-b]pyridinium 3-oxide hexafluorophosphate) (HATU).

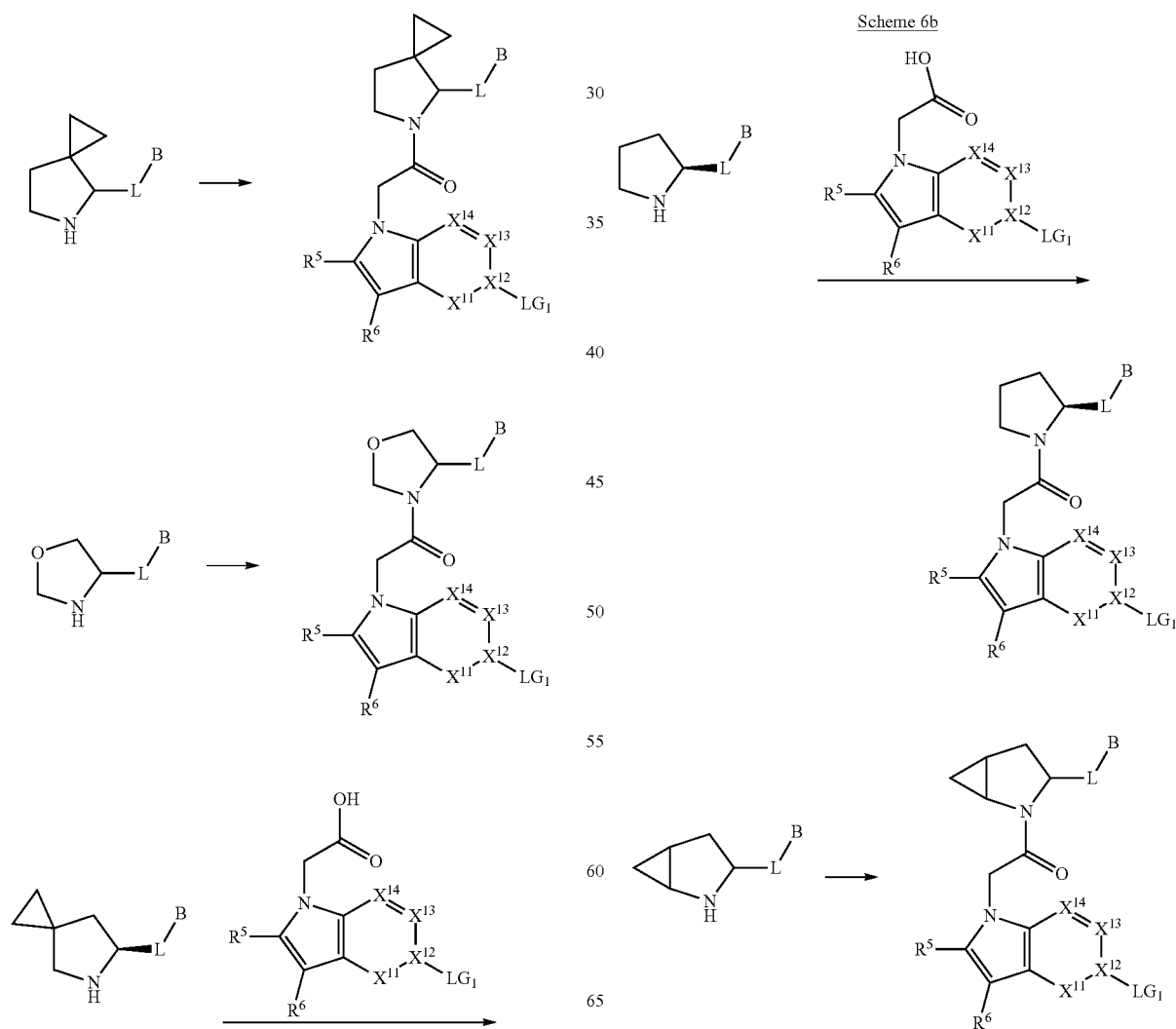

Scheme 6a

Scheme 6b

91
-continued

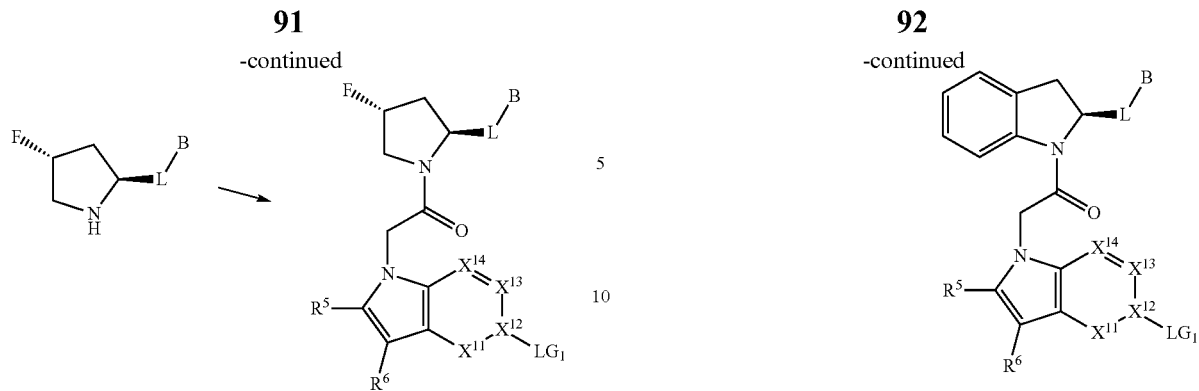

92
-continued

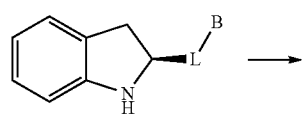

As illustrated in Scheme 6b, the central-LB synthons and carboxylic acid (C(O)-A) are combined and treated with an organic solvent, a base, and coupling agent. In one embodiment, the solvent is DMF. In one embodiment, the base is N,N-diisopropylethylamine. In one embodiment the coupling reagent is (1-[bis(dimethylamino)methylene]-1H-1,2,3-triazolo[4,5-b]pyridinium 3-oxide hexafluorophosphate) (HATU).

Example 7. Synthesis of Alkynes of Formula I

Scheme 7a

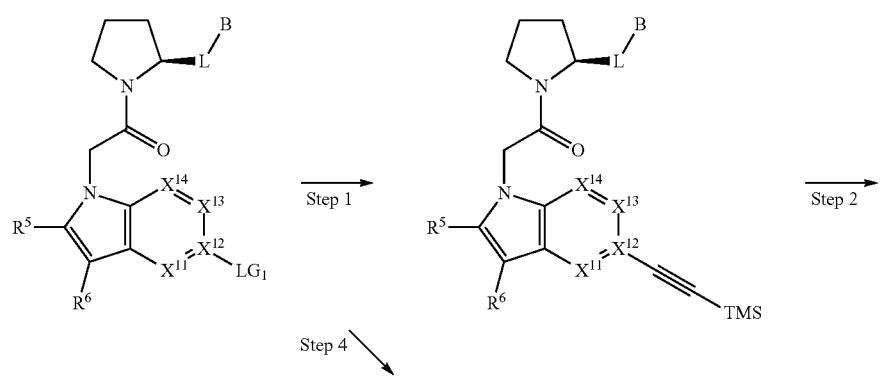

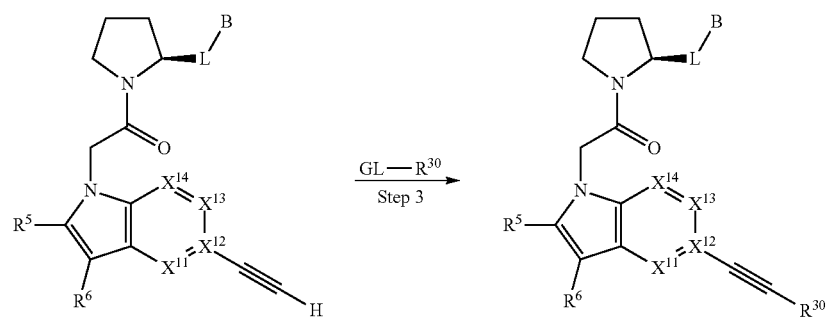

As an example, the proline derivative from Example 6 Scheme 6b is treated with two organometallic catalysts, trimethylsilylacetylene, a base and organic solvent at an elevated temperature to generate a trimethylsilyl protected alkyne. In one embodiment, the first organometallic catalyst is copper iodide. In one embodiment, the second organometallic catalyst is tetrakis(triphenylphosphine)palladium (0). In one embodiment, the base is triethylamine. In one embodiment, the organic solvent is DMF. In one embodiment, the reaction is deoxygenated by bubbling argon into the pressure vessel. In one embodiment, the reaction is treated at an elevated temperature. In one embodiment, the reaction is treated at about 80 to about 105° C. In Step 2, the trimethylsilyl protected akyne is treated with a fluoride reagent and an organic solvent. In one embodiment, the fluoride reagent is tetrabutylammonium fluoride. In one embodiment, the organic solvent is tetrahydrofuran. In Step 3, the alkyne is treated with LG-$R^{30}$, two organometallic catalysts, a base, and an organic solvent at an elevated temperature. In one embodiment, the first organometallic catalyst is copper iodide. In one embodiment, the second organometallic catalyst is bis(triphenylphosphine)palladium (II) dichloride. In one embodiment, the base is triethylamine. In one embodiment, the organic solvent is DMF. In one embodiment, the elevated temperature is at about 80 to about 95° C. In one embodiment the LG $R^{30}$ group is an heteroaryl halide. In one embodiment, the LG-$R^{30}$ group is an aryl halide. This chemistry is illustrated in Scheme 7a.

In an alternate embodiment, the proline derivative from Example 6 Scheme 6b is treated with two organometallic catalysts, an alkyne, a base and organic solvent at an elevated temperature to generate an alkyne of Formula I. In one embodiment, the first organometallic catalyst is copper iodide. In one embodiment, the second organometallic catalyst is tetrakis(triphenylphosphine)palladium(0). In one embodiment, the base is triethylamine. In one embodiment, the organic solvent is DMF. In one embodiment, the reaction is deoxygenated by bubbling argon into the pressure vessel. In one embodiment, the reaction is treated at an elevated temperature. In one embodiment, the reaction is treated at about 80 to about 105° C.

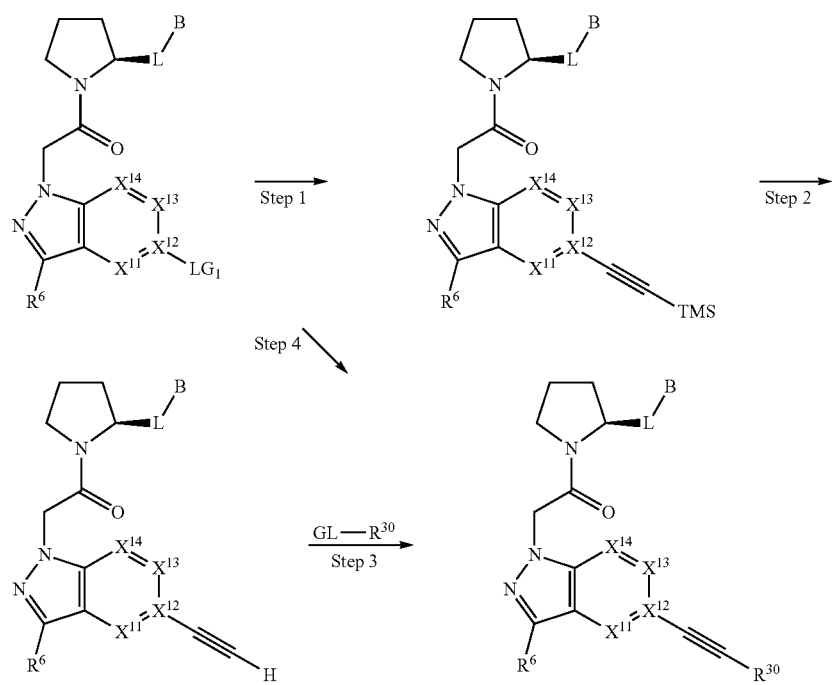

Scheme 7b

The proline derivative from Example 6 Scheme 6b is treated with two organometallic catalysts, trimethylsilylacetylene, a base and organic solvent at an elevated temperature to generate a trimethylsilyl protected alkyne. In one embodiment, the first organometallic catalyst is copper iodide. In one embodiment, the second organometallic catalyst is tetrakis(triphenylphosphine)palladium(0). In one embodiment, the base is triethylamine. In one embodiment, the organic solvent is DMF. In one embodiment, the reaction is deoxygenated by bubbling argon into the pressure vessel. In one embodiment, the reaction is treated at an elevated temperature. In one embodiment, the reaction is treated at about 80 to about 105° C. In Step 2, the trimethylsilyl protected akyne is treated with a fluoride reagent and an organic solvent. In one embodiment, the fluoride reagent is tetrabutylammonium fluoride. In one embodiment, the organic solvent is tetrahydrofuran. In Step 3, the alkyne is treated with LG-$R^{30}$, two organometallic catalysts, a base, and an organic solvent at an elevated temperature. In one embodiment, the first organometallic catalyst is copper iodide. In one embodiment, the second organometallic catalyst is bis(triphenylphosphine)palladium(II) dichloride. In one embodiment, the base is triethylamine. In one embodiment, the organic solvent is DMF. In one embodiment, the elevated temperature is at about 80 to about 95° C. In one embodiment the LG $R^{30}$ group is an heteroaryl halide. In one embodiment, the LG-$R^{30}$ group is an aryl halide. This chemistry is illustrated in Scheme 7b.

In an alternate embodiment, the proline derivative from Example 6 Scheme 6b is treated with two organometallic catalysts, an alkyne, a base and organic solvent at an elevated temperature to generate an alkyne of Formula I. In one embodiment, the first organometallic catalyst is copper iodide. In one embodiment, the second organometallic catalyst is tetrakis(triphenylphosphine)palladium(0). In one embodiment, the base is triethylamine. In one embodiment, the organic solvent is DMF. In one embodiment, the reaction is deoxygenated by bubbling argon into the pressure vessel. In one embodiment, the reaction is treated at an elevated temperature. In one embodiment, the reaction is treated at about 80 to about 105° C.

In an alternative embodiment, a TMS alkyne from Example 7 Scheme 7a or 7b can be treated with an inorganic fluoride, an organic solvent and carbon dioxide to generate a carboxylic acid. In one embodiment, the inorganic fluoride is cesium fluoride. In one embodiment, the organic solvent is dimethyl sulfoxide. The resulting carboxylic acid can be treated with a sulfonamide anion to generate a compound of Formula I.

Example 8. Synthesis of 1A. (2S,4R)-tert-butyl 2-((3-chloro-2-fluoro-benzyl)carbamoyl)-4-fluoropyrrolidine-1-carboxylate

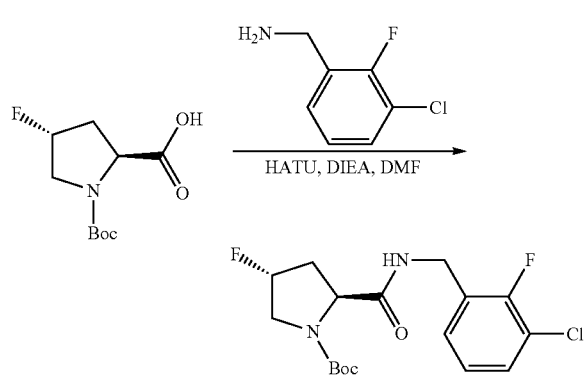

(2S,4R)-1-(tert-butoxycarbonyl)-4-fluoropyrrolidine-2-carboxylic acid (2.33 gm, 10 mmol) was dissolved in DMF (50 ml) and $^i$Pr$_2$NEt (8.6 ml, 5 eq.) was added, followed by the addition of (3-chloro-2-fluorophenyl) methanamine (3.18 gm 20 mmol) at 5° C. Then HATU (8 gm, 2.1 eq) was added slowly at same temperature. The reaction mixture was then stirred for 18 h at RT. After completion of the reaction monitored by HPLC, The reaction mixture was diluted with 1M citric acid solution (200 ml+NaCl solid 20 gm) and extracted with DCM (150 mL×2), the organic layer was then washed with an aqueous solution of NaHCO$_3$ (100 ml) and washed with water (100 ml), brine (100 ml) and dried over Na$_2$SO$_4$ and concentrated under reduced pressure. The remaining residue was purified by column chromatography (eluted with DCM/EtOAc) to give (2S,4R)-tert-butyl 2-((3-chloro-2-fluorobenzyl)carbamoyl)-4-fluoropyrrolidine-1-carboxylate. 1B. (2S,4R)—N-(3-CHLORO-2-FLUOROBENZYL)-4-FLUOROPYRROLIDINE-2-CARBOXAMIDE HYDROCHLORIDE (A).

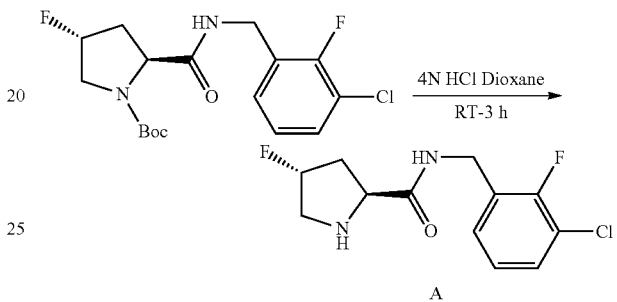

(2S,4R)-tert-butyl 2-((3-chloro-2-fluorobenzyl)carbamoyl)-4-fluoropyrrolidine-1-carboxylate (500 mg) was taken in 4N HCl dioxane (30 ml) and resulting reaction mixture was stirred at rt for 3 h. After completion of the reaction monitored by HPLC solvent was removed under reduced pressure. The residue, A, was used for next reaction.

Example 9. Synthesis of (2S,4R)-1-(2-(3-Acetyl-5-(pyrimidin-2-ylethynyl)-1H-indol-1-yl)acetyl)-N-(3-chloro-2-fluorobenzyl)-4-fluoropyrrolidine-2-carboxamide

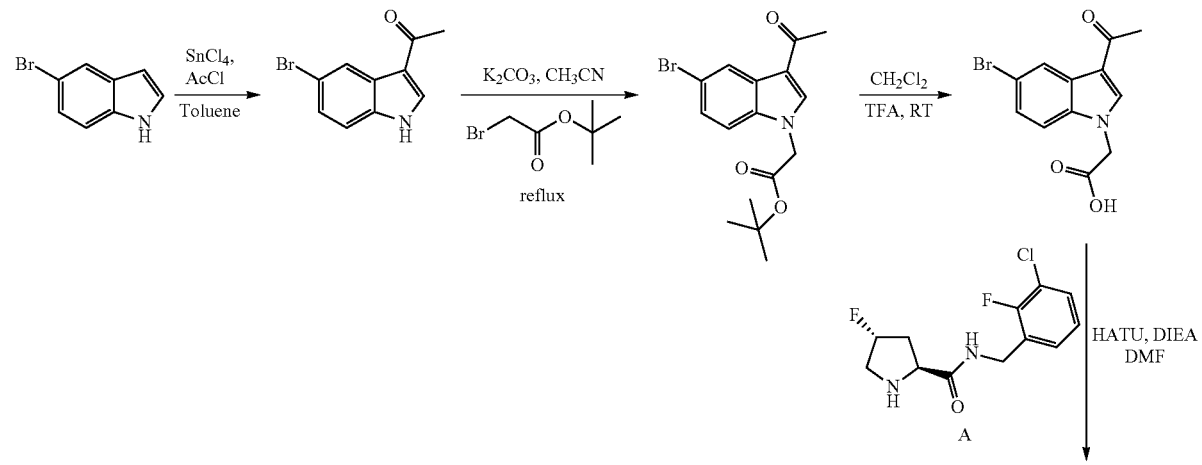

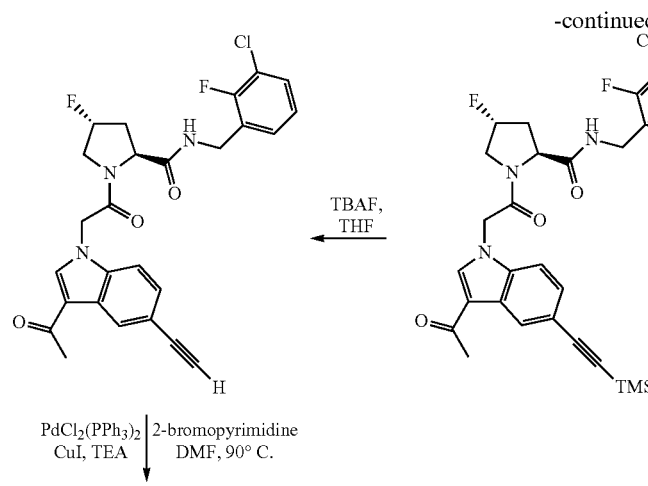
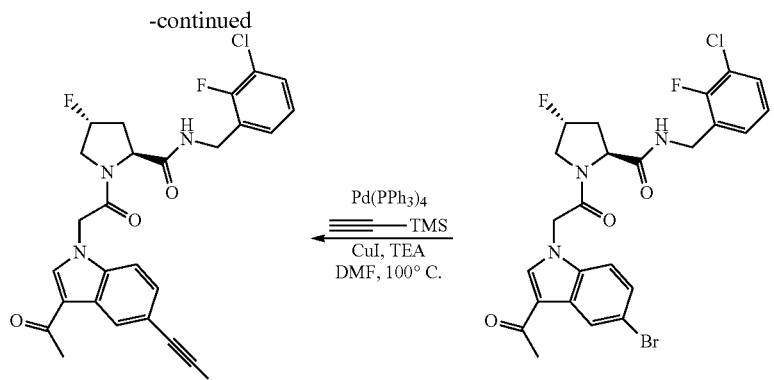

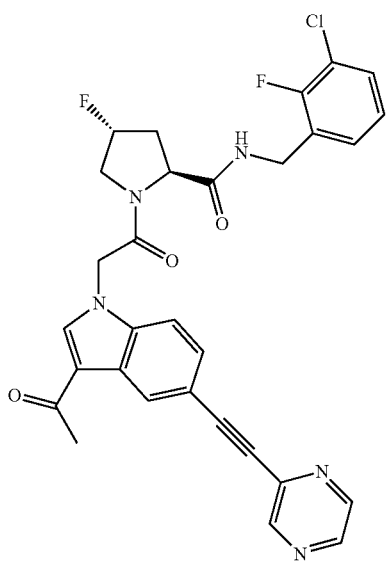

1-(5-Bromo-1H-indol-3-yl)ethanone (2) was prepared from 5-bromoindole according to the procedure published by MacKay et al. (MacKay, J. A.; Bishop, R.; Rawal, V. H. *Org. Lett.* 2005, 7, 3421-3424.)

A mixture of 3.9 g (16.4 mmol) of 1-(5-bromo-1H-indol-3-yl)ethanone, 2.63 mL (18.02 mmol) of tert-butyl bromoacetate and 2.50 g (18.02 mmol) potassium carbonate in anhydrous acetonitrile (80 mL) was refluxed for 5 h. The reaction mixture was then cooled to RT and the solvent was removed under reduced pressure. The residue was taken in 1:1 mixture of $CH_2Cl_2$ and water (100 mL: 100 mL). The two layers were separated and the organic layer was washed with water (2×100 mL). Finally, the organic layer was dried ($Na_2SO_4$) and concentrated. The resulting residue was stirred with 50 mL of heptane for 30 min., cooled in an ice bath and filtered, washing the solid with cold heptane (10 mL). This cream colored solid was dried under high vacuum to give 5.6 g of product tert-Butyl 2-(3-acetyl-5-bromo-1H-indol-1-yl)acetate.

4.5 g of tert-Butyl 2-(3-acetyl-5-bromo-1H-indol-1-yl) acetate was stirred in 1:1 mixture of $CH_2Cl_2$-TFA (90 mL) at RT for 4 h. The volatiles were removed under reduced pressure. The residue was dissolved in 45 mL of DMF. 4.16 g (13.4 mmol) of hydrochloride salt of 5 was added to this solution, followed by 11 mL of N,N-diisopropylethylamine (63.7 mmol). The reaction mixture was cooled in an ice bath and 5.82 g of (15.3 mmol) HATU was added. Following the addition of HATU, the cooling bath was removed and the reaction mixture was stirred overnight at RT. This reaction mixture was then poured in 450 mL of 1.0 M aq. citric acid solution. The separated product was isolated by filtration and the solid was washed thoroughly with water. This gray solid was dried under high vacuum to give 7.4 g of product (2S,4R)-1-(2-(3-Acetyl-5-bromo-1H-indol-1-yl)acetyl)-N-(3-chloro-2-fluorobenzyl)-4-fluoropyrrolidine-2-carboxamide.

A mixture of 1 g (1.8 mmol) of (2S,4R)-1-(2-(3-Acetyl-5-bromo-1H-indol-1-yl)acetyl)-N-(3-chloro-2-fluorobenzyl)-4-fluoropyrrolidine-2-carboxamide, 0.419 g (0.36 mmol) of tetrakis(triphenylphosphine)palladium(0), 0.138 g 0.72 mmol) of cuprous iodide in DMF (10 mL) was deoxygenated by bubbling argon in a pressure vessel. Triethylamine (2.53 mL, 18.1 mmol) and 2.56 mL (18.1 mmol) of ethynyltrimethylsilane were added under argon. The pressure vessel was capped and heated at 100° C. overnight. Then the reaction mixture was cooled to RT and the solvent was removed under reduced pressure. The residue was purified by column chromatography (silica gel, 0-2% MeOH in $CH_2Cl_2$) to give 0.56 g of (2S,4R)-1-(2-(3-Acetyl-5-((trimethylsilyl)ethynyl)-1H-indol-1-yl)acetyl)-N-(3-chloro-2-fluorobenzyl)-4-fluoropyrrolidine-2-carboxamide as a yellow solid.

To a solution of (2S,4R)-1-(2-(3-Acetyl-5-((trimethylsilyl)ethynyl)-1H-indol-1-yl)acetyl)-N-(3-chloro-2-fluorobenzyl)-4-fluoropyrrolidine-2-carboxamide (0.5 g, 1 mmol) in THF (5 mL) was added 1.5 mL of 1.0 M tetrabutylammonium fluoride in THF at RT. The reaction mixture was stirred for 1 h. The solvent was removed under reduced pressure and the residue was purified by column chromatography (silica gel, 0-2% MeOH in $CH_2Cl_2$) to give 0.26 g of (2S,4R)-1-(2-(3-acetyl-5-ethynyl-1H-indol-1-yl)acetyl)-N-(3-chloro-2-fluorobenzyl)-4-fluoropyrrolidine-2-carboxamide as a light yellow solid.

A mixture of 0.16 g (1.0 mmol) of 2-bromopyrimidine, 0.141 g (0.2 mmol) of $PdCl_2(PPh_3)_2$, 0.043 g (0.23 mmol) of cuprous iodide in DMF (4 mL) was deoxygenated by bubbling argon in a pressure vessel. Triethylamine (2.0 mL) and 0.250 g (0.5 mmol) of (2S,4R)-1-(2-(3-Acetyl-5-ethynyl-1H-indol-1-yl)acetyl)-N-(3-chloro-2-fluorobenzyl)-4-fluoropyrrolidine-2-carboxamide were added under argon. The pressure vessel was capped and heated at 100° C. overnight. Then the reaction mixture was cooled to RT and the solvent was removed under reduced pressure. The residue was purified by column chromatography (silica gel, 0-4.5% MeOH in $CH_2Cl_2$) to give 35 mg of the desired product (2S,4R)-1-(2-(3-acetyl-5-(pyrimidin-2-ylethynyl)-1H-indol-1-yl)acetyl)-N-(3-chloro-2-fluorobenzyl)-4-fluoropyrrolidine-2-carboxamide as a light red solid. $^1$H NMR (400 MHz, DMSO-$d_6$, 300 K): (major rotamer) δ: 1.99-2.18 (m, 1H), 2.46 (s, 3H), 3.92 (ddd, J=24.4, 12.4, 2.8 Hz, 1H), 4.26 (dd, J=12.8, 20.8 Hz, 1H), 4.32 (dd, J=28.4, 6.0 Hz, 1H), 4.39-4.49 (m, 2H), 5.24 (d, J=17.2 Hz, 1H), 5.45 (d, J=17.2 Hz, 1H), 5.51 (d, J=52.8 Hz, 1H), 6.96 (t, J=7.2 Hz, 1H), 7.23 (t, J=6.4 Hz, 1H), 7.40-7.51 (m, 4H), 7.59 (d, J=8.4 Hz, 1H), 8.36 (s, 1H), 8.47 (d, J=0.8 Hz, 1H), 8.61 (t, J=5.6 Hz, 1H), 8.85 (d, J=4.8 Hz, 2H). $^{31}$F NMR (376 MHz, DMSO-$d_6$, 300 K): (major rotamer) δ: −121.7, −176.1. LC (method 1): $t_R$=1.73 min. LC/MS (EI) m/z: [M+H]$^+$ calcd for $C_{30}H_{24}ClF_2N_5O_3$, 575.9. found, 576.4.

Example 10: Additional Syntheses of Non-Limiting Examples of Alkyne Compounds of Formula I Compound 2: 3-(3-Acetyl-1-(2-((2S,4R)-2-((3-chloro-2-fluorobenzyl)carbamoyl)-4-fluoropyrrolidin-1-yl)-2-oxoethyl)-1H-indol-5-yl)propiolic acid

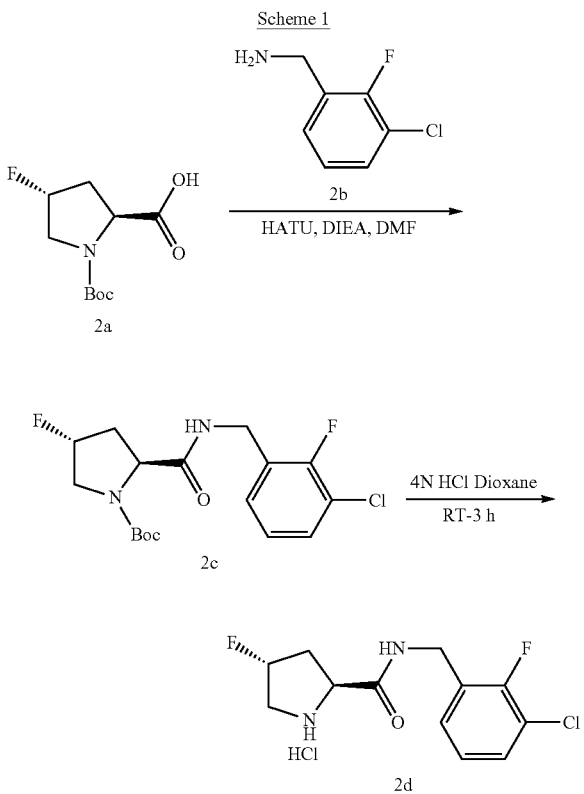

As shown in Scheme 1, (2S,4R)-1-(tert-butoxycarbonyl)-4-fluoropyrrolidine-2-carboxylic acid (2a, 2.33 g) was dissolved in DMF (50 ml) and DIEA (8.6 ml) was added, followed by the addition of (3-chloro-2-fluorophenyl)methanamine (2b, 3.18 gm) at 5° C. Then HATU (8 gm) was added slowly at same temperature. The reaction mixture was then stirred for 18 h at RT. After completion of the reaction monitored by HPLC, The reaction mixture was diluted with 1M citric acid solution (200 ml+NaCl solid 20 gm) and extracted with DCM (150 mL×2), the organic layer was then washed with an aqueous solution of $NaHCO_3$ (100 ml) and washed with water (100 ml), brine (100 ml) and dried over $Na_2SO_4$ and concentrated under reduced pressure. The remaining residue was purified by column chromatography (eluent: DCM/EtOAc) to give (2S,4R)-tert-butyl 2-((3-chloro-2-fluorobenzyl)carbamoyl)-4-fluoropyrrolidine-1-carboxylate (2c).

(2S,4R)-tert-butyl 2-((3-chloro-2-fluorobenzyl)carbamoyl)-4-fluoropyrrolidine-1-carboxylate (500 mg) was taken in 4N HCl dioxane (30 ml) and resulting reaction mixture was stirred at RT for 3 h. After completion of the reaction, solvent was removed under reduced pressure. The residue, 2d, was used for next reaction.

Scheme 2

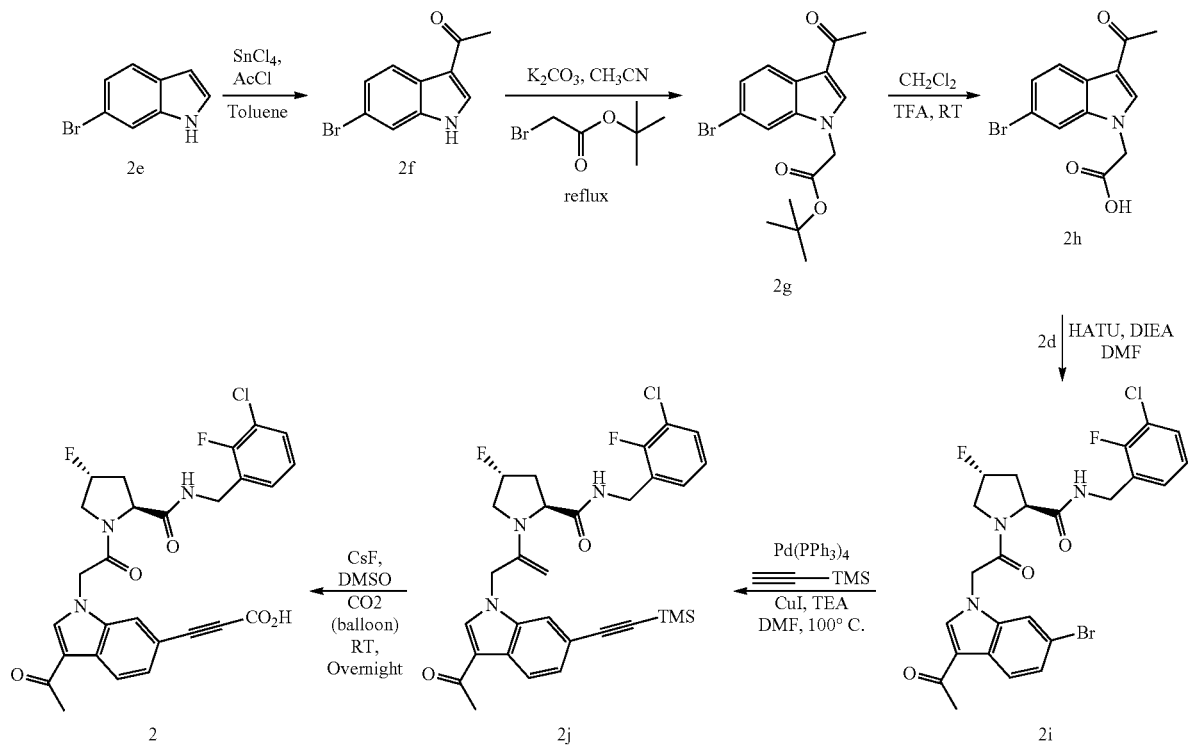

As shown in scheme 2, 1-(6-Bromo-1H-indol-3-yl)ethanone (2f) was prepared from 6-bromoindole (2e) according to the procedure published by MacKay et al. (MacKay, J. A.; Bishop, R.; Rawal, V. H. Org. Lett. 2005, 7, 3421-3424.)

A mixture of 0.5 g of 1-(6-bromo-1H-indol-3-yl)ethanone, 0.35 mL of tert-butyl bromoacetate and 0.318 g potassium carbonate in anhydrous acetonitrile (10 mL) was refluxed for 5 h. The reaction mixture was then cooled to RT and diluted with dichloromethane. $K_2CO_3$ was filtered off and the filtrate was concentrated under reduced pressure. The residue was purified by chromatography over silica gel (eluent: 0-25% EtOAc in hexanes) to get 0.7 g of white solid of tButyl 2-(3-acetyl-5-bromo-1H-indol-1-yl)acetate (2g).

Compound 2e (31.0 g) was taken in 4.0 N HCl in dioxane and stirred overnight at RT. Then 150 mL of additional 4.0 N HCl in dioxane was added and stirred for 6 h at RT. The volatiles were then removed under reduced pressure and the residue was dried under high vacuum to get 25.3 g of 2-(3-acetyl-6-bromo-1H-indol-1-yl)acetic acid (2h).

Compound 2h (25.3 g) was dissolved in 250 mL of DMF. 27.86 g of hydrochloride salt of 2d was added to this solution, followed by 83.82 mL of N,N-diisopropylethylamine. The reaction mixture was cooled in an ice bath and 38.98 g of HATU was added. Following the addition of HATU, the cooling bath was removed and the reaction mixture was stirred for 1 h at RT. This reaction mixture was then poured in 250 mL of 1.0 M aq. citric acid solution. The separated product was isolated by filtration and the solid was washed thoroughly with water. This cream solid was dried under high vacuum to give 48 g of product (2S,4R)-1-(2-(3-Acetyl-6-bromo-1H-indol-1-yl)acetyl)-N-(3-chloro-2-fluorobenzyl)-4-fluoropyrrolidine-2-carboxamide (2i). This solid was then stirred with 250 mL of EtOAc for 30 min at RT and filtered, washing the solid with 60 mL of EtOAc to get 45 g of the product 2i.

A mixture of 0.8 g of (2S,4R)-1-(2-(3-Acetyl-6-bromo-1H-indol-1-yl)acetyl)-N-(3-chloro-2-fluorobenzyl)-4-fluoropyrrolidine-2-carboxamide (2i), 0.669 g of $Pd(PPh_3)_4$, 0.124 g of cuprous iodide in DMF (8 mL) was deoxygenated by bubbling argon in a pressure vessel. Triethylamine (4 mL), and 2.6 mL of ethynyltrimethylsilane were added under argon. The pressure vessel was capped and heated at 100° C. overnight. Then the reaction mixture was cooled to RT and the solvent was removed under reduced pressure. The residue was purified by chromatography over silica gel (eluent: 0-2.5% MeOH in $CH_2Cl_2$) to give 0.68 g of (2S, 4R)-1-(2-(3-Acetyl-6-((trimethylsilyl)ethynyl)-1H-indol-1-yl)acetyl)-N-(3-chloro-2-fluorobenzyl)-4-fluoropyrrolidine-2-carboxamide (2j) as orange yellow solid.

Synthesized following the procedure of Kobayashi et al (Kobayashi et al, Org. Biomol. Chem. 2013, 11, 3773-3775). A flask was charged with 96 mg of CsF in anhydrous DMSO (3 mL) under $CO_2$ atmosphere. Then 0.3 g of 2j was added and stirred under $CO_2$ atmosphere in a balloon overnight at RT. The reaction mixture was diluted with water (30 mL) and extracted with dichloromethane. The aq. layer was acidified with aq. 6N HCl at 0° C. and extracted with EtOAc. Then the EtOAc layer was dried ($Na_2SO_4$) and concentrated. The residue was purified by chromatography over silica gel (eluent: 0-3.2% MeOH in $CH_2Cl_2$) to get 75 mg of 3-(3-Acetyl-1-(2-((2 S,4R)-2-((3-chloro-2-fluorobenzyl)carbamoyl)-4-fluoropyrrolidin-1-yl)-2-oxoethyl)-1H-indol-5-yl) propiolic acid (2) as cream colored solid. $^1$H NMR (400 MHz, DMSO-$d_6$, 300 K): (major rotamer) δ 2.05-2.18 (m, 1H), 2.45 (s, 3H), 2.50-2.58 (m, 1H), 3.87-4.08 (m, 1H), 4.11-4.16 (m, 1H), 4.23-4.29 (m, 1H), 4.35-4.49 (m, 2H), 5.25 (d, J=17.2 Hz, 1H), 5.45 (d, J=17.2 Hz, 1H), 5.52 (d, J=53.2 Hz, 1H), 6.90 (t, J=8 Hz, 1H), 7.19 (t, J=6.8 Hz, 1H), 7.33-7.55 (m, 2H), 7.91 (s, 1H), 8.23 (d, J=8.4 Hz, 1H), 8.39 (s, 1H), 8.61 (t, J=5.6 Hz, 1H), 13.70 (brs, 1H). $^{19}$F NMR (376 MHz, DMSO-$d_6$, 300 K): (major rotamer) δ −121.8, −176.1. LC (method 1): $t_R$=1.53 min. LC/MS (EI) m/z: [M+H]$^+$ calcd for $C_{27}H_{22}ClF_2N_3O_5$, 542. found, 542.

Compound 6: 3-(3-Acetyl-1-(2-((2 S,4R)-2-((3-chloro-2-fluorobenzyl)carbamoyl)-4-fluoropyrrolidin-1-yl)-2-oxoethyl)-1H-indol-5-yl)propiolic acid Scheme 3:

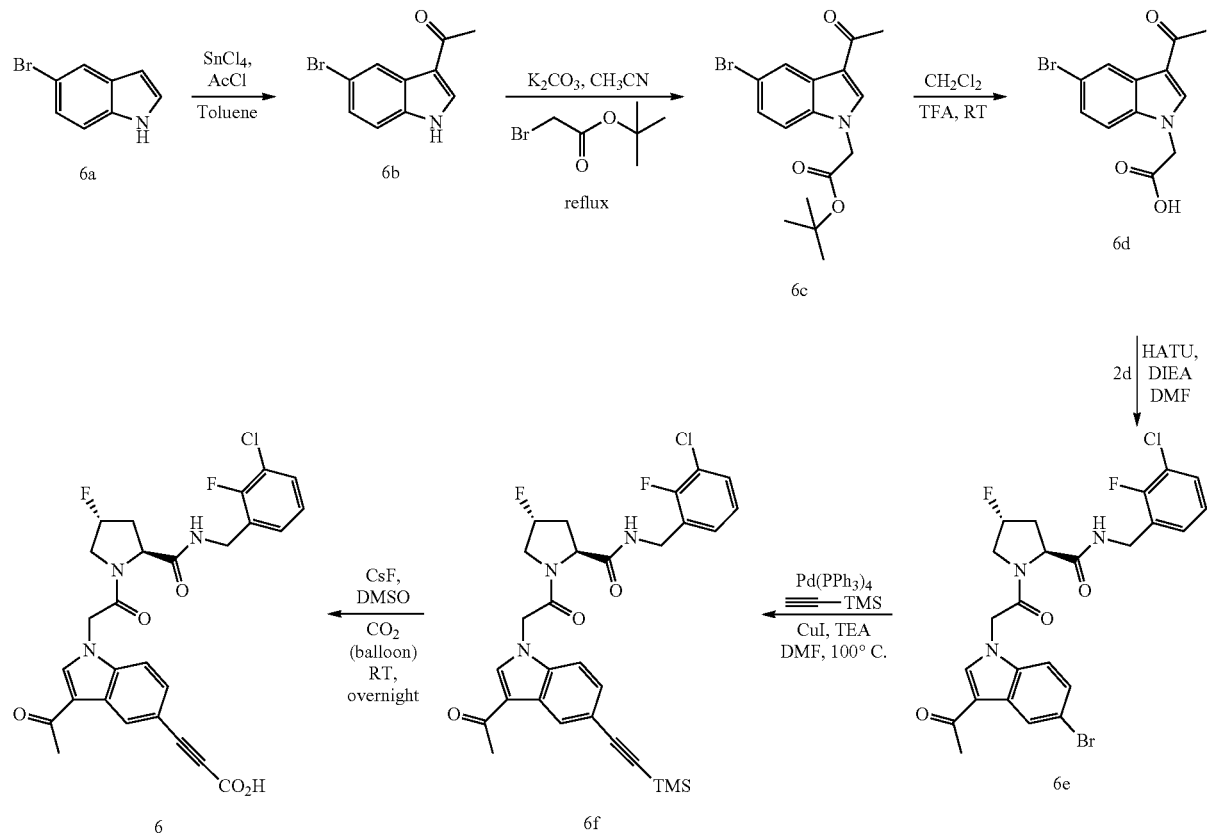

Same procedure as for the synthesis of compound 2 was followed, except the starting material was 5-bromoindole 6a.

1-(5-Bromo-1H-indol-3-yl)ethanone (6b) was prepared from 5-bromoindole according to the procedure published by MacKay et al. (MacKay, J. A.; Bishop, R.; Rawal, V. H. Org. Lett. 2005, 7, 3421-3424.)

A mixture of 3.9 g of 1-(5-bromo-1H-indol-3-yl)ethanone, 2.63 mL of tert-butyl bromoacetate and 2.50 g potassium carbonate in anhydrous acetonitrile (80 mL) was refluxed for 5 h. The reaction mixture was then cooled to RT and the solvent was removed under reduced pressure. The residue was taken in 1:1 mixture of $CH_2Cl_2$ and water (100 mL: 100 mL). The two layers were separated and the organic layer was washed with water (2×100 mL). Finally, the organic layer was dried ($Na_2SO_4$) and concentrated. The resulting residue was stirred with 50 mL of heptane for 30 min., cooled in an ice bath and filtered, washing the solid with cold heptane (10 mL). This cream colored solid was dried under high vacuum to give 5.6 g of product tert-Butyl 2-(3-acetyl-5-bromo-1H-indol-1-yl)acetate (6c).

tert-Butyl 2-(3-acetyl-5-bromo-1H-indol-1-yl)acetate (6c, 4.5 g) was stirred in 1:1 mixture of $CH_2Cl_2$-TFA (90 mL) at RT for 4 h. The volatiles were removed under reduced pressure. The residue was dissolved in 45 mL of DMF. 4.16 g (13.4 mmol) of hydrochloride salt of 2d was added to this solution, followed by 11 mL of N,N-diisopropylethylamine (63.7 mmol). The reaction mixture was cooled in an ice bath and 5.82 g of (15.3 mmol) HATU was added. Following the addition of HATU, the cooling bath was removed and the reaction mixture was stirred overnight at RT. This reaction mixture was then poured in 450 mL of 1.0 M aq. citric acid solution. The separated product was isolated by filtration and the solid was washed thoroughly with water. This gray solid was dried under high vacuum to give 7.4 g of product (2S,4R)-1-(2-(3-Acetyl-5-bromo-1H-indol-1-yl)acetyl)-N-(3-chloro-2-fluorobenzyl)-4-fluoropyrrolidine-2-carboxamide (6e).

A mixture of 1 g of (2S,4R)-1-(2-(3-Acetyl-5-bromo-1H-indol-1-yl)acetyl)-N-(3-chloro-2-fluorobenzyl)-4-fluoropyrrolidine-2-carboxamide (6e), 0.419 g of tetrakis(triphenylphosphine)palladium(0), 0.138 g of cuprous iodide in DMF (10 mL) was deoxygenated by bubbling argon in a pressure vessel. Triethylamine (2.53 mL) and 2.56 mL of ethynyltrimethylsilane were added under argon. The pressure vessel was capped and heated at 100° C. overnight. Then the reaction mixture was cooled to RT and the solvent was removed under reduced pressure. The residue was purified by column chromatography over silica gel (eluent: 0-2% MeOH in $CH_2Cl_2$) to give 0.56 g of (2S,4R)-1-(2-(3-acetyl-5-((trimethylsilyl)ethynyl)-1H-indol-1-yl)acetyl)-N-(3-chloro-2-fluorobenzyl)-4-fluoropyrrolidine-2-carboxamide (6f) as a yellow solid.

Synthesized following the procedure of Kobayashi et al (Kobayashi et al, Org. Biomol. Chem. 2013, 11, 3773-3775) as described for 2. A flask was charged with 176 mg of CsF in anhydrous DMSO (5 mL) under $CO_2$ atmosphere. Then 0.55 g of 6f was added and stirred under CO$_2$ atmosphere in a balloon overnight at RT. The reaction mixture was diluted with water (30 mL) and extracted with dichloromethane. The aq. layer was acidified with aq. 6N HCl at 0° C. and extracted with EtOAc. Then the EtOAc layer was dried (Na$_2$SO$_4$) and concentrated. The residue was washed with dichloromethane to get 130 mg of 3-(3-Acetyl-1-(2-((2S, 4R)-2-((3-chloro-2-fluorobenzyl)carbamoyl)-4-fluoropyrrolidin-1-yl)-2-oxoethyl)-1H-indol-5-yl)propiolic acid (6) as light orange solid. $^1$H NMR (400 MHz, DMSO-d$_6$, 300 K): (major rotamer) δ 2.05-2.18 (m, 1H), 2.45 (s, 3H), 2.49-2.58 (m, 1H), 3.84-3.97 (m, 1H), 4.09-4.18 (m, 1H), 4.23-4.28 (m, 1H), 4.34-4.49 (m, 2H), 5.23 (d, J=17.2 Hz, 1H), 5.43 (d, J=17.2 Hz, 1H), 5.50 (d, J=52.4 Hz, 1H), 6.96 (t, J=7.6 Hz, 1H), 7.22 (t, J=6.4 Hz, 1H), 7.42-7.44 (m, 2H), 7.57 (d, J=8.4 Hz, 1H), 8.36 (s, 1H), 8.44 (d, J=1.2 Hz, 1H), 8.59 (t, J=6 Hz, 1H), 13.58 (brs, 1H). $^{19}$F NMR (376 MHz, DMSO-d$_6$, 300 K): (major rotamer) δ −121.7, −176.1. LC (method 1): $t_R$=1.26 min. LC/MS (EI) m/z: [M+H]$^+$ calcd for C$_{27}$H$_{22}$ClF$_2$N$_3$O$_5$, 542. found, 542.

Compound 8: (2S,4R)-1-(2-(3-acetyl-5-(3-(ethylsulfonamido)-3-oxoprop-1-yn-1-yl)-1H-indol-1-yl)acetyl)-N-(3-chloro-2-fluorobenzyl)-4-fluoropyrrolidine-2-carboxamide Scheme 4:

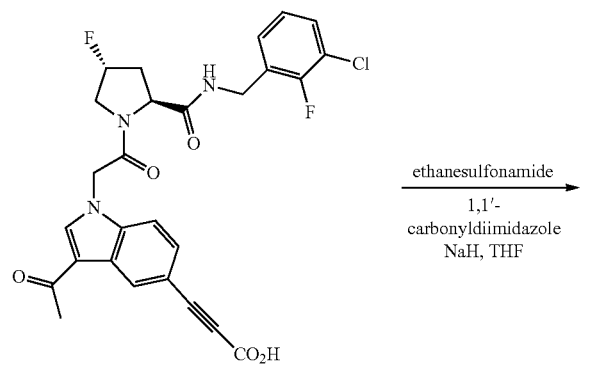

1,1'-Carbonyldiimidazole (20 mg) was added with stirring to a heterogeneous solution of 6 (50 mg) in THF (4 mL) and stirred overnight at room temperature.

In another round bottom flask, NaH (15 mg) was added portion-wise to an ice cooled solution of ethanesulfonamide (50 mg) in THF (2 mL). After the addition of NaH was complete, the cooling bath was removed and the reaction mixture was stirred at RT for 1 h. This sulfonamide anion was then added to the flask containing the activated ester of 6 drop-wise. The resulting reaction mixture was stirred overnight at RT and the volatiles were removed under reduced pressure. The residue was purified by chromatography over silica gel (eluent: 0-8.5% MeOH in dichloromethane). 10 mg of 8 was obtained as a light yellow solid.

$^1$H NMR (400 MHz, DMSO-d$_6$, 300 K): (major rotamer) δ 1.18-1.28 (m, 5H), 1.95-2.17 (m, 1H), 2.45 (s, 3H), 2.42-2.48 (m, 1H), 3.87-3.99 (m, 1H), 4.09-4.18 (m, 1H), 4.26 (dd, J=10, 5.6 Hz, 1H), 4.34-4.51 (m, 2H), 5.22 (d, J=17.2 Hz, 1H), 5.43 (d, J=17.2 Hz, 1H), 5.51 (d, J=52.4 Hz, 1H), 6.97 (t, J=4.8 Hz, 1H), 7.22 (t, J=7.2 Hz, 1H), 7.39-7.48 (m, 2H), 7.55 (d, J=8 Hz, 1H), 8.35 (s, 1H), 8.45 (brs, 1H), 8.59 (t, J=6 Hz, 1H). $^{19}$F NMR (376 MHz, DMSO-d$_6$, 300 K): (major rotamer) δ −121.7, −176.1. LC (method 1): $t_R$=1.73 min. LC/MS (EI) m/z: [M+H]$^+$ calcd for C$_{29}$H$_{72}$ClF$_2$N$_4$O$_6$S, 633. found 633.

Compound 9: (2S,4R)-1-(2-(3-Acetyl-5-(pyrimidin-2-ylethynyl)-1H-indol-1-yl)acetyl)-N-(3-chloro-2-fluorobenzyl)-4-fluoropyrrolidine-2-carboxamide Scheme 5:

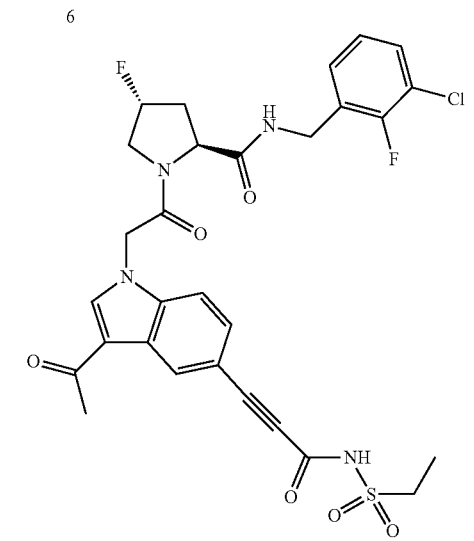

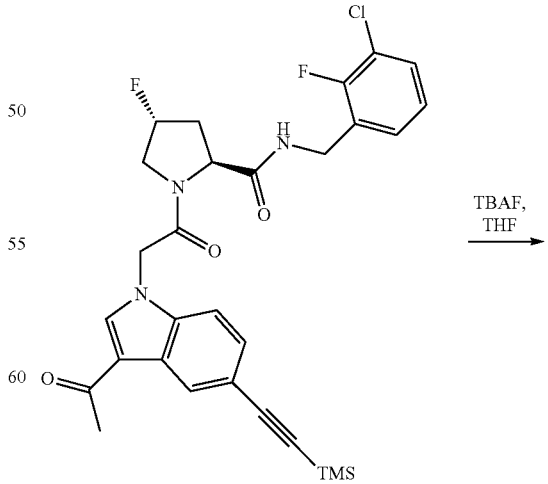

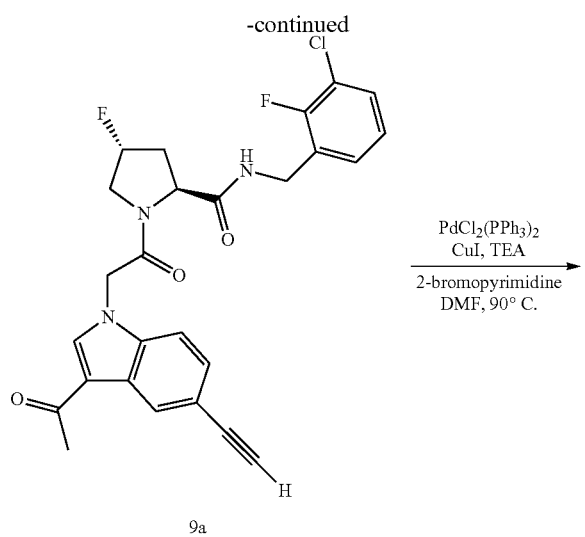

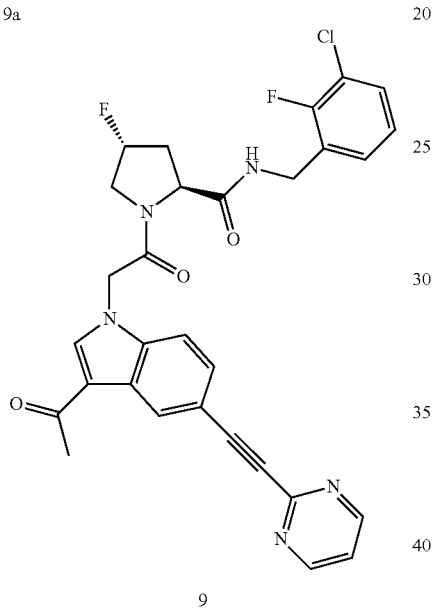

To a solution of (2S,4R)-1-(2-(3-Acetyl-5-((trimethylsilyl)ethynyl)-1H-indol-1-yl)acetyl)-N-(3-chloro-2-fluorobenzyl)-4-fluoropyrrolidine-2-carboxamide (6f, synthesized as described for compound 6, in scheme 3) (0.5 g) in THF (5 mL) was added 1.5 mL of 1.0 M tetrabutylammonium fluoride in THF at RT. The reaction mixture was stirred for 1 h. The solvent was removed under reduced pressure and the residue was purified by column chromatography over silica gel (eluent: 0-2% MeOH in $CH_2Cl_2$) to give 0.26 g of (2S, 4R)-1-(2-(3-acetyl-5-ethynyl-1H-indol-1-yl)acetyl)-N-(3-chloro-2-fluorobenzyl)-4-fluoropyrrolidine-2-carboxamide (9a) as a light yellow solid.

A mixture of 0.16 g of 2-bromopyrimidine, 0.141 g of $PdCl_2(PPh_3)_2$, 0.043 g of cuprous iodide in DMF (4 mL) was deoxygenated by bubbling argon in a pressure vessel. Triethylamine (2.0 mL) and 0.250 g of (2S,4R)-1-(2-(3-Acetyl-5-ethynyl-1H-indol-1-yl)acetyl)-N-(3-chloro-2-fluorobenzyl)-4-fluoropyrrolidine-2-carboxamide (9a) were added under argon. The pressure vessel was capped and heated at 90° C. overnight. Then the reaction mixture was cooled to RT and the solvent was removed under reduced pressure. The residue was purified by column chromatography over silica gel (eluent: 0-4.5% MeOH in $CH_2Cl_2$) to give 35 mg of the desired product (2S,4R)-1-(2-(3-Acetyl-5-(pyrimidin-2-ylethynyl)-1H-indol-1-yl)acetyl)-N-(3-chloro-2-fluorobenzyl)-4-fluoropyrrolidine-2-carboxamide (9) as a light orange solid. $^1$H NMR (400 MHz, DMSO-$d_6$, 300 K): (major rotamer) δ 1.99-2.18 (m, 1H), 2.46 (s, 3H), 3.92 (ddd, J=24.4, 12.4, 2.8 Hz, 1H), 4.26 (dd, J=12.8, 20.8 Hz, 1H), 4.32 (dd, J=28.4, 6.0 Hz, 1H), 4.39-4.49 (m, 2H), 5.24 (d, J=17.2 Hz, 1H), 5.45 (d, J=17.2 Hz, 1H), 5.51 (d, J=52.8 Hz, 1H), 6.96 (t, J=7.2 Hz, 1H), 7.23 (t, J=6.4 Hz, 1H), 7.40-7.51 (m, 4H), 7.59 (d, J=8.4 Hz, 1H), 8.36 (s, 1H), 8.47 (d, J=0.8 Hz, 1H), 8.61 (t, J=5.6 Hz, 1H), 8.85 (d, J=4.8 Hz, 2H). $^{31}$F NMR (376 MHz, DMSO-$d_6$, 300 K): (major rotamer) δ −121.7, −176.1. LC (method 1): $t_R$=1.74 min. LC/MS (EI) m/z: [M+H]$^+$ calcd for $C_{30}H_{24}ClF_2N_5O_3$, 576. found, 576.

Compound 10: (2S,4R)-1-(2-(3-acetyl-6-(3-(ethylsulfonamido)-3-oxoprop-1-yn-1-yl)-1H-indol-1-yl)acetyl)-N-(3-chloro-2-fluorobenzyl)-4-fluoropyrrolidine-2-carboxamide Scheme 6:

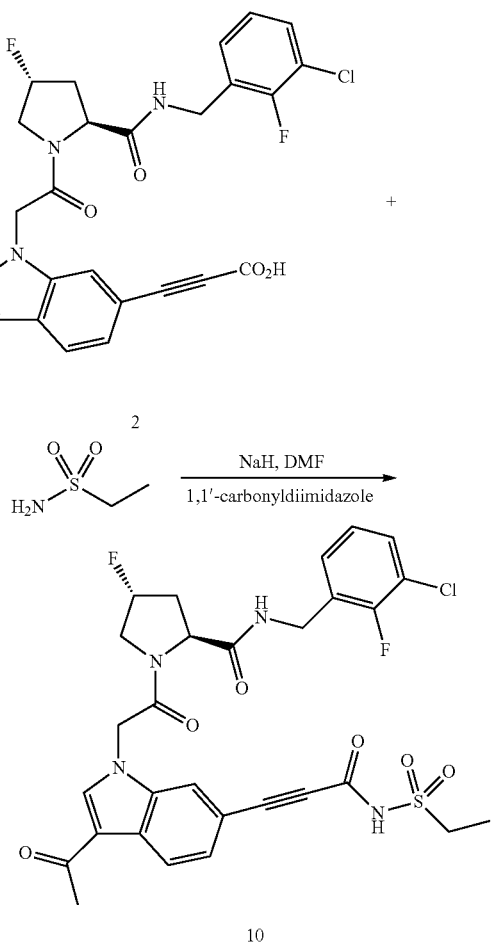

Compound 10 was synthesized using the procedure similar to the synthesis of compound 8. Thus, 100 mg of 2 in DMF was coupled with 93 mg of ethanesulfonamide using 45 mg of 1,1'-carbonyldiimidazole and 37 mg of NaH. The reaction mixture was poured into 50 mL of water and acidified with 2N aq. HCl. The separated solid was isolated by filtration, washed successively with water and tert-butyl-methyl ether. The solid was dried under high vacuum to yield 11 mg of 10 as brown solid.

$^1$H NMR (400 MHz, DMSO-$d_6$, 300 K): (major rotamer) δ 1.11-1.22 (m, 5H), 2.01-2.19 (m, 1H), 2.45 (s, 3H), 2.48-2.51 (m, 1H), 3.86-3.98 (m, 1H), 4.09-4.17 (m, 1H), 4.26 (dd, J=10, 6 Hz, 1H), 4.34-4.49 (m, 2H), 5.25 (d, J=17.2 Hz, 1H), 5.44 (d, J=17.2 Hz, 1H), 5.51 (d, J=53.2 Hz, 1H), 6.95 (t, J=8 Hz, 1H), 7.21 (t, J=6 Hz, 1H), 7.38-7.43 (m, 2H), 7.91 (s, 1H), 8.25 (d, J=8.4 Hz, 1H), 8.39 (s, 1H), 8.61 (t, J=5.6 Hz, 1H). $^{19}$F NMR (376 MHz, DMSO-$d_6$, 300 K): (major rotamer) δ −121.8, −176.0. LC (method 1): $t_R$=1.73 min. LC/MS (EI) m/z: [M+H]$^+$ calcd for $C_{29}H_{27}ClF_2N_4O_6S$, 633. found 633.

Compound 22: 1-(2-((2S,4R)-2-((2'-chloro-2-fluoro-[1,1'-biphenyl]-3-yl)carbamoyl)-4-fluoropyrrolidin-1-yl)-2-oxoethyl)-5-(pyrimidin-2-ylethynyl)-1H-indazole-3-carboxamide Compound 22c was prepared following similar procedure to the synthesis of 6f. 7.0 g of 22b was coupled with 28 mL of trimethylsilylacetylene using 4.69 g of Pd(PPh$_3$)$_4$, 1.5 g of cuprous iodide and 28 mL of triethylamine in 70 mL of DMF at 100° C. overnight. After removal of the solvent, the crude product was purified by column chromatography over silica gel (eluent: 0-1% MeOH in dichloromethane) to get 15 g of 22c.

Compound 22d was synthesized following the same procedure as for the synthesis of 9a. So, 1.6 g of 22c was deprotected using 3.0 mL of 1.0 M TBAF in THF at 0° C. for 15 min. Crude product was purified by chromatography over silica gel (eluent: 0-2.5% MeOH in dichloromethane) to get 1.09 g of 22d as cream-colored solid.

A mixture of 0.31 g of 2-bromopyrimidine, 0.282 g of PdCl$_2$(PPh$_3$)$_2$, 0.086 g of cuprous iodide in DMF (4 mL) was deoxygenated by bubbling argon in a pressure vessel. Triethylamine (1.5 mL) and 0.3 g of 22d were added under argon. The pressure vessel was capped and heated at 90° C.

Scheme 7:

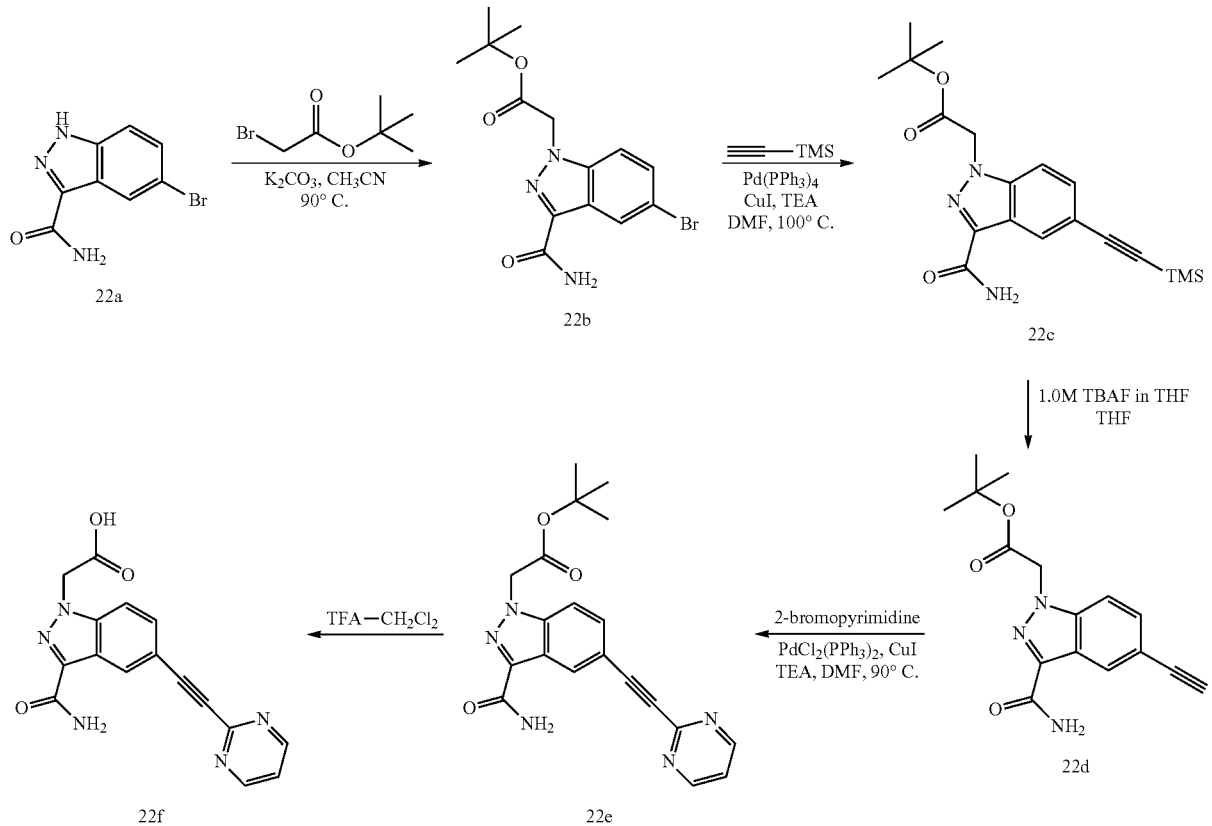

Compound 22b was prepared using the procedure similar to the synthesis of 6c. Thus, 23.5 g of 22a was coupled with 17.3 mL of tert-butyl bromoacetate using 32.5 g of potassium carbonate in 470 mL of acetonitrile at 90° C. for 3 h. Then the solvent was removed and water was added to the residue. The product was isolated by filtration, washed with water and dried. Finally, the product was washed with 2:1 mixture of tert-butylmethyl ether and heptane to get 29 g of 22b.

overnight. Then the reaction mixture was cooled to RT and the solvent was removed under reduced pressure. The residue was purified by column chromatography over silica gel (eluent: 0-2% MeOH in CH$_2$Cl$_2$) to give 0.15 g of the desired product tert-butyl 2-(3-carbamoyl-5-(pyrimidin-2-ylethynyl)-1H-indazol-1-yl)acetate (22e) light orange solid.

A solution of 1.81 g of 22e in CH$_2$Cl$_2$ (3 mL) and TFA (3 mL) was stirred for 2 h at RT. Then the volatiles were removed under reduced pressure. The residue 2-(3-Carbamoyl-5-(pyrimidin-2-ylethynyl)-1H-indazol-1-yl)acetic acid, 22f, was used as such for the next step.

Scheme 8:

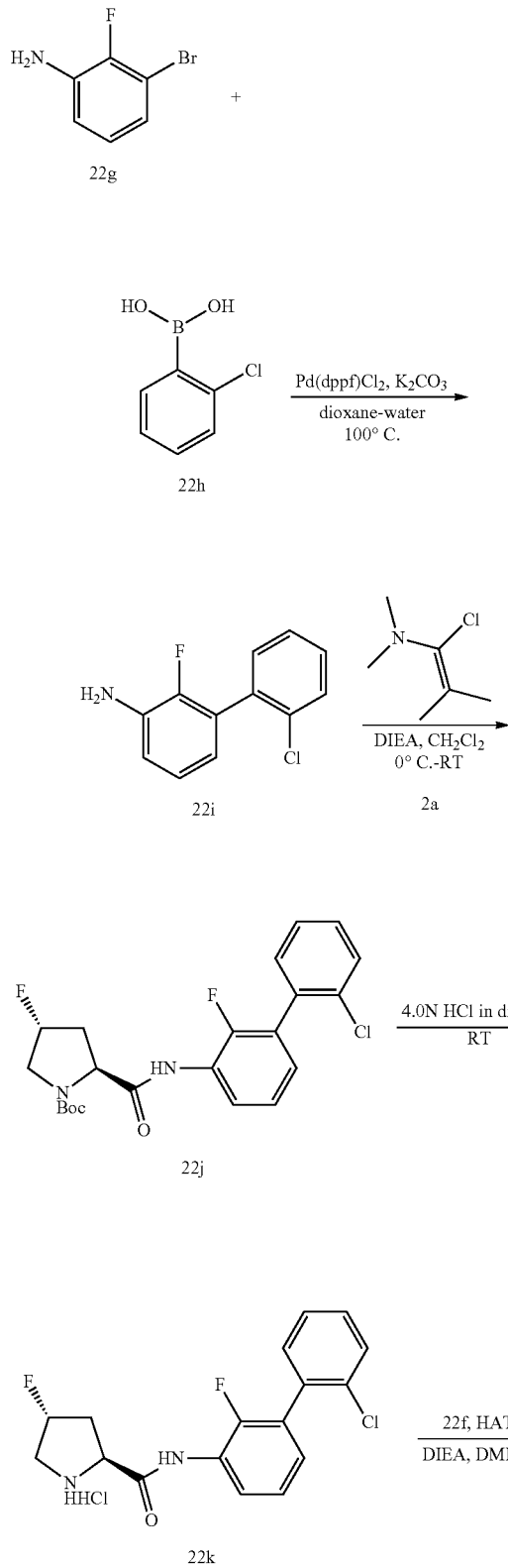

-continued

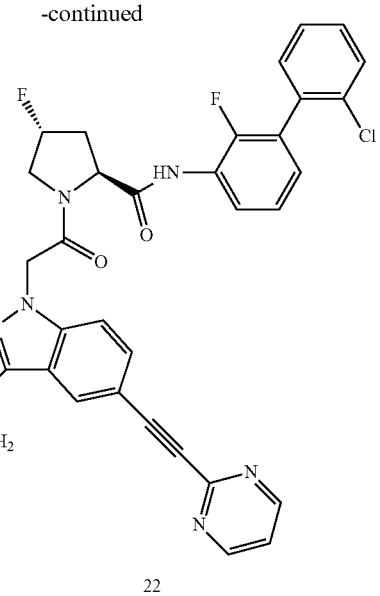

22

3-Bromo-2-fluoroaniline (22g, 30 g) and 2-chlorophenylboronic acid, 22h (61.75 g), Pd(dppf)Cl$_2$ (19.25 g) and K$_2$CO$_3$ (91 g) were taken in a round bottom flask kept under argon. 400 mL of dioxane and 100 mL of water were added to this mixture. The mixture was bubbled with argon for 5 min and heated with stirring at 100° C. overnight. Then the reaction mixture was filtered through a Celite® pad and the filtrate was concentrated under reduced pressure. The residue was purified by chromatography over silica gel (eluent: 0-0.5% MeOH in CH$_2$Cl$_2$) to get a white oil. 300 mL of saturated HCl in methanol was added to this oil and the solvent was evaporated to get 30 g of the hydrochloride salt of 22i as white solid.

To an ice cold solution of (2S,4R)-1-(tert-butoxycarbonyl)-4-fluoropyrrolidine-2-carboxylic acid (2a, 24.64 g) in 600 mL of CH$_2$Cl$_2$, Ghosez's reagent (15.4 mL) was added drop-wise with stirring. The stirring was continued for 3 h. at same temperature. Then solid hydrochloride salt of 22i (30 g) was added, followed by 55.2 mL of DIEA (3 equiv.). The cooling bath was removed and the reaction mixture was stirred overnight at RT. The solvent was co-evaporated with 30 mL of MeOH. The crude product was purified by chromatography over silica gel (eluent: 10-50% CH$_2$Cl$_2$ in hexanes, then dichloromethane) to get 37 g of 22j as white solid.

A solution of 35.6 g of compound 22j in 400 mL of 4.0 N HCl in dioxane was stirred at RT for 4 h. The thick heterogeneous mixture was then concentrated under reduced pressure. The residue was sonicated with 350 mL of dichloromethane and filtered and the solid washed with 250 mL of dichloromethane. The isolated solid was dried under high vacuum to get 29.2 g of 22k as white solid.

Compound 22f from above and 1.69 g of 22k were taken in 20 mL of DMF. 4 mL of DIEA was added to this reaction mixture and cooled in an ice bath. HATU (2.09 g) was added to this cooled solution. After the addition of HATU, the cooling bath was removed and the reaction mixture was stirred at RT for 1 h. DMF was removed under reduced pressure and the residue was purified by chromatography over silica gel (eluent: 0-2.5% MeOH in dichloromethane) to get 2.46 g of 1-(2-((2S,4R)-2-((2'-chloro-2-fluoro-[1,1'- biphenyl]-3-yl)carbamoyl)-4-fluoropyrrolidin-1-yl)-2-oxo-ethyl)-5-(pyrimidin-2-ylethynyl)-1H-indazole-3-carboxamide (22).

$^1$H NMR (400 MHz, DMSO-d$_6$, 300 K): (major rotamer) δ 2.08-2.29 (m, 1H), 2.55-2.63 (m, 1H), 3.90-4.03 (m, 1H), 4.24 (dd, J=21.6, 12 Hz, 1H), 4.78 (t, J=8.4 Hz, 1H), 5.56 (d, J=52.8 Hz, 1H), 5.53 (d, J=17.2 Hz, 1H), 5.74 (d, J=17.2 Hz, 1H), 7.07 (t, J=8 Hz, 1H), 7.23 (t, J=8 Hz, 1H), 7.37-7.54 (m, 5H), 7.58-7.61 (m, 1H), 7.65 (dd, J=8.8, 1.6 Hz, 1H), 7.77 (dd, J=8.8, 0.4 Hz, 1H), 7.79 (brs, 1H), 7.97 (t, J=6.8 Hz, 1H), 8.48 (d, J=2.4 Hz, 1H), 8.87 (d, J=4.8 Hz, 2H), 9.99 (s, 1H). $^{19}$F NMR (376 MHz, DMSO-d$_6$, 300 K): (major rotamer) δ −126.6,−175.8. LC (method 1): t$_R$=1.99 min. LC/MS (EI) m/z: [M+H]$^+$ calcd for C$_{33}$H$_{24}$ClF$_2$N$_7$O$_3$, 640. found 640.

Compound 27: 1-(2-(((1R,3S,5R)-3-((2'-Chloro-2-fluoro-[1,1'-biphenyl]-3-yl)carbamoyl)-2-azabicyclo[3.1.0]hexan-2-yl)-2-oxoethyl)-5-(pyrimidin-2-yl-ethynyl)-1H-indazole-3-carboxamide Scheme 9:

Scheme 10:

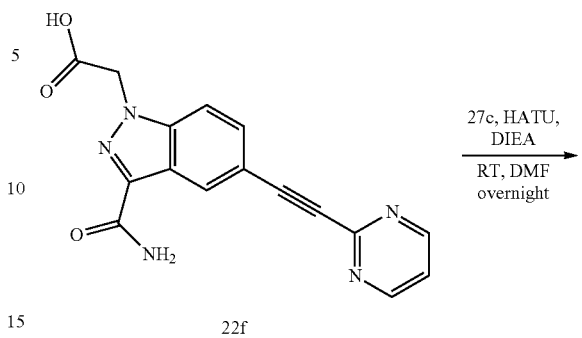

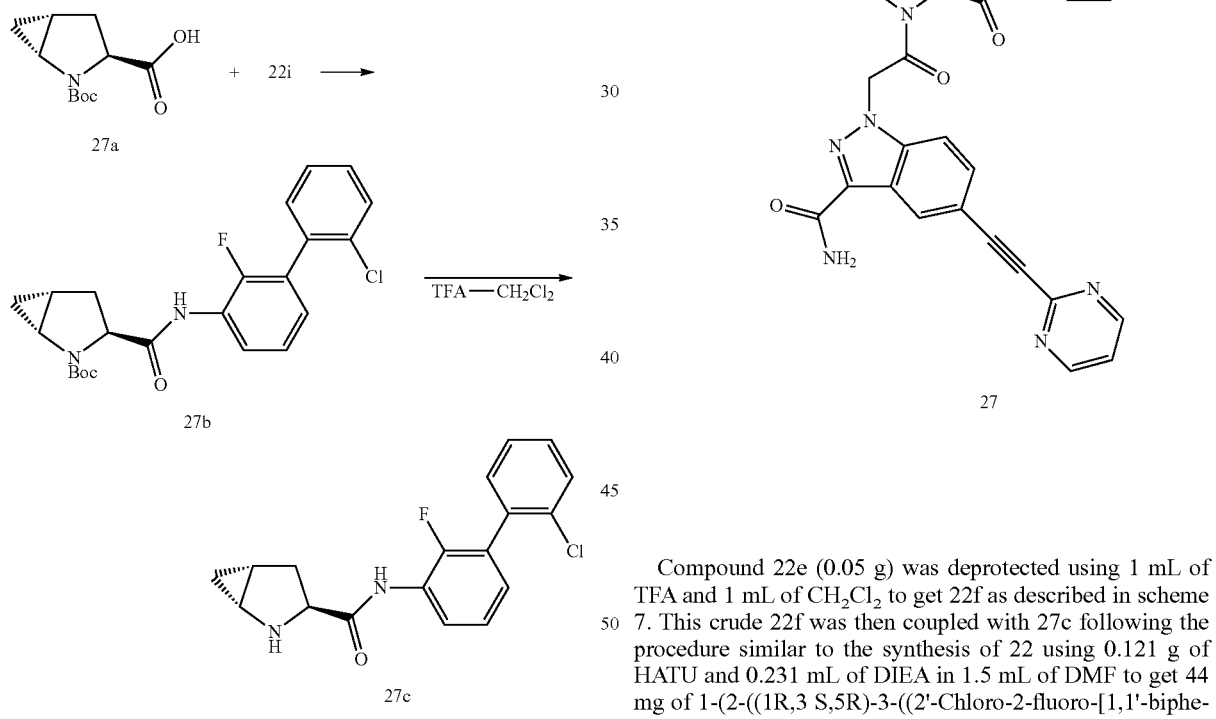

(1R,3S,5R)-2-(tert-butoxycarbonyl)-2-azabicyclo[3.1.0]hexane-3-carboxylic acid (27a) was coupled with 22i using Ghosez's reagent as described in synthesis of 22j (scheme 8). Thus, 0.2 g of 27a was coupled with 0.249 g of hydrochloride salt of 22i using 0.128 mL of Ghosez's reagent to get 0.3 g of 27b as colorless solid.

A solution of 0.114 g of 27b in CH$_2$Cl$_2$ (1.0 mL) and TFA (1.0 mL) was stirred for 30 min. Then the volatiles were removed under reduced pressure. The residue, 27c, was used as such for the next step.

Compound 22e (0.05 g) was deprotected using 1 mL of TFA and 1 mL of CH$_2$Cl$_2$ to get 22f as described in scheme 7. This crude 22f was then coupled with 27c following the procedure similar to the synthesis of 22 using 0.121 g of HATU and 0.231 mL of DIEA in 1.5 mL of DMF to get 44 mg of 1-(2-(((1R,3 S,5R)-3-((2'-Chloro-2-fluoro-[1,1'-biphenyl]-3-yl)carbamoyl)-2-azabicyclo[3.1.0]hexan-2-yl)-2-oxoethyl)-5-(pyrimidin-2-ylethynyl)-1H-indazole-3-carboxamide (27) as white solid.

$^1$H NMR (400 MHz, CD$_3$OD, 300 K): (major rotamer) δ 0.649 (br, 1H), 1.09-1.12 (m, 1H), 2.02-2.07 (m, 1H), 2.41-2.58 (m, 2H), 3.69-3.77 (m, 1H), 4.65 (dd, J=8.8, 4.8 Hz, 1H), 5.67 (d, J=17.2 Hz, 1H), 5.78 (d, J=17.2 Hz, 1H), 7.09 (t, J=7.2 Hz, 1H), 7.22 (t, J=8 Hz, 1H), 7.30-7.36 (m, 3H), 7.41 (t, J=5.2 Hz, 1H), 7.47-7.49 (m, 1H), 7.69 (dd, J=18, 8.8 Hz, 2H), 7.97 (t, J=7.6 Hz, 1H), 8.57 (s, 1H), 8.84 (d, J=5.2 Hz, 2H). $^{19}$F NMR (376 MHz, CD$_3$OD, 300 K): (major rotamer) δ −128.8. LC (method 1): t$_R$=2.10 min. LC/MS (EI) m/z: [M+H]$^+$ calcd for C$_{34}$H$_{25}$ClFN$_7$O$_3$, 634. found 634.

Compound 28: 1-(2-((2S,4R)-2-((3-(3-chloropyridin-2-yl)-2-fluorophenyl)carbamoyl)-4-fluoropyrrolidin-1-yl)-2-oxoethyl)-5-(pyrimidin-2-ylethynyl)-1H-indazole-3-carboxamide Scheme 11:

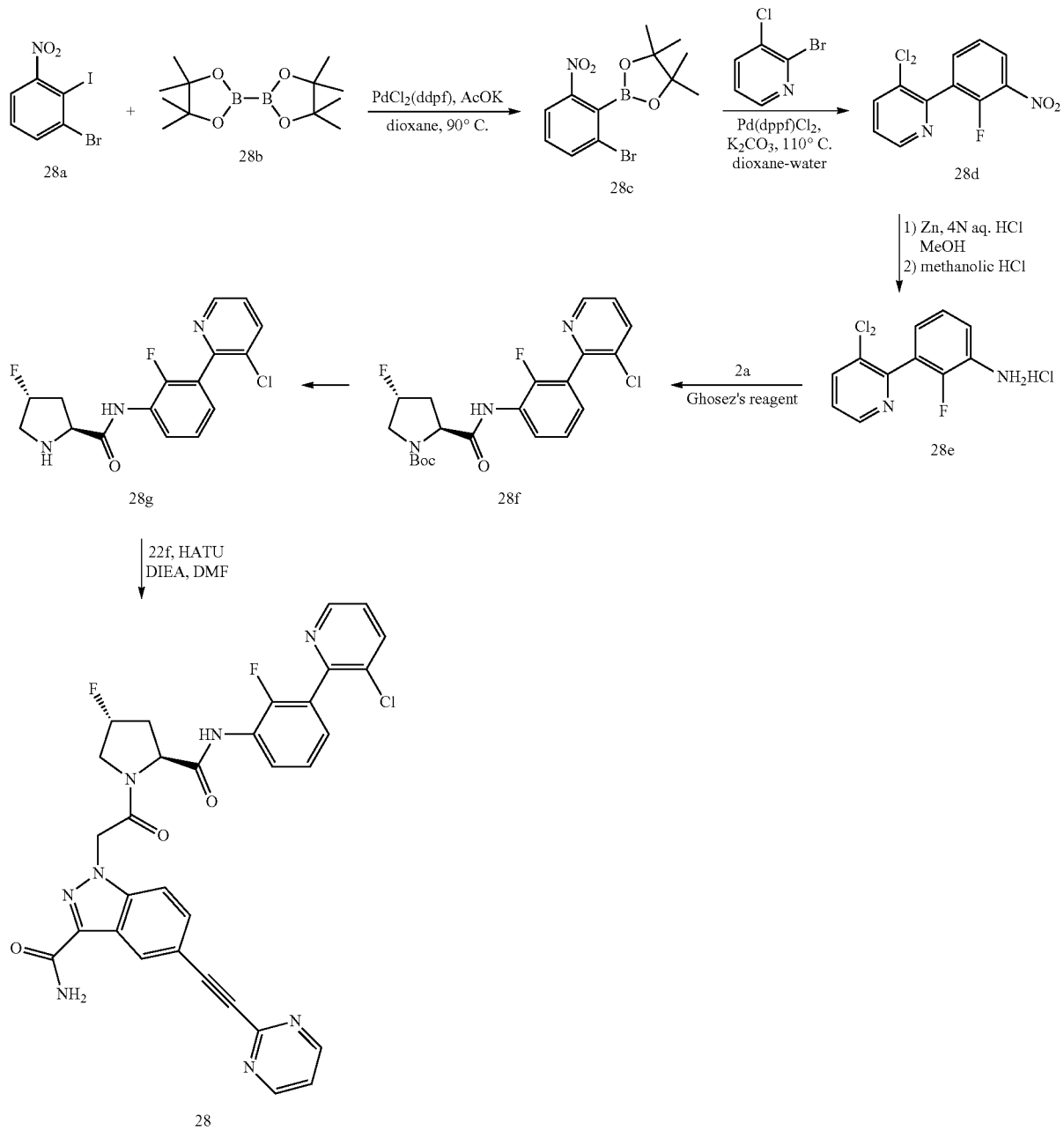

A mixture of 2.5 g of nitrobromide (28a), 7.21 g of bis(pinacolato)diboron, 1.24 g of PdCl₂(dppf), 3.35 g of potassium acetate in dioxane (25 mL) was deoxygenated by bubbling argon in a pressure vessel. The pressure vessel was capped and heated at 90° C. overnight. Then the reaction mixture was cooled to RT and the solvent was removed under reduced pressure. The residue was diluted with dichloromethane and water. The organic layer was dried (Na₂SO₄) and concentrated. The crude product was purified by chromatography over silica gel (eluent: 20% EtOAc in hexanes) to get 2.94 g of 28c.

Same procedure as for the synthesis of 22i was followed, except that the reaction mixture was heated at 110° C. for 2 days. Thus, 2.8 g of 28c was coupled with 2.02 g of 2-bromo-2-chloropyridine using 85 mg of Pd(dppf)Cl₂ and 3.63 g of potassium carbonate in dioxane-water. Purification of crude product by chromatography over silica gel gave 2.25 g of 28d.

Compound 28d (2.25 g) was taken in 1:1 mixture of MeOH-4 N aq. HCl (60 mL) and 5.8 g of Zn powder was added to this reaction mixture. This heterogeneous reaction mixture was stirred overnight at RT. Finally, the reaction mixture was carefully neutralized with sat. aq. NaHCO$_3$, the volatiles were removed under reduced pressure and the residue was extracted with EtOAc. Then the organic layer was dried (Na$_2$SO$_4$) and concentrated. The crude product was purified by chromatography over silica gel and the product was dissolved in methanolic HCl and taken to dryness to get 2.2 g of 28e.

(2S,4R)-1-(tert-butoxycarbonyl)-4-fluoropyrrolidine-2-carboxylic acid (2a) was coupled with amine 28e using Ghosez's reagent following procedure described for synthesis of 22j (scheme 8). Thus, 0.249 g of compound 2a was coupled with 0.292 g of amine 28e using 0.145 mL of Ghosez's reagent, after chromatographic purification, to get 0.286 g of 28f.

fluoropyrrolidin-1-yl)-2-oxoethyl)-5-(pyrimidin-2-ylethynyl)-1H-indazole-3-carboxamide (28).
$^1$H NMR (400 MHz, DMSO-d$_6$, 300 K): (major rotamer) δ 2.12-2.29 (m, 1H), 2.58-2.63 (m, 1H), 3.90-4.02 (m, 1H), 4.23 (dd, J=21.6, 12.4 Hz, 1H), 4.76 (t, J=8 Hz, 1H), 5.53 (d, J=17.6 Hz, 1H), 5.55 (d, J=52.8 Hz, 1H), 5.73 (d, J=17.6 Hz, 1H), 7.18 (t, J=6.8 Hz, 1H), 7.25 (t, J=8 Hz, 1H), 7.49-7.53 (m, 3H), 7.63 (d, J=8.8 Hz, 1H), 7.77 (d, J=8.8 Hz, 1H), 7.78 (brs, 1H), 8.08 (d, J=8 Hz, 1H), 8.25 (brs, 1H), 8.46 (s, 1H), 8.64 (d, J=4.8 Hz, 1H), 8.86 (d, J=4.8 Hz, 2H), 10.01 (s, 1H). $^{19}$F NMR (376 MHz, DMSO-d$_6$, 300 K): (major rotamer) δ -126.9, -175.9. LC (method 1): t$_R$=1.54 min. LC/MS (EI) m/z: [M+H]$^+$ calcd for C$_{32}$H$_{23}$ClF$_2$N$_8$O$_3$, 641. found 641.

Compound 39: 1-(2-((2S,4R)-2-((6-bromopyridin-2-yl)carbamoyl)-4-fluoropyrrolidin-1-yl)-2-oxoethyl)-5-(pyrimidin-2-ylethynyl)-1H-indazole-3-carboxamide

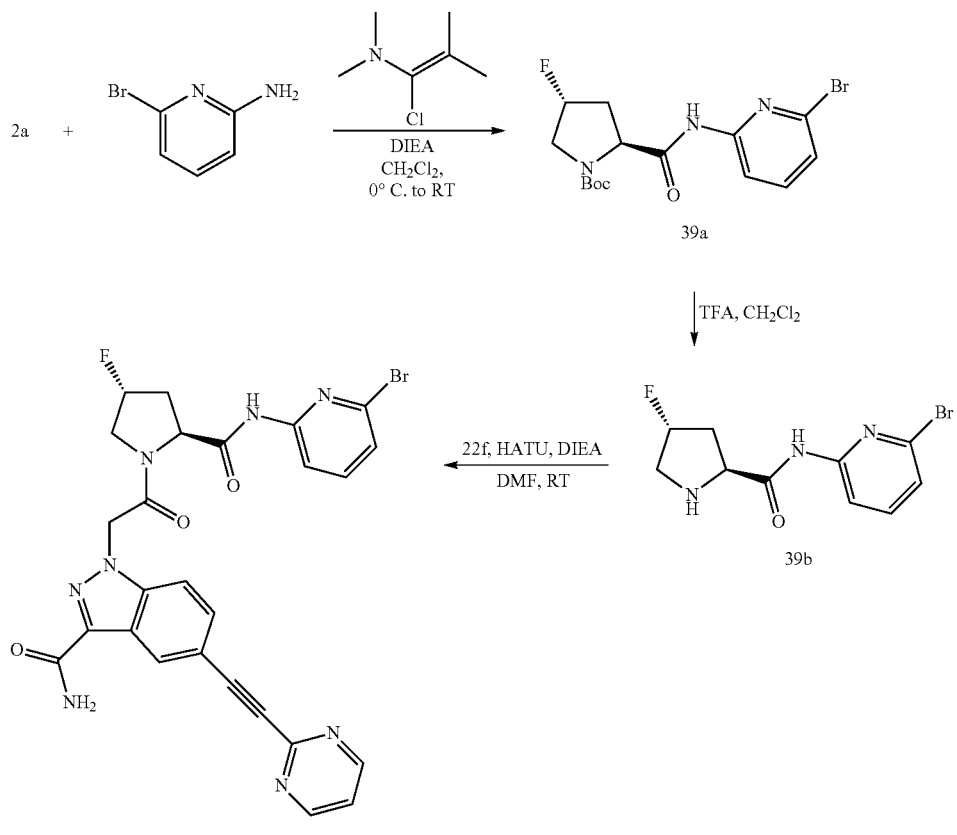

Scheme 12:

Compound 28f (0.286 g) was deprotected using 3 mL of TFA and 3 mL of dichloromethane to get 28g. Similarly, 0.240 g of 22e was hydrolyzed using 3 mL of TFA and 3 mL of dichloromethane to get crude 22f. Finally 22f was coupled with 28g as described for the synthesis of 22 using 0.298 g of HATU and 1 mL of DIEA in 5 mL of DMF. After the removal of DMF, the residue was purified by chromatography over silica gel (eluent: 0-3% MeOH in dichloromethane) to get 200 mg of 1-(2-((2 S,4R)-2-((3-(3-chloropyridin-2-yl)-2-fluorophenyl)carbamoyl)-4-

2-Amino-6-bromopyridine (0.191 g) was coupled with 0.23 g of trans-fluoroproline 2a using 0.146 mL of Ghosez's reagent in presence of 0.522 ml of DIEA following the procedure used for the synthesis of 22j. Crude product was purified by chromatography over silica gel (eluent: 0-0.1% MeOH in dichloromethane) to get 0.2 g of 39a as white solid.

0.05 g of 22e and 65 mg of 39a were deprotected following procedure described for compound 22 (schemes 7 and 8). Coupling was done using the same procedure that was used for the synthesis of 22. Crude product was purified by chromatography over silica gel (eluent: 0-4% MeOH in dichloromethane) gave 50 mg of 1-(2-((2S,4R)-2-((6-bromopyridin-2-yl)carbamoyl)-4-fluoropyrrolidin-1-yl)-2-oxoethyl)-5-(pyrimidin-2-ylethynyl)-1H-indazole-3-carboxamide (39) as cream colored solid.

$^1$H NMR (400 MHz, CD$_3$OD, 300 K): (major rotamer) δ 2.16-2.37 (m, 1H), 2.68-2.73 (m, 1H), 3.95-4.09 (m, 1H), 4.17-4.30 (m, 1H), 4.76 (t, J=8.4 Hz, 1H), 5.49 (d, J=52 Hz, 1H), 5.49 (d, J=17.2 Hz, 1H), 5.64 (d, J=17.2 Hz, 1H), 7.27 (d, J=7.6 Hz, 1H), 7.47 (t, J=4.8 Hz, 1H), 7.61 (t, J=8 Hz, 1H), 7.71 (s, 2H), 8.08 (d, J=8 Hz, 1H), 8.59 (s, 1H), 8.82 (d, J=4.8 Hz, 1H). $^{19}$F NMR (376 MHz, CD$_3$OD, 300 K): (major rotamer) δ −178.6. LC (method 1): $t_R$=1.48 min. LC/MS (EI) m/z: [M+]+ calcd for C$_{26}$H$_2$O BrFN$_8$O$_3$, 591. found 591.

Compound 41: 1-(2-((1R,3S,5R)-3-((6-bromopyridin-2-yl)carbamoyl)-2-azabicyclo[3.1.0]hexan-2-yl)-2-oxoethyl)-5-(pyrimidin-2-ylethynyl)-1H-indazole-3-carboxamide 1.5 g of 27a was coupled with 1.26 g of 2-amino-6-bromopyridine using 961 μL of Ghosez's reagent as described for the synthesis of 22j. Crude product was purified by chromatography over silica gel (eluent: 0-0.1% MeOH in dichloromethane) to get 1.5 g of 41a as a white solid.

Compound 22e (0.05 g) and 56 mg of 41a were deprotected as described for compound 22 (scheme 7& 8). Coupling was done using the same procedure that was used for the synthesis of 22. Crude product was purified by chromatography over silica gel (eluent: 0-3% MeOH in dichloromethane) to get 50 mg of 1-(2-((1R,3S,5R)-3-((6-bromopyridin-2-yl)carbamoyl)-2-azabicyclo[3.1.0]hexan-2-yl)-2-oxoethyl)-5-(pyrimidin-2-ylethynyl)-1H-indazole-3-carboxamide (41) as white solid. $^1$H NMR (400 MHz, DMSO-d$_6$, 300 K): (major rotamer) δ 0.76 (brs, 1H), 0.99-1.05 (m, 1H), 1.86-1.92 (m, 1H), 2.07-2.29 (m, 2H), 3.80 (br, 1H), 4.45 (dd, J=8.8, 5.2 Hz, 1H), 5.54 (d, J=17.2 Hz, 1H), 5.87 (d, J=17.2 Hz, 1H), 7.32 (d, J=8 Hz, 1H), 7.50-7.53 (m, 2H), 7.68 (d, J=9.2 Hz, 1H), 7.72 (d, J=7.6 Hz, 1H), 7.79 (d, J=8.8 Hz, 2H), 8.02 (d, J=8 Hz, 1H), 8.46 (s, 1H), 8.85 (d, J=4.8 Hz, 2H), 10.76 (s, 1H). LC (method 1): $t_R$=1.60 min. LC/MS (EI) m/z: [M+]+ calcd for C$_{27}$H$_{21}$BrFN$_8$O$_3$, 585. found 585.

Scheme 13:

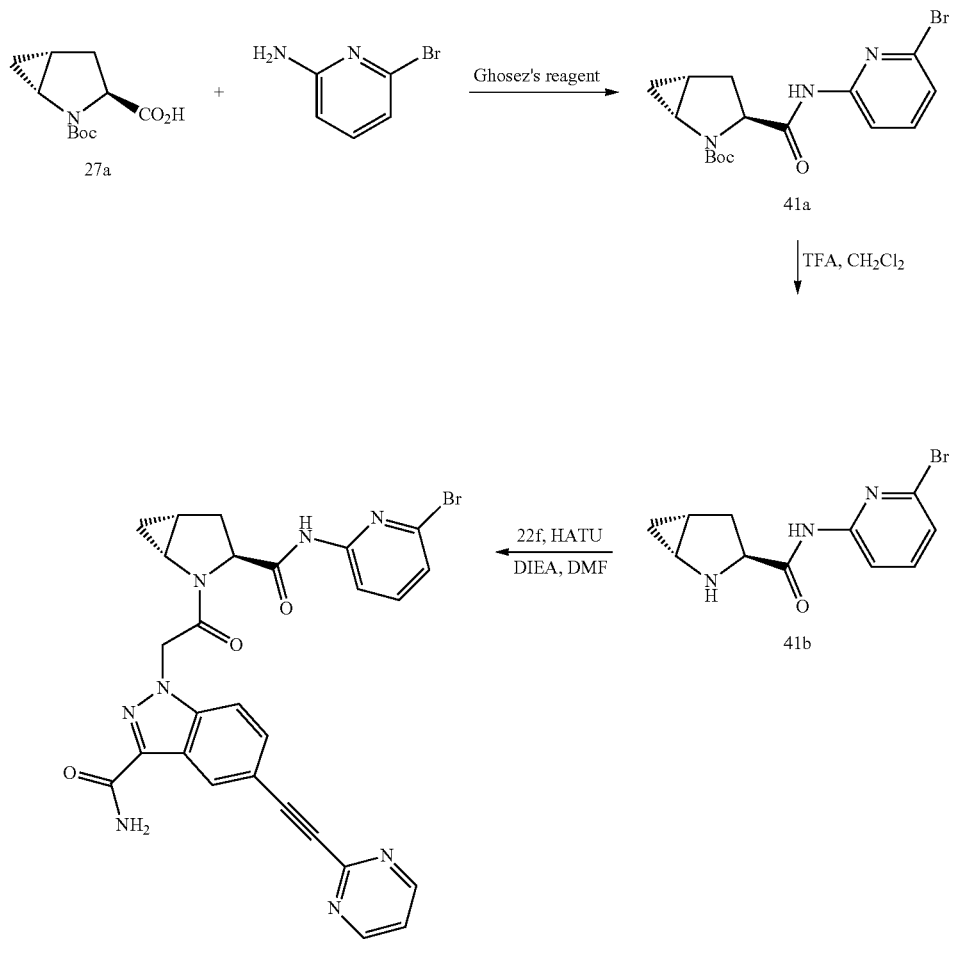

41

121

Compound 46: 1-(2-((2S,4R)-2-((6-bromopyridin-2-yl)carbamoyl)-4-fluoropyrrolidin-1-yl)-2-oxoethyl)-5-((5-fluoropyrimidin-2-yl)ethynyl)-1H-indazole-3-carboxamide Scheme 14:

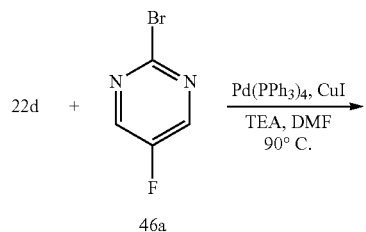

22d +  → (Pd(PPh₃)₄, CuI, TEA, DMF, 90° C.)

46a

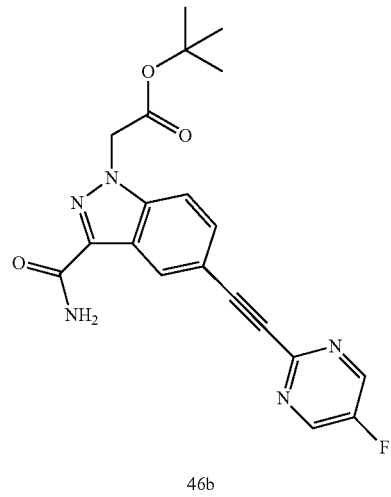

46b

TFA, CH₂Cl₂ →

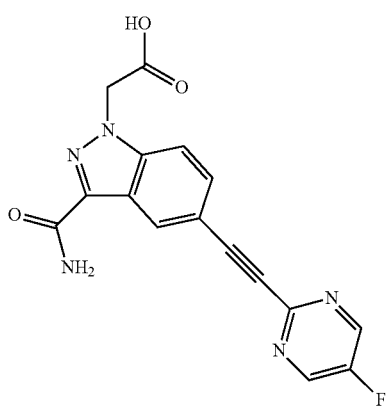

46c

↓ 39b, HATU DIEA, DMF

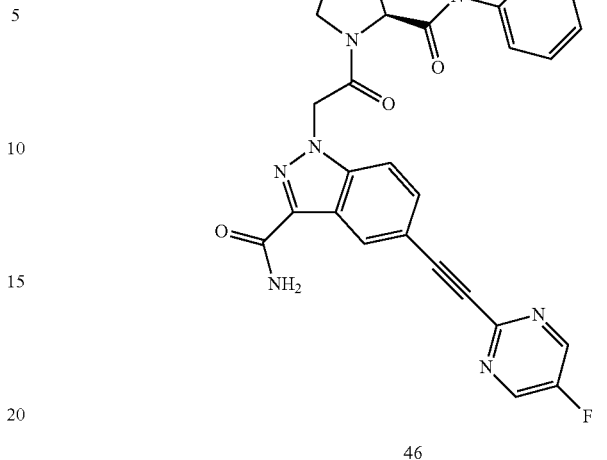

46

Procedure similar to the synthesis of 22e was followed. Thus, 0.1 g of 22d was coupled with 0.592 g of bromopyrimidine 46a in presence of 77 mg of Pd(PPh₃)₄, 25 mg of CuI and 0.245 mL of TEA in 2 mL of DMF at 90° C. Crude product was purified by chromatography over silica gel (eluent: 0-2% MeOH in dichloromethane) to get 0.13 g of 46b as cream colored solid.

Compound 46b (31 g) and 37 mg of 39a were deprotected as described for compound 22 (scheme 7&8). Coupling was done using the same procedure that was used for the synthesis of 22. Crude product was purified by chromatography over silica gel (eluent: 0-2.5% MeOH in dichloromethane) to get 36 mg of 1-(2-((2S,4R)-2-((6-bromopyridin-2-yl)carbamoyl)-4-fluoropyrrolidin-1-yl)-2-oxoethyl)-5-((5-fluoropyrimidin-2-yl)ethynyl)-1H-indazole-3-carboxamide (46) as white solid.

$^1$H NMR (400 MHz, DMSO-$d_6$, 300 K): (major rotamer) δ 2.03-2.23 (m, 1H), 2.52-2.56 (m 1H), 3.88-4.03 (m, 1H), 4.21 (dd, J=22.4, 12.8 Hz, 1H), 4.66 (t, J=8 Hz, 1H), 5.53 (d, J=52.8 Hz, 1H), 5.52 (d, J=17.2 Hz, 1H), 5.73 (d, J=17.2 Hz, 1H), 7.33 (d, J=7.6 Hz, 1H), 7.53 (s, 1H), 7.66-7.69 (m, 1H), 7.72 (d, J=8 Hz, 1H), 7.78 (d, J=8 Hz, 1H), 7.84 (s, 1H), 8.02 (d, J=8 Hz, 1H), 8.45 (s, 1H), 8.96 (d, J=0.8 Hz, 2H), 11.02 (s, 1H). $^{19}$F NMR (376 MHz, DMSO-$d_6$, 300 K): (major rotamer) δ −135.7, −175.7. LC (method 1): $t_R$=1.69 min. LC/MS (EI) m/z: [M+H]$^+$ calcd for $C_{26}H_{19}BrF_2N_6O_3$, 609. found 609.

Compound 49: 1-(2-((2S,4R)-2-((2'-chloro-2,4'-difluoro-[1,1'-biphenyl]-3-yl)carbamoyl)-4-fluoropyrrolidin-1-yl)-2-oxoethyl)-5-(pyrimidin-2-ylethynyl)-1H-indazole-3-carboxamide Scheme 15:

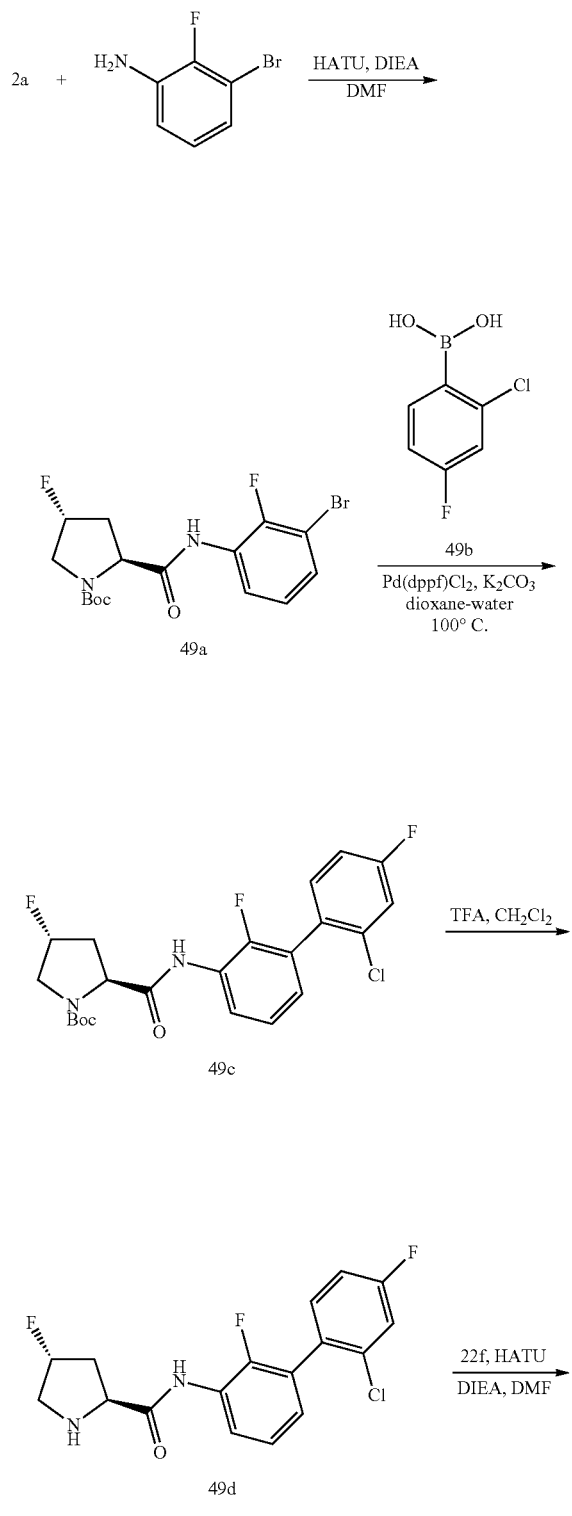

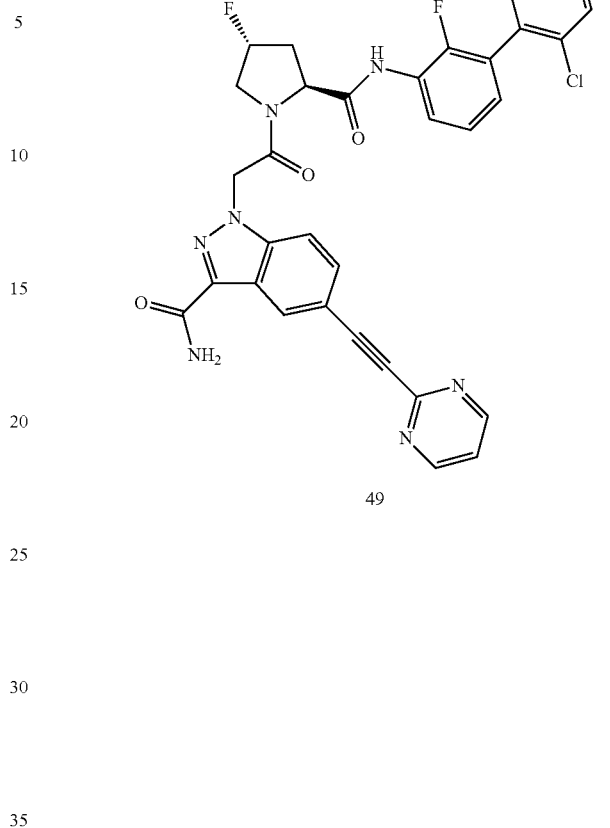

Same procedure as for the synthesis of 2c in scheme 1 was followed. Thus, 1.0 g of 3-bromo-2-fluoroaniline was coupled with 1.35 g of trans-fluoroproline 2a in presence of 2.4 g of HATU in DMF to get 0.695 g of 49a.

Prepared following the procedure for the synthesis of 22i (scheme 8). Thus, 0.3 g of 49a was coupled with 0.387 g of boronic acid 49b using 0.108 g of Pd(dppf)Cl$_2$ and 0.512 g of K$_2$CO$_3$ in dioxane-water to get 280 mg of 49c.

0.150 g of 49c and 0.137 g of 22e were deprotected as described in synthesis of compound 22 (schemes 7, 8). Coupling was done using the same procedure that was used for the synthesis of 22 to get 1-(2-((2S,4R)-2-((2'-Chloro-2,4'-difluoro-[1,1'-biphenyl]-3-yl)carbamoyl)-4-fluoropyrrolidin-1-yl)-2-oxoethyl)-5-(pyrimidin-2-ylethynyl)-1H-indazole-3-carboxamide (49). $^1$H NMR (400 MHz, DMSO-d$_6$, 300 K): (major rotamer) δ 2.11-2.28 (m, 1H), 2.53-2.60 (m, 1H), 3.89-4.02 (m, 1H), 4.23 (dd, J=21.6, 12.8 Hz, 1H), 4.77 (t, J=8.4 Hz, 1H), 5.55 (d, J=52.4 Hz, 1H), 5.52 (d, J=17.2 Hz, 1H), 5.73 (d, J=17.2 Hz, 1H), 7.06 (t, J=7.2 Hz, 1H), 7.22 (t, J=8 Hz, 1H), 7.42-7.46 (m, 1H), 7.52 (t, J=4.8 Hz, 1H), 7.57-7.66 (m, 4H), 7.76 (d, J=9.2 Hz, 1H), 7.78 (s, 1H), 7.97 (t, J=7.6 Hz, 1H), 8.46 (s, 1H), 8.86 (d, J=4.8 Hz, 2H), 9.99 (s, 1H). $^{19}$F NMR (376 MHz, DMSO-d$_6$, 300 K): (major rotamer) δ -111.6, -126.7, -175.9. LC (method 1): $t_R$=2.04 min. LC/MS (EI) m/z: [M+H]$^+$ calcd for $C_{33}H_{23}ClF_3N_7O_3$, 658. found 658.

Compound 64: 1-(2-((1R,3S,5R)-3-((2'-chloro-2,4'-difluoro-[1,1'-biphenyl]-3-yl)carbamoyl)-2-azabicyclo[3.1.0]hexan-2-yl)-2-oxoethyl)-5-((5-fluoropyrimidin-2-yl)ethynyl)-1H-indazole-3-carboxamide
Scheme 16:
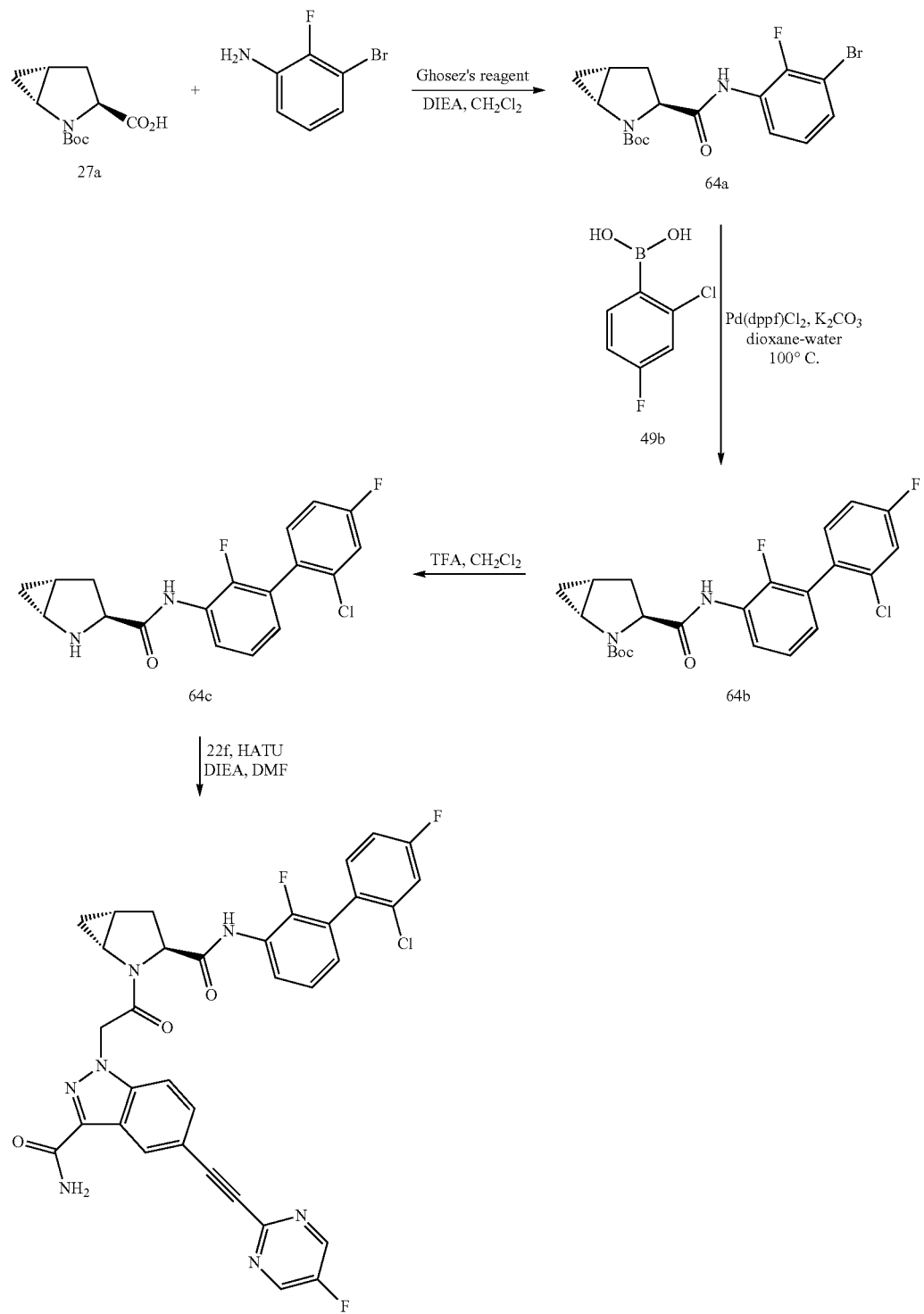

The acid 27a was coupled with 3-bromo-2fluoroaniline using Ghosez's reagent as described for the synthesis of 22j.

Same procedure as for the synthesis of 49c was followed. Thus 0.210 g of 64a was coupled with 0.275 g of 49b in presence of 77 mg of Pd(dppf)Cl$_2$ to get 0.184 g of 64b.

Compound 64b (0.136 g) and 0.100 g of 46b were deprotected as described in synthesis of compound 22 (scheme 7&8). Coupling was done using the same procedure that was used for the synthesis of 22 to give 1-(2-((1R,3S,5R)-3-((2'-Chloro-2,4'-difluoro-[1,1'-biphenyl]-3-yl)carbamoyl)-2-azabicyclo[3.1.0]hexan-2-yl)-2-oxoethyl)-5-((5-fluoropyrimidin-2-yl)ethynyl)-1H-indazole-3-carboxamide (64). $^1$H NMR (400 MHz, DMSO-d$_6$, 300 K): (major rotamer) δ 0.8 (m, 1H), 1.01-1.05 (m, 1H), 1.85-1.95 (m, 1H), 2.28-2.31 (m, 2H), 3.79 (t, J=4.8 Hz, 1H), 4.54 (t, J=6.4 Hz, 1H), 5.55 (d, J=17.2 Hz, 1H), 5.87 (d, J=17.2 Hz, 1H), 7.08 (t, J=6.8 Hz, 1H), 7.23 (t, J=8 Hz, 1H), 7.31-7.35 (m, 1H), 7.45 (t, J=8.8 Hz, 1H), 7.51 (s, 1H), 7.59 (dd, J=8.8, 2.4 Hz, 1H), 7.64 (d, J=8.8 Hz, 1H), 7.78 (d, J=8.8 Hz, 1H), 7.79 (s, 1H), 7.92 (t, J=7.6 Hz, 1H), 8.46 (s, 1H), 8.96 (s, 2H), 9.75 (s, 1H). $^{19}$F NMR (376 MHz, DMSO-d$_6$, 300 K): (major rotamer) δ −111.6, −126.5, −135.7. LC (method 1): $t_R$=2.56 min. LC/MS (EI) m/z: [M+H]$^+$ calcd for C$_{34}$H$_{23}$ClF$_3$N$_7$O$_3$, 670. found 670.

Compound 65: 1-(2-((1R,3S,5R)-3-((6-bromopyridin-2-yl)carbamoyl)-2-azabicyclo[3.1.0]hexan-2-yl)-2-oxoethyl)-5-((4-fluoropyridin-2-yl)ethynyl)-1H-indazole-3-carboxamide Scheme 17:

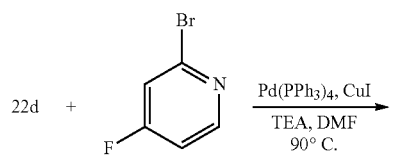

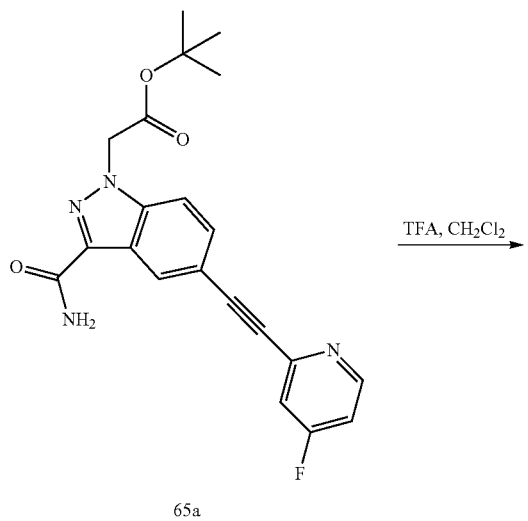

65a

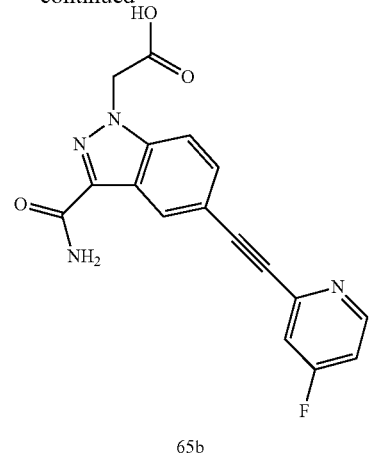

65b

|41b, HATU
DIEA, DMF

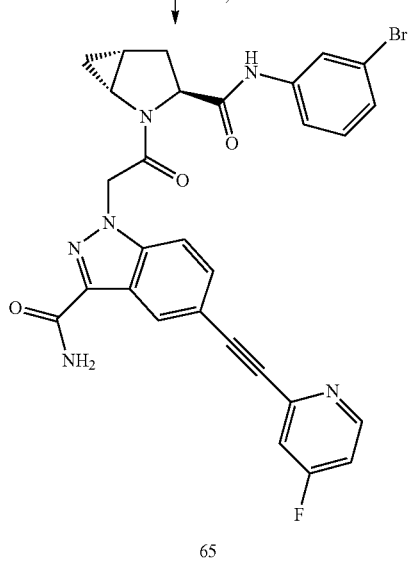

65

Procedure similar to the synthesis of 22e was followed. Thus, 0.1 g of 22d was coupled with 0.589 g of 2-bromo-4-fluoropyridine in presence of 77 mg of Pd(PPh$_3$)$_4$, 25 mg of CuI and 0.245 mL of TEA in 2 mL of DMF at 90° C. Crude product was purified by chromatography over silica gel (eluent: 0-1.5% MeOH in dichloromethane) to get 0.12 g of 65a as orange solid.

0.05 g of 65a and 0.53 g of 41a were deprotected as described in synthesis of compound 22 (scheme 7&8). Coupling was done using the same procedure that was used for the synthesis of 22. 53 mg of 1-(2-((1R,3S,5R)-3-((6-Bromopyridin-2-yl)carbamoyl)-2-azabicyclo[3.1.0]hexan-2-yl)-2-oxoethyl)-5-((4-fluoropyridin-2-yl)ethynyl)-1H-indazole-3-carboxamide (65) was isolated as white solid.

$^1$H NMR (400 MHz, DMSO-d$_6$, 300 K): (major rotamer) δ 0.75 (brm, 1H), 0.99-1.02 (m, 1H), 1.87-1.91 (m, 1H), 2.19-2.24 (m, 1H), 2.29-2.35 (m, 1H), 3.80 (t, J=4.8 Hz, 1H), 4.45 (dd, J=8.8, 5.2 Hz, 1H), 5.53 (d, J=17.2 Hz, 1H), 5.86 (d, J=17.2 Hz, 1H), 7.32 (d, J=8 Hz, 1H), 7.36-7.40 (m, 1H), 7.49 (s, 1H), 7.65 (d, J=8.8 Hz, 1H), 7.69-7.73 (m, 2H), 7.78 (d, J=9.2 Hz, 1H), 7.79 (s, 1H), 8.02 (d, J=8 Hz, 1H), 8.46 (s, 1H), 8.64 (dd, J=8.8, 6 Hz, 1H). $^{19}$F NMR (376 MHz, DMSO-d$_6$, 300 K): (major rotamer) δ −103. LC (method 1): $t_R$=2.41 min. LC/MS (EI) m/z: [M+H]$^+$ calcd for C$_{28}$H$_{21}$BrFN$_7$O$_3$, 603. found 603.

Example 11. Non-Limiting Examples of Compounds of Formula I

Table 1 shows illustrative compounds of Formula I with characterizing data. The assay of Example 12 was used to determine the $IC_{50}$'s of the compounds. Other standard factor D inhibition assays are also available. Three *s are used to denote compounds with an $IC_{50}$ less than 1 micromolar; two s indicate compound with an $IC_{50}$ between 1 micromolar and 10 micromolar, and one * denotes compounds with an $IC_{50}$ greater than 10 micromolar.

TABLE 1

| Cmp No. | Structure | Name | $IC_{50}$ | RT min (Method A or B) | MS (M + 1) |
|---|---|---|---|---|---|
| 1 | 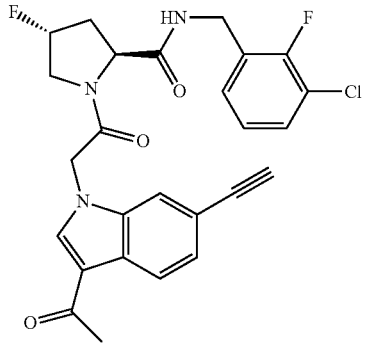 [SMILES: C#Cc1ccc2c(C(C)=O)cn(CC(=O)N3C[C@H](F)C[C@H]3C(=O)NCc3cccc(Cl)c3F)c2c1] | (2S,4R)-1-(2-(3-acetyl-6-ethynyl-1H-indol-1-yl)acetyl)-N-(3-chloro-2-fluorobenzyl)-4-fluoropyrrolidine-2-carboxamide | *** | 1.97 (A) | 498 |
| 2 | 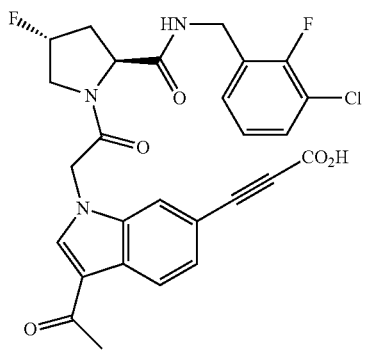 [SMILES: CC(=O)c1cn(CC(=O)N2C[C@H](F)C[C@H]2C(=O)NCc2cccc(Cl)c2F)c2cc(C#CC(=O)O)ccc12] | 3-(3-acetyl-1-(2-((2S,4R)-2-(3-chloro-2-fluorobenzylcarbamoyl)-4-fluoropyrrolidin-1-yl)-2-oxoethyl)-1H-indol-6-yl)propiolic acid | *** | 1.52 (A) | 542 |
| 3 | 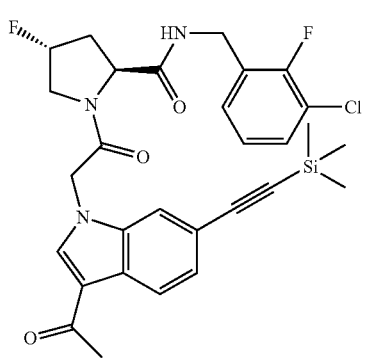 [SMILES: CC(=O)c1cn(CC(=O)N2C[C@H](F)C[C@H]2C(=O)NCc2cccc(Cl)c2F)c2cc(C#C[Si](C)(C)C)ccc12] | (2S,4R)-1-(2-(3-acetyl-6-((trimethylsilyl)ethynyl)-1H-indol-1-yl)acetyl)-N-(3-chloro-2-fluorobenzyl)-4-fluoropyrrolidine-2-carboxamide | *** | 2.71 (A) | 570 |
| 4 | 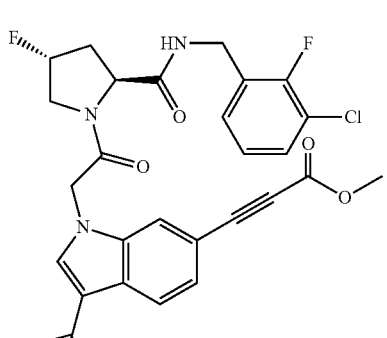 | methyl 3-(3-acetyl-1-(2-((2S,4R)-2-(3-chloro-2-fluorobenzylcarbamoyl)-4-fluoropyrrolidin-1-yl)-2-oxoethyl)-1H-indol-6-yl)propiolate | *** | 1.91 (A) | 556 |

TABLE 1-continued

| Cmp No. | Structure | Name | IC$_{50}$ | RT min (Method A or B) | MS (M + 1) |
|---|---|---|---|---|---|
| 5 | 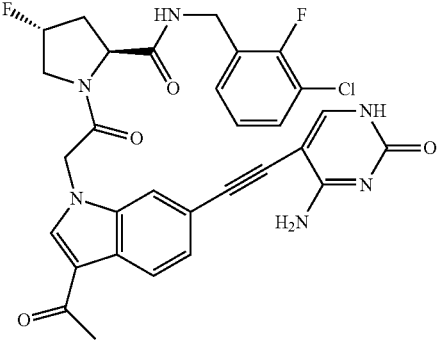 [SMILES: CC(=O)c1cn(CC(=O)N2C[C@H](F)C[C@H]2C(=O)NCc2cccc(Cl)c2F)c2cc(C#Cc3c[nH]c(=O)nc3N)ccc12] | (2S,4R)-1-(2-(3-acetyl-6-((4-amino-2-oxo-1,2-dihydropyrimidin-5-yl)ethynyl)-1H-indol-1-yl)acetyl)-N-(3-chloro-2-fluorobenzyl)-4-fluoropyrrolidine-2-carboxamide | *** | 1.02 (A) | 607 |
| 6 | 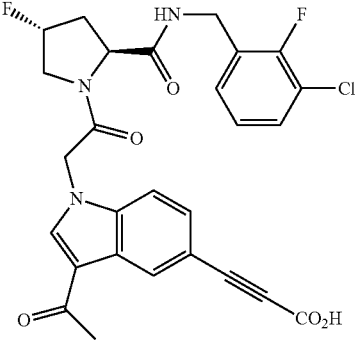 [SMILES: CC(=O)c1cn(CC(=O)N2C[C@H](F)C[C@H]2C(=O)NCc2cccc(Cl)c2F)c2ccc(C#CC(=O)O)cc12] | 3-(3-acetyl-1-(2-((2S,4R)-2-(3-chloro-2-fluorobenzylcarbamoyl)-4-fluoropyrrolidin-1-yl)-2-oxoethyl)-1H-indol-5-yl)propiolic acid | *** | 1.26 (A) | 542 |
| 7 | 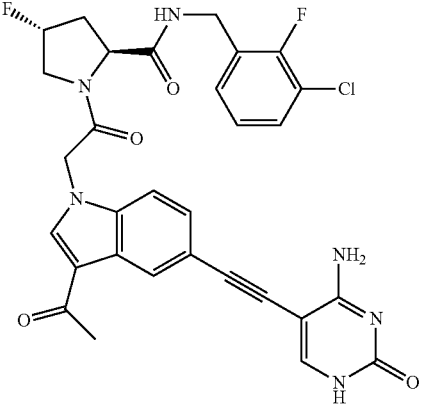 [SMILES: CC(=O)c1cn(CC(=O)N2C[C@H](F)C[C@H]2C(=O)NCc2cccc(Cl)c2F)c2ccc(C#Cc3c[nH]c(=O)nc3N)cc12] | (2S,4R)-1-(2-(3-acetyl-5-((4-amino-2-oxo-1,2-dihydropyrimidin-5-yl)ethynyl)-1H-indol-1-yl)acetyl)-N-(3-chloro-2-fluorobenzyl)-4-fluoropyrrolidine-2-carboxamide | *** | 1.17 (A) | 607 |

TABLE 1-continued

| Cmp No. | Structure | Name | IC$_{50}$ | RT min (Method A or B) | MS (M + 1) |
|---|---|---|---|---|---|
| 8 | 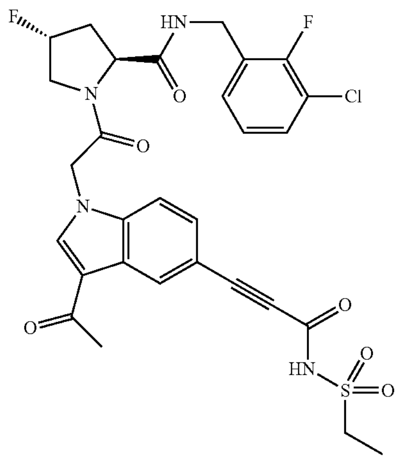 [SMILES: CCS(=O)(=O)NC(=O)C#Cc1ccc2c(c1)c(C(C)=O)cn2CC(=O)N1C[C@H](F)C[C@H]1C(=O)NCc1cccc(Cl)c1F] | (2S,4R)-1-(2-(3-acetyl-5-(3-(ethylsulfonamido)-3-oxoprop-1-ynyl)-1H-indol-1-yl)acetyl)-N-(3-chloro-2-fluorobenzyl)-4-fluoropyrrolidine-2-carboxamide | *** | 1.73 (A) | 633 |
| 9 | 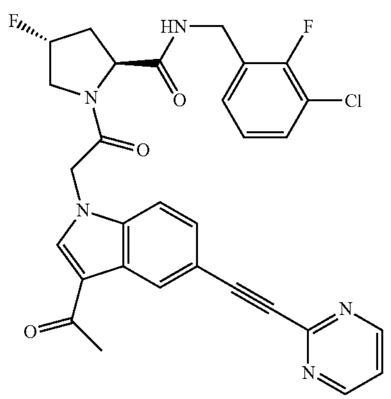 [SMILES: CC(=O)c1cn(CC(=O)N2C[C@H](F)C[C@H]2C(=O)NCc2cccc(Cl)c2F)c2ccc(C#Cc3ncccn3)cc12] | (2S,4R)-1-(2-(3-acetyl-5-(pyrimidin-2-ylethynyl)-1H-indol-1-yl)acetyl)-N-(3-chloro-2-fluorobenzyl)-4-fluoropyrrolidine-2-carboxamide | *** | 1.74 (A) | 576 |
| 10 | 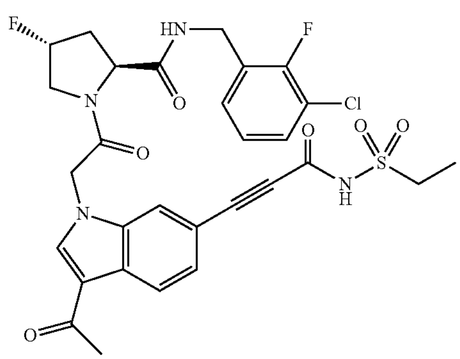 [SMILES: CCS(=O)(=O)NC(=O)C#Cc1ccc2c(C(C)=O)cn(CC(=O)N3C[C@H](F)C[C@H]3C(=O)NCc3cccc(Cl)c3F)c2c1] | (2S,4R)-1-(2-(3-acetyl-6-(3-(ethylsulfonamido)-3-oxoprop-1-ynyl)-1H-indol-1-yl)acetyl)-N-(3-chloro-2-fluorobenzyl)-4-fluoropyrrolidine-2-carboxamide | *** | 1.73 (A) | 633 |
| 11 | 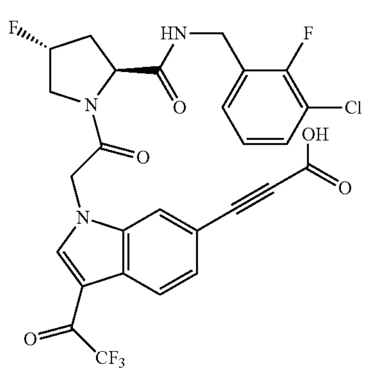 [SMILES: O=C(O)C#Cc1ccc2c(C(=O)C(F)(F)F)cn(CC(=O)N3C[C@H](F)C[C@H]3C(=O)NCc3cccc(Cl)c3F)c2c1] | 3-(1-(2-((2S,4R)-2-(3-chloro-2-fluorobenzylcarbamoyl)-4-fluoropyrrolidin-1-yl)-2-oxoethyl)-3-(2,2,2-trifluoroacetyl)-1H-indol-6-yl)propiolic acid | *** | 2.11 (A) | 596 |

TABLE 1-continued

| Cmp No. | Structure | Name | IC$_{50}$ | RT min (Method A or B) | MS (M + 1) |
|---|---|---|---|---|---|
| 12 | 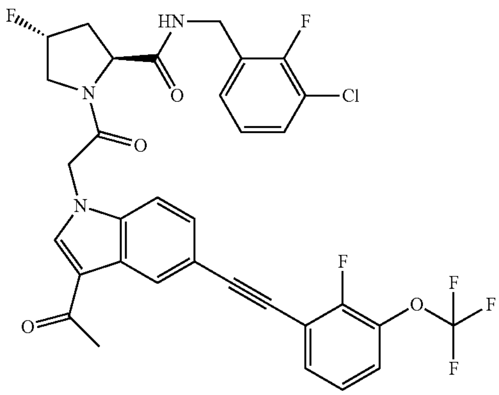 [SMILES: CC(=O)c1cn(CC(=O)N2C[C@H](F)C[C@H]2C(=O)NCc2cccc(Cl)c2F)c2ccc(C#Cc3cccc(OC(F)(F)F)c3F)cc12] | (2S,4R)-1-(2-(3-acetyl-5-((2-fluoro-3-(trifluoromethoxy)phenyl)ethynyl)-1H-indol-1-yl)acetyl)-N-(3-chloro-2-fluorobenzyl)-4-fluoropyrrolidine-2-carboxamide | ** | 2.83 (A) | 676 |
| 13 | 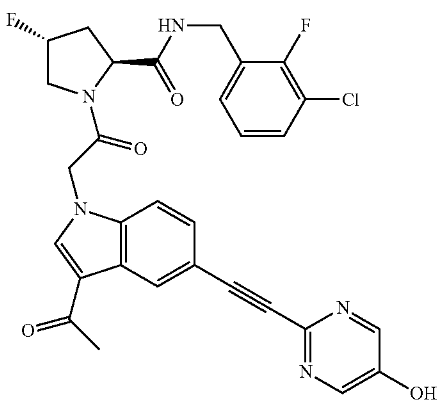 [SMILES: CC(=O)c1cn(CC(=O)N2C[C@H](F)C[C@H]2C(=O)NCc2cccc(Cl)c2F)c2ccc(C#Cc3ncc(O)cn3)cc12] | (2S,4R)-1-(2-(3-acetyl-5-((5-hydroxypyrimidin-2-yl)ethynyl)-1H-indol-1-yl)acetyl)-N-(3-chloro-2-fluorobenzyl)-4-fluoropyrrolidine-2-carboxamide | *** | 1.44 (A) | 592 |
| 14 | 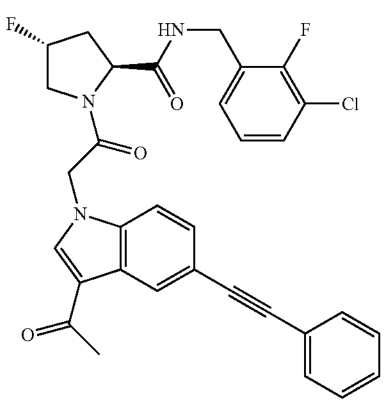 [SMILES: CC(=O)c1cn(CC(=O)N2C[C@H](F)C[C@H]2C(=O)NCc2cccc(Cl)c2F)c2ccc(C#Cc3ccccc3)cc12] | (2S,4R)-1-(2-(3-acetyl-5-(phenylethynyl)-1H-indol-1-yl)acetyl)-N-(3-chloro-2-fluorobenzyl)-4-fluoropyrrolidine-2-carboxamide | *** | 2.54 (A) | 574 |

TABLE 1-continued

| Cmp No. | Structure | Name | IC$_{50}$ | RT min (Method A or B) | MS (M + 1) |
|---|---|---|---|---|---|
| 15 | 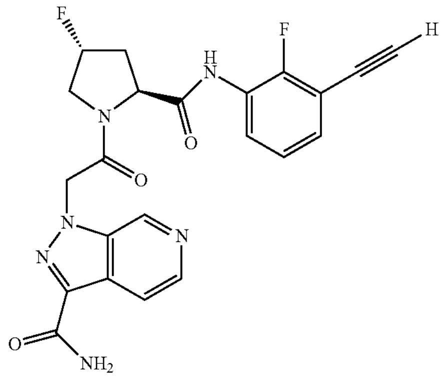 [SMILES: C#Cc1cccc(NC(=O)[C@@H]2C[C@@H](F)CN2C(=O)Cn2nc(C(N)=O)c3ccncc32)c1F] | 1-(2-((2S,4R)-2-(3-ethynyl-2-fluorophenylcarbamoyl)-4-fluoropyrrolidin-1-yl)-2-oxoethyl)-1H-pyrazolo[3,4-c]pyridine-3-carboxamide | *** | 0.91 (A) | 453 |
| 16 | 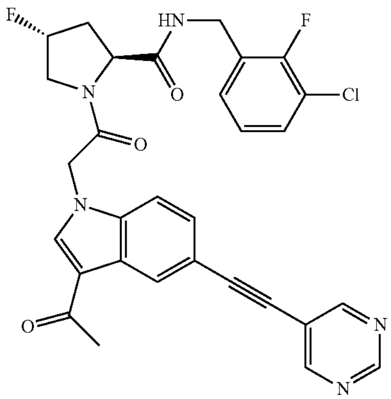 [SMILES: CC(=O)c1cn(CC(=O)N2C[C@H](F)C[C@H]2C(=O)NCc2cccc(Cl)c2F)c2ccc(C#Cc3cncnc3)cc12] | (2S,4R)-1-(2-(3-acetyl-5-(pyrimidin-5-ylethynyl)-1H-indol-1-yl)acetyl)-N-(3-chloro-2-fluorobenzyl)-4-fluoropyrrolidine-2-carboxamide | *** | 1.84 (A) | 576 |
| 17 | 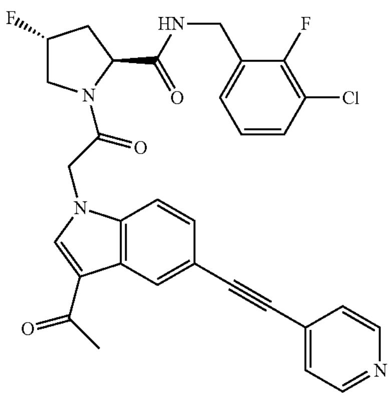 [SMILES: CC(=O)c1cn(CC(=O)N2C[C@H](F)C[C@H]2C(=O)NCc2cccc(Cl)c2F)c2ccc(C#Cc3ccncc3)cc12] | (2S,4R)-1-(2-(3-acetyl-5-(pyridin-4-ylethynyl)-1H-indol-1-yl)acetyl)-N-(3-chloro-2-fluorobenzyl)-4-fluoropyrrolidine-2-carboxamide | *** | 1.52 (A) | 575 |
| 18 | 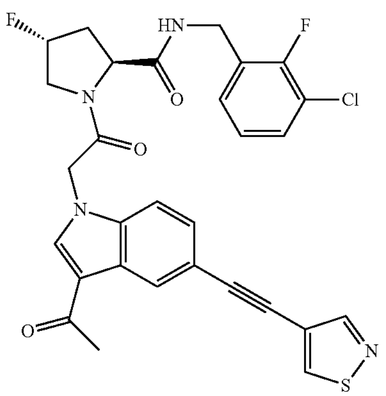 [SMILES: CC(=O)c1cn(CC(=O)N2C[C@H](F)C[C@H]2C(=O)NCc2cccc(Cl)c2F)c2ccc(C#Cc3cnsc3)cc12] | (2S,4R)-1-(2-(3-acetyl-5-(isothiazol-4-ylethynyl)-1H-indol-1-yl)acetyl)-N-(3-chloro-2-fluorobenzyl)-4-fluoropyrrolidine-2-carboxamide | *** | 2.18 (A) | 581 |

TABLE 1-continued

| Cmp No. | Structure | Name | IC$_{50}$ | RT min (Method A or B) | MS (M + 1) |
|---|---|---|---|---|---|
| 19 | 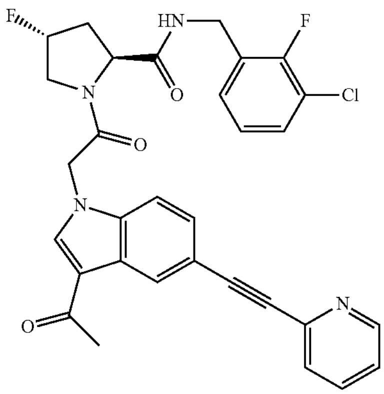 | (2S,4R)-1-(2-(3-acetyl-5-(pyridin-2-ylethynyl)-1H-indol-1-yl)acetyl)-N-(3-chloro-2-fluorobenzyl)-4-fluoropyrrolidine-2-carboxamide | *** | 1.86 (A) | 575 |
| 20 | 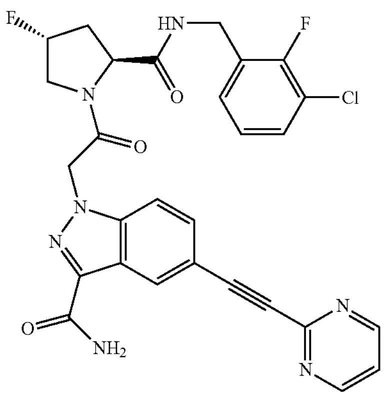 [SMILES: NC(=O)c1nn(CC(=O)N2C[C@H](F)C[C@H]2C(=O)NCc2cccc(Cl)c2F)c2ccc(C#Cc3ncccn3)cc12] | 1-(2-((2S,4R)-2-(3-chloro-2-fluorobenzylcarbamoyl)-4-fluoropyrrolidin-1-yl)-2-oxoethyl)-5-(pyrimidin-2-ylethynyl)-1H-indazole-3-carboxamide | *** | 1.52 (A) | 578 |
| 21 | 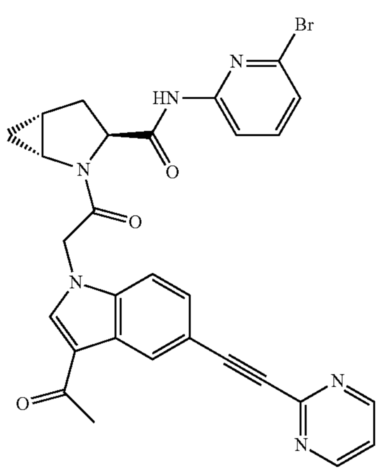 [SMILES: CC(=O)c1cn(CC(=O)N2[C@@H]3C[C@@H]3C[C@H]2C(=O)Nc2cccc(Br)n2)c2ccc(C#Cc3ncccn3)cc12] | (1R,3S,5R)-2-(2-(3-acetyl-5-(pyrimidin-2-ylethynyl)-1H-indol-1-yl)acetyl)-N-(6-bromopyridin-2-yl)-2-azabicyclo[3.1.0]hexane-3-carboxamide | *** | 1.84 (A) | 583 |

TABLE 1-continued

| Cmp No. | Structure | Name | IC$_{50}$ | RT min (Method A or B) | MS (M + 1) |
|---|---|---|---|---|---|
| 22 | 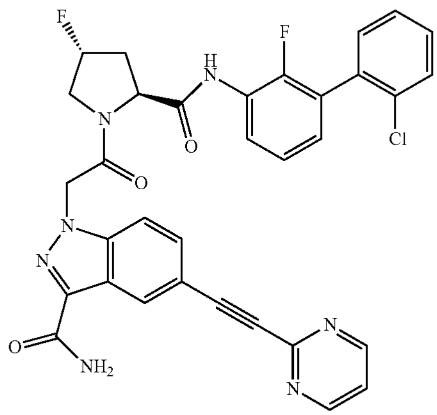 [SMILES: NC(=O)c1nn(CC(=O)N2C[C@H](F)C[C@H]2C(=O)Nc2cccc(-c3ccccc3Cl)c2F)c2ccc(C#Cc3ncccn3)cc12] | 1-(2-((2S,4R)-2-(2'-chloro-2-fluorobiphenyl-3-ylcarbamoyl)-4-fluoropyrrolidin-1-yl)-2-oxoethyl)-5-(pyrimidin-2-ylethynyl)-1H-indazole-3-carboxamide | *** | 1.99 (A) | 640 |
| 23 | 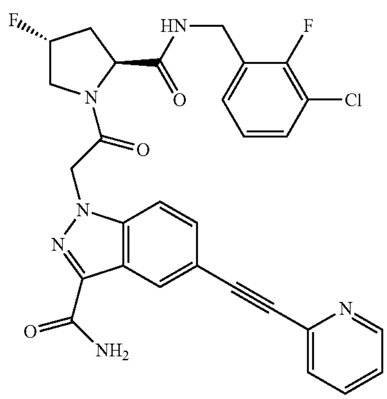 | 1-(2-((2S,4R)-2-(3-chloro-2-fluorobenzylcarbamoyl)-4-fluoropyrrolidin-1-yl)-2-oxoethyl)-5-(pyridin-2-ylethynyl)-1H-indazole-3-carboxamide | *** | 1.66 (A) | 577 |
| 24 | 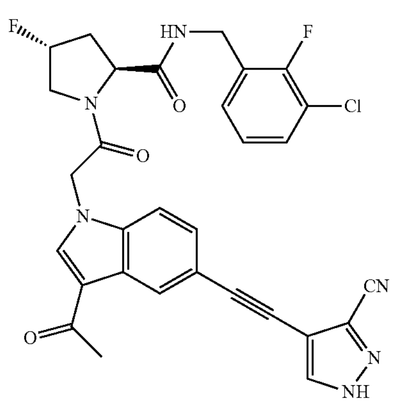 [SMILES: CC(=O)c1cn(CC(=O)N2C[C@H](F)C[C@H]2C(=O)NCc2cccc(Cl)c2F)c2ccc(C#Cc3c[nH]nc3C#N)cc12] | (2S,4R)-1-(2-(3-acetyl-5-((3-cyano-1H-pyrazol-4-yl)ethynyl)-1H-indol-1-yl)acetyl)-N-(3-chloro-2-fluorobenzyl)-4-fluoropyrrolidine-2-carboxamide | *** | 1.84 (A) | 589 |

TABLE 1-continued

| Cmp No. | Structure | Name | IC$_{50}$ | RT min (Method A or B) | MS (M + 1) |
|---|---|---|---|---|---|
| 25 | 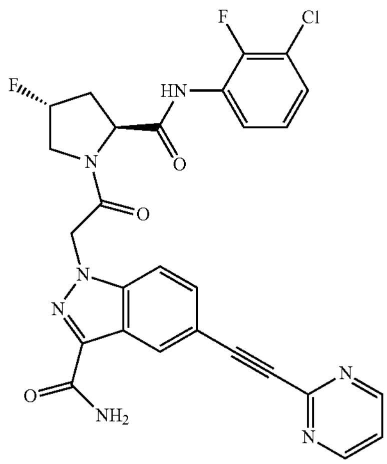 [SMILES: NC(=O)c1nn(CC(=O)N2C[C@H](F)C[C@H]2C(=O)Nc2cccc(Cl)c2F)c2ccc(C#Cc3ncccn3)cc12] | 1-(2-((2S,4R)-2-(3-chloro-2-fluorophenylcarbamoyl)-4-fluoropyrrolidin-1-yl)-2-oxoethyl)-5-(pyrimidin-2-ylethynyl)-1H-indazole-3-carboxamide | *** | 1.56 (A) | 564 |
| 26 | 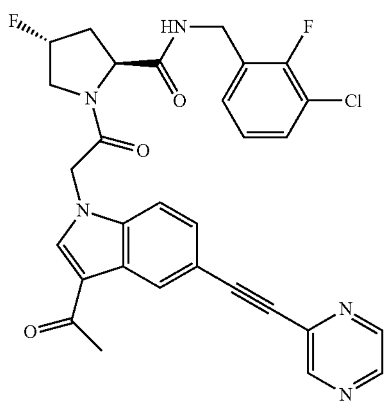 [SMILES: CC(=O)c1cn(CC(=O)N2C[C@H](F)C[C@H]2C(=O)NCc2cccc(Cl)c2F)c2ccc(C#Cc3cnccn3)cc12] | (2S,4R)-1-(2-(3-acetyl-5-(pyrazin-2-ylethynyl)-1H-indol-1-yl)acetyl)-N-(3-chloro-2-fluorobenzyl)-4-fluoropyrrolidine-2-carboxamide | *** | 1.86 (A) | 576 |
| 27 | 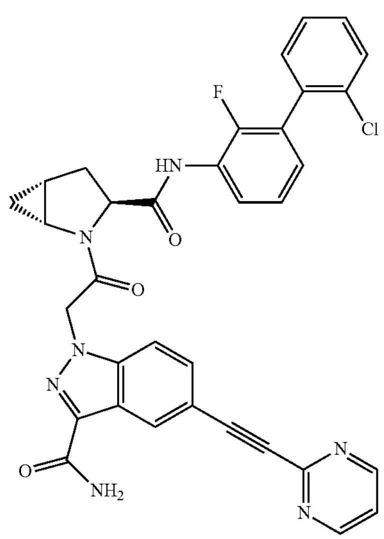 [SMILES: NC(=O)c1nn(CC(=O)N2[C@@H]3C[C@@H]3C[C@H]2C(=O)Nc2cccc(-c3ccccc3Cl)c2F)c2ccc(C#Cc3ncccn3)cc12] | 1-(2-((1R,3S,5R)-3-(2'-chloro-2-fluorobiphenyl-3-ylcarbamoyl)-2-azabicyclo[3.1.0]hexan-2-yl)-2-oxoethyl)-5-(pyrimidin-2-ylethynyl)-1H-indazole-3-carboxamide | *** | 2.10 (A) | 634 |

TABLE 1-continued

| Cmp No. | Structure | Name | IC$_{50}$ | RT min (Method A or B) | MS (M + 1) |
|---|---|---|---|---|---|
| 28 | 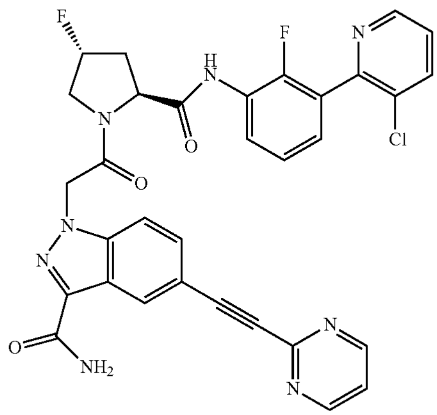 [SMILES: NC(=O)c1nn(CC(=O)N2C[C@H](F)C[C@H]2C(=O)Nc2cccc(-c3ncccc3Cl)c2F)c2ccc(C#Cc3ncccn3)cc12] | 1-(2-((2S,4R)-2-(3-(3-chloropyridin-2-yl)-2-fluorophenylcarbamoyl)-4-fluoropyrrolidin-1-yl)-2-oxoethyl)-5-(pyrimidin-2-ylethynyl)-1H-indazole-3-carboxamide | *** | 1.54 (A) | 641 |
| 29 | 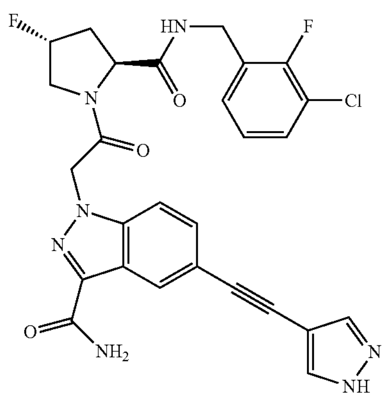 [SMILES: NC(=O)c1nn(CC(=O)N2C[C@H](F)C[C@H]2C(=O)NCc2cccc(Cl)c2F)c2ccc(C#Cc3cn[nH]c3)cc12] | 5-((1H-pyrazol-4-yl)ethynyl)-1-(2-((2S,4R)-2-(3-chloro-2-fluorobenzylcarbamoyl)-4-fluoropyrrolidin-1-yl)-2-oxoethyl)-1H-indazole-3-carboxamide | *** | 1.49 (A) | 566 |
| 30 | 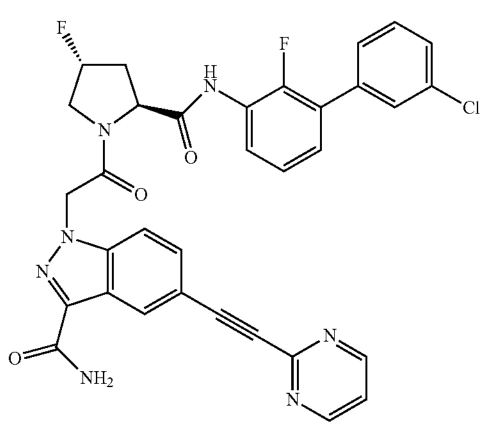 [SMILES: NC(=O)c1nn(CC(=O)N2C[C@H](F)C[C@H]2C(=O)Nc2cccc(-c3cccc(Cl)c3)c2F)c2ccc(C#Cc3ncccn3)cc12] | 1-(2-((2S,4R)-2-(3'-chloro-2-fluorobiphenyl-3-ylcarbamoyl)-4-fluoropyrrolidin-1-yl)-2-oxoethyl)-5-(pyrimidin-2-ylethynyl)-1H-indazole-3-carboxamide | *** | 2.10 (A) | 640 |

TABLE 1-continued

| Cmp No. | Structure | Name | IC$_{50}$ | RT min (Method A or B) | MS (M + 1) |
|---|---|---|---|---|---|
| 31 | 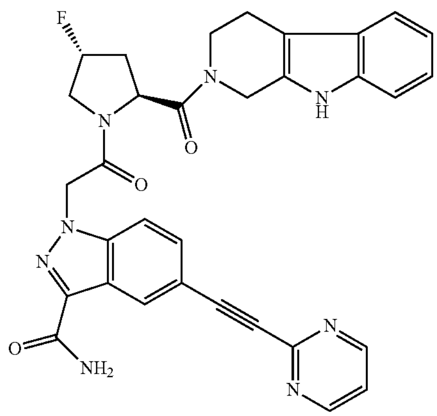 [SMILES: NC(=O)c1nn(CC(=O)N2C[C@H](F)C[C@H]2C(=O)N2CCc3c([nH]c4ccccc34)C2)c2ccc(C#Cc3ncccn3)cc12] | 1-(2-((2S,4R)-4-fluoro-2-(2,3,4,9-tetrahydro-1H-pyrido[3,4-b]indole-2-carbonyl)pyrrolidin-1-yl)-2-oxoethyl)-5-(pyrimidin-2-ylethynyl)-1H-indazole-3-carboxamide | * | 1.65 (A) | 591 |
| 32 | 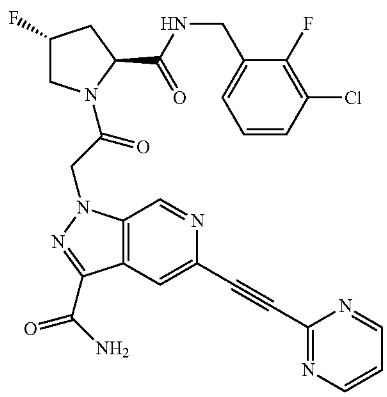 [SMILES: NC(=O)c1nn(CC(=O)N2C[C@H](F)C[C@H]2C(=O)NCc2cccc(Cl)c2F)c2cnc(C#Cc3ncccn3)cc12] | 1-(2-((2S,4R)-2-(3-chloro-2-fluorobenzylcarbamoyl)-4-fluoropyrrolidin-1-yl)-2-oxoethyl)-5-(pyrimidin-2-ylethynyl)-1H-pyrazolo[3,4-c]pyridine-3-carboxamide | *** | 1.32 (A) | 579 |
| 33 | 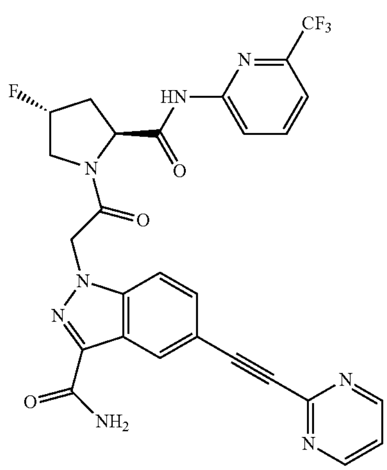 [SMILES: NC(=O)c1nn(CC(=O)N2C[C@H](F)C[C@H]2C(=O)Nc2cccc(C(F)(F)F)n2)c2ccc(C#Cc3ncccn3)cc12] | 1-(2-((2S,4R)-4-fluoro-2-(6-(trifluoromethyl)pyridin-2-ylcarbamoyl)pyrrolidin-1-yl)-2-oxoethyl)-5-(pyrimidin-2-ylethynyl)-1H-indazole-3-carboxamide | *** | 1.61 (A) | 581 |

TABLE 1-continued

| Cmp No. | Structure | Name | IC$_{50}$ | RT min (Method A or B) | MS (M + 1) |
|---|---|---|---|---|---|
| 34 | 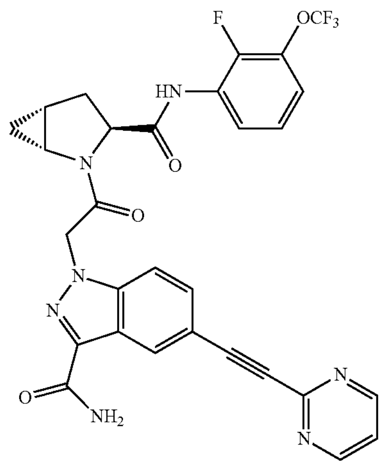 [SMILES: NC(=O)c1nn(CC(=O)N2[C@@H]3C[C@@H]3C[C@H]2C(=O)Nc2cccc(OC(F)(F)F)c2F)c2ccc(C#Cc3ncccn3)cc12] | 1-(2-((1R,3S,5R)-3-(2-fluoro-3-(trifluoromethoxy)phenyl-carbamoyl)-2-azabicyclo[3.1.0]hexan-2-yl)-2-oxoethyl)-5-(pyrimidin-2-ylethynyl)-1H-indazole-3-carboxamide | *** | 1.87 (A) | 608 |
| 35 | 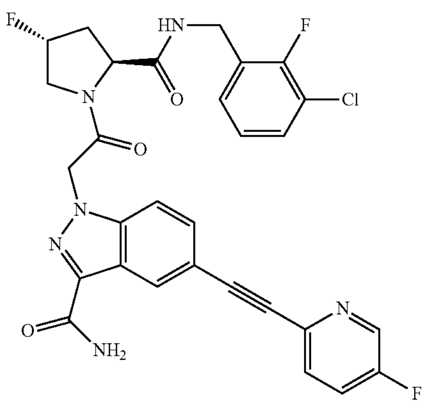 [SMILES: NC(=O)c1nn(CC(=O)N2C[C@H](F)C[C@H]2C(=O)NCc2cccc(Cl)c2F)c2ccc(C#Cc3ccc(F)cn3)cc12] | 1-(2-((2S,4R)-2-(3-chloro-2-fluorobenzylcarbamoyl)-4-fluoropyrrolidin-1-yl)-2-oxoethyl)-5-((5-fluoropyridin-2-yl)ethynyl)-1H-indazole-3-carboxamide | *** | 1.91 (A) | 595 |
| 36 | 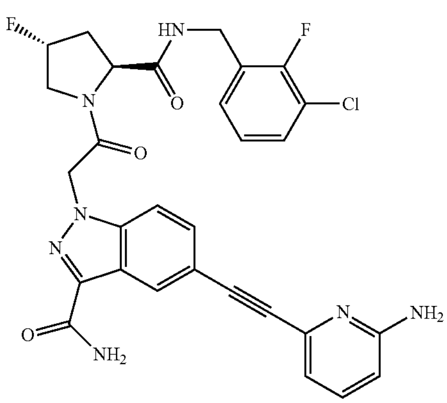 [SMILES: NC(=O)c1nn(CC(=O)N2C[C@H](F)C[C@H]2C(=O)NCc2cccc(Cl)c2F)c2ccc(C#Cc3cccc(N)n3)cc12] | 5-((6-aminopyridin-2-yl)ethynyl)-1-(2-((2S,4R)-2-(3-chloro-2-fluorobenzylcarbamoyl)-4-fluoropyrrolidin-1-yl)-2-oxoethyl)-1H-indazole-3-carboxamide | *** | 1.27 (A) | 592 |

| Cmp No. | Structure | Name | IC$_{50}$ | RT min (Method A or B) | MS (M + 1) |
|---|---|---|---|---|---|
| 37 | 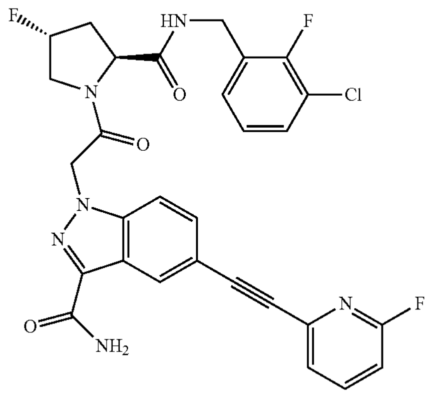 [SMILES: NC(=O)c1nn(CC(=O)N2C[C@H](F)C[C@H]2C(=O)NCc2cccc(Cl)c2F)c2ccc(C#Cc3cccc(F)n3)cc12] | 1-(2-((2S,4R)-2-(3-chloro-2-fluorobenzylcarbamoyl)-4-fluoropyrrolidin-1-yl)-2-oxoethyl)-5-((6-fluoropyridin-2-yl)ethynyl)-1H-indazole-3-carboxamide | *** | 1.96 (A) | 595 |
| 38 | 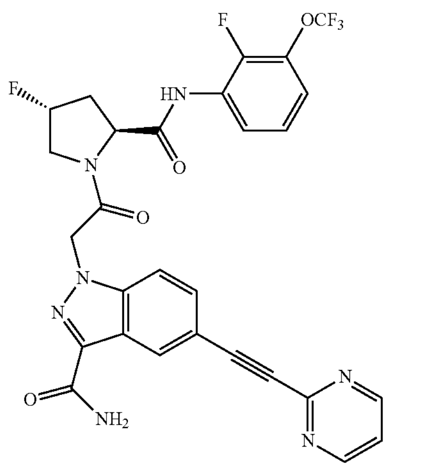 [SMILES: NC(=O)c1nn(CC(=O)N2C[C@H](F)C[C@H]2C(=O)Nc2cccc(OC(F)(F)F)c2F)c2ccc(C#Cc3ncccn3)cc12] | 1-(2-((2S,4R)-4-fluoro-2-(2-fluoro-3-(trifluoromethoxy)phenylcarbamoyl)pyrrolidin-1-yl)-2-oxoethyl)-5-(pyrimidin-2-ylethynyl)-1H-indazole-3-carboxamide | *** | 1.77 (A) | 614 |
| 39 | 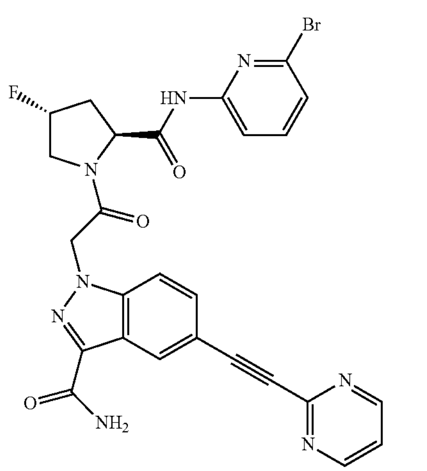 | 1-(2-((2S,4R)-2-(6-bromopyridin-2-ylcarbamoyl)-4-fluoropyrrolidin-1-yl)-2-oxoethyl)-5-(pyrimidin-2-ylethynyl)-1H-indazole-3-carboxamide | *** | 1.48 (A) | 591 |

TABLE 1-continued

| Cmp No. | Structure | Name | IC$_{50}$ | RT min (Method A or B) | MS (M + 1) |
|---|---|---|---|---|---|
| 40 | 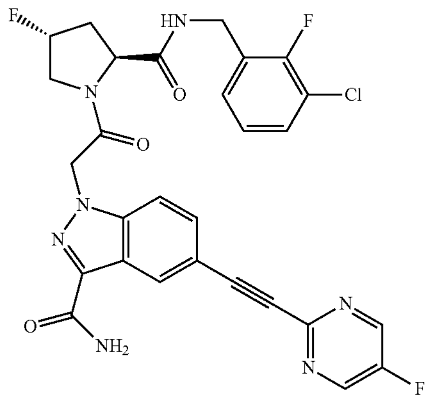 | 1-(2-((2S,4R)-2-(3-chloro-2-fluorobenzylcarbamoyl)-4-fluoropyrrolidin-1-yl)-2-oxoethyl)-5-((5-fluoropyrimidin-2-yl)ethynyl)-1H-indazole-3-carboxamide | *** | 1.73 (A) | 596 |
| 41 | 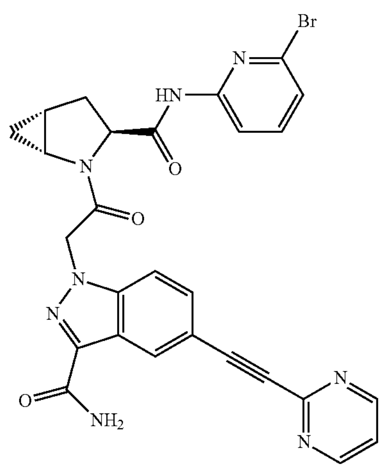 | 1-(2-((1R,3S,5R)-3-(6-bromopyridin-2-ylcarbamoyl)-2-azabicyclo[3.1.0]hexan-2-yl)-2-oxoethyl)-5-(pyrimidin-2-ylethynyl)-1H-indazole-3-carboxamide | *** | 1.60 (A) | 585 |
| 42 | 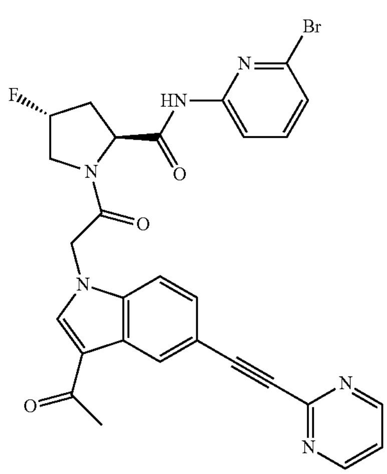 [SMILES: CC(=O)c1cn(CC(=O)N2C[C@H](F)C[C@H]2C(=O)Nc2cccc(Br)n2)c2ccc(C#Cc3ncccn3)cc12] | (2S,4R)-1-(2-(3-acetyl-5-(pyrimidin-2-ylethynyl)-1H-indol-1-yl)acetyl)-N-(6-bromopyridin-2-yl)-4-fluoropyrrolidine-2-carboxamide | *** | 1.70 (A) | 589 |

TABLE 1-continued

| Cmp No. | Structure | Name | IC$_{50}$ | RT min (Method A or B) | MS (M + 1) |
|---|---|---|---|---|---|
| 43 | 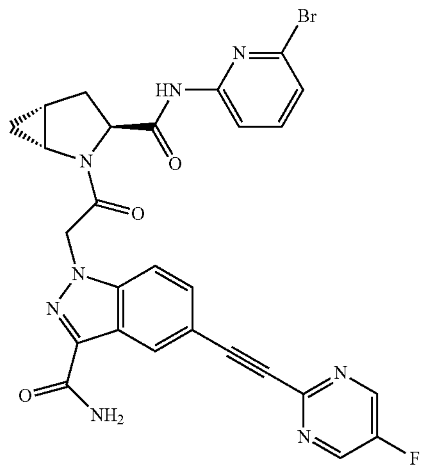 [SMILES: NC(=O)c1nn(CC(=O)N2[C@@H]3C[C@@H]3C[C@H]2C(=O)Nc2cccc(Br)n2)c2ccc(C#Cc3ncc(F)cn3)cc12] | 1-(2-((1R,3S,5R)-3-(6-bromopyridin-2-ylcarbamoyl)-2-azabicyclo[3.1.0]hexan-2-yl)-2-oxoethyl)-5-((5-fluoropyrimidin-2-yl)ethynyl)-1H-indazole-3-carboxamide | *** | 1.81 (A) | 603 |
| 44 | 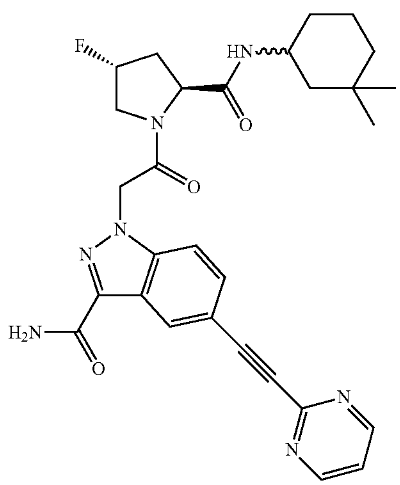 [SMILES: CC1(C)CCCC(NC(=O)[C@@H]2C[C@@H](F)CN2C(=O)Cn2nc(C(N)=O)c3cc(C#Cc4ncccn4)ccc32)C1] | 1-(2-((2S,4R)-2-(3,3-dimethylcyclohexylcarbamoyl)-4-fluoropyrrolidin-1-yl)-2-oxoethyl)-5-(pyrimidin-2-ylethynyl)-1H-indazole-3-carboxamide | *** | 1.69 (A) | 546 |
| 45 | 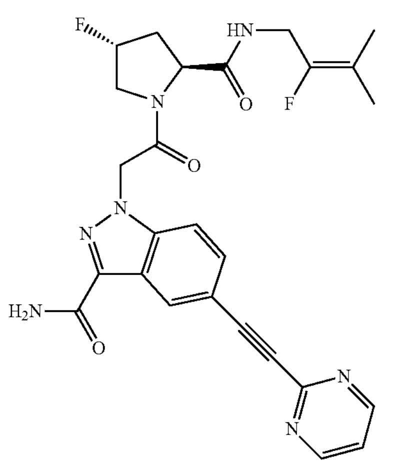 [SMILES: CC(C)=C(F)CNC(=O)[C@@H]1C[C@@H](F)CN1C(=O)Cn1nc(C(N)=O)c2cc(C#Cc3ncccn3)ccc21] | 1-(2-((2S,4R)-4-fluoro-2-(2-fluoro-3-methylbut-2-enylcarbamoyl)pyrrolidin-1-yl)-2-oxoethyl)-5-(pyrimidin-2-ylethynyl)-1H-indazole-3-carboxamide | *** | 1.31 (A) | 522 |

TABLE 1-continued

| Cmp No. | Structure | Name | IC$_{50}$ | RT min (Method A or B) | MS (M + 1) |
|---|---|---|---|---|---|
| 46 | 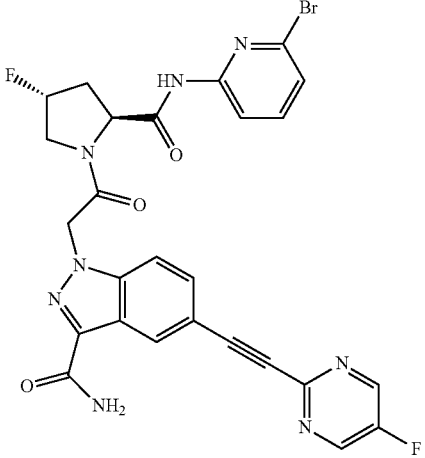 [SMILES: NC(=O)c1nn(CC(=O)N2C[C@H](F)C[C@H]2C(=O)Nc2cccc(Br)n2)c2ccc(C#Cc3ncc(F)cn3)cc12] | 1-(2-((2S,4R)-2-(6-bromopyridin-2-ylcarbamoyl)-4-fluoropyrrolidin-1-yl)-2-oxoethyl)-5-((5-fluoropyrimidin-2-yl)ethynyl)-1H-indazole-3-carboxamide | *** | 1.69 (A) | 609 |
| 47 | 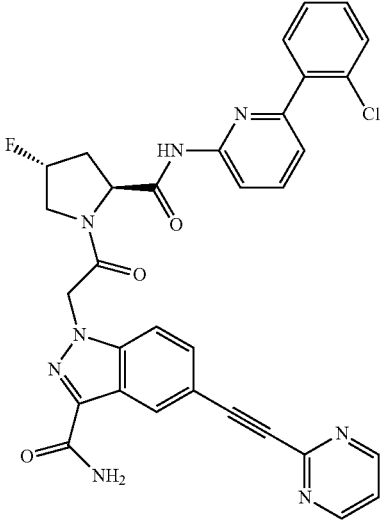 [SMILES: NC(=O)c1nn(CC(=O)N2C[C@H](F)C[C@H]2C(=O)Nc2cccc(-c3ccccc3Cl)n2)c2ccc(C#Cc3ncccn3)cc12] | 1-(2-((2S,4R)-2-(6-(2-chlorophenyl)pyridin-2-ylcarbamoyl)-4-fluoropyrrolidin-1-yl)-2-oxoethyl)-5-(pyrimidin-2-ylethynyl)-1H-indazole-3-carboxamide | *** | 1.91 (A) | 623 |
| 48 | 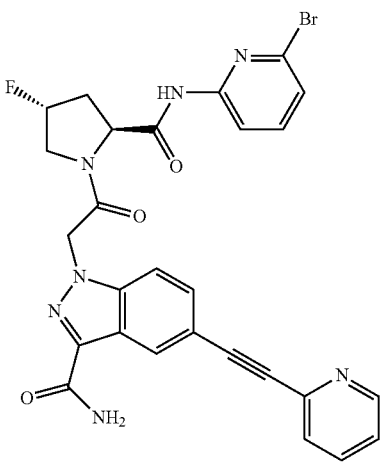 [SMILES: NC(=O)c1nn(CC(=O)N2C[C@H](F)C[C@H]2C(=O)Nc2cccc(Br)n2)c2ccc(C#Cc3ccccn3)cc12] | 1-(2-((2S,4R)-2-(6-bromopyridin-2-ylcarbamoyl)-4-fluoropyrrolidin-1-yl)-2-oxoethyl)-5-(pyridin-2-ylethynyl)-1H-indazole-3-carboxamide | *** | 1.60 (A) | 590 |

| Cmp No. | Structure | Name | IC$_{50}$ | RT min (Method A or B) | MS (M + 1) |
|---|---|---|---|---|---|
| 49 | 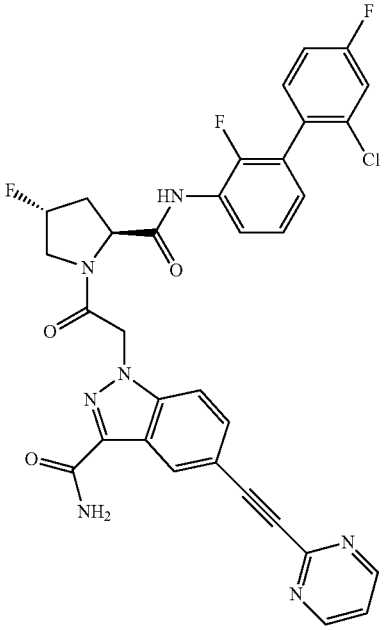 [SMILES: NC(=O)c1nn(CC(=O)N2C[C@H](F)C[C@H]2C(=O)Nc2cccc(-c3ccc(F)cc3Cl)c2F)c2ccc(C#Cc3ncccn3)cc12] | 1-(2-((2S,4R)-2-(2'-chloro-2,4'-difluorobiphenyl-3-ylcarbamoyl)-4-fluoropyrrolidin-1-yl)-2-oxoethyl)-5-(pyrimidin-2-ylethynyl)-1H-indazole-3-carboxamide | *** | 2.04 (A) | 658 |
| 50 | 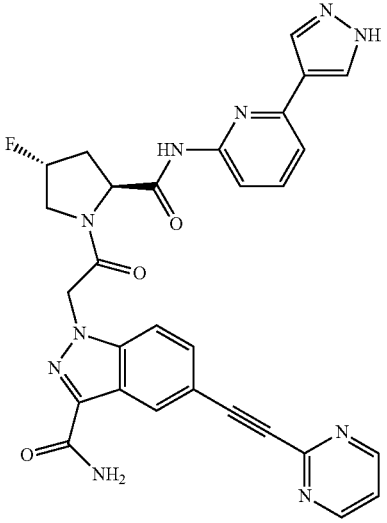 [SMILES: NC(=O)c1nn(CC(=O)N2C[C@H](F)C[C@H]2C(=O)Nc2cccc(-c3cn[nH]c3)n2)c2ccc(C#Cc3ncccn3)cc12] | 1-(2-((2S,4R)-2-(6-(1H-pyrazol-4-yl)pyridin-2-ylcarbamoyl)-4-fluoropyrrolidin-1-yl)-2-oxoethyl)-5-(pyrimidin-2-ylethynyl)-1H-indazole-3-carboxamide | *** | 1.11 (A) | 579 |

TABLE 1-continued

| Cmp No. | Structure | Name | IC$_{50}$ | RT min (Method A or B) | MS (M + 1) |
|---|---|---|---|---|---|
| 51 | 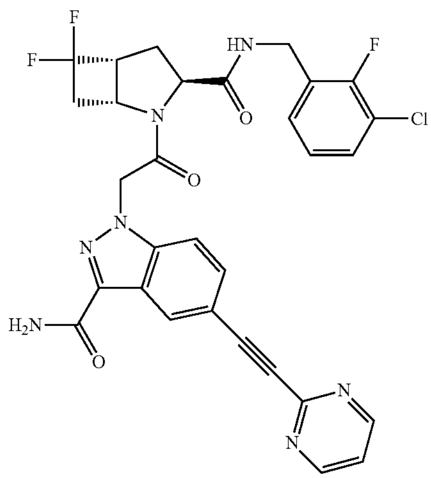 [SMILES: NC(=O)c1nn(CC(=O)N2[C@@H]3CC(F)(F)[C@@H]3C[C@H]2C(=O)NCc2cccc(Cl)c2F)c2ccc(C#Cc3ncccn3)cc12] | 1-(2-((1R,3S,5R)-3-(3-chloro-2-fluorobenzylcarbamoyl)-6,6-difluoro-2-azabicyclo[3.2.0]heptan-2-yl)-2-oxoethyl)-5-(pyrimidin-2-ylethynyl)-1H-indazole-3-carboxamide | ** | 1.79 (A) | 622 |
| 52 | 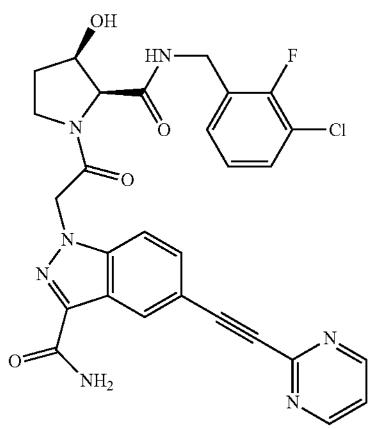 [SMILES: NC(=O)c1nn(CC(=O)N2CC[C@@H](O)[C@H]2C(=O)NCc2cccc(Cl)c2F)c2ccc(C#Cc3ncccn3)cc12] | 1-(2-((2S,3R)-2-(3-chloro-2-fluorobenzylcarbamoyl)-3-hydroxypyrrolidin-1-yl)-2-oxoethyl)-5-(pyrimidin-2-ylethynyl)-1H-indazole-3-carboxamide | *** | 1.28 (A) | 576 |
| 53 | 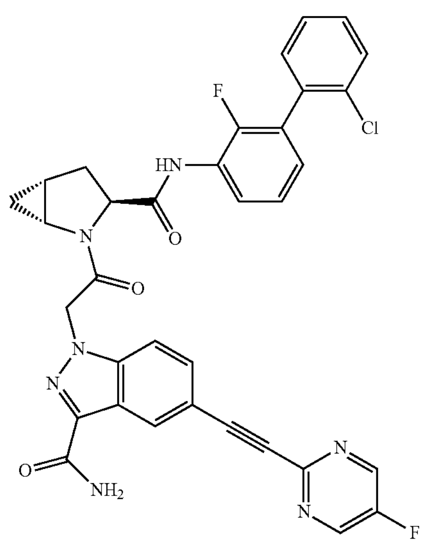 [SMILES: NC(=O)c1nn(CC(=O)N2[C@@H]3C[C@@H]3C[C@H]2C(=O)Nc2cccc(-c3ccccc3Cl)c2F)c2ccc(C#Cc3ncc(F)cn3)cc12] | 1-(2-((1R,3S,5R)-3-(2'-chloro-2-fluorobiphenyl-3-ylcarbamoyl)-2-azabicyclo[3.1.0]hexan-2-yl)-2-oxoethyl)-5-((5-fluoropyrimidin-2-yl)ethynyl)-1H-indazole-3-carboxamide | *** | 2.31 (A) | 652 |

TABLE 1-continued

| Cmp No. | Structure | Name | IC50 | RT min (Method A or B) | MS (M + 1) |
|---|---|---|---|---|---|
| 54 | 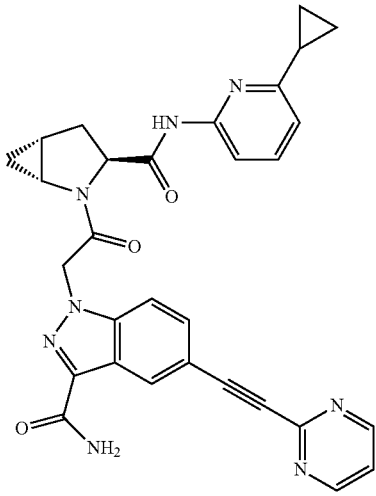 [SMILES: NC(=O)c1nn(CC(=O)N2[C@@H]3C[C@@H]3C[C@H]2C(=O)Nc2cccc(C3CC3)n2)c2ccc(C#Cc3ncccn3)cc12] | 1-(2-((1R,3S,5R)-3-(6-cyclopropylpyridin-2-ylcarbamoyl)-2-azabicyclo[3.1.0]hexan-2-yl)-2-oxoethyl)-5-(pyrimidin-2-ylethynyl)-1H-indazole-3-carboxamide | *** | 1.62 (A) | 547 |
| 55 | 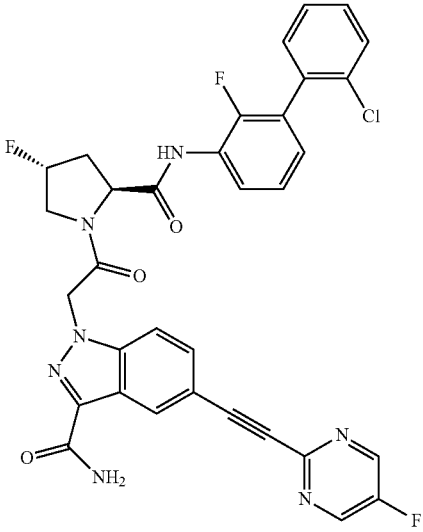 [SMILES: NC(=O)c1nn(CC(=O)N2C[C@H](F)C[C@H]2C(=O)Nc2cccc(-c3ccccc3Cl)c2F)c2ccc(C#Cc3ncc(F)cn3)cc12] | 1-(2-((2S,4R)-2-(2'-chloro-2-fluorobiphenyl-3-ylcarbamoyl)-4-fluoropyrrolidin-1-yl)-2-oxoethyl)-5-((5-fluoropyrimidin-2-yl)ethynyl)-1H-indazole-3-carboxamide | *** | 2.20 (A) | 658 |
| 56 | 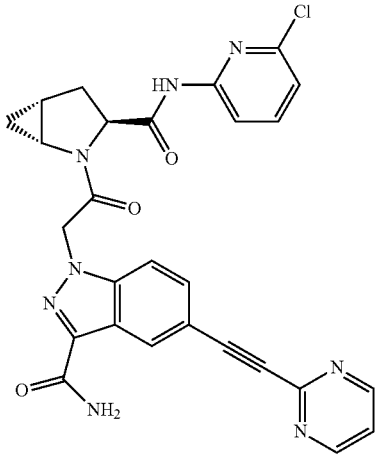 | 1-(2-((1R,3S,5R)-3-(6-chloropyridin-2-ylcarbamoyl)-2-azabicyclo[3.1.0]hexan-2-yl)-2-oxoethyl)-5-(pyrimidin-2-ylethynyl)-1H-indazole-3-carboxamide | *** | 1.56 (A) | 541 |

TABLE 1-continued

| Cmp No. | Structure | Name | IC$_{50}$ | RT min (Method A or B) | MS (M + 1) |
|---|---|---|---|---|---|
| 57 | 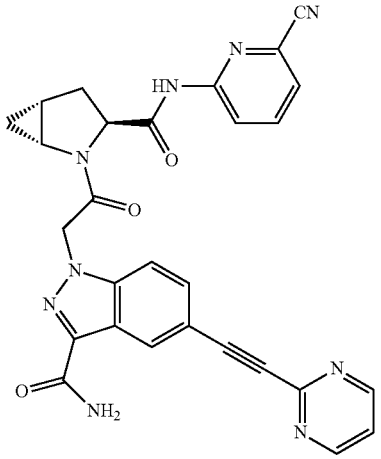 | 1-(2-((1R,3S,5R)-3-(6-cyanopyridin-2-ylcarbamoyl)-2-azabicyclo[3.1.0]hexan-2-yl)-2-oxoethyl)-5-(pyrimidin-2-ylethynyl)-1H-indazole-3-carboxamide | *** | 1.39 (A) | 532 |
| 58 | 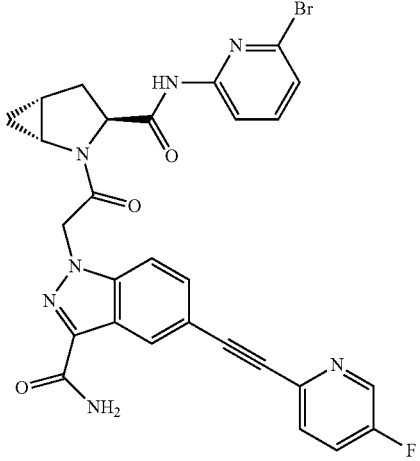 [SMILES: NC(=O)c1nn(CC(=O)N2[C@@H]3C[C@@H]3C[C@H]2C(=O)Nc2cccc(Br)n2)c2ccc(C#Cc3ccc(F)cn3)cc12] | 1-(2-((1R,3S,5R)-3-(6-bromopyridin-2-ylcarbamoyl)-2-azabicyclo[3.1.0]hexan-2-yl)-2-oxoethyl)-5-((5-fluoropyridin-2-yl)ethynyl)-1H-indazole-3-carboxamide | *** | 2.01 (A) | 602 |
| 59 | 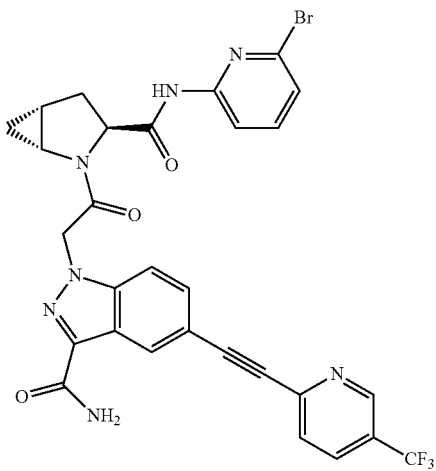 [SMILES: NC(=O)c1nn(CC(=O)N2[C@@H]3C[C@@H]3C[C@H]2C(=O)Nc2cccc(Br)n2)c2ccc(C#Cc3ccc(C(F)(F)F)cn3)cc12] | 1-(2-((1R,3S,5R)-3-(6-bromopyridin-2-ylcarbamoyl)-2-azabicyclo[3.1.0]hexan-2-yl)-2-oxoethyl)-5-((5-(trifluoromethyl)pyridin-2-yl)ethynyl)-1H-indazole-3- | *** | 2.33 (A) | 654 |

TABLE 1-continued

| Cmp No. | Structure | Name | IC$_{50}$ | RT min (Method A or B) | MS (M + 1) |
|---|---|---|---|---|---|
| 60 | 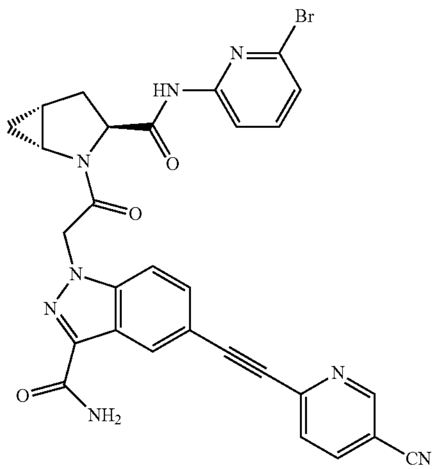 [SMILES: N#Cc1ccc(C#Cc2ccc3c(c2)c(C(N)=O)nn3CC(=O)N2[C@@H]3C[C@@H]3C[C@H]2C(=O)Nc2cccc(Br)n2)nc1] | 1-(2-((1R,3S,5R)-3-(6-bromopyridin-2-ylcarbamoyl)-2-azabicyclo[3.1.0]hexan-2-yl)-2-oxoethyl)-5-((5-cyanopyridin-2-yl)ethynyl)-1H-indazole-3-carboxamide | *** | 1.93 (A) | 609 |
| 61 | 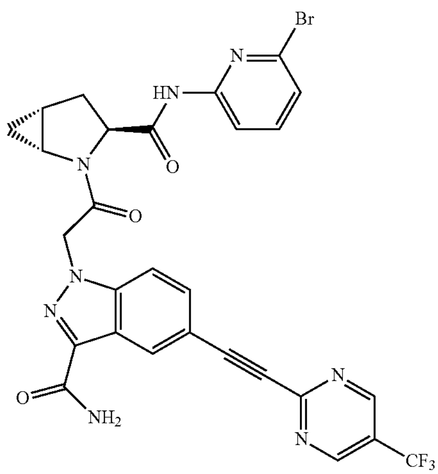 [SMILES: NC(=O)c1nn(CC(=O)N2[C@@H]3C[C@@H]3C[C@H]2C(=O)Nc2cccc(Br)n2)c2ccc(C#Cc3ncc(C(F)(F)F)cn3)cc12] | 1-(2-((1R,3S,5R)-3-(6-bromopyridin-2-ylcarbamoyl)-2-azabicyclo[3.1.0]hexan-2-yl)-2-oxoethyl)-5-((5-(trifluoromethyl)pyrimidin-2-yl)ethynyl)-1H-indazole-3-carboxamide | *** | 2.17 (A) | 653 |
| 62 | 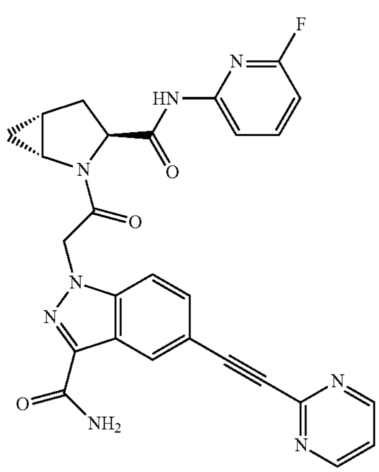 | 1-(2-((1R,3S,5R)-3-(6-fluoropyridin-2-ylcarbamoyl)-2-azabicyclo[3.1.0]hexan-2-yl)-2-oxoethyl)-5-(pyrimidin-2-ylethynyl)-1H-indazole-3-carboxamide | *** | 1.44 (A) | 525 |

TABLE 1-continued
| Cmp No. | Structure | Name | IC$_{50}$ | RT min (Method A or B) | MS (M + 1) |
|---|---|---|---|---|---|
| 63 | 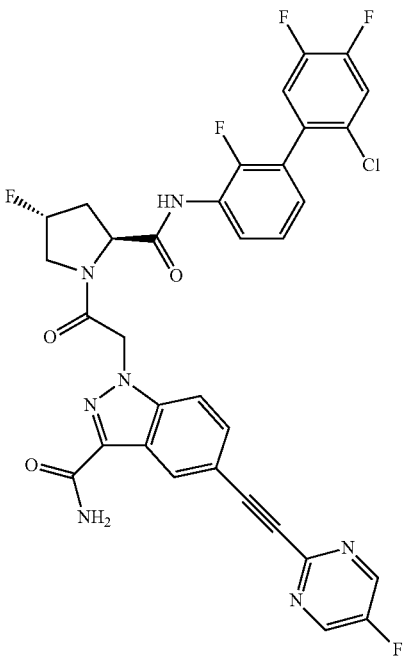 [SMILES: NC(=O)c1nn(CC(=O)N2C[C@H](F)C[C@H]2C(=O)Nc2cccc(-c3cc(F)c(F)cc3Cl)c2F)c2ccc(C#Cc3ncc(F)cn3)cc12] | 1-(2-((2S,4R)-2-(2'-chloro-2,4',5'-trifluorobiphenyl-3-ylcarbamoyl)-4-fluoropyrrolidin-1-yl)-2-oxoethyl)-5-((5-fluoropyrimidin-2-yl)ethynyl)-1H-indazole-3-carboxamide | *** | 2.32 (A) | 694 |
| 64 | 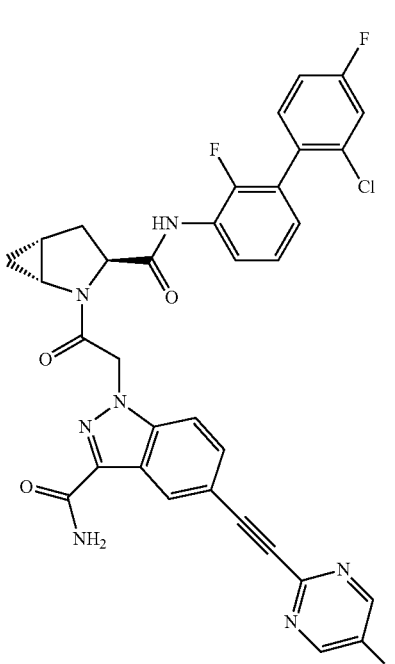 | 1-(2-((1R,3S,5R)-3-(2'-chloro-2,4'-difluorobiphenyl-3-ylcarbamoyl)-2-azabicyclo[3.1.0]hexan-2-yl)-2-oxoethyl)-5-((5-fluoropyrimidin-2-yl)ethynyl)-1H-indazole-3-carboxamide | *** | 2.56 (A) | 670 |

TABLE 1-continued

| Cmp No. | Structure | Name | IC$_{50}$ | RT min (Method A or B) | MS (M + 1) |
|---|---|---|---|---|---|
| 65 | 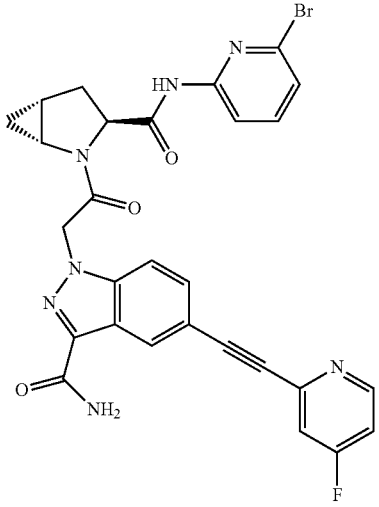 [SMILES: NC(=O)c1nn(CC(=O)N2[C@@H]3C[C@@H]3C[C@H]2C(=O)Nc2cccc(Br)n2)c2ccc(C#Cc3cc(F)ccn3)cc12] | 1-(2-((1R,3S,5R)-3-(6-bromopyridin-2-ylcarbamoyl)-2-azabicyclo[3.1.0]hexan-2-yl)-2-oxoethyl)-5-((4-fluoropyridin-2-yl)ethynyl)-1H-indazole-3-carboxamide | *** | 2.41 (A) | 604 |
| 66 | 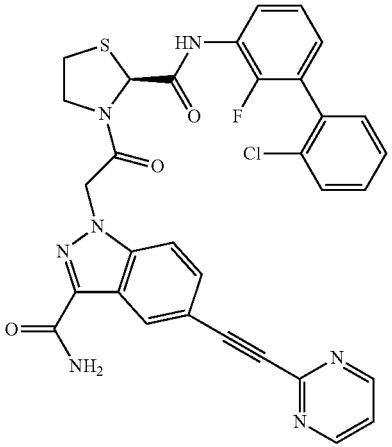 [SMILES: NC(=O)c1nn(CC(=O)N2CCS[C@H]2C(=O)Nc2cccc(-c3ccccc3Cl)c2F)c2ccc(C#Cc3ncccn3)cc12] | (S)-3-(2-(3-carbamoyl-5-(pyrimidin-2-ylethynyl)-1H-indazol-1-yl)acetyl)-N-(2'-chloro-2-fluorobiphenyl-3-yl)thiazolidine-2-carboxamide | *** | 2.47 (A) | 640 |
| 67 | 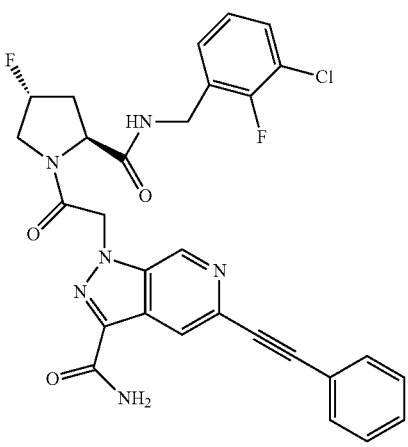 [SMILES: NC(=O)c1nn(CC(=O)N2C[C@H](F)C[C@H]2C(=O)NCc2cccc(Cl)c2F)c2cnc(C#Cc3ccccc3)cc12] | 1-(2-((2S,4R)-2-(3-chloro-2-fluorobenzylcarbamoyl)-4-fluoropyrrolidin-1-yl)-2-oxoethyl)-5-(phenylethynyl)-1H-pyrazolo[3,4-c]pyridine-3-carboxamide | *** | 2.46 (A) | 577 |

TABLE 1-continued

| Cmp No. | Structure | Name | IC$_{50}$ | RT min (Method A or B) | MS (M + 1) |
|---|---|---|---|---|---|
| 68 | 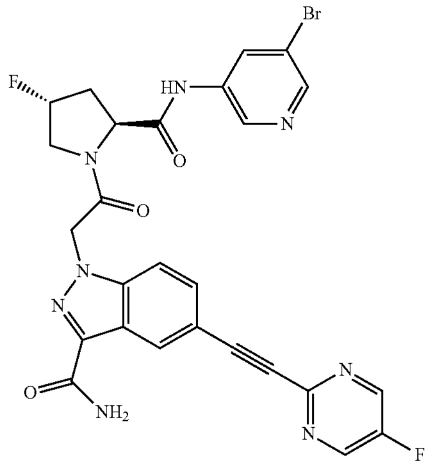 [SMILES: NC(=O)c1nn(CC(=O)N2C[C@H](F)C[C@H]2C(=O)Nc2cncc(Br)c2)c2ccc(C#Cc3ncc(F)cn3)cc12] | 1-(2-((2S,4R)-2-(5-bromopyridin-3-ylcarbamoyl)-4-fluoropyrrolidin-1-yl)-2-oxoethyl)-5-((5-fluoropyrimidin-2-yl)ethynyl)-1H-indazole-3-carboxamide | *** | 2.03 (A) | 609 |
| 69 | 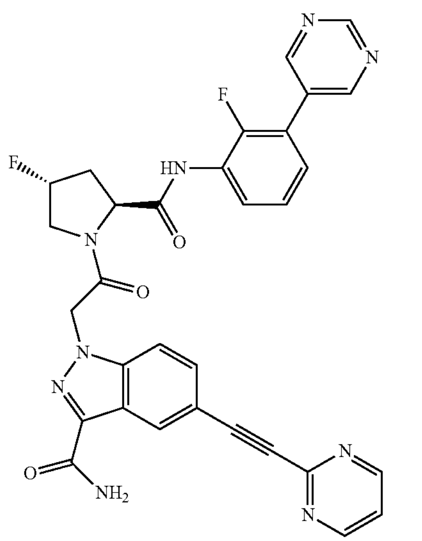 [SMILES: NC(=O)c1nn(CC(=O)N2C[C@H](F)C[C@H]2C(=O)Nc2cccc(-c3cncnc3)c2F)c2ccc(C#Cc3ncccn3)cc12] | 1-(2-((2S,4R)-4-fluoro-2-(2-fluoro-3-(pyrimidin-5-yl)phenylcarbamoyl)pyrrolidin-1-yl)-2-oxoethyl)-5-(pyrimidin-2-ylethynyl)-1H-indazole-3-carboxamide | *** | 1.16 (A) | 608 |
| 70 | 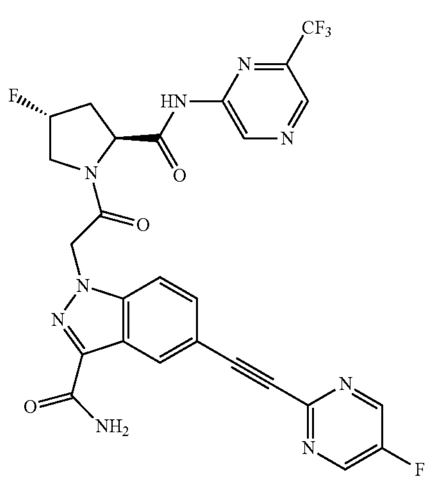 [SMILES: NC(=O)c1nn(CC(=O)N2C[C@H](F)C[C@H]2C(=O)Nc2cncc(C(F)(F)F)n2)c2ccc(C#Cc3ncc(F)cn3)cc12] | 1-(2-((2S,4R)-4-fluoro-2-(6-(trifluoromethyl)pyrazin-2-ylcarbamoyl)pyrrolidin-1-yl)-2-oxoethyl)-5-((5-fluoropyrimidin-2-yl)ethynyl)-1H-indazole-3-carboxamide | *** | 1.65 (A) | 600 |

TABLE 1-continued

| Cmp No. | Structure | Name | IC$_{50}$ | RT min (Method A or B) | MS (M + 1) |
|---|---|---|---|---|---|
| 71 | 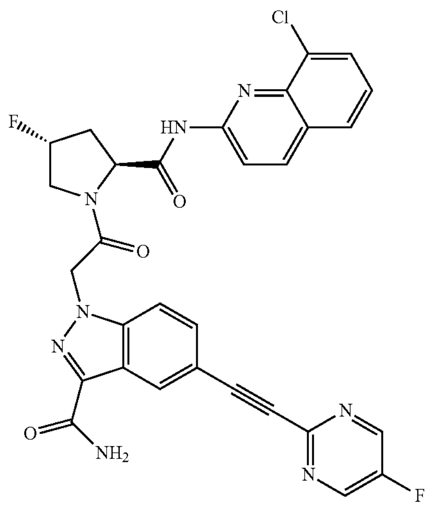 [SMILES: NC(=O)c1nn(CC(=O)N2C[C@H](F)C[C@H]2C(=O)Nc2ccc3cccc(Cl)c3n2)c2ccc(C#Cc3ncc(F)cn3)cc12] | 1-(2-((2S,4R)-2-(8-chloroquinolin-2-ylcarbamoyl)-4-fluoropyrrolidin-1-yl)-2-oxoethyl)-5-((5-fluoropyrimidin-2-yl)ethynyl)-1H-indazole-3-carboxamide | *** | 1.94 (A) | 615 |
| 72 | 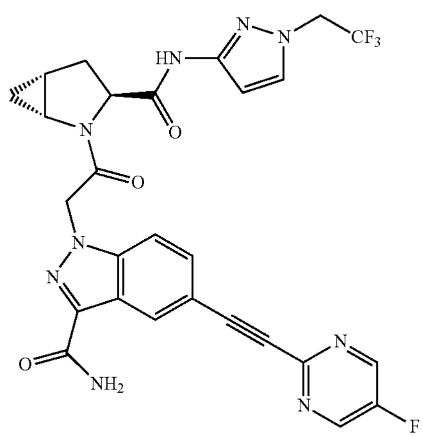 [SMILES: NC(=O)c1nn(CC(=O)N2[C@@H]3C[C@@H]3C[C@H]2C(=O)Nc2ccn(CC(F)(F)F)n2)c2ccc(C#Cc3ncc(F)cn3)cc12] | 5-((5-fluoropyrimidin-2-yl)ethynyl)-1-(2-oxo-2-((1R,3S,5R)-3-(1-(2,2,2-trifluoroethyl)-1H-pyrazol-3-ylcarbamoyl)-2-azabicyclo[3.1.0]hexan-2-yl)ethyl)-1H-indazole-3-carboxamide | *** | 1.54 (A) | 596 |
| 73 | 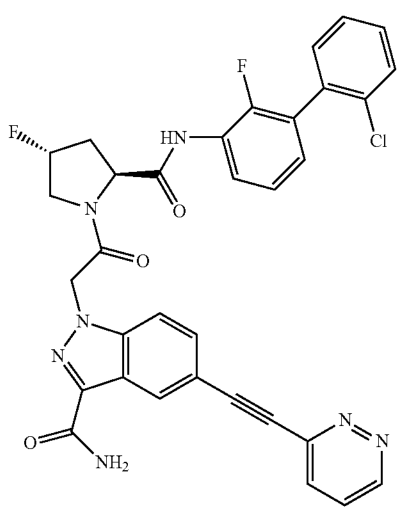 [SMILES: NC(=O)c1nn(CC(=O)N2C[C@H](F)C[C@H]2C(=O)Nc2cccc(-c3ccccc3Cl)c2F)c2ccc(C#Cc3cccnn3)cc12] | 1-(2-((2S,4R)-2-(2'-chloro-2-fluorobiphenyl-3-ylcarbamoyl)-4-fluoropyrrolidin-1-yl)-2-oxoethyl)-5-(pyridazin-3-ylethynyl)-1H-indazole-3-carboxamide | *** | 1.93 (A) | 640 |

TABLE 1-continued

| Cmp No. | Structure | Name | IC$_{50}$ | RT min (Method A or B) | MS (M + 1) |
|---|---|---|---|---|---|
| 74 | 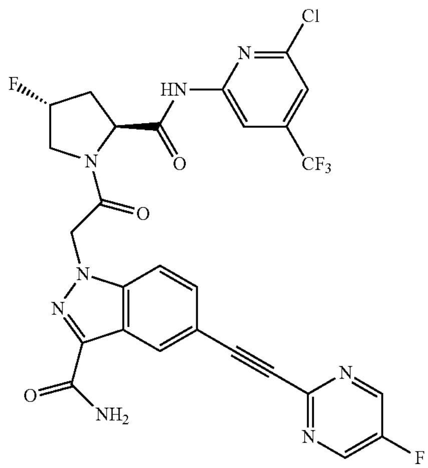 [SMILES: NC(=O)c1nn(CC(=O)N2C[C@H](F)C[C@H]2C(=O)Nc2cc(C(F)(F)F)cc(Cl)n2)c2ccc(C#Cc3ncc(F)cn3)cc12] | 1-(2-((2S,4R)-2-(6-chloro-4-(trifluoromethyl)pyridin-2-ylcarbamoyl)-4-fluoropyrrolidin-1-yl)-2-oxoethyl)-5-((5-fluoropyrimidin-2-yl)ethynyl)-1H-indazole-3-carboxamide | *** | 2.06 (A) | 633 |
| 75 | 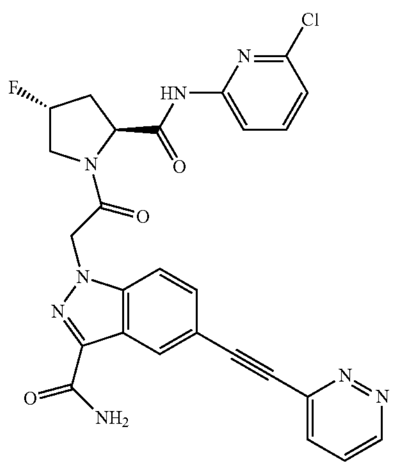 [SMILES: NC(=O)c1nn(CC(=O)N2C[C@H](F)C[C@H]2C(=O)Nc2cccc(Cl)n2)c2ccc(C#Cc3cccnn3)cc12] | 1-(2-((2S,4R)-2-(6-chloropyridin-2-ylcarbamoyl)-4-fluoropyrrolidin-1-yl)-2-oxoethyl)-5-(pyridazin-3-ylethynyl)-1H-indazole-3-carboxamide | *** | 1.37 (A) | 547 |
| 76 | 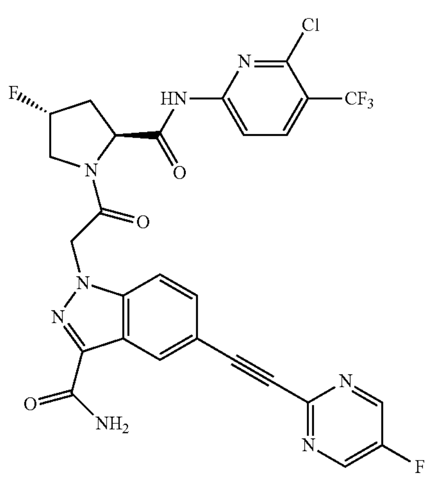 [SMILES: NC(=O)c1nn(CC(=O)N2C[C@H](F)C[C@H]2C(=O)Nc2ccc(C(F)(F)F)c(Cl)n2)c2ccc(C#Cc3ncc(F)cn3)cc12] | 1-(2-((2S,4R)-2-(6-chloro-5-(trifluoromethyl)pyridin-2-ylcarbamoyl)-4-fluoropyrrolidin-1-yl)-2-oxoethyl)-5-((5-fluoropyrimidin-2-yl)ethynyl)-1H-indazole-3-carboxamide | *** | 2.05 (A) | 633 |

TABLE 1-continued

| Cmp No. | Structure | Name | IC$_{50}$ | RT min (Method A or B) | MS (M + 1) |
|---|---|---|---|---|---|
| 77 | 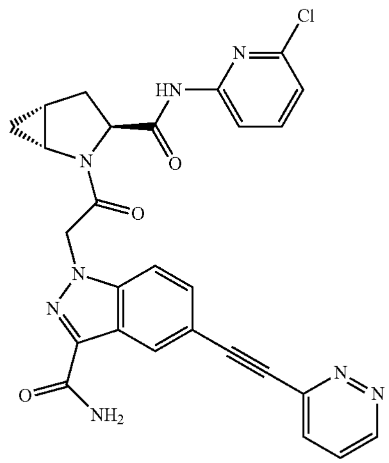 [SMILES: NC(=O)c1nn(CC(=O)N2[C@@H]3C[C@@H]3C[C@H]2C(=O)Nc2cccc(Cl)n2)c2ccc(C#Cc3cccnn3)cc12] | 1-(2-((1R,3S,5R)-3-(6-chloropyridin-2-ylcarbamoyl)-2-azabicyclo[3.1.0]hexan-2-yl)-2-oxoethyl)-5-(pyridazin-3-ylethynyl)-1H-indazole-3-carboxamide | *** | 1.48 (A) | 541 |
| 78 | 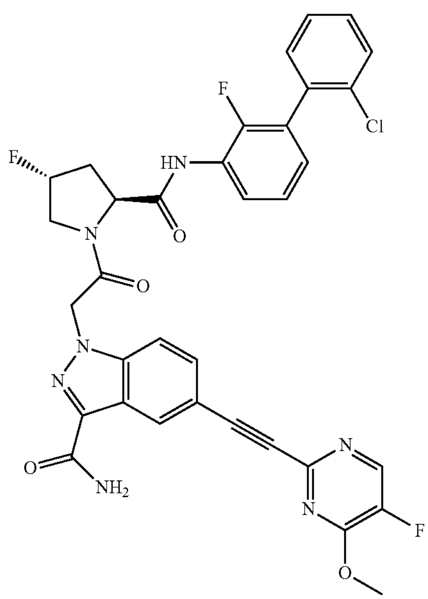 [SMILES: COc1nc(C#Cc2ccc3c(c2)c(C(N)=O)nn3CC(=O)N2C[C@H](F)C[C@H]2C(=O)Nc2cccc(-c3ccccc3Cl)c2F)ncc1F] | 1-(2-((2S,4R)-2-(2'-chloro-2-fluorobiphenyl-3-ylcarbamoyl)-4-fluoropyrrolidin-1-yl)-2-oxoethyl)-5-((5-fluoro-4-methoxypyrimidin-2-yl)ethynyl)-1H-indazole-3-carboxamide | *** | 2.37 (A) | 688 |
| 79 | 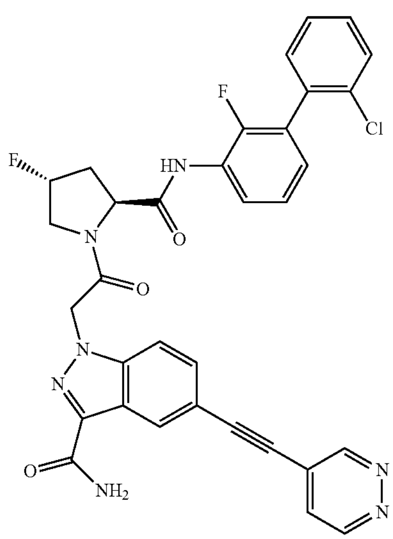 [SMILES: NC(=O)c1nn(CC(=O)N2C[C@H](F)C[C@H]2C(=O)Nc2cccc(-c3ccccc3Cl)c2F)c2ccc(C#Cc3ccnnc3)cc12] | 1-(2-((2S,4R)-2-(2'-chloro-2-fluorobiphenyl-3-ylcarbamoyl)-4-fluoropyrrolidin-1-yl)-2-oxoethyl)-5-(pyridazin-4-ylethynyl)-1H-indazole-3-carboxamide | *** | 1.93 (A) | 640 |

TABLE 1-continued

| Cmp No. | Structure | Name | IC$_{50}$ | RT min (Method A or B) | MS (M + 1) |
|---|---|---|---|---|---|
| 80 | 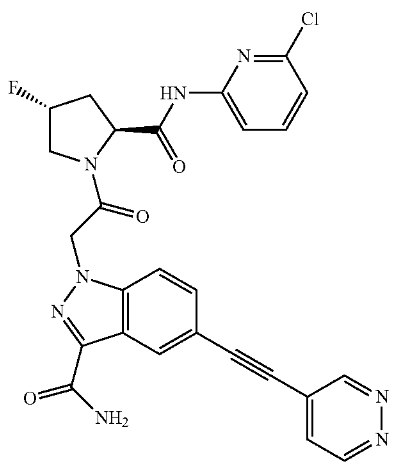 [SMILES: NC(=O)c1nn(CC(=O)N2C[C@H](F)C[C@H]2C(=O)Nc2cccc(Cl)n2)c2ccc(C#Cc3ccnnc3)cc12] | 1-(2-((2S,4R)-2-(6-chloropyridin-2-ylcarbamoyl)-4-fluoropyrrolidin-1-yl)-2-oxoethyl)-5-(pyridazin-4-ylethynyl)-1H-indazole-3-carboxamide | *** | 1.37 (A) | 547 |
| 81 | 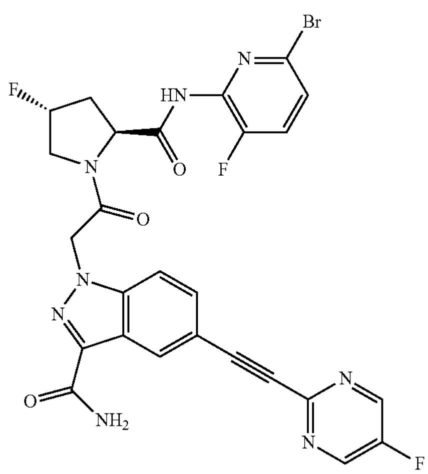 [SMILES: NC(=O)c1nn(CC(=O)N2C[C@H](F)C[C@H]2C(=O)Nc2nc(Br)ccc2F)c2ccc(C#Cc3ncc(F)cn3)cc12] | 1-(2-((2S,4R)-2-(6-chloro-3-fluoropyridin-2-ylcarbamoyl)-4-fluoropyrrolidin-1-yl)-2-oxoethyl)-5-((5-fluoropyrimidin-2-yl)ethynyl)-1H-indazole-3-carboxamide | *** | 1.44 (A) | 583 |
| 82 | 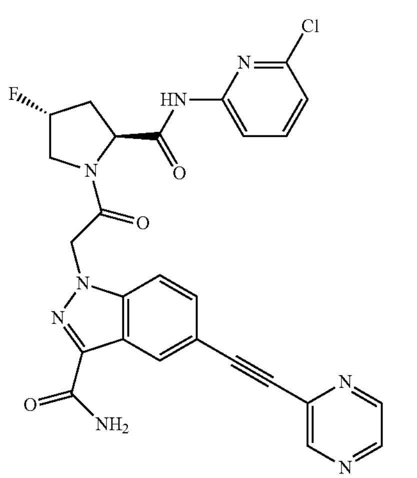 [SMILES: NC(=O)c1nn(CC(=O)N2C[C@H](F)C[C@H]2C(=O)Nc2cccc(Cl)n2)c2ccc(C#Cc3cnccn3)cc12] | 1-(2-((2S,4R)-2-(6-chloropyridin-2-ylcarbamoyl)-4-fluoropyrrolidin-1-yl)-2-oxoethyl)-5-(pyrazin-2-ylethynyl)-1H-indazole-3-carboxamide | *** | 1.53 (A) | 547 |

TABLE 1-continued

| Cmp No. | Structure | Name | IC$_{50}$ | RT min (Method A or B) | MS (M + 1) |
|---|---|---|---|---|---|
| 83 | 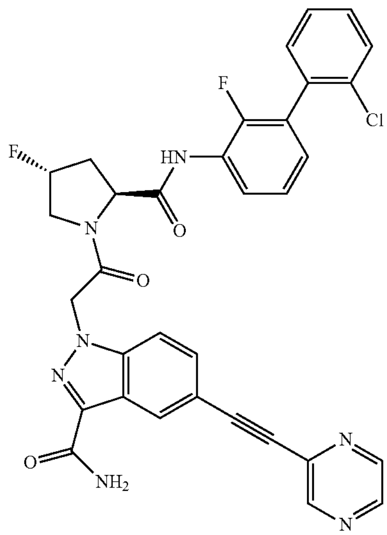 [SMILES: NC(=O)c1nn(CC(=O)N2C[C@H](F)C[C@H]2C(=O)Nc2cccc(-c3ccccc3Cl)c2F)c2ccc(C#Cc3cnccn3)cc12] | 1-(2-((2S,4R)-2-(2'-chloro-2-fluorobiphenyl-3-ylcarbamoyl)-4-fluoropyrrolidin-1-yl)-2-oxoethyl)-5-(pyrazin-2-ylethynyl)-1H-indazole-3-carboxamide | *** | 2.08 (A) | 640 |
| 84 | 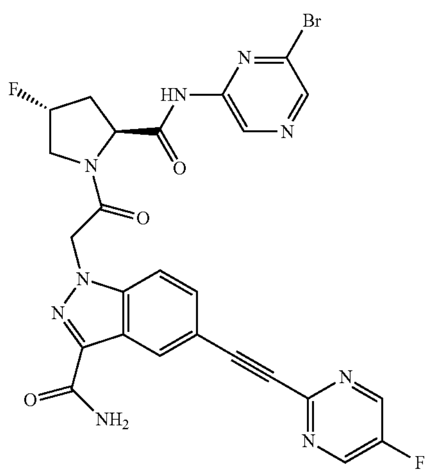 [SMILES: NC(=O)c1nn(CC(=O)N2C[C@H](F)C[C@H]2C(=O)Nc2cncc(Br)n2)c2ccc(C#Cc3ncc(F)cn3)cc12] | 1-(2-((2S,4R)-2-(6-bromopyrazin-2-ylcarbamoyl)-4-fluoropyrrolidin-1-yl)-2-oxoethyl)-5-((5-fluoropyrimidin-2-yl)ethynyl)-1H-indazole-3-carboxamide | *** | 1.52 (A) | 611 |
| 85 | 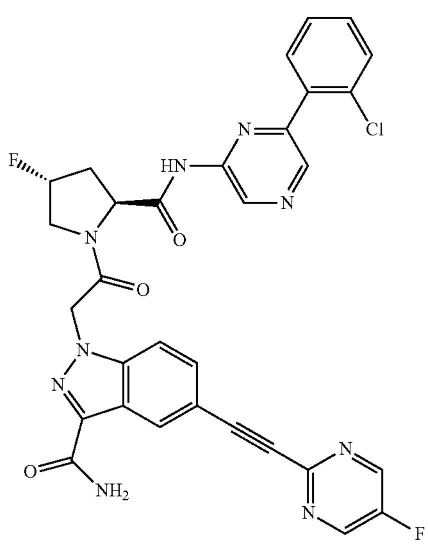 [SMILES: NC(=O)c1nn(CC(=O)N2C[C@H](F)C[C@H]2C(=O)Nc2cncc(-c3ccccc3Cl)n2)c2ccc(C#Cc3ncc(F)cn3)cc12] | 1-(2-((2S,4R)-2-(6-(2-chlorophenyl)pyrazin-2-ylcarbamoyl)-4-fluoropyrrolidin-1-yl)-2-oxoethyl)-5-((5-fluoropyrimidin-2-yl)ethynyl)-1H-indazole-3-carboxamide | *** | 1.88 (A) | 642 |

TABLE 1-continued

| Cmp No. | Structure | Name | IC$_{50}$ | RT min (Method A or B) | MS (M + 1) |
|---|---|---|---|---|---|
| 86 | 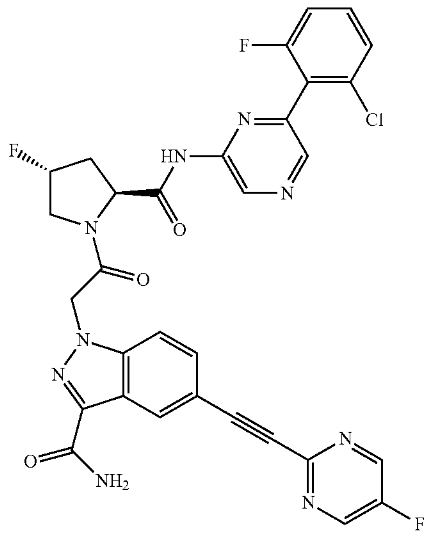 [SMILES: NC(=O)c1nn(CC(=O)N2C[C@H](F)C[C@H]2C(=O)Nc2cncc(-c3c(F)cccc3Cl)n2)c2ccc(C#Cc3ncc(F)cn3)cc12] | 1-(2-((2S,4R)-2-(6-(2-chloro-6-fluorophenyl)pyrazin-2-ylcarbamoyl)-4-fluoropyrrolidin-1-yl)-2-oxoethyl)-5-((5-fluoropyrimidin-2-yl)ethynyl)-1H-indazole-3-carboxamide | *** | 1.87 (A) | 660 |
| 87 | 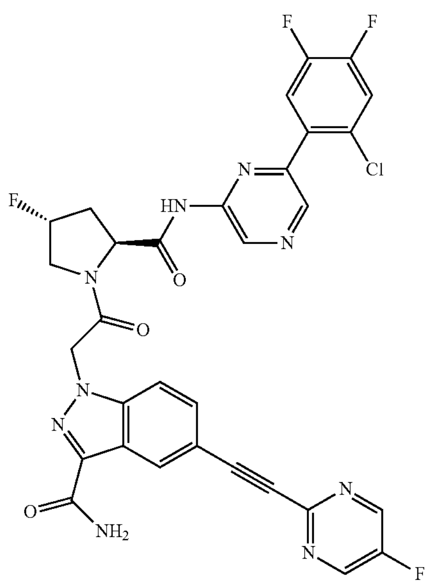 [SMILES: NC(=O)c1nn(CC(=O)N2C[C@H](F)C[C@H]2C(=O)Nc2cncc(-c3cc(F)c(F)cc3Cl)n2)c2ccc(C#Cc3ncc(F)cn3)cc12] | 1-(2-((2S,4R)-2-(6-(2-chloro-4,5-difluorophenyl)pyrazin-2-ylcarbamoyl)-4-fluoropyrrolidin-1-yl)-2-oxoethyl)-5-((5-fluoropyrimidin-2-yl)ethynyl)-1H-indazole-3-carboxamide | *** | 2.01 (A) | 678 |
| 88 | 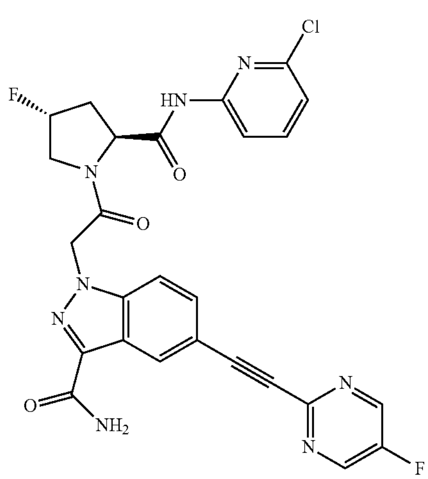 [SMILES: NC(=O)c1nn(CC(=O)N2C[C@H](F)C[C@H]2C(=O)Nc2cccc(Cl)n2)c2ccc(C#Cc3ncc(F)cn3)cc12] | 1-(2-((2S,4R)-2-(6-chloropyridin-2-ylcarbamoyl)-4-fluoropyrrolidin-1-yl)-2-oxoethyl)-5-((5-fluoropyrimidin-2-yl)ethynyl)-1H-indazole-3-carboxamide | *** | 1.64 (A) | 565 |

| Cmp No. | Structure | Name | IC$_{50}$ | RT min (Method A or B) | MS (M + 1) |
|---|---|---|---|---|---|
| 89 | 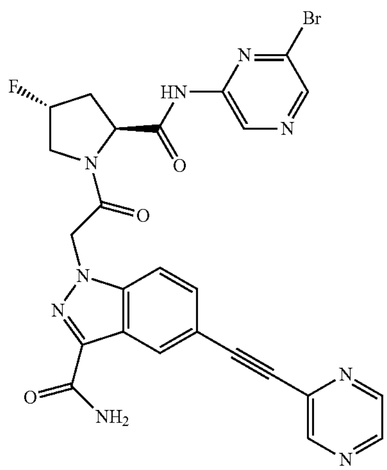 [SMILES: NC(=O)c1nn(CC(=O)N2C[C@H](F)C[C@H]2C(=O)Nc2cncc(Br)n2)c2ccc(C#Cc3cnccn3)cc12] | 1-(2-((2S,4R)-2-(6-bromopyrazin-2-ylcarbamoyl)-4-fluoropyrrolidin-1-yl)-2-oxoethyl)-5-(pyrazin-2-ylethynyl)-1H-indazole-3-carboxamide | *** | 1.41 (A) | 594 |
| 90 | 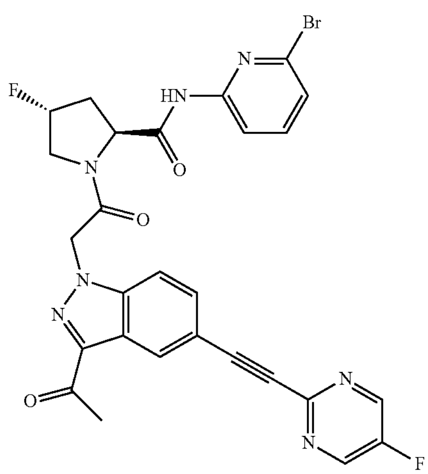 [SMILES: CC(=O)c1nn(CC(=O)N2C[C@H](F)C[C@H]2C(=O)Nc2cccc(Br)n2)c2ccc(C#Cc3ncc(F)cn3)cc12] | (2S,4R)-1-(2-(3-acetyl-5-((5-fluoropyrimidin-2-yl)ethynyl)-1H-indazol-1-yl)acetyl)-N-(6-bromopyridin-2-yl)-4-fluoropyrrolidine-2-carboxamide | *** | 2.14 (A) | 608 |
| 91 | 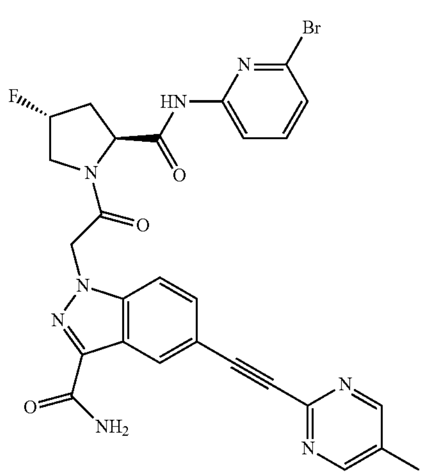 [SMILES: Cc1cnc(C#Cc2ccc3c(c2)c(C(N)=O)nn3CC(=O)N2C[C@H](F)C[C@H]2C(=O)Nc2cccc(Br)n2)nc1] | 1-(2-((2S,4R)-2-(6-bromopyridin-2-ylcarbamoyl)-4-fluoropyrrolidin-1-yl)-2-oxoethyl)-5-((5-methylpyrimidin-2-yl)ethynyl)-1H-indazole-3-carboxamide | *** | 1.68 (A) | 605 |

TABLE 1-continued

| Cmp No. | Structure | Name | IC$_{50}$ | RT min (Method A or B) | MS (M + 1) |
|---|---|---|---|---|---|
| 92 | 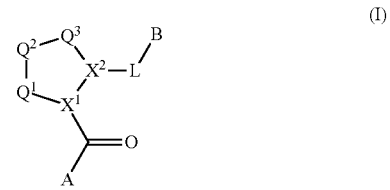 | 1-(2-((2S,4R)-2-(6-bromopyridin-2-ylcarbamoyl)-4-fluoropyrrolidin-1-yl)-2-oxoethyl)-5-((2-methoxypyrimidin-5-yl)ethynyl)-1H-indazole-3-carboxamide | *** | 1.83 (A) | 623 |

Example 12. Human Factor D Assay

Human factor D (purified from human serum, Complement Technology, Inc.) at 80 nM final concentration is incubated with test compound at various concentrations for 5 minutes at room temperature in 50 mM Tris, 1M NaCl, pH 7.5. A synthetic substrate Z-L-Lys-SBzl and DTNB (Ellman's reagent) are added to final concentrations of 100 μM each. The increase in color is recorded at OD$_{405}$ nm in a microplate in kinetic mode over 30 minutes with 30 second time points in a spectrofluorimeter. IC$_{50}$ values are calculated by non-linear regression from the percentage of inhibition of complement factor D activity as a function of test compound concentration.

Example 13. Hemolysis Assay

The hemolysis assay was previously described by G. Ruiz-Gomez, et al., J. Med. Chem. (2009) 52: 6042-6052. In the assay red blood cells (RBC), rabbit erythrocyctes (purchased from Complement Technologies), are washed using GVB Buffer (0.1% gelatin, 5 mM Veronal, 145 mM NaCl, 0.025% NaN$_3$, pH 7.3) plus 10 mM final Mg-EGTA. Cells are used at a concentration of 1×10$^8$ cells/mL. Prior to the hemolysis assay, the optimum concentration of Normal Human Serum (NHS) needed to achieve 100% lysis of rabbit erythrocytes is determined by titration. NHS (Complement Technologies) is incubated with inhibitor for 15 min at 37° C., rabbit erythrocytes in buffer were added and incubated for an additional 30 min at 37° C. Positive control (100% lysis) consists of serum and RBC and negative control (0% lysis) of Mg-EGTA buffer and RBC only. Samples are centrifuged at 2000 g for 5 min, and supernatants collected. Optical density of the supernatant is monitored at 405 nm using a UV/visible spectrophotometer. Percentage lysis in each sample is calculated relative to positive control (100% lysis).

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

What is claimed is:
1. A compound of Formula I

(I)

or a pharmaceutically acceptable salt thereof, wherein:
   $Q^1$ is $C(R^1R^{1'})$;
   $Q^2$ is $C(R^2R^{2'})$;
   $Q^3$ is $C(R^3R^{3'})$;
   $X^1$ is N and $X^2$ is CH;
   $R^1$, $R^{1'}$, $R^2$, $R^{2'}$, $R^3$, and $R^{3'}$ are independently chosen from hydrogen, halogen, hydroxyl, nitro, cyano, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —C$_0$-C$_4$alkylNR$^9$R$^{10}$, —C(O)OR$^9$, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, $C_1$-$C_2$haloalkyl, and $C_1$-$C_2$haloalkoxy;
   $R^9$ and $R^{10}$ are independently chosen at each occurrence from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl);
   or $R^1$ and $R^2$ form a 3- to 6-membered carbocyclic or aryl ring;
   or $R^2$ and $R^3$ form a 3- to 6-membered carbocyclic ring;
   or $R^1$ and $R^{1'}$, or $R^2$ and $R^{2'}$, or $R^3$ and $R^{3'}$ form a 3- to 6-membered carbocyclic spiro ring;
   or $R^1$ and $R^{1'}$, or $R^2$ and $R^{2'}$, or $R^3$ and $R^{3'}$ form a 3- to 6-membered heterocyclic spiro ring;
   each of which ring is unsubstituted or substituted with 1 or more substituents independently chosen from halogen, hydroxyl, cyano, —COOH, $C_1$-$C_4$alkyl, $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy;

or $R^1$ and $R^{1'}$, $R^2$ and $R^{2'}$, or $R^3$ and $R^{3'}$ form a carbonyl group;

or $R^1$ and $R^2$ or $R^2$ and $R^3$ form a carbon-carbon double bond;

A is a group selected from:

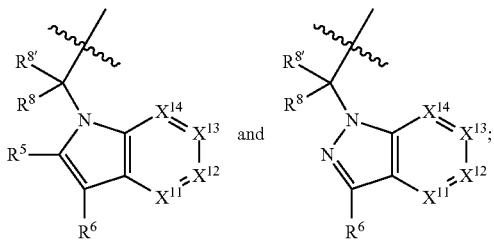

$R^5$ and $R^6$ are independently selected from —CHO, —C(O)NH$_2$, —C(O)NH(CH$_3$), $C_2$-$C_6$alkanoyl, hydrogen, hydroxyl, halogen, cyano, nitro, —COOH, —SO$_2$NH$_2$, vinyl, $C_1$-$C_6$alkyl, $C_2$-$C_6$alkenyl, $C_1$-$C_6$alkoxy, —$C_0$-$C_4$alkyl($C_3$-$C_7$cycloalkyl), —C(O) $C_0$-$C_4$alkyl($C_3$-$C_7$cycloalkyl), —P(O)(OR$^9$)$_2$, —OC(O)R$^9$, —C(O)OR$^9$, —C(O)N(CH$_2$CH$_2$R$^9$)(R$^{10}$), —NR$^9$C(O)R$^{10}$, phenyl, or 5- to 6-membered heteroaryl;

$R^8$ and $R^{8'}$ are independently chosen from hydrogen, halogen, hydroxyl, $C_1$-$C_6$alkyl, —$C_0$-$C_4$alkyl($C_3$-$C_7$cycloalkyl), $C_1$-$C_6$alkoxy, and ($C_1$-$C_4$alkylamino)$C_0$-$C_2$alkyl; or $R^8$ and $R^{8'}$ are taken together to form an oxo group; or $R^8$ and $R^{8'}$ can be taken together with the carbon that they are bonded to form a 3-membered carbocyclic ring;

$X^{11}$ is N or CR$^{11}$;
$X^{12}$ is CR$^{12}$;
$X^{13}$ is CR$^{13}$;
$X^{14}$ is N or CR$^{14}$;

one of $R^{12}$ and $R^{13}$ is chosen from $R^{31}$ and the other of $R^{12}$ and $R^{13}$ is chosen from $R^{32}$;

$R^{31}$ is chosen from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)OR$^9$, $C_1$-$C_6$thioalkyl, —$C_0$-$C_4$alkylNR$^9$R$^{10}$, —C(O) NR$^9$R$^{10}$, —SO$_2$R$^9$, —SO$_2$NR$^9$R$^{10}$, —OC(O)R$^9$, and —C(NR$^9$)NR$^9$R$^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —CONH$_2$ $C_1$-$C_2$haloalkyl, and $C_1$-$C_2$haloalkoxy, and each of which $R^{31}$ is also optionally substituted with one substituent chosen from phenyl and 4- to 7-membered heterocycle containing 1, 2, or 3 heteroatoms independently chosen from N, O, and S; which phenyl or 4- to 7-membered heterocycle is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy;

$R^{32}$ is

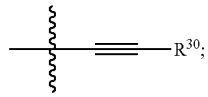

$R^{11}$ and $R^{14}$ are independently chosen at each occurrence from hydrogen, halogen, hydroxyl, nitro, cyano, —O(PO)(OR$^9$)$_2$, —(PO)(OR$^9$)$_2$, $C_1$-$C_6$alkyl, $C_2$-$C_6$alkenyl, $C_2$-$C_6$alkynyl, $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy;

$R^{21}$ and $R^{22}$ are independently chosen at each occurrence from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O) OC$_1$-$C_6$alkyl, —$C_1$-$C_4$alkylOC(O)$C_1$-$C_6$alkyl, —$C_1$-$C_4$alkylC(O)OC$_1$-$C_6$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle) $C_0$-$C_4$alkyl having 1, 2, or 3 heteroatoms independently chosen from N, O, and S;

$R^{23}$ is independently chosen at each occurrence from $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S;

$R^{24}$ and $R^{25}$ are taken together with the nitrogen to which they are attached to form a 4- to 7-membered monocyclic heterocycloalkyl group, or a 6- to 10-membered bicyclic heterocyclic group having fused, spiro, or bridged rings;

$R^{30}$ is independently chosen at each occurrence from hydrogen, $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S; (5- or 6-membered unsaturated or aromatic heterocycle)$C_0$-$C_4$alkyl having 1, 2, or 3 heteroatoms independently chosen from N, O, and S; COOH, Si(CH$_3$)$_3$, COOR$^{30a}$, $C_2$-$C_6$alkanoyl, —B(OH)$_2$, —C(O)(CH$_2$)$_{1-4}$S(O)R$^{21}$, —P(O)(OR$^{21}$) (OR$^{22}$), —P(O)(OR$^{21}$)R$^{22}$, —P(O)R$^{21}$R$^{22}$, —NR$^9$P(O) (NHR$^{21}$)(NHR$^{22}$), —NR$^9$P(O)(OR$^{21}$)(NHR$^{22}$), —NR$^9$P(O)(R$^{21}$)(R$^{22}$), —C(S)R$^{21}$, —NR$^{21}$SO$_2$R$^{22}$, —NR$^9$S(O)NR$^{10}$R$^{22}$, —NR$^9$SO$_2$NR$^{10}$R$^{22}$, —SO$_2$NR$^9$COR$^{22}$, —SO$_2$NR$^9$CONR$^{21}$R$^{22}$, —NR$^{21}$SO$_2$R$^{22}$, —C(O)NR$^{21}$SO$_2$R$^{22}$, —C(NH$_2$) NR$^9$R$^{22}$, —C(NH$_2$)NR$^9$S(O)$_2$R$^{22}$, —NR$^9$C(O)OR$^{10}$, —NR$^{21}$OC(O)R$^{22}$, —(CH$_2$)$_{1-4}$C(O)NR$^{21}$R$^{22}$, —C(O) R$^{24}$R$^{25}$, —NR$^9$C(O)R$^{21}$, —C(O)R$^{21}$, —NR$^9$C(O) NR$^9$R$^{10}$, —NR$^9$C(O)NR$^{24}$R$^{25}$, —(CH$_2$)$_{1-4}$OC(O)R$^{21}$;

$R^{30a}$ is $C_1$-$C_6$alkyl, $C_2$-$C_6$alkenyl, $C_2$-$C_6$alkynyl, ($C_3$-$C_7$cycloalkyl)$C_0$-$C_4$alkyl-, (aryl)$C_0$-$C_4$alkyl-, (3- to 7-membered heterocycloalkyl)$C_0$-$C_4$alkyl- having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S;

L is

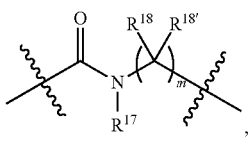

where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently chosen from hydrogen, halogen, hydroxymethyl, and methyl; and m is 0, 1, 2, or 3;

B is a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl) each of which B is unsubstituted or substituted with one or more substituents independently chosen from $R^{33}$ and $R^{34}$, and 0 or 1 substituents chosen from $R^{35}$ and $R^{36}$;

$R^{33}$ is independently chosen from halogen, hydroxyl, —COOH, cyano, $C_1$-$C_6$alkyl, $C_2$-$C_6$alkanoyl, $C_1$-$C_6$alkoxy, —$C_0$-$C_4$alkylN$R^9R^{10}$, —$SO_2R^9$, $C_1$-$C_2$haloalkyl, and $C_1$-$C_2$haloalkoxy;

$R^{34}$ is independently chosen from nitro, $C_2$-$C_6$alkenyl, $C_2$-$C_6$alkynyl, $C_1$-$C_6$thioalkyl, -J$C_3$-$C_7$cycloalkyl, —B(OH)$_2$, -JC(O)NR$^9$R$^{23}$, -JOSO$_2$R$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$) -JNR$^9$P(O)(OR$^{21}$)(NHR$^{22}$), -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)NR$^{22}$, -JC(NH$_2$)NR$^9$S(O)$_2$R$^{22}$, -JOC(O)NR$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)R$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_{1-4}$OC(O)R$^{21}$, and -JC(O)OR$^{23}$; each of which $R^{34}$ may be unsubstituted or substituted with one or more substituents independently chosen from halogen, hydroxyl, nitro, cyano, amino, oxo, —B(OH)$_2$, —Si(CH$_3$)$_3$, —COOH, —CONH$_2$, —P(O)(OH)$_2$, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy;

$R^{35}$ is independently chosen from naphthyl, naphthyloxy, indanyl, (4- to 7-membered heterocycloalkyl)$C_0$-$C_4$alkyl containing 1 or 2 heteroatoms chosen from N, O, and S, and bicyclic heterocycle containing 1, 2, or 3 heteroatoms independently chosen from N, O, and S, and containing 4- to 7-ring atoms in each ring; each of which $R^{35}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, $C_1$-$C_2$haloalkyl, and $C_1$-$C_2$haloalkoxy; and $R^{36}$ is independently chosen from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently chosen from N, O, B, and S, each of which $R^{36}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, —OSi(CH$_3$)$_2$C(CH$_3$)$_3$, —Si(CH$_3$)$_2$C(CH$_3$)$_3$, $C_1$-$C_2$haloalkyl, and $C_1$-$C_2$haloalkoxy; and J is independently selected at each occurrence from a covalent bond, $C_1$-$C_4$alkylene, —O$C_1$-$C_4$alkylene, $C_2$-$C_4$alkenylene, and $C_2$-$C_4$alkynylene.

2. A method for the treatment of a disorder mediated by complement factor D, comprising administering an effective amount to a host in need thereof of a compound of claim 1, optionally in a pharmaceutically acceptable carrier.

3. The method of claim 2, wherein the host is a human.

4. The method of claim 2, wherein the disorder is age-related macular degeneration (AMD).

5. The method of claim 2, wherein the disorder is retinal degeneration.

6. The method of claim 2, wherein the disorder is an ophthalmic disease.

7. The method of claim 2, wherein the disorder is paroxysmal nocturnal hemoglobinuria (PNH).

8. The method of claim 2, wherein the disorder is multiple sclerosis.

9. The method of claim 2, wherein the disorder is arthritis.

10. The method of claim 2, wherein the disorder is rheumatoid arthritis.

11. The method of claim 2, wherein the disorder is a respiratory disease or a cardiovascular disease.

12. The compound of claim 1, wherein the

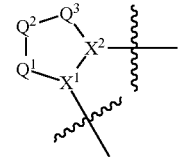

ring is selected from:

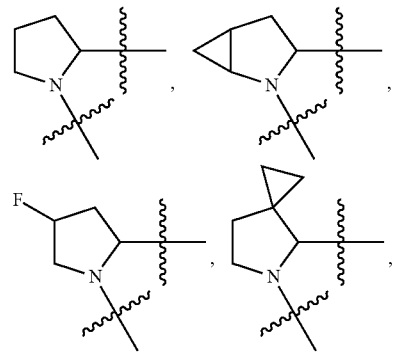

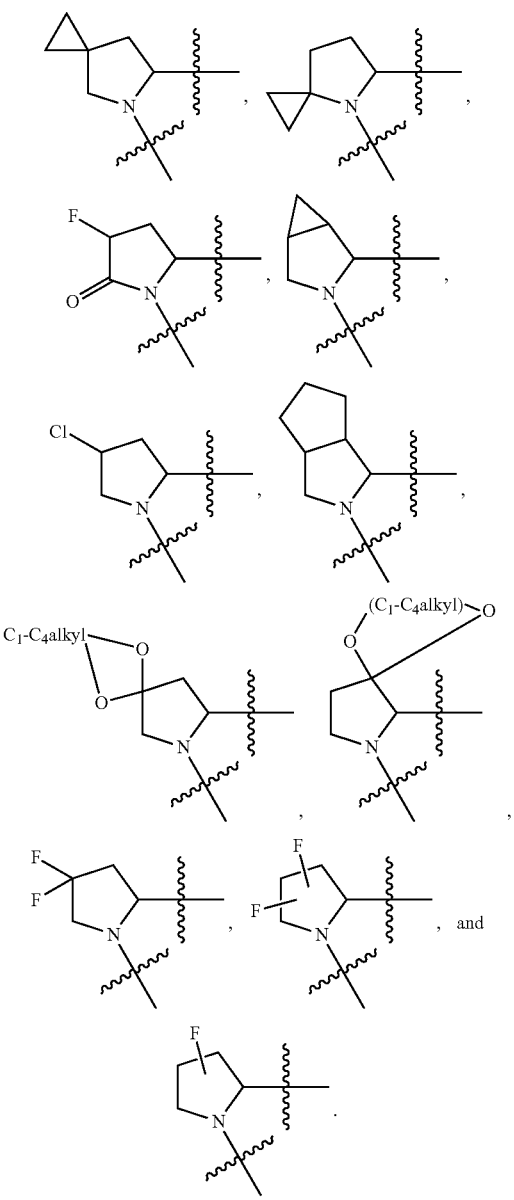

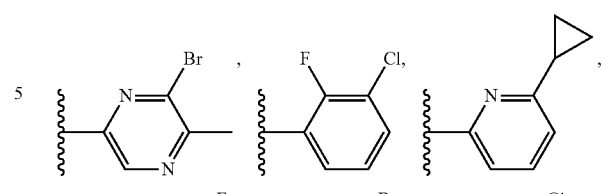

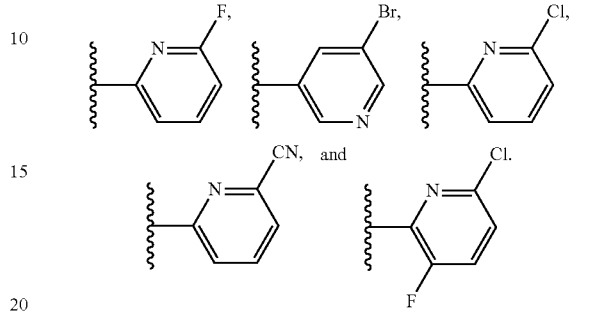

16. The compound of claim 1, wherein B is selected from:

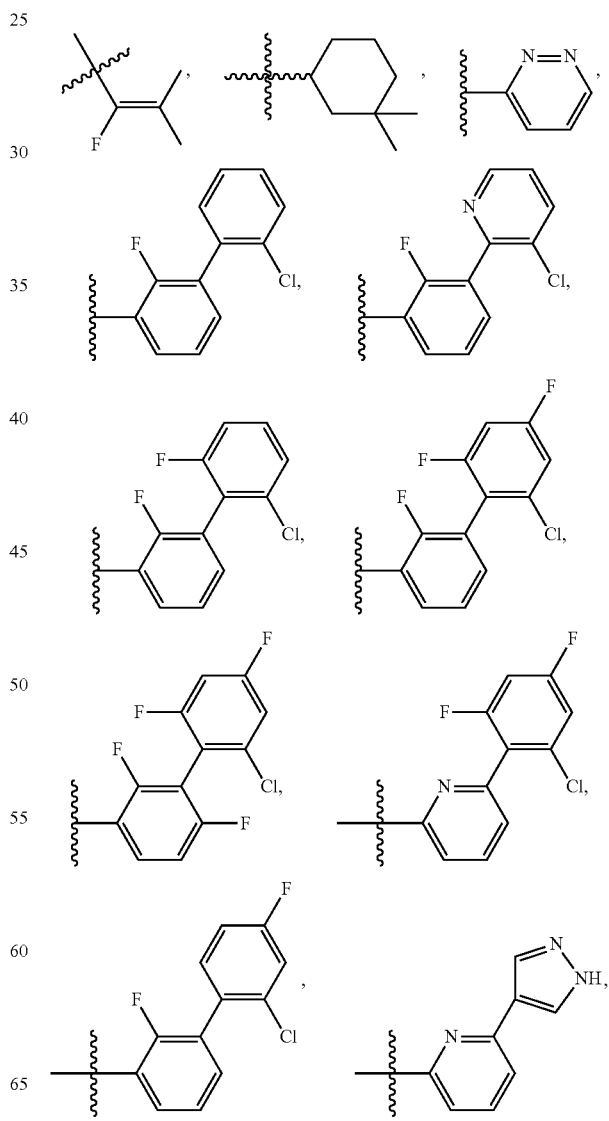

13. The compound of claim 1, wherein $R^1$ and $R^{1'}$ or $R^3$ and $R^{3'}$ can together form a 3- to 6-membered carbocyclic spiro ring or a 3- to 6-membered heterocyclic spiro ring containing 1 or 2 heteroatoms independently chosen from N, O, or S.

14. The compound of claim 1, wherein $R^2$ and $R^{2'}$ can together to form a 3- to 6-membered carbocyclic spiro ring; or $R^2$ and $R^{2'}$ are taken together to form a 3- to 6-membered heterocyclic spiro ring.

15. The compound of claim 1, wherein B is selected from:

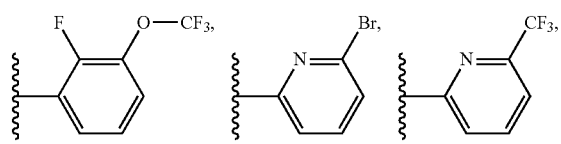

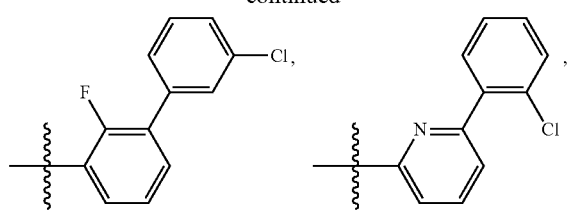
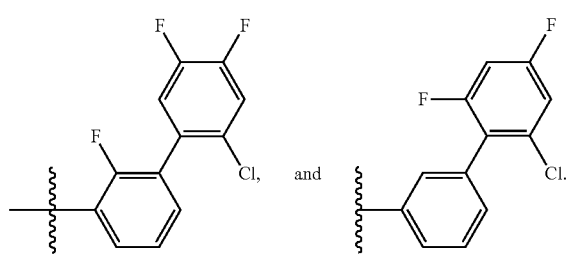
17. The compound of claim 1, wherein B is selected from:
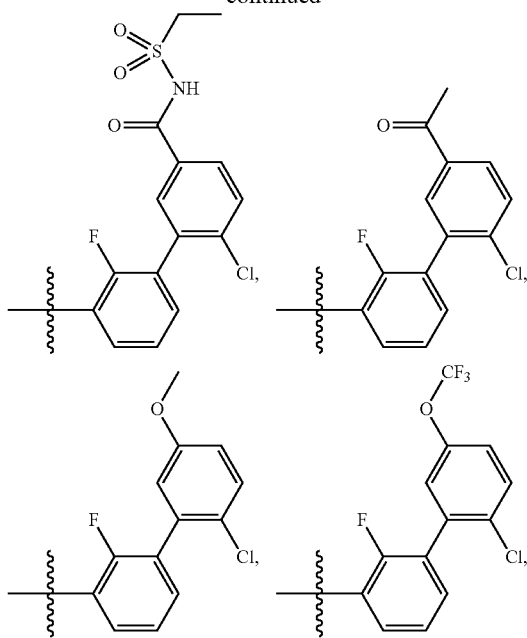
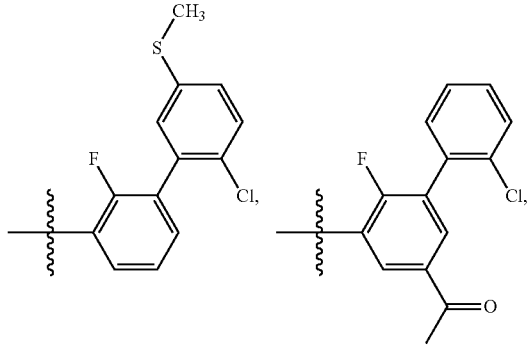
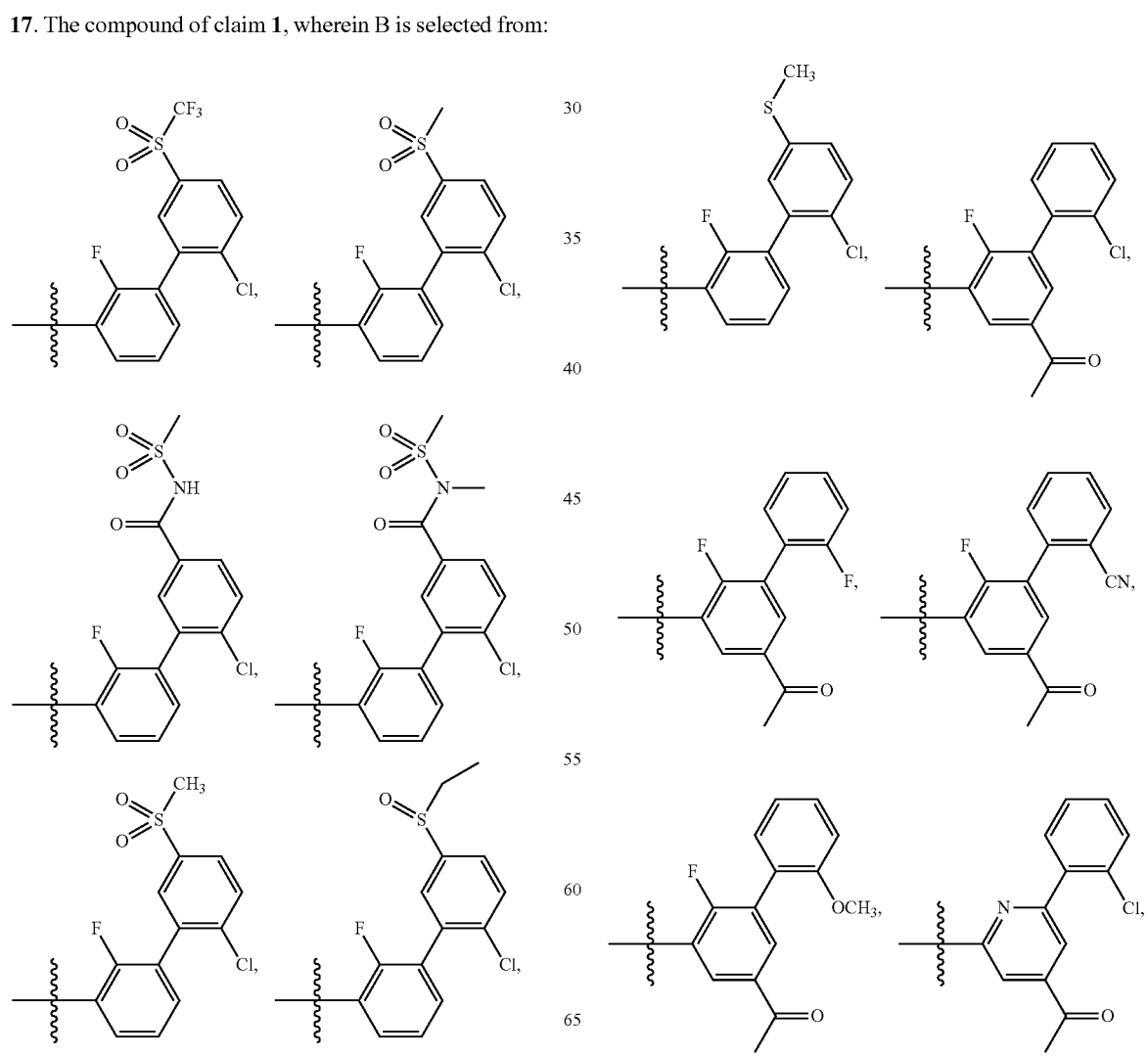

-continued
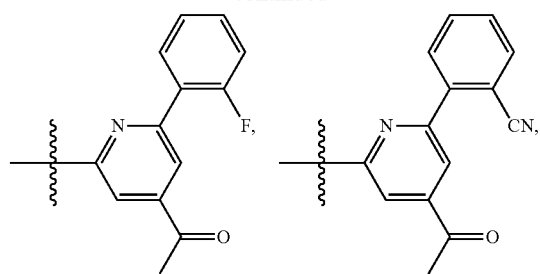
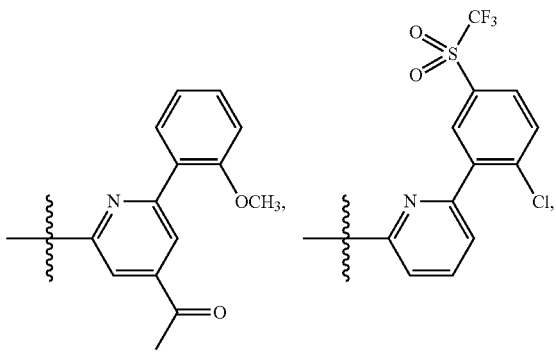
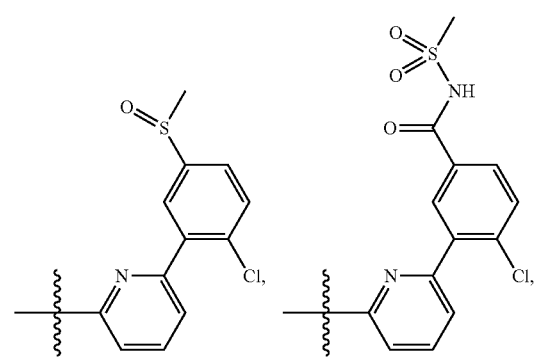
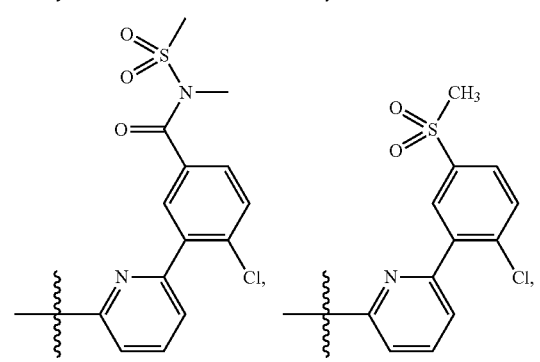
-continued
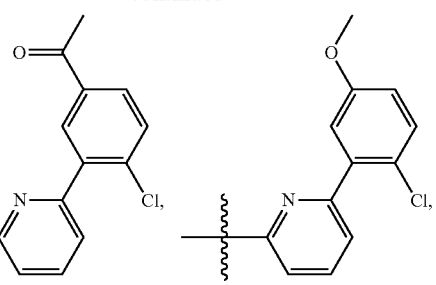
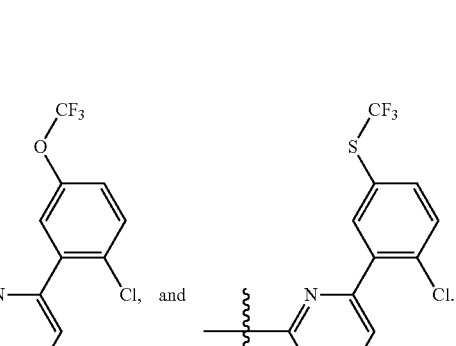
18. The compound of claim 1, wherein B is selected from:
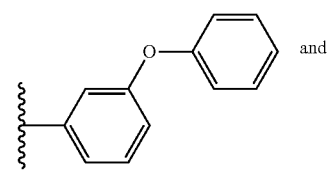
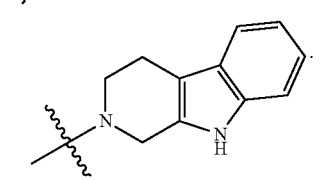
19. The compound of claim 1, wherein B is selected from:
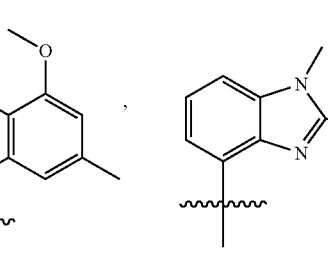
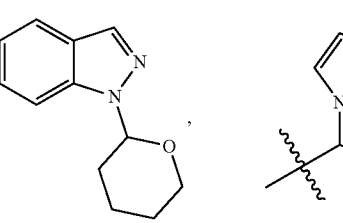

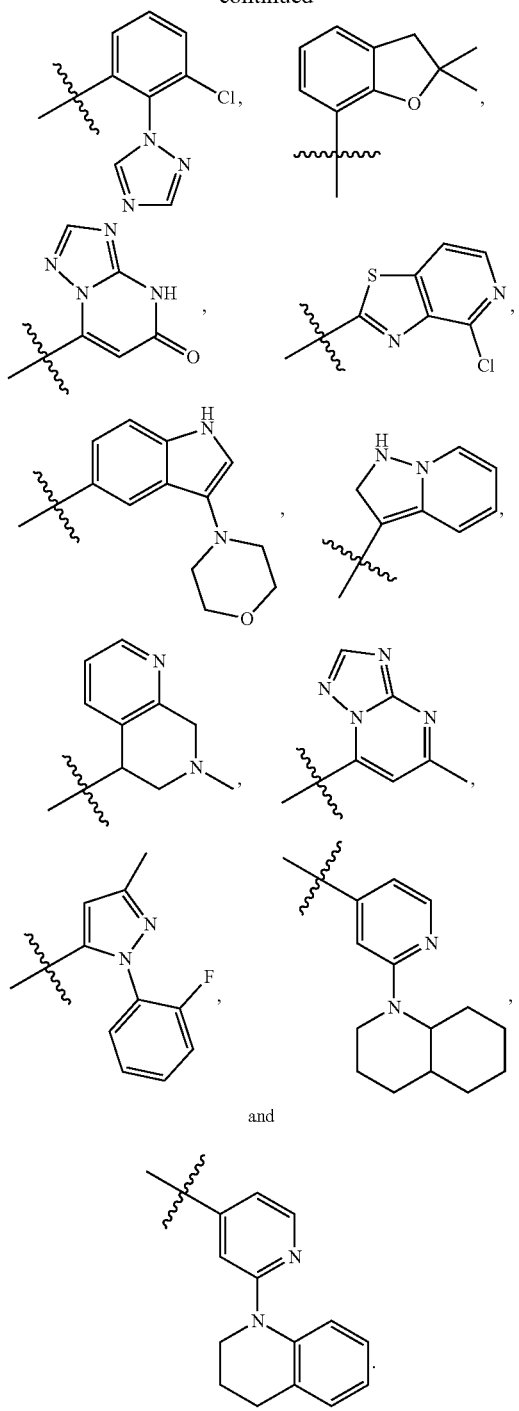
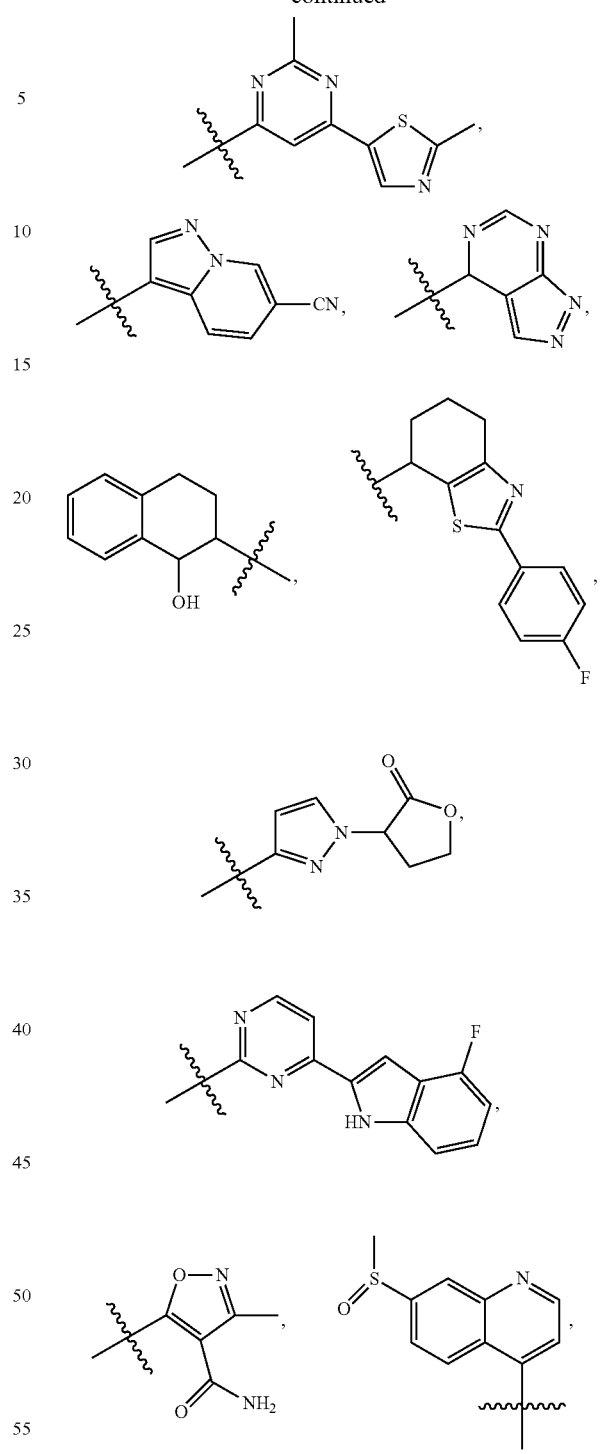
20. The compound of claim 1, wherein B is selected from:
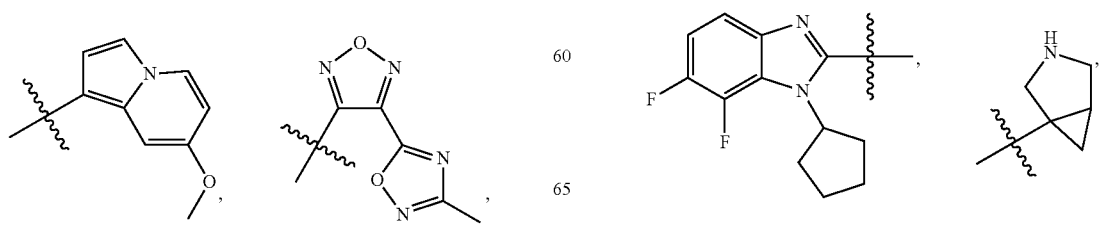

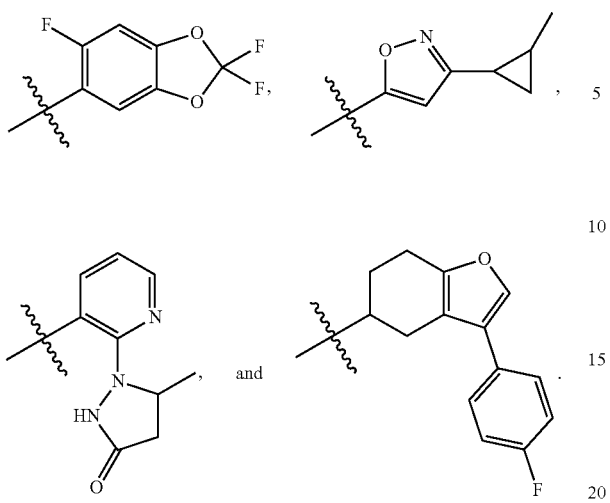

21. The compound of claim 1 of Formula IB

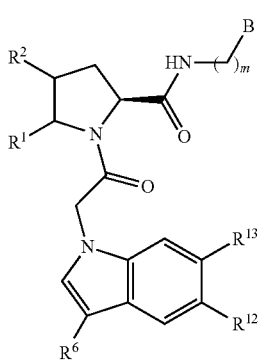
(IB)

or a pharmaceutically acceptable salt thereof.

22. The compound of claim 1 of Formula IC

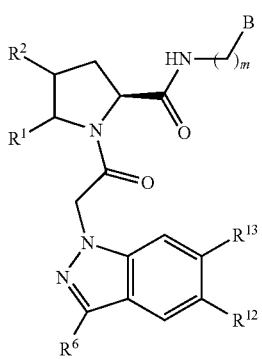
(IC)

or a pharmaceutically acceptable salt thereof.

23. The compound of claim 1, wherein A is

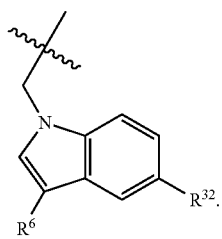

24. The compound of claim 1, wherein A is

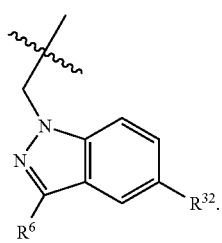

25. The compound of claim 1, wherein B is —($C_0$-$C_4$alkyl)(aryl), —($C_0$-$C_4$alkyl)(heteroaryl), or —($C_0$-$C_4$alkyl)(biphenyl) each of which B is unsubstituted or substituted with one or more substituents independently chosen from $R^{33}$ and $R^{34}$, and 0 or 1 substituents chosen from $R^{35}$ and $R^{36}$.

26. The compound of claim 25, wherein B is —($CH_2$)(aryl) substituted with two substituents independently chosen from $R^{33}$ and $R^{34}$.

27. The compound of claim 26, wherein $R^{33}$ is halogen.

28. The compound of claim 27, wherein there are two $R^{33}$ substituents and one is chlorine and the other is fluorine.

29. The compound of claim 25, wherein B is aryl or heteroaryl each of which B is unsubstituted or substituted with one or more substituents independently chosen from $R^{33}$ and $R^{34}$.

30. The compound of claim 29, wherein B is aryl.

31. The compound of claim 29, wherein B is heteroaryl.

32. The compound of claim 31, wherein heteroaryl is 2-pyridine.

33. The compound of claim 32, wherein 2-pyridine is substituted with one substituent independently chosen from $R^{33}$.

34. The compound of claim 33, wherein $R^{33}$ is halogen.

35. The compound of claim 34, wherein A is

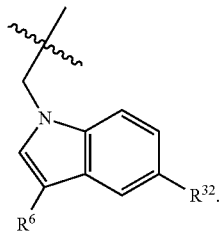

36. The compound of claim 34, wherein A is
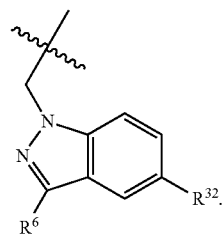
37. The compound of claim 28, wherein A is
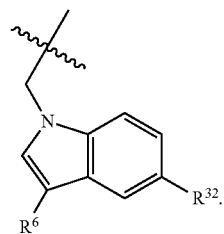
38. The compound of claim 28, wherein A is
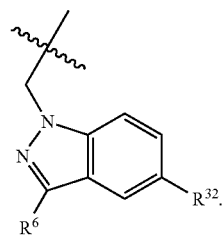
39. The compound of claim 1, wherein the compound is:
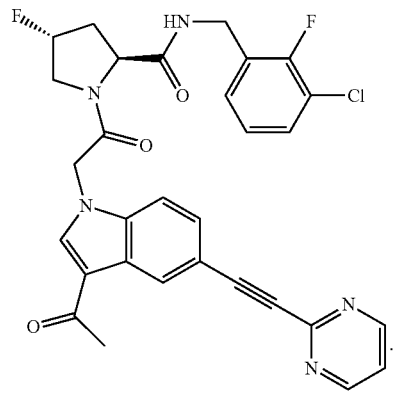 [SMILES: CC(=O)c1cn(CC(=O)N2C[C@H](F)C[C@H]2C(=O)NCc2cccc(Cl)c2F)c2ccc(C#Cc3ncccn3)cc12]
40. The compound of claim 1, wherein the compound is:
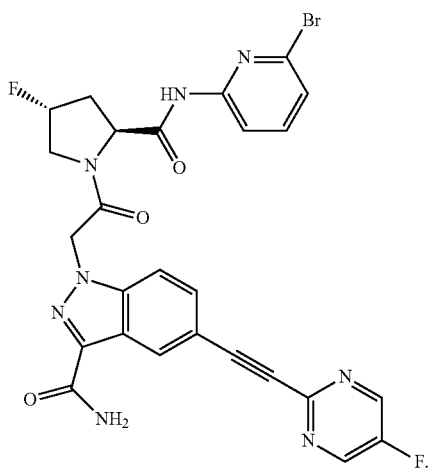 [SMILES: NC(=O)c1nn(CC(=O)N2C[C@H](F)C[C@H]2C(=O)Nc2cccc(Br)n2)c2ccc(C#Cc3ncc(F)cn3)cc12]
* * * * *